US010980755B2

(12) United States Patent
England et al.

(10) Patent No.: US 10,980,755 B2
(45) Date of Patent: Apr. 20, 2021

(54) LRH-1 MODULATORS

(71) Applicant: THE REGENTS OF THE UNIVERSITY OF CALIFORNIA, Oakland, CA (US)

(72) Inventors: Pamela M. England, San Francisco, CA (US); Felipe de Jesus Cortez, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/758,549

(22) PCT Filed: Sep. 9, 2016

(86) PCT No.: PCT/US2016/051159

§ 371 (c)(1),
(2) Date: Mar. 8, 2018

(87) PCT Pub. No.: WO2017/044889

PCT Pub. Date: Mar. 16, 2017

(65) Prior Publication Data

US 2018/0243245 A1 Aug. 30, 2018

Related U.S. Application Data

(60) Provisional application No. 62/216,950, filed on Sep. 10, 2015, provisional application No. 62/217,343, filed on Sep. 11, 2015.

(51) Int. Cl.

| | |
|---|---|
| ***C07C 235/60*** | (2006.01) |
| ***A61K 31/166*** | (2006.01) |
| ***C07D 333/24*** | (2006.01) |
| ***C07D 333/22*** | (2006.01) |
| ***C07D 207/337*** | (2006.01) |
| ***C07D 213/56*** | (2006.01) |
| ***C07C 317/46*** | (2006.01) |
| ***C07C 311/29*** | (2006.01) |
| ***C07D 231/12*** | (2006.01) |
| ***A61P 9/00*** | (2006.01) |
| ***A61P 3/10*** | (2006.01) |
| ***A61P 29/00*** | (2006.01) |
| ***A61P 35/00*** | (2006.01) |
| ***A61K 31/381*** | (2006.01) |
| ***A61K 31/40*** | (2006.01) |
| ***A61K 31/415*** | (2006.01) |
| ***A61K 31/4418*** | (2006.01) |

(52) U.S. Cl.

CPC .......... *A61K 31/166* (2013.01); *A61K 31/381* (2013.01); *A61K 31/40* (2013.01); *A61K 31/415* (2013.01); *A61K 31/4418* (2013.01); *A61P 3/10* (2018.01); *A61P 9/00* (2018.01); *A61P 29/00* (2018.01); *A61P 35/00* (2018.01); *C07C 235/60* (2013.01); *C07C 311/29* (2013.01); *C07C 317/46* (2013.01); *C07D 207/337* (2013.01); *C07D 213/56* (2013.01); *C07D 231/12* (2013.01); *C07D 333/22* (2013.01); *C07D 333/24* (2013.01)

(58) Field of Classification Search

CPC .................................................... C07C 235/60

See application file for complete search history.

(56) References Cited

U.S. PATENT DOCUMENTS

| | | | | |
|---|---|---|---|---|
| 3,161,612 | A * | 12/1964 | Ley | C08L 7/00 524/248 |
| 4,380,629 | A | 4/1983 | Yamashita et al. | |
| 2003/0069242 | A1 | 4/2003 | Toriyabe et al. | |
| 2006/0035944 | A1 * | 2/2006 | Muto | A61K 31/167 514/365 |
| 2009/0247534 | A1 | 10/2009 | Serrano-Wu et al. | |
| 2011/0124559 | A1 | 5/2011 | Cowan et al. | |
| 2011/0281866 | A1 | 11/2011 | Ren et al. | |

FOREIGN PATENT DOCUMENTS

| | | | | |
|---|---|---|---|---|
| JP | 2000086677 A * | 3/2000 | | |
| WO | WO-9741197 A1 * | 11/1997 | | C11D 3/362 |

OTHER PUBLICATIONS

Faust et al. "Derivatives of Salicylamide" Journal of the American Pharmaceutical Association, 1956, vol. XLV, No. 8, pp. 514-517.*

Kanamori et al. "Contribution of the intramolecular hydrogen bond to the shift of the pKa value and the oxidation potential of phenols and phenolate anions" Org. Biomol. Chem., 2005,3, 1453-1459. (Year: 2005).*

Shaw et al. "A New Iron(III)—Salen Catalyst for Enantioselective Conia-ene Carbocyclization", JACS, 2014, vol. 136, No. 39, pp. 13578-13581.*

England, P. M. et al. (Jun. 2014). "Poster Board #LBSA-0437: Identification of New Ligand Scaffolds for the Nuclear Receptor LRH-1," presented at the ICE ENDO Conference Jun. 2014, 1 page.

International Search Report dated Jan. 13, 2017 for PCT Application No. PCT/US2016/051159, filed Sep. 9, 2016, 5 pages.

Written Opinion dated Jan. 13, 2017 for PCT Application No. PCT/US2016/051159, filed Sep. 9, 2016, 6 pages.

* cited by examiner

*Primary Examiner* — Joseph R Kosack

(74) *Attorney, Agent, or Firm* — Mintz Levin Cohn Ferris Glovsky and Popeo, P.C.

(57) ABSTRACT

Disclosed herein are compositions and methods for modulating the liver receptor homolog-1.

10 Claims, 15 Drawing Sheets

Specification includes a Sequence Listing.

| Compund | $R_1$ | $R_2$ | $R_3$ |
|---|---|---|---|
| 1 | iPr | iPr | propyl |
| 2 | iPr | iPr | butyl |
| 3 | iPr | iPr | pentyl |
| 4 | iPr | H | propyl |
| 5 | H | iPr | propyl |
| 6 | tBu | H | propyl |
| 7 | H | tBu | propyl |
| 8 (PME8) | tBu | tBu | propyl |
| 9 (PME9) | tBu | tBu | butyl |
| 10 (PME10) | tBu | tBu | pentyl |

FIG. 13

| Name | Accession | Forward 5'-3' | Reverse 5'-3' |
|---|---|---|---|
| GAPDH | NM_008084 | GGCGCGCGTCATCAG (SEQ ID NO:1) | TGACCAGGCGCCCAATAC (SEQ ID NO:2) |
| TBP | NM_003194 | CGAATATAATCCCAAGCG GTTT (SEQ ID NO:3) | TGGTTCGTGGCTCTCTTAT CC (SEQ ID NO:4) |
| NR5A2 (hLRH-1) | NM_205860 | CAGAGAAAGCGTTGTCCT TACTG (SEQ ID NO:5) | TTATTCCTTCCTCCACGCA TT (SEQ ID NO:6) |
| CYP24A1 | NM_000782 | ACGCCTCAGATGGTGGTA TT (SEQ ID NO:7) | GATGGTGCTGACACAGGT GA (SEQ ID NO:8) |

10.14 analog
(no disulfide, terminal CH3)

15.31 overlay 10.14

10.28 analog
(no disulfide, terminal CH3,
no chiral center)

SEQUENCE LISTING

```
<160> NUMBER OF SEQ ID NOS: 9

<210> SEQ ID NO 1
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 1

ggcgcgcgtc atcag                                                    15


<210> SEQ ID NO 2
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 2

tgaccaggcg cccaatac                                                 18


<210> SEQ ID NO 3
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 3

cgaatataat cccaagcggt tt                                            22


<210> SEQ ID NO 4
<211> LENGTH: 21
<212> TYPE: DNA
<213> ORGANISM: Artificial Sequence
```

<220> FEATURE:
<223> OTHER INFORMATION: Synthetic polynucleotide

<400> SEQUENCE: 4
tggttcgtgg ctctcttatc c 21

<210> SEQ ID NO 5
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 5
cagagaaagc gttgtcctta ctg 23

<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 6
ttattccttc ctccacgcat t 21

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
acgcctcaga tggtggtatt 20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
gatggtgctg acacaggtga 20

<210> SEQ ID NO 9
<211> LENGTH: 541
<212> TYPE: PRT
<213> ORGANISM: Homo sapiens

<400> SEQUENCE: 9

```
Met Ser Ser Asn Ser Asp Thr Gly Asp Leu Gln Glu Ser Leu Lys His
1               5                   10                  15

Gly Leu Thr Pro Ile Gly Ala Gly Leu Pro Asp Arg His Gly Ser Pro
            20                  25                  30

Ile Pro Ala Arg Gly Arg Leu Val Met Leu Pro Lys Val Glu Thr Glu
        35                  40                  45

Ala Leu Gly Leu Ala Arg Ser His Gly Glu Gln Gly Gln Met Pro Glu
    50                  55                  60

Asn Met Gln Val Ser Gln Phe Lys Met Val Asn Tyr Ser Tyr Asp Glu
65                  70                  75                  80

Asp Leu Glu Glu Leu Cys Pro Val Cys Gly Asp Lys Val Ser Gly Tyr
```

-continued

```
                85                  90                  95

His Tyr Gly Leu Leu Thr Cys Glu Ser Cys Lys Gly Phe Phe Lys Arg
            100                 105                 110

Thr Val Gln Asn Asn Lys Arg Tyr Thr Cys Ile Glu Asn Gln Asn Cys
        115                 120                 125

Gln Ile Asp Lys Thr Gln Arg Lys Arg Cys Pro Tyr Cys Arg Phe Gln
    130                 135                 140

Lys Cys Leu Ser Val Gly Met Lys Leu Glu Ala Val Arg Ala Asp Arg
145                 150                 155                 160

Met Arg Gly Gly Arg Asn Lys Phe Gly Pro Met Tyr Lys Arg Asp Arg
                165                 170                 175

Ala Leu Lys Gln Gln Lys Lys Ala Leu Ile Arg Ala Asn Gly Leu Lys
            180                 185                 190

Leu Glu Ala Met Ser Gln Val Ile Gln Ala Met Pro Ser Asp Leu Thr
        195                 200                 205

Ile Ser Ser Ala Ile Gln Asn Ile His Ser Ala Ser Lys Gly Leu Pro
    210                 215                 220

Leu Asn His Ala Ala Leu Pro Pro Thr Asp Tyr Asp Arg Ser Pro Phe
225                 230                 235                 240

Val Thr Ser Pro Ile Ser Met Thr Met Pro Pro His Gly Ser Leu Gln
                245                 250                 255

Gly Tyr Gln Thr Tyr Gly His Phe Pro Ser Arg Ala Ile Lys Ser Glu
            260                 265                 270

Tyr Pro Asp Pro Tyr Thr Ser Ser Pro Glu Ser Ile Met Gly Tyr Ser
        275                 280                 285

Tyr Met Asp Ser Tyr Gln Thr Ser Ser Pro Ala Ser Ile Pro His Leu
    290                 295                 300

Ile Leu Glu Leu Leu Lys Cys Glu Pro Asp Glu Pro Gln Val Gln Ala
305                 310                 315                 320

Lys Ile Met Ala Tyr Leu Gln Gln Glu Gln Ala Asn Arg Ser Lys His
                325                 330                 335

Glu Lys Leu Ser Thr Phe Gly Leu Met Cys Lys Met Ala Asp Gln Thr
            340                 345                 350

Leu Phe Ser Ile Val Glu Trp Ala Arg Ser Ser Ile Phe Phe Arg Glu
        355                 360                 365

Leu Lys Val Asp Asp Gln Met Lys Leu Leu Gln Asn Cys Trp Ser Glu
    370                 375                 380

Leu Leu Ile Leu Asp His Ile Tyr Arg Gln Val Val His Gly Lys Glu
385                 390                 395                 400

Gly Ser Ile Phe Leu Val Thr Gly Gln Gln Val Asp Tyr Ser Ile Ile
                405                 410                 415

Ala Ser Gln Ala Gly Ala Thr Leu Asn Asn Leu Met Ser His Ala Gln
            420                 425                 430

Glu Leu Val Ala Lys Leu Arg Ser Leu Gln Phe Asp Gln Arg Glu Phe
        435                 440                 445

Val Cys Leu Lys Phe Leu Val Leu Phe Ser Leu Asp Val Lys Asn Leu
    450                 455                 460

Glu Asn Phe Gln Leu Val Glu Gly Val Gln Glu Gln Val Asn Ala Ala
465                 470                 475                 480

Leu Leu Asp Tyr Thr Met Cys Asn Tyr Pro Gln Gln Thr Glu Lys Phe
                485                 490                 495

Gly Gln Leu Leu Leu Arg Leu Pro Glu Ile Arg Ala Ile Ser Met Gln
            500                 505                 510
```

-continued

```
Ala Glu Glu Tyr Leu Tyr Tyr Lys His Leu Asn Gly Asp Val Pro Tyr
        515                 520                 525

Asn Asn Leu Leu Ile Glu Met Leu His Ala Lys Arg Ala
    530                 535                 540
```

LRH-1 MODULATORS

CROSS-REFERENCES TO RELATED APPLICATIONS

This application is a national stage application under 35 U.S.C. 371 of international application PCT/US2016/051159, filed Sep. 9, 2016, which claims the benefit of U.S. Provisional Application Nos. 62/216,950, filed Sep. 10, 2015, and 62/217,343, filed Sep. 11, 2015, all of which are incorporated herein by reference in their entirety for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048536-573N01US_ST25.TXT, created Mar. 8, 2018, 6,622 bytes, machine format IBM-PC, MS-Windows operating system, is hereby incorporated herein by reference in its entirety.

BACKGROUND

Liver receptor homolog-1 (LRH-1) is a ligand-activated nuclear receptor that plays essential roles in human physiology and represents a therapeutic target for several diseases. Endogenous phospholipid ligands for this receptor are neither optimal for probing LRH-1 biology nor viable as drug leads.

LRH-1 plays a critical role in embryonic development and is highly expressed in adult intestine, liver, exocrine pancreas, and ovary. In intestinal crypt cells, LRH-1 controls cell proliferation and differentiation and is a potential therapeutic target for inflammatory bowel disease. In the liver, LRH-1 functions as a crucial regulator of enzymes controlling bile acid biosynthesis, cholesterol homeostasis, and the acute phase response, and is a target for the treatment of liver and cardiovascular disease. In the pancreas and ovaries, LRH-1 controls cell proliferation and differentiation, and is a target for cancers. Thus, there is need in the art for effective LRH-1 modulators. Disclosed herein are solutions to these and other problems in the art.

BRIEF SUMMARY

In an aspect is provided a compound having the formula:

(I)

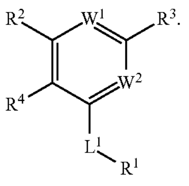

$W^1$ and $W^2$ are independently CH or N. $L^1$ is independently a bond, —O—, —NH—, —C(O)—, —C(O)NH—, —NHC(O)—, —S—, —NHC(O)NH—, substituted or unsubstituted alkylene, substituted or unsubstituted heteroalkylene. $R^1$ is independently a hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{10}$, —$SO_{v1}NR^7R^8$, —$NHNR^7R^8$, —$ONR^7R^8$, —NHC═(O)$NHNR^7R^8$, —NHC═(O)$NR^7R^8$, —NHC═($NR^9$)$NR^7R^8$, —$N(O)_{m1}$, —$NR^7R^8$, —C(O)$R^9$, —C(O)—$OR^9$, —C(O)$NR^7R^8$, —$OR^{10}$, —$NR^7SO_2R^{10}$, —$NR^7C$═(O)$R^9$, —$NR^7C$(O)—$OR^9$, —$NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. E is an electrophilic moiety. $R^2$ is independently a hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{14}$, —$SO_{v2}NR^{11}R^{12}$, —$NHNR^{11}R^{12}$, —$ONR^{11}R^{12}$, —NHC═(O)$NHNR^{11}R^{12}$, —NHC═(O)$NR^{11}R^{12}$, —NHC═($NR^{13}$)$NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}C$═(O)$R^{13}$, —$NR^{11}C$(O)—$OR^{13}$, —$NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{18}$, —$SO_{v3}NR^{15}R^{16}$, —$NHNR^{15}R^{16}$, —$ONR^{15}R^{16}$, —NHC═(O)$NHNR^{15}R^{16}$, —NHC═(O)$NR^{15}R^{16}$, —NHC═($NR^{17}$)$NR^{15}R^{16}$, —$N(O)_{m3}$, —$NR^{15}R^{16}$, —C(O)$R^{17}$, —C(O)—$OR^{17}$, —C(O)$NR^{15}R^{16}$, —$OR^{18}$, —$NR^{15}SO_2R^{18}$, —$NR^{15}C$═(O)$R^{17}$, —$NR^{15}C$(O)—$OR^{17}$, —$NR^{15}OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{22}$, —$SO_{v4}NR^{19}R^{20}$, —$NHNR^{19}R^{20}$, —$ONR^{19}R^{20}$, —NHC═(O)$NHNR^{19}R^{20}$, —NHC═(O)$NR^{19}R^{20}$, —NHC═($NR^{21}$)$NR^{19}R^{20}$, —$N(O)_{m4}$, —$NR^{19}R^{20}$, —C(O)$R^{21}$, —C(O)$OR^{21}$, —C(O)$NR^{19}R^{20}$, —$OR^{22}$, —$NR^{19}SO_2R^{22}$, —$NR^{19}C$═(O)$R^{21}$, —$NR^{19}C$(O)$OR^{21}$, —$NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —$CHX_2$, —$CH_2X$, —$OCX_3$, —$OCH_2X$, —$OCHX_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(NH)$NH_2$, —NHC═(O)$NH_2$, —$NHSO_2H$, —NHC═(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl. The symbols m1, m2, m3, m4, v1, v2, v3, and v4 are independently 1 or 2. The symbols n1, n2, n3, and n4 are independently an integer from 0 to 4. X, $X^1$, $X^2$, $X^3$, and $X^4$ are independently —Cl, —Br, —I, or —F. In embodiments, $L^1$-$R^1$ does not include a disulfide bond.

In an aspect is provided a compound having the formula:

(IIa)

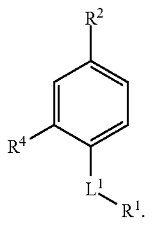

$R^1$, $R^2$, $R^4$, and $L^1$ are as described herein, including in embodiments.

In an aspect is provided a compound having the formula:

(IIb)

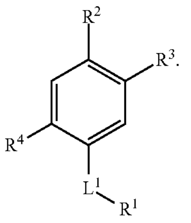

$R^1$, $R^2$, $R^3$, $R^4$, and $L^1$ are as described herein, including in embodiments. In embodiments, $L^1$-$R^1$ does not include a disulfide bond.

In an aspect is provided a compound having the formula:

(IIc)

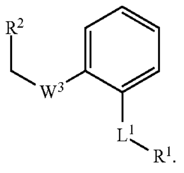

$R^1$, $R^2$, and $L^1$ are as described herein, including in embodiments. $W^3$ is O, NH, $CH_2$, or S. In embodiments, $L^1$-$R^1$ does not include a disulfide bond.

In an aspect is provided a compound having the formula:

(IId)

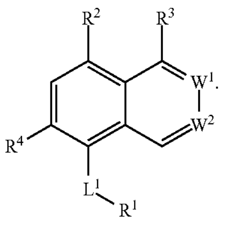

$W^1$, $W^2$, $R^1$, $R^2$, $R^3$, $R^4$, and $L^1$ are as described herein, including in embodiments. In embodiments, $L^1$-$R^1$ does not include a disulfide bond.

In an aspect is provided a compound having the formula:

(IIe)

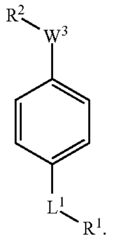

$W^3$, $R^1$, $R^2$, and $L^1$ are as described herein, including in embodiments. In embodiments, $L^1$-$R^1$ does not include a disulfide bond.

In an aspect is provided a compound having the formula:

(IIf)

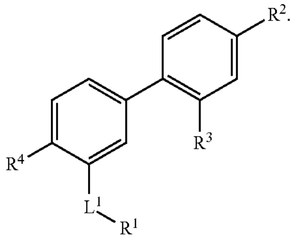

$R^1$, $R^2$, $R^3$, $R^4$, and $L^1$ are as described herein, including in embodiments. In embodiments, $L^1$-$R^1$ does not include a disulfide bond.

In an aspect is provided a compound having the formula:

(IIg)

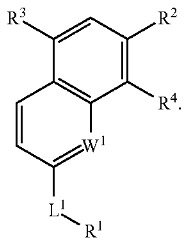

$W^1$, $R^1$, $R^2$, $R^3$, $R^4$, and $L^1$ are as described herein, including in embodiments. In embodiments, $L^1$-$R^1$ does not include a disulfide bond.

In an aspect is provided an LRH-1 agonist having the formula:

(I)

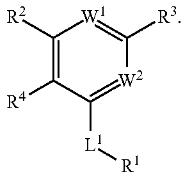

$W^1$ and $W^2$ are independently CH or N. $L^1$ is independently a bond, —O—, —NH—, —C(O)—, —C(O)NH—, —NHC(O)—, —S—, —NHC(O)NH—, substituted or unsubstituted alkylene, substituted or unsubstituted heteroalkylene. $R^1$ is independently a hydrogen, halogen, —$CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—NHC{=}(NR^9)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. E is an electrophilic moiety. $R^2$ is independently a hydrogen, halogen, $—CX^2_3$, $—CHX^2$, $—CH_2X^2$, $—OCX^2_3$, $—OCH_2X$, $—OCHX^2$, —CN, $—SO_{n2}R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—NHC{=}(NR^{13})NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—NHC{=}(NR^{17})NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{22}$, $—SO_{v4}NR^{19}R^{20}$, $—NHNR^{19}R^{20}$, $—ONR^{19}R^{20}$, $—NHC{=}(O)NHNR^{19}R^{20}$, $—NHC{=}(O)NR^{19}R^{20}$, $—NHC{=}(NR^{21})NR^{19}R^{20}$, $—N(O)_{m4}$, $—NR^{19}R^{20}$, $—C(O)R^{21}$, $—C(O)OR^{21}$, $—C(O)NR^{19}R^{20}$, $—OR^{22}$, $—NR^{19}SO_2R^{22}$, $—NR^{19}C{=}(O)R^{21}$, $—NR^{19}C(O)OR^{21}$, $—NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^0$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, $—CHX_2$, $—CH_2X$, $—OCX_3$, $—OCH_2X$, $—OCHX_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(NH)NH_2$, $—NHC{=}(O)NH_2$, $—NHSO_2H$, $—NHC{=}(O)H$, $—NHC(O)—OH$, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl. The symbols m1, m2, m3, m4, v1, v2, v3, and v4 are independently 1 or 2. The symbols n1, n2, n3, and n4 are independently an integer from 0 to 4. X, $X^1$, $X^2$, $X^3$, and $X^4$ are independently —Cl, —Br, —I, or —F. In embodiments, $L^1$-$R^1$ does not include a disulfide bond.

In another aspect is provided a pharmaceutical composition including a pharmaceutically acceptable excipient and a compound or LRH-1 agonist, or a pharmaceutically acceptable salt thereof, as described herein, including embodiments.

In another aspect is provided a method of treating a nuclear receptor activity-associated disease in a subject in need of such treatment, the method including administering a compound or LRH-1 agonist, or a pharmaceutically acceptable salt thereof, as described herein, including embodiments (e.g., in an aspect, embodiment, example, table, figure, or claim).

In another aspect is provided a method of treating a disease associated with LRH-1 activity in a subject in need of the treatment, the method including administering an effective amount of a compound or LRH-1 agonist, or a pharmaceutically acceptable salt thereof, as described herein.

In another aspect is provided a method of treating a disease associated with aberrant LRH-1 activity in a subject in need of the treatment, the method including administering an effective amount of a compound or LRH-1 agonist, or a pharmaceutically acceptable salt thereof, as described herein.

In another aspect is provided a method of treating a inflammatory bowel disease in a subject in need of the treatment, the method including administering an effective amount of a compound or LRH-1 agonist, or a pharmaceutically acceptable salt thereof, as described herein. In embodiments, the disease is Crohn's disease, microscopic colitis, diversion colitis, indeterminate colitis, Behçet's disease, ulcerative colitis.

In another aspect is provided a method of treating diabetes (e.g., type II) in a subject in need of the treatment, the method including administering an effective amount of a compound or LRH-1 agonist, or a pharmaceutically acceptable salt thereof, as described herein.

In another aspect is provided a method of treating cancer in a subject in need of the treatment, the method including administering an effective amount of a compound or LRH-1 agonist, or a pharmaceutically acceptable salt thereof, as described herein. In embodiments, the cancer is prostate cancer, pancreatic cancer, breast cancer (e.g., triple negative breast cancer), colon cancer, liver cancer, bladder cancer, stomach cancer, esophageal cancer, rectal cancer, gastrointestinal cancer, ovarian cancer, or intestinal cancer.

In another aspect is provided a method of treating an inflammatory disease in a subject in need of the treatment, the method including administering an effective amount of a compound or LRH-1 agonist, or a pharmaceutically acceptable salt thereof, as described herein.

In another aspect is provided a method of treating a metabolic disease in a subject in need of the treatment, the method including administering an effective amount of a compound or LRH-1 agonist, or a pharmaceutically acceptable salt thereof, as described herein.

In another aspect is provided a method of treating a cardiovascular disease in a subject in need of the treatment, the method including administering an effective amount of a compound or LRH-1 agonist, or a pharmaceutically acceptable salt thereof, as described herein.

In embodiments, the method of treatment is a method of prevention. In embodiments, the compounds set forth herein are provided as pharmaceutical compositions including the compound and a pharmaceutically acceptable excipient.

In another aspect is provided a method of treating arteriosclerosis in a subject in need of the treatment, the method including administering an effective amount of a compound described herein.

In an aspect is provided a method of treating fatty liver disease in a subject in need of said treatment, said method comprising administering an effective amount of a compound as described herein.

In another aspect is provided a method of inhibiting LRH-1 activity in a subject in need thereof, including administering to the subject an effective amount of a compound or LRH-1 agonist, or a pharmaceutically acceptable salt thereof as described herein.

In another aspect is provided a method of activating LRH-1 activity in a subject in need thereof, including administering to the subject an effective amount of a compound or LRH-1 agonist, or a pharmaceutically acceptable salt thereof as described herein.

In another aspect is provided a method of increasing the level of activity of LRH-1 (e.g., relative to the level of activity in the absence of the compound) in a subject in need thereof, including administering to the subject an effective amount of a compound or LRH-1 agonist, or a pharmaceutically acceptable salt thereof as described herein.

In another aspect is provided a method of modulating LRH-1 activity, including contacting a cell with a compound or LRH-1 agonist, or a pharmaceutically acceptable salt thereof, as described herein.

BRIEF DESCRIPTION OF THE DRAWINGS

FIG. 7A: Relative expression levels of the hLRH-1 target gene CYP24A1 with increasing treatment times of PME8 (10 μM) compared to the DMSO control (black bar) ranging from 3-24 h. Corresponding expression levels of hLRH-1 transcripts in each time condition are shown in right panel without (−Dox) or with (+Dox) induction of exogenous hLRH-1. FIG. 7B: Levels of CYP24A1 with DMSO or with increasing concentrations of RJW100 and PME8 treatment for 16 h without (−Dox) or with (+Dox) induction of exogenous hLRH-1. Data are representative of at least three independent experiments with error bars representing SEM, P values=****<0.0001.

FIG. 13. RT-qPCR Primer Sequences (Example 6). Sequence legend: GAPDH (forward): SEQ ID NO: 1; GAPDH (reverse): SEQ ID NO:2; TBP (forward): SEQ ID NO:3; TBP (reverse): SEQ ID NO:4; NR5A2 9 (hLRH-1) (forward): SEQ ID NO:5; NR5A2 (hLRH-1) (reverse): SEQ ID NO:6; CYP24A1 (forward): SEQ ID NO:7; CYP24A1 (reverse): SEQ ID NO:8.

DETAILED DESCRIPTION

A. Definitions

Figure 1A:
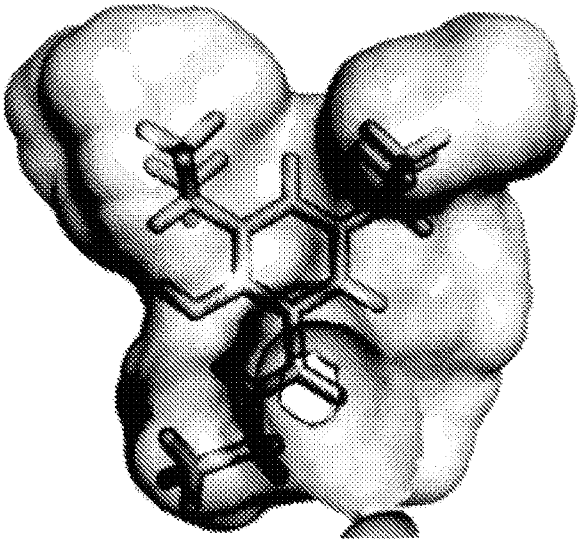
FIGS. 1A-1D. Computational model showing orientation of and space around example compound in the hLRH-1 pocket. Computational model of compound covalently bound to LRH-1 through a disulfide bond to $Cys^{346}$; Van der Walls surface represents all protein within 4.5 Å of the ligand; structure of compound and cartoon derived from the model illustrating the binding site for the compound is framed by helices 3, 5 and 11 and may include a polar interaction with the backbone carbonyl of $Met^{345}$.
Figure 1B:
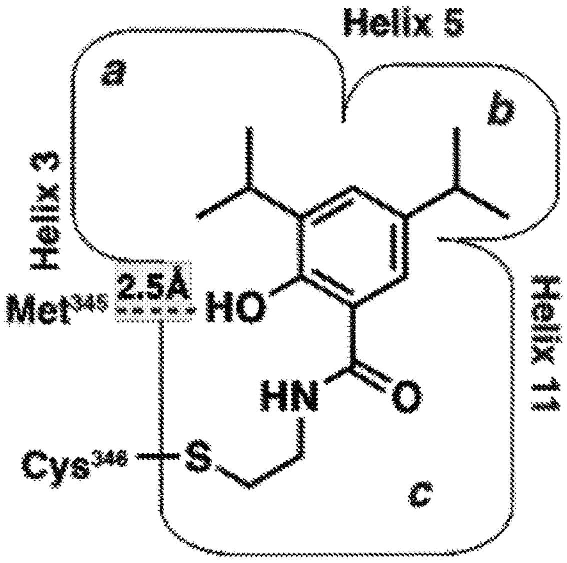
Figure 1C:
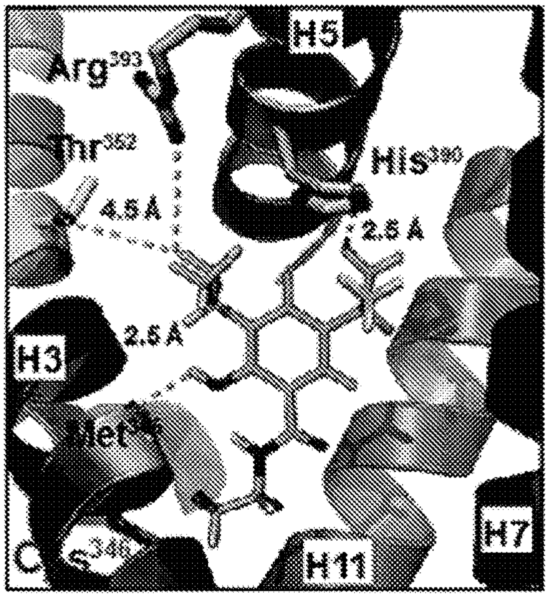
Figure 1D:
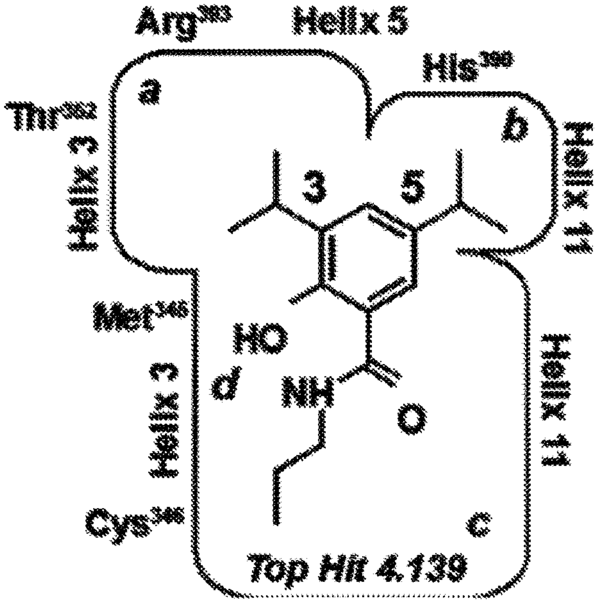

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g., selected from the group consisting of O, N, P, Si, and S, and wherein the nitrogen and sulfur atoms may optionally be oxidized, and the nitrogen heteroatom may optionally be quaternized). The heteroatom(s) (e.g., O, N, P, S, and Si) may be placed at any interior position of the heteroalkyl group or at the position at which the alkyl group is attached to the remainder of the molecule. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH=CH—O—CH_3$, $—Si(CH_3)_3$, $—CH_2—CH=N—OCH_3$, $—CH=CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', -halogen, —SiR'R"R'", —OC(O)R', —C(O)R', —$CO_2$R', —CONR'R", —OC(O)N R'R", —NR"C(O)R', —NR'—C(O)NR"R'", —NR"C($O)_2$R', —NR—C(NR'R"R'")═NR"", —NR—C(NR'R")═NR'", —S(O)R', —S($O)_2$R', —$S(O)_2NR'R''$, —$NRSO_2R'$, —NR'NR"R'", —ONR'R", —NR'C═(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2R'$, —CONR'R", —OC (O)NR'R", —NR"C(O)R', —NR'—C (O)NR"R'", —NR"$C(O)_2R'$, —NR—C(NR'R"R'")═NR"", —NR—C(NR'R")═NR'", —S(O)R', —$S(O)_2R'$, —$S(O)_2NR'R''$, —$NRSO_2R'$, —NR'NR"R'", —ONR'R", —NR'C═(O)NR"NR'"R"", —CN, —$NO_2$, —R', —$N_3$, —$CH(Ph)_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2NR'$—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'— $(C''R''R''')_d$—, where s and d are independently integers of from 0 to 3, and X' is —O—, —NR'—, —S—, —S(O)—, —$S(O)_2$—, or —$S(O)_2NR'$—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "$\sim\sim$" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with LRH-1 activity. Certain methods described herein may treat diseases associated with LRH-1 activity (e.g., cancer) by inhibiting LRH-1 activity. Certain methods described herein may treat diseases associated with LRH-1 activity by inhibiting ligand binding to LRH-1. Certain methods described herein may treat diseases associated with LRH-1 activity by increasing LRH-1 activity. For example, certain methods herein treat cancer. For example certain methods herein treat cancer by decreasing a symptom of cancer. Symptoms of cancer would be known or may be determined by a person of ordinary skill in the art. For example, certain methods herein treat an inflammatory disease (e.g., inflammatory bowel disease). For example certain methods herein treat an inflammatory disease by decreasing a symptom of the inflammatory disease (e.g., inflammatory bowel disease). Symptoms of an inflammatory disease (e.g., inflammatory bowel disease) would be known or may be determined by a person of ordinary skill in the art. For example, certain methods herein treat a metabolic disease (e.g., diabetes, type II diabetes). For example certain methods herein treat a metabolic disease (e.g., diabetes, type II diabetes) by decreasing a symptom of the metabolic disease. Symptoms of a metabolic disease (e.g., diabetes, type II diabetes) would be known or may be determined by a person of ordinary skill in the art. For example, certain methods herein treat a cardiovascular disease. For example certain methods herein treat a cardiovascular disease by decreasing a symptom of the cardiovascular disease. Symptoms of a cardiovascular disease would be known or may be determined by a person of ordinary skill in the art. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with LRH-1 activity may be treated with an agent (e.g. compound as described herein) effective for modulating the level of LRH-1 activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is an LRH-1 antagonist. In embodiments, a modulator is an LRH-1 inhibitor. In embodiments, a modulator is an LRH-1 covalent modifier. In embodiments, a modulator is an LRH-1 agonist. In embodiments, a modulator is an LRH-1 activator. In embodiments, a modulator is an anti-inflammatory disease (e.g, IBD) agent. In embodiments, a modulator is an anti-metabolic disease (e.g., diabetes, type II diabetes) agent. In embodiments, a modulator is an anti-cardiovascular disease agent.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}In$, $^{90}Y$, or $^{131}I$, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of LRH-1 activity. In some embodiments, the disease is inflammatory bowel disease. In some embodiments, the disease is diabetes (e.g., type II). In some embodiments, the disease is a metabolic disease. In some embodiments, the disease is an inflammatory disease. In some embodiments, the disease is a cardiovascular disease. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is prostate cancer, liver cancer, intestinal cancer, breast cancer, pancreatic cancer, bladder cancer, gall bladder cancer, or colon cancer.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "metabolic disease" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, pelvic inflammatory disease, reperfusion injury, sarcoidosis, transplant rejection, interstitial cystitis, atherosclerosis, and atopic dermatitis.

As used herein, the term "cardiovascular disease" refers to a disease or condition in which the function of a subject's cardiovascular system becomes impaired. Examples of cardiovascular diseases that may be treated with a compound, pharmaceutical composition, or method described herein include congestive heart failure; arrhythmogenic syndromes (e.g., paroxysmal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

Example of Amino Acid Classification

Small/Aliphatic residues: Gly, Ala, Val, Leu, Ile
Cyclic Imino Acid: Pro
Hydroxyl-containing Residues: Ser, Thr
Acidic Residues: Asp, Glu
Amide Residues: Asn, Gln
Basic Residues: Lys, Arg
Imidazole Residue: His
Aromatic Residues: Phe, Tyr, Trp
Sulfur-containing Residues: Met, Cys In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. For example, a selected residue in a selected protein corresponds to Cys346 of human LRH-1 when the selected residue occupies the same essential spatial or other structural relationship as Cys346 in human LRH-1. In some embodiments, where a selected protein is aligned for maximum homology with the human LRH-1 protein, the position in the aligned selected protein aligning with Cys346 is said to correspond to Cys346. Instead of a primary sequence alignment, a three dimensional structural alignment can also be used, e.g., where the structure of the selected protein is aligned for maximum correspondence with the human LRH-1 protein and the overall structures compared. In this case, an amino acid that occupies the same essential position as Cys346 in the structural model is said to correspond to the Cys346 residue.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J Microencapsul.* 13:293-306, 1996; Chonn, *Curr. Opin. Biotechnol.* 6:698-708, 1995; Ostro, *Am. J Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer, inflammatory disease, IBD, diabetes (e.g. type II) or aberrant LRH-1 activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

The term "liver receptor homolog-1" or "LRH-1" or "NR5A2" refers to a nuclear receptor commonly referred to by the same name. The term "LRH-1" may refer to the nucleotide sequence or protein sequence of human LRH-1 (e.g., Entrez 2494, Uniprot 000482, RefSeq NM_205860, or RefSeq NP_995582). The term "LRH-1" includes both the wild-type form of the nucleotide sequences or proteins as well as any mutants thereof. In some embodiments, "LRH-1" is wild-type LRH-1. In some embodiments, "LRH-1" is one or more mutant forms. The term "LRH-1" XYZ refers to a nucleotide sequence or protein of a mutant LRH-1 wherein the Y numbered amino acid of LRH-1 that normally has an X amino acid in the wildtype, instead has a Z amino acid in the mutant. In embodiments, an LRH-1 is the human LRH-1. In embodiments, the LRH-1 has the nucleotide sequence corresponding to reference number GI:451172091. In embodiments, the LRH-1 has the nucleotide sequence corresponding to RefSeq NM_205860.2. In embodiments, the LRH-1 has the protein sequence corresponding to reference number GI:45545405. In embodiments, the LRH-1 has the amino acid sequence corresponding to RefSeq NP_995582.1. In embodiments, the LRH-1 has the following amino acid sequence:

(SEQ ID NO: 9)

```
MSSNSDTGDLQESLKHGLTPIGAGLPDRHGSPIPARGRLVMLPKVETEAL
GLARSHGEQGQMPENMQVSQFKMVNYSYDEDLEELCPVCGDKVSGYHYGL
LTCESCKGFFKRTVQNNKRYTCIENQNCQIDKTQRKRCPYCRFQKCLSVG
MKLEAVRADRMRGGRNKFGPMYKRDRALKQQKKALIRANGLKLEAMSQVI
QAMPSDLTISSAIQNIHSASKGLPLNHAALPPTDYDRSPFVTSPISMTMP
PHGSLQGYQTYGHFPSRAIKSEYPDPYTSSPESIMGYSYMDSYQTSSPAS
IPHLILELLKCEPDEPQVQAKIMAYLQQEQANRSKHEKLSTFGLMCKMAD
QTLFSIVEWARSSIFFRELKVDDQMKLLQNCWSELLILDHIYRQVVHGKE
GSIFLVTGQQVDYSIIASQAGATLNNLMSHAQELVAKLRSLQFDQREFVC
LKFLVLFSLDVKNLENFQLVEGVQEQVNAALLDYTMCNYPQQTEKFGQLL
LRLPEIRAISMQAEEYLYYKHLNGDVPYNNLLIEMLHAKRA.
```

In embodiments, the LRH-1 is a mutant LRH-1. In embodiments, the mutant LRH-1 is associated with a disease that is not associated with wildtype LRH-1. In embodiments, the LRH-1 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above.

The term "electrophilic moiety" is used in accordance with its plain ordinary chemical meaning and refers to a monovalent chemical group that is electrophilic (i.e. a moiety attracted to electrons). Electrophiles may be positively charged or neutral and have vacant orbitals that are attracted to electronic rich centers. In embodiments, an electrophilic moiety is a monovalent chemical group capable of forming a covalent bond (e.g., reversible or irreversible) with a Cys, Asp, Glu, Tyr, Ser, or Lys sidechain of a nuclear receptor (e.g., LRH-1). In embodiments an electrophilic moiety is a monovalent chemical group capable of forming a covalent bond (e.g., reversible or irreversible) with a Cys residue. In embodiments an electrophilic moiety is a monovalent chemical group capable of forming a covalent bond (e.g., reversible or irreversible) with an LRH-1 Cys residue (e.g., Cys346).

The term "LRH-1 agonist" as used herein refers to a compound which is capable of detectably increasing the expression or activity of LRH-1. The agonist can increase expression or activity 10%, 20%, 30%, 40%, 50%, 60%, 70%, 80%, 90% or more in comparison to a control (e.g., in the absence of the LRH-1 agonist). In certain instances, expression or activity is 1.5-fold, 2-fold, 3-fold, 4-fold, 5-fold, 10-fold or higher than the expression or activity in the absence of the agonist. In embodiments an LRH-1 agonist increases the expression of LRH-1 relative to a control (e.g., the absence of the LRH-1 agonist). In embodiments an LRH-1 agonist increases the activity (e.g., transcriptional activity, transcriptional activation, DNA binding, nuclear translocation, co-activator binding, repressor disassociation, ligand binding, or oligomerization) of LRH-1 relative to a control (e.g., the absence of the LRH-1 agonist). In embodiments, the LRH-1 agonist increases the level of an ATP-binding cassette protein. In embodiments, the LRH-1 agonist increases the level of Mesenchyme Homeobox 1 (MEOX1), G0/G1 Switch 2 (G0S2), steroidogenic acute regulatory protein (StAR), small/short heterodimer partner (SHP), cholesterol 7α-hydroxylase (CYP7A1), 1,25-dihydroxyvitamin D3 24-hydroxylase (CYP24A1), ATP-binding cassette sub-family B member 11 (ABCB11), ATP-binding cassette sub-family G member 5 (ABCG5), or ATP-binding cassette sub-family G member 8 (ABCG8). In embodiments, the LRH-1 agonist increases the level of CYP24A1. In embodiments, the LRH-1 agonist increases the level of CYP24A1 relative to control. In embodiments, the LRH-1 agonist increases the level of CYP24A1 relative to the absence of the LRH-1 agonist. In embodiments, the LRH-1 agonist increases the level of CYP24A1 activity. In embodiments, the LRH-1 agonist increases the level of CYP24A1 activity relative to control. In embodiments, the LRH-1 agonist increases the level of CYP24A1 activity relative to the absence of the LRH-1 agonist. In embodiments, the LRH-1 is a human LRH-1.

The term "disulfide bond" is used in accordance with its plain ordinary meaning and refers to two adjacent covalently bonded sulfur atoms having the formula

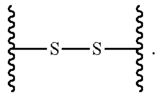

B. Compounds

In an aspect is provided a compound having the formula:

(I)

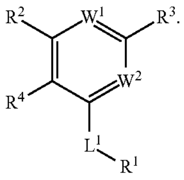

$W^1$ and $W^2$ are independently CH or N. $L^1$ is independently a bond, —O—, —NH—, —C(O)—, —C(O)NH—, —NHC(O)—, —S—, —NHC(O)NH—, substituted or unsubstituted alkylene, substituted or unsubstituted heteroalkylene. $R^1$ is independently a hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—NHC{=}(NR^9)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. E is an electrophilic moiety. $R^2$ is independently a hydrogen, halogen, $—CX^2_3$, $—CHX^2_2$, $—CH_2X^2$, $—OCX^2_3$, $—OCH_2X^2$, $—OCHX^2_2$, —CN, $—SO_2R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—NHC{=}(NR^{13})NR^{11}R^{12}$, $—N(O)_{m2}$, $—NR^{11}R^{12}$, $—C(O)R^{13}$, $—C(O)—OR^{13}$, —C(O)NR"11R$^1$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—NHC{=}(NR^{17})NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{22}$, $—SO_{v4}NR^{19}R^{20}$, $—NHNR^{19}R^{20}$, $—ONR^{19}R^{20}$, $—NHC{=}(O)NHNR^{19}R^{20}$, $—NHC{=}(O)NR^{19}R^{20}$, $—NHC{=}(NR^{21})NR^{19}R^{20}$, $—N(O)_{m4}$, $—NR^{19}R^{20}$, $—C(O)R^{21}$, $—C(O)OR^{21}$, $—C(O)NR^{19}R^{20}$, $—OR^{22}$, $—NR^{19}SO_2R^{22}$, $—NR^{19}C{=}(O)R^{21}$, $—NR^{19}C(O)OR^{21}$, $—NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, $—CHX_2$, $—CH_2X$, $—OCX_3$, $—OCH_2X$, $—OCHX_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(NH)NH_2$, $—NHC{=}(O)NH_2$, $—NHSO_2H$, $—NHC{=}(O)H$, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl. The symbols m1, m2, m3, m4, v1, v2, v3, and v4 are independently 1 or 2. The symbols n1, n2, n3, and n4 are independently an integer from 0 to 4. X, $X^1$, $X^2$, $X^3$, and $X^4$ are independently —Cl, —Br, —I, or —F. In embodiments, $L^1$-$R^1$ does not include a disulfide bond.

In embodiments, $W^1$ is CH. In embodiments, $W^1$ is N. In embodiments, $W^2$ is CH. In embodiments, $W^2$ is N.

In embodiments, $L^1$ is independently a bond, —O—, —NH—, —C(O)—, —C(O)NH—, —NHC(O)—, —S—, —NHC(O)NH—, substituted or unsubstituted $C_1$-$C_5$ alkylene, substituted or unsubstituted 2 to 5 membered heteroalkylene. In embodiments, $L^1$ is independently a bond. In embodiments, $L^1$ is independently —O—. In embodiments, $L^1$ is independently —NH—. In embodiments, $L^1$ is independently —C(O)—. In embodiments, $L^1$ is independently —C(O)NH—. In embodiments, $L^1$ is independently —NHC(O)—. In embodiments, $L^1$ is independently —S—. In embodiments, $L^1$ is independently —NHC(O)NH—. In embodiments, $L^1$ is independently substituted or unsubstituted alkylene. In embodiments, $L^1$ is independently substituted or unsubstituted heteroalkylene. In embodiments, $L^1$ is independently substituted alkylene. In embodiments, $L^1$ is independently substituted heteroalkylene. In embodiments, $L^1$ is independently unsubstituted alkylene. In embodiments, $L^1$ is independently unsubstituted heteroalkylene. In embodiments, $L^1$ is independently substituted or unsubstituted $C_1$-$C_5$ alkylene. In embodiments, $L^1$ is independently substituted or unsubstituted 2 to 5 membered heteroalkylene. In embodiments, $L^1$ is independently substituted $C_1$-$C_5$ alkylene. In embodiments, $L^1$ is independently substituted 2 to 5 membered heteroalkylene. In embodiments, $L^1$ is independently unsubstituted $C_1$-$C_5$ alkylene. In embodiments, $L^1$ is independently unsubstituted 2 to 5 membered heteroalkylene. In embodiments, $L^1$ is independently a bond, —O—, —NH—, —C(O)—, —C(O)NH—, —NHC(O)—, —S—, —NHC(O)NH—, substituted or unsubstituted $C_1$-$C_3$ alkylene, substituted or unsubstituted 2 to 3 membered heteroalkylene. In embodiments, $L^1$ is independently substituted or unsubstituted $C_1$-$C_3$ alkylene. In embodiments, $L^1$ is substituted or unsubstituted 2 to 3 membered heteroalkylene. In embodiments, $L^1$ is independently unsubstituted $C_1$-$C_3$ alkylene. In embodiments, $L^1$ is unsubstituted 2 to 3 membered heteroalkylene. In embodiments, $L^1$ is independently a bond or —C(O)NH—. In embodiments, $L^1$ is unsubstituted methylene. In embodiments, $L^1$ is unsubstituted ethylene. In embodiments, $L^1$ is unsubstituted propylene. In embodiments, $L^1$ does not include a disulfide bond.

In embodiments, $R^1$ is independently halogen, $—CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—NHC{=}(NR^9)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently halogen. In embodiments, $R^1$ is independently $—CX^1_3$. In embodiments, $R^1$ is independently $—CHX^1_2$. In embodiments, $R^1$ is independently $—CH_2X^1$. In embodiments, $R^1$ is independently $—OCX^1_3$. In embodiments, $R^1$ is independently $—OCH_2X^1$. In embodiments, $R^1$ is independently $—OCHX^1_2$. In embodiments, $R^1$ is independently —CN. In embodiments, $R^1$ is independently $—SO_{n1}R^{10}$. In embodiments, $R^1$ is independently $—SO_{v1}NR^7R^8$. In embodiments, $R^1$ is independently $—NHNR^7R^8$. In embodiments, $R^1$ is independently $—ONR^7R^8$. In embodiments, $R^1$ is independently $—NHC{=}(O)NHNR^7R^8$. In embodiments, $R^1$ is independently $—NHC{=}(O)NR^7R^8$. In embodiments, $R^1$ is independently $—NHC{=}(NR^9)NR^7R^8$. In embodiments, $R^1$ is independently $—N(O)_{m1}$. In embodiments, $R^1$ is independently $—NR^7R^8$. In embodiments, $R^1$ is independently $—C(O)R^9$. In embodiments, $R^1$ is independently $—C(O)—OR^9$. In embodiments, $R^1$ is independently $—C(O)NR^7R^8$. In embodiments, $R^1$ is independently $—OR^{10}$. In embodiments, $R^1$ is independently $—NR^7SO_2R^{10}$. In embodiments, $R^1$ is independently $—NR^7C{=}(O)R^9$. In embodiments, $R^1$ is independently $—NR^7C(O)—OR^9$. In embodiments, $R^1$ is independently $—NR^7OR^9$. In embodiments, $R^1$ is independently —SH. In embodiments, $R^1$ is independently $—SO_2CH_3$. In embodiments, $R^1$ is independently $—SO_2NH_2$. In embodiments, $R^1$ is independently $—N(O)_2$. In embodiments, $R^1$ is independently $—NH_2$. In embodiments, $R^1$ is independently $—C(O)CH_3$. In embodiments, $R^1$ is independently —C(O)OH. In embodiments, $R^1$ is independently $—C(O)NH_2$. In embodiments, $R^1$ is independently —OH. In embodiments, $R^1$ is independently E. In embodiments, $R^1$ is independently substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^1$ is independently substituted or unsubstituted $C_1$-$C_8$ alkyl. In embodiments, $R^1$ is independently substituted or unsubstituted 2 to 8 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, $R^1$ is independently unsubstituted $C_1$-$C_8$ alkyl. In embodiments, $R^1$ is independently unsubstituted 2 to 8 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$-$C_{10}$ aryl. In embodiments, $R^1$ is independently unsubstituted 5 to 10 membered heteroaryl. In embodiments, $R^1$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently substituted or unsubstituted $C_1$-$C_6$ alkyl or substituted or unsubstituted 2 to 6 membered heteroalkyl. In embodiments, $R^1$ is independently substituted or unsubstituted $C_1$-$C_5$ alkyl, or substituted or unsubstituted 2 to 5 membered alkoxy. In embodiments, $R^1$ is independently substituted or unsubstituted $C_1$-$C_5$ alkyl. In embodiments, $R^1$ is independently substituted or unsubstituted $C_4$-$C_5$ alkyl. In embodiments, $R^1$ is independently substituted or unsubstituted $C_4$-$C_6$ alkyl.

In embodiments, $R^1$ is independently unsubstituted butyl, unsubstituted pentyl, unsubstituted hexyl, unsubstituted propoxy, unsubstituted butoxy, or unsubstituted pentoxy. In embodiments, $R^1$ is independently unsubstituted propyl, unsubstituted butyl, unsubstituted pentyl, unsubstituted hexyl, unsubstituted propoxy, unsubstituted butoxy, or unsubstituted pentoxy. In embodiments, $R^1$ is independently unsubstituted butyl. In embodiments, $R^1$ is independently unsubstituted n-butyl. In embodiments, $R^1$ is independently unsubstituted isobutyl. In embodiments, $R^1$ is independently unsubstituted t-butyl. In embodiments, $R^1$ is independently unsubstituted pentyl. In embodiments, $R^1$ is independently unsubstituted n-pentyl. In embodiments, $R^1$ is independently unsubstituted isopentyl. In embodiments, $R^1$ is independently unsubstituted hexyl. In embodiments, $R^1$ is independently unsubstituted n-hexyl. In embodiments, $R^1$ is independently unsubstituted isohexyl. In embodiments, $R^1$ is independently unsubstituted propoxy. In embodiments, $R^1$ is independently unsubstituted n-propoxy. In embodiments, $R^1$ is independently unsubstituted isopropoxy. In embodiments, $R^1$ is independently unsubstituted butoxy. In embodiments, $R^1$ is independently unsubstituted butoxy. In embodiments, $R^1$ is independently unsubstituted n-butoxy. In embodiments, $R^1$ is independently unsubstituted isobutoxy. In embodiments, $R^1$ is independently unsubstituted tert-butoxy. In embodiments, $R^1$ is independently unsubstituted pentoxy. In embodiments, $R^1$ is independently unsubstituted n-pentoxy. In embodiments, $R^1$ is independently unsubstituted isopentoxy. In embodiments, $R^1$ does not include a disulfide bond.

In embodiments, E is

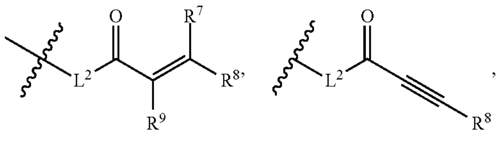
,

-continued

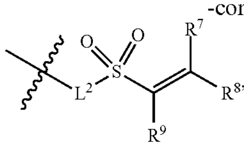
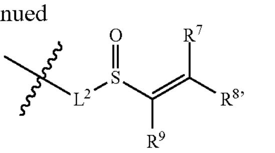
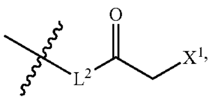
or
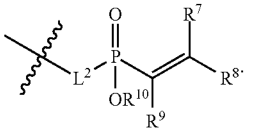

In embodiments, $L^2$ is a bond, —O—, —C(O)—, —S—, —SO—, —$S(O)_2$—, —N(H)—, —NHC(O)—, —C(O)NH—, —$SO_2NH$—, —$NHSO_2$—, —OC(O)NH—, —NHC(O)O—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is independently —SO—. In embodiments, $L^2$ is independently —$S(O)_2$—. In embodiments, $L^2$ is independently —$SO_2NH$—. In embodiments, $L^2$ is independently —$NHSO_2$—. In embodiments, $L^2$ is independently —OC(O)NH—. In embodiments, $L^2$ is independently —NHC(O)O—. In embodiments, $L^2$ is independently —NHC(O)NH—. In embodiments, $L^2$ is independently a bond. In embodiments, $L^2$ is independently —O—. In embodiments, $L^2$ is independently —NH—. In embodiments, $L^2$ is independently —C(O)—. In embodiments, $L^2$ is independently —C(O)NH—. In embodiments, $L^2$ is independently —NHC(O)—. In embodiments, $L^2$ is independently —S—. In embodiments, $L^2$ is independently —NHC(O)NH—. In embodiments, $L^2$ is independently substituted or unsubstituted $C_1$-$C_5$ alkylene. In embodiments, $L^2$ is independently substituted or unsubstituted 2 to 5 membered heteroalkylene. In embodiments, $L^2$ is independently substituted $C_1$-$C_5$ alkylene. In embodiments, $L^2$ is independently substituted 2 to 5 membered heteroalkylene. In embodiments, $L^2$ is independently unsubstituted $C_1$-$C_5$ alkylene. In embodiments, $L^2$ is independently unsubstituted 2 to 5 membered heteroalkylene. In embodiments, $L^2$ is independently a bond, —O—, —NH—, —C(O)—, —C(O)NH—, —NHC(O)—, —S—, —NHC(O)NH—, substituted or unsubstituted $C_1$-$C_3$ alkylene, substituted or unsubstituted 2 to 3 membered heteroalkylene. In embodiments, $L^2$ is independently substituted or unsubstituted $C_1$-$C_3$ alkylene. In embodiments, $L^2$ is substituted or unsubstituted 2 to 3 membered heteroalkylene. In embodiments, $L^2$ is independently unsubstituted $C_1$-$C_3$ alkylene. In embodiments, $L^2$ is unsubstituted 2 to 3 membered heteroalkylene. In embodiments, $L^2$ is independently a bond or —C(O)NH—. In embodiments, $L^2$ is unsubstituted methylene. In embodiments, $L^2$ is unsubstituted ethylene. In embodiments, $L^2$ is unsubstituted propylene. In embodiments, $L^2$ is a bond. In embodiments, $L^2$ is —NH—. In embodiments, $L^2$ is —$N(CH_3)$—. In embodiments, $L^2$ is

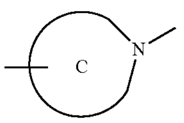
.

Ring C is a substituted or unsubstituted heterocycloalkylene or substituted or unsubstituted heteroarylene. In embodiments, Ring C is an unsubstituted heterocycloalkylene. In embodiments, Ring C is an unsubstituted heteroarylene. In embodiments, Ring C is substituted heterocycloalkylene. In embodiments, Ring C is substituted heteroarylene. In embodiments, Ring C is an unsubstituted 5 to 7 membered heterocycloalkylene. In embodiments, Ring C is an unsubstituted 5 to 6 membered heteroarylene.

In embodiments, E is

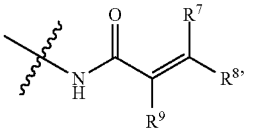
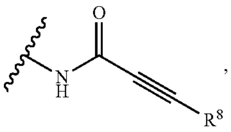
,
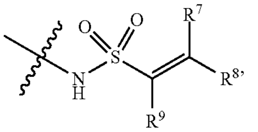
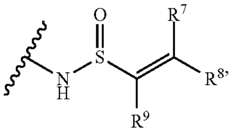
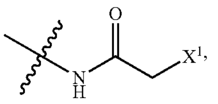
or
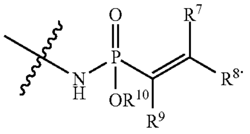

In embodiments, E is

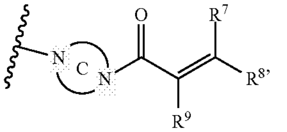
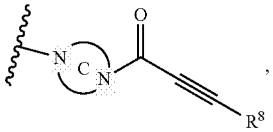
,
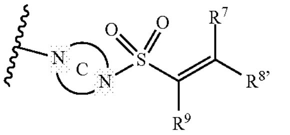
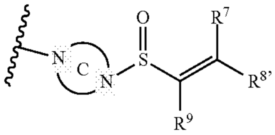
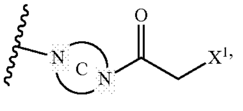
or
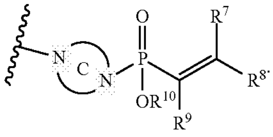

In embodiments, Ring C is an unsubstituted heterocycloalkylene. In embodiments, Ring C is substituted heterocycloalkylene. In embodiments, Ring C is an unsubstituted 5 to 7 membered heterocycloalkylene. In embodiments, Ring C is a substituted 5 to 7 membered heterocycloalkylene. In embodiments, Ring C is an unsubstituted 5 membered heterocycloalkylene. In embodiments, Ring C is a substituted 5 membered heterocycloalkylene. In embodiments, Ring C is an unsubstituted 6 membered heterocycloalkylene. In embodiments, Ring C is a substituted 6 membered heterocycloalkylene. In embodiments, Ring C is an unsubstituted 7 membered heterocycloalkylene. In embodiments, Ring C is a substituted 7 membered heterocycloalkylene. In embodiments, Ring C is a $R^{30}$-substituted 5 to 7 membered heterocycloalkylene. In embodiments, Ring C is a $R^{30}$-substituted 5 membered heterocycloalkylene. In embodiments, Ring C is a $R^{30}$-substituted 6 membered heterocycloalkylene. In embodiments, Ring C is a $R^{30}$-substituted 7 membered heterocycloalkylene. In embodiments, Ring C is a $R^{30}$-substituted 5 to 7 membered heterocycloalkylene. In embodiments, Ring C is a $R^{30}$- substituted 5 membered heterocycloalkylene. In embodiments, Ring C is a $R^{30}$-substituted 6 membered heterocycloalkylene. In embodiments, Ring C is a $R^{30}$-substituted 7 membered heterocycloalkylene.

In some embodiments, E includes a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted dialdehyde moiety, substituted or unsubstituted nitrogen mustard moiety, substituted or unsubstituted propargyl moiety, substituted or unsubstituted propargylamide moiety, —CN, —$NO_2$, 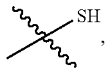, or 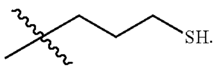

In some embodiments, E is a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro ($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted dialdehyde moiety, substituted or unsubstituted nitrogen mustard moiety, substituted or unsubstituted propargyl moiety, substituted or unsubstituted propargylamide moiety, —SH, —CN, or —$NO_2$.

In some embodiments, E comprises a cyano, an unsubstituted vinyl sulfone moiety, unsubstituted vinyl sulfonamide moiety, unsubstituted fluoro($C_1$-$C_4$)alkylketone moiety, unsubstituted chloro($C_1$-$C_4$)alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted dialdehyde moiety, unsubstituted nitrogen mustard moiety, unsubstituted propargyl moiety, or unsubstituted propargylamide moiety. In some embodiments, E is a cyano, an unsubstituted vinyl sulfone moiety, unsubstituted vinyl sulfonamide moiety, unsubstituted fluoro($C_1$-$C_4$)alkylketone moiety, unsubstituted chloro($C_1$-$C_4$)alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted dialdehyde moiety, unsubstituted nitrogen mustard moiety, unsubstituted propargyl moiety, or unsubstituted propargylamide moiety.

In embodiments, $R^2$ is independently a halogen, —$CX^2_3$, —$CHX^2_2$, —$CH_2X^2$, —$OCX^2_3$, —$OCH_2X^2$, —$OCHX^2_2$, —CN, —$SO_{n2}R^{14}$, —$SO_{v2}NR^{11}R^{12}$, —$NHNR^{11}R^{12}$, —$ONR^{11}R^{12}$, —NHC═(O)$NHNR^{11}R^{12}$, —NHC═(O)$NR^{11}R^{12}$, —NHC═($NR^{13}$)$NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}C$═(O)$R^{13}$, —$NR^{11}C$(O)—$OR^{13}$, —$NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is independently a halogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$OCX^2_3$. In embodiments, $R^2$ is independently —$OCH_2X^2$. In embodiments, $R^2$ is independently —$OCHX^{22}$. In embodiments, $R^2$ is independently —CN. In embodiments, $R^2$ is independently —$SO_{n2}R^{14}$. In embodiments, $R^2$ is independently —$SO_{v2}NR^{11}R^{12}$. In embodiments, $R^2$ is independently —$NHNR^{11}R^{12}$. In embodiments, $R^2$ is independently —$ONR^{11}R^{12}$. In embodiments, $R^2$ is independently —NHC═(O)$NHNR^{11}R^{12}$. In embodiments, $R^2$ is independently —NHC═(O)$NR^{11}R^{12}$. In embodiments, $R^2$ is independently —NHC═($NR^{13}$)$NR^{11}R^{12}$. In embodiments, $R^2$ is independently —$N(O)_{m2}$. In embodiments, $R^2$ is independently —$NR^{11}R^{12}$. In embodiments, $R^2$ is independently —C(O)$R^{13}$. In embodiments, $R^2$ is independently —C(O)—$OR^{13}$. In embodiments, $R^2$ is independently —C(O)$NR^{11}R^{12}$. In embodiments, $R^2$ is independently —$OR^{14}$. In embodiments, $R^2$ is independently —$NR^{11}SO_2R^{14}$. In embodiments, $R^2$ is independently —$NR^{11}C$═(O)$R^{13}$. In embodiments, $R^2$ is independently —$NR^{11}C$(O)—$OR^{13}$. In embodiments, $R^2$ is independently —$NR^{11}OR^{13}$. In embodiments, $R^2$ is independently —SH. In embodiments, $R^2$ is independently —$SO_2CH_3$. In embodiments, $R^2$ is independently —$SO_2NH_2$. In embodiments, $R^2$ is independently —$N(O)_2$. In embodiments, $R^2$ is independently —$NH_2$. In embodiments, $R^2$ is independently —C(O)$CH_3$. In embodiments, $R^2$ is independently —C(O)OH. In embodiments, $R^2$ is independently —C(O)$NH_2$. In embodiments, $R^2$ is independently —$O_H$. In embodiments, $R^2$ is independently a halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(NH)$NH_2$, —NHC═(O)$NH_2$, —$NHSO_2H$, —NHC═(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is independently a halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —CO $NH_2$, —$NO_2$, —SH, —$NHNH_2$, —NHC(O)$NH_2$, —NHC═(NH)$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently —$CF_3$, —CN, —OH, —$NH_2$, —COOH, —$CONH_2$, —$NO_2$, —SH, —$NHNH_2$, —NHC(O)$NH_2$, —NHC═(NH)$NH_2$, —$OCF_3$, substituted or unsubstituted $C_1$-$C_4$ alkyl or substituted or unsubstituted 2 to 4 membered heteroalkyl. In embodiments, $R^2$ is independently —$CF_3$, —CN, —OH, —$NH_2$, —COOH, —$CONH_2$, —$NO_2$, —SH, —$NHNH_2$, —NHC(O)$NH_2$, —NHC═(NH)$NH_2$, —$OCF_3$, unsubstituted isopropyl, unsubstituted isobutyl, unsubstituted tert-butyl, unsubstituted propoxy, or unsubstituted butoxy. In embodiments, $R^2$ is independently unsubstituted isopropyl or unsubstituted tert-butyl. In embodiments, $R^2$ is independently unsubstituted isopropyl. In embodiments, $R^2$ is independently unsubstituted tert-butyl. In embodiments, $R^2$ is independently unsubstituted isobutyl. In embodiments, $R^2$ is independently substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^2$ is independently substituted or unsubstituted $C_1$-$C_8$ alkyl. In embodiments, $R^2$ is independently substituted or unsubstituted 2 to 8 membered heteroalkyl. In embodiments, $R^2$ is independently substituted or unsubstituted $C_3$-$C_8$ cycloalkyl. In embodiments, $R^2$ is independently substituted or unsubstituted 3 to 8 membered heterocycloalkyl. In embodiments, $R^2$ is independently substituted or unsubstituted $C_6$-$C_{10}$ aryl. In embodiments, $R^2$ is independently substituted or unsubstituted 5 to 10 membered heteroaryl. In embodiments, $R^2$ is independently unsubstituted $C_1$-$C_8$ alkyl. In embodiments, $R^2$ is independently unsubstituted 2 to 8 membered heteroalkyl. In embodiments, $R^2$ is independently unsubstituted $C_3$-$C_8$ cycloalkyl. In embodiments, $R^2$ is independently unsubstituted 3 to 8 membered heterocycloalkyl. In embodiments, $R^2$ is independently unsubstituted $C_6$-$C_{10}$ aryl. In embodiments, $R^2$ is independently unsubstituted 5 to 10 membered heteroaryl. In embodiments, $R^2$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently substituted or unsubstituted $C_1$-$C_6$ alkyl or substituted or unsubstituted 2 to 6 membered heteroalkyl. In embodiments, $R^2$ is independently substituted or unsubstituted $C_1$-$C_5$ alkyl, substituted or unsubstituted 2 to 5 membered alkoxy. In embodiments, $R^2$ is independently unsubstituted butyl, unsubstituted pentyl, unsubstituted hexyl, unsubstituted propoxy, unsubstituted butoxy, or unsubstituted pentoxy. In embodiments, $R^2$ is independently unsubstituted butyl. In embodiments, $R^2$ is independently unsubstituted t-butyl. In embodiments, $R^2$ is independently unsubstituted pentyl. In embodiments, $R^2$ is independently unsubstituted hexyl. In embodiments, $R^2$ is independently unsubstituted propoxy. In embodiments, $R^2$ is independently unsubstituted butoxy. In embodiments, $R^2$ is independently unsubstituted pentoxy. In embodiments, $R^2$ is independently a hydrogen.

In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$OCX^2_3$. In embodiments, $R^2$ is independently —$OCH_2X^2$. In embodiments, $R^2$ is independently —$OCHX^2_2$. In embodiments, $R^2$ is independently —$CF_3$. In embodiments, $R^2$ is independently —$CCl_3$. In embodiments, $R^2$ is independently —$CBr_3$. In embodiments, $R^2$ is independently —$CI_3$. In embodiments, $R^2$ is independently —NHC═($NR^{13}$)$NR^{11}R^{12}$. In embodiments, $R^2$ is independently —NHC═(NH)$NH_2$. In embodiments, $R^2$ is independently —NHC═(O)$NH_2$. In embodiments, $R^2$ is independently —NHC═(O)$NR^{11}R^{12}$. In embodiments, $R^2$ is independently —C(O)$OR^{13}$. In embodiments, $R^2$ is independently —C(O)OH. In embodiments, $R^2$ is independently —C(O)$NR^{11}R^{12}$. In embodiments, $R^2$ is independently —C(O)$NH_2$. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently substituted or unsubstituted aryl or substituted or unsubstituted heteroaryl. In embodiments, $R^2$ is independently substituted or unsubstituted phenyl. In embodiments, $R^2$ is independently substituted or unsubstituted 5 to 6 membered heteroaryl. In embodiments, $R^2$ is independently unsubstituted phenyl. In embodiments, $R^2$ is independently unsubstituted 5 to 6 membered heteroaryl. In embodiments, $R^2$ is independently substituted or unsubstituted imidazolyl. In embodiments, $R^2$ is independently substituted or unsubstituted indolyl. In embodiments, $R^2$ is independently substituted or unsubstituted benzoxazolyl. In embodiments, $R^2$ is independently substituted or unsubstituted pyridyl. In embodiments, $R^2$ is independently substituted or unsubstituted thienyl. In embodiments, $R^2$ is independently substituted or unsubstituted heteroaryl. In embodiments, $R^2$ is independently substituted or unsubstituted 5 to 6 membered heteroaryl. In embodiments, $R^2$ is independently substituted or unsubstituted pyrrolyl. In embodiments, $R^2$ is independently substituted or unsubstituted thienyl. In embodiments, $R^2$ is independently substituted or unsubstituted furanyl. In embodiments, $R^2$ is independently substituted or unsubstituted pyrazolyl. In embodiments, $R^2$ is independently substituted or unsubstituted pyridyl. In embodiments, $R^2$ is independently substituted or unsubstituted phenyl. In embodiments, $R^2$ is independently substituted or unsubstituted imidazolyl. In embodiments, $R^2$ is independently substituted or unsubstituted oxazolyl. In embodiments, $R^2$ is independently substituted or unsubstituted isoxazolyl. In embodiments, $R^2$ is independently substituted or unsubstituted thiazolyl. In embodiments, $R^2$ is independently substituted or unsubstituted triazolyl. In embodiments, $R^2$ is independently substituted or unsubstituted pyridyl. In embodiments, $R^2$ is independently substituted or unsubstituted phenyl.

$R^2$ may independently be substituted or unsubstituted benzyl. $R^2$ may independently be substituted benzyl. $R^2$ may independently be benzyl wherein the phenyl is substituted with one or more substituents independently selected from halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(NH)$NH_2$, —NHC═(O) $NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^2$ may independently be benzyl wherein the phenyl is substituted with one or more substituents independently selected from halogen, —$CF_3$, —CN, —OH, —$NH_2$, —COOH, —$CONH_2$, —$NO_2$, —SH, —$SO_3H$, —$SO_4H$, $—SO_2NH_2$, $—NHNH_2$, $—ONH_2$, $—NHC═(O)NHNH_2$, $—NHC═(NH)NH_2$, $—NHC═(O)\ NH_2$, $—NHSO_2H$, $—NHC═(O)H$, —NHC(O)—OH, —NHOH, $—OCF_3$, $—OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, and substituted or unsubstituted 5 to 6 membered heteroaryl. $R^2$ may independently be benzyl wherein the phenyl is independently substituted with one halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(NH)NH_2$, $—NHC═(O)\ NH_2$, $—NHSO_2H$, —NHC═(O)H, —NHC(O)—OH, —NHOH, $—OCF_3$, $—OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^2$ may independently be methyl substituted with a substituted or unsubstituted phenyl or substituted or unsubstituted 5 to 6 membered heteroaryl. $R^2$ may independently be methyl substituted with a substituted or unsubstituted phenyl or substituted or unsubstituted 5 to 6 membered heteroaryl wherein the phenyl or heteroaryl is optionally substituted with halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(NH)NH_2$, $—NHC═(O)\ NH_2$, $—NHSO_2H$, —NHC═(O)H, —NHC(O)—OH, —NHOH, $—OCF_3$, $—OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl.

$R^2$ may independently be $—SO_2R^{14}$. $R^2$ may independently be $—SO_2NR^{11}R^{12}$. $R^2$ may independently be $—C(O)R^{13}$. $R^2$ may independently be $—C(O)OR^{13}$. $R^2$ may independently be $—C(O)NR^{11}R^{12}$. Each $R^{11}$, $R^{12}$, $R^{13}$, or $R^{14}$ may independently be substituted or unsubstituted cycloalkyl, substituted or unsubstituted heterocycloalkyl, substituted or unsubstituted aryl, or substituted or unsubstituted heteroaryl. Each $R^{11}$, $R^{12}$, $R^{13}$, or $R^{14}$ may independently be substituted or unsubstituted aryl or substituted or unsubstituted heteroaryl. Each $R^{11}$, $R^{12}$, $R^{13}$, or $R^{14}$ may independently be unsubstituted cycloalkyl, unsubstituted heterocycloalkyl, unsubstituted aryl, or unsubstituted heteroaryl. Each $R^{11}$, $R^{12}$, $R^{13}$, or $R^{14}$ may independently be substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. Each $R^{11}$, $R^{12}$, $R^{13}$, or $R^{14}$ may independently be unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. Each $R^{11}$, $R^{12}$, $R^{13}$, or $R^{14}$ may independently be substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^{11}$, $R^{12}$, $R^{13}$, or $R^{14}$ may independently be unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. Each $R^{11}$, $R^{12}$, $R^{13}$, or $R^{14}$ may independently be substituted or unsubstituted 5 to 6 membered heteroaryl. Each $R^{11}$, $R^{12}$, $R^{13}$, or $R^{14}$ may independently be unsubstituted 5 to 6 membered heteroaryl. Each $R^{11}$, $R^{12}$, $R^{13}$, or $R^{14}$ may independently be substituted or unsubstituted 5 membered heteroaryl. Each $R^{11}$, $R^{12}$, $R^{13}$, or $R^{14}$ may independently be substituted or unsubstituted 6 membered heteroaryl. Each $R^{11}$, $R^{12}$, $R^{13}$, or $R^{14}$ may independently be 5 to 6 membered heteroaryl substituted with halogen, $—CF_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC═(O)NHNH_2$, $—NHC═(NH)NH_2$, $—NHC═(O)\ NH_2$, $—NHSO_2H$, —NHC═(O)H, —NHC(O)—OH, —NHOH, $—OCF_3$, $—OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each $R^{11}$, $R^{12}$, $R^{13}$, or $R^{14}$ may independently be 5 to 6 membered heteroaryl substituted with halogen, $—CF_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC═(O)NHNH_2$, $—NHC═(NH)NH_2$, $—NHC═(O)\ NH_2$, $—NHSO_2H$, —NHC═(O)H, —NHC(O)—OH, —NHOH, $—OCF_3$, $—OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^{11}$, $R^{12}$, $R^{13}$, or $R^{14}$ may independently be substituted or unsubstituted thienyl. Each $R^{11}$, $R^{12}$, $R^{13}$, or $R^{14}$ may independently be thienyl substituted with halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(NH)NH_2$, $—NHC═(O)\ NH_2$, $—NHSO_2H$, —NHC═(O)H, —NHC(O)—OH, —NHOH, $—OCF_3$, $—OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Each $R^{11}$, $R^{12}$, $R^{13}$, or $R^{14}$ may independently be thienyl substituted with halogen, $—CF_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC═(O)NHNH_2$, $—NHC═(NH)NH_2$, $—NHC═(O)\ NH_2$, $—NHSO_2H$, —NHC═(O)H, —NHC(O)—OH, —NHOH, $—OCF_3$, $—OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^{11}$, $R^{12}$, $R^{13}$, or $R^{14}$ may independently be unsubstituted thienyl.

In embodiments, $R^2$ is substituted or unsubstituted phenyl. In embodiments, $R^2$ is $R^{33}$-substituted phenyl. In embodiments, $R^{33}$ is independently halogen. In embodiments, $R^{33}$ is independently 4-halogen. In embodiments, $R^{33}$ is independently 4-Cl.

In embodiments, $R^2$ is substituted or unsubstituted heteroaryl. In embodiments, $R^2$ is substituted or unsubstituted 5 to 6 membered heteroaryl. In embodiments, $R^2$ is unsubstituted 5 to 6 membered heteroaryl. In embodiments, $R^2$ is substituted 5 to 6 membered heteroaryl. In embodiments, $R^2$ is $R^{33}$-substituted 5 to 6 membered heteroaryl. In embodiments, $R^2$ is substituted or unsubstituted pyrrolyl. In embodiments, $R^2$ is unsubstituted pyrrolyl. In embodiments, $R^2$ is substituted pyrrolyl. In embodiments, $R^2$ is $R^{33}$-substituted pyrrolyl. In embodiments, $R^2$ is substituted or unsubstituted thienyl. In embodiments, $R^2$ is unsubstituted thienyl. In embodiments, $R^2$ is substituted thienyl. In embodiments, $R^2$ is $R^{33}$-substituted thienyl. In embodiments, $R^2$ is substituted or unsubstituted furanyl. In embodiments, $R^2$ is unsubstituted furanyl. In embodiments, $R^2$ is substituted furanyl. In embodiments, $R^2$ is $R^{33}$-substituted furanyl. In embodiments, $R^2$ is substituted or unsubstituted pyrazolyl. In embodiments, $R^2$ is unsubstituted pyrazolyl. In embodiments, $R^2$ is substituted pyrazolyl. In embodiments, $R^2$ is $R^{33}$-substituted pyrazolyl. In embodiments, $R^2$ is unsubstituted pyridyl. In embodiments, $R^2$ is substituted pyridyl. In embodiments, $R^2$ is $R^{33}$-substituted pyridyl. In embodiments, $R^2$ is unsubstituted phenyl. In embodiments, $R^2$ is substituted phenyl. In embodiments, $R^2$ is $R^{33}$-substituted phenyl. In embodiments, $R^2$ is unsubstituted imidazolyl. In embodiments, $R^2$ is substituted imidazolyl. In embodiments, $R^2$ is $R^{33}$-substituted imidazolyl. In embodiments, $R^2$ is unsubstituted oxazolyl. In embodiments, $R^2$ is substituted oxazolyl. In embodiments, $R^2$ is $R^{33}$-substituted oxazolyl. In embodiments, $R^2$ is unsubstituted isoxazolyl. In embodiments, $R^2$ is substituted isoxazolyl. In embodiments, $R^2$ is $R^{33}$-substituted isoxazolyl. In embodiments, $R^2$ is unsubstituted thiazolyl. In embodiments, $R^2$ is substituted thiazolyl. In embodiments, $R^2$ is $R^{33}$-substituted thiazolyl. In embodiments, $R^2$ is unsubstituted triazolyl. In embodiments, $R^2$ is substituted triazolyl. In embodiments, $R^2$ is $R^{33}$-substituted triazolyl. In embodiments, $R^2$ is unsubstituted pyridyl. In embodiments, $R^2$ is substituted pyridyl. In embodiments, $R^2$ is $R^{33}$-substituted pyridyl. In embodiments, $R^2$ is unsubstituted phenyl. In embodiments, $R^2$ is substituted phenyl. In embodiments, $R^2$ is $R^{33}$-substituted phenyl.

In embodiments, $R^2$ is substituted or unsubstituted pyridyl. In embodiments, $R^2$ is unsubstituted pyridyl. In embodiments, $R^2$ is substituted or unsubstituted pyrid-2-yl. In embodiments, $R^2$ is substituted or unsubstituted pyrid-3-yl. In embodiments, $R^2$ is substituted or unsubstituted pyrid-4-yl. In embodiments, $R^2$ is substituted or unsubstituted pyridyl. In embodiments, $R^2$ is unsubstituted pyridin-2-yl. In embodiments, $R^2$ is unsubstituted pyridin-3-yl. In embodiments, $R^2$ is unsubstituted pyridin-4-yl. In embodiments, $R^2$ is unsubstituted pyridyl. In embodiments, $R^2$ is substituted or unsubstituted $C_1$-$C_6$ alkyl. In embodiments, $R^2$ is substituted $C_1$-$C_6$ alkyl. In embodiments, $R^2$ is unsubstituted $C_1$-$C_6$ alkyl. In embodiments, $R^2$ is $R^{33}$-substituted $C_1$-$C_6$ alkyl. In embodiments, $R^2$ is substituted or unsubstituted $C_1$-$C_4$ alkyl. In embodiments, $R^2$ is substituted $C_1$-$C_4$ alkyl. In embodiments, $R^2$ is unsubstituted $C_1$-$C_4$ alkyl. In embodiments, $R^2$ is $R^{33}$-substituted $C_1$-$C_4$ alkyl. In embodiments, $R^2$ is substituted or unsubstituted $C_3$-$C_5$ alkyl. In embodiments, $R^2$ is substituted $C_3$-$C_5$ alkyl. In embodiments, $R^2$ is unsubstituted $C_3$-$C_5$ alkyl. In embodiments, $R^2$ is $R^{33}$-substituted $C_3$-$C_5$ alkyl. In embodiments, $R^2$ is substituted methyl. In embodiments, $R^2$ is substituted ethyl. In embodiments, $R^2$ is substituted propyl. In embodiments, $R^2$ is substituted isopropyl. In embodiments, $R^2$ is substituted butyl. In embodiments, $R^2$ is substituted pentyl. In embodiments, $R^2$ is substituted tert-butyl. In embodiments, $R^2$ is substituted isopropyl. In embodiments, $R^2$ is substituted isopentyl. In embodiments, $R^2$ is substituted iso-butyl. In embodiments, $R^2$ is substituted n-butyl. In embodiments, $R^2$ is substituted n-propyl. In embodiments, $R^2$ is substituted n-pentyl. In embodiments, $R^2$ is $R^{33}$-substituted methyl. In embodiments, $R^2$ is $R^{33}$-substituted ethyl. In embodiments, $R^2$ is $R^{33}$-substituted propyl. In embodiments, $R^2$ is $R^{33}$-substituted isopropyl. In embodiments, $R^2$ is $R^{33}$-substituted butyl. In embodiments, $R^2$ is $R^{33}$-substituted pentyl. In embodiments, $R^2$ is $R^{33}$-substituted tert-butyl. In embodiments, $R^2$ is $R^{33}$-substituted isopropyl. In embodiments, $R^2$ is $R^{33}$-substituted isopentyl. In embodiments, $R^2$ is $R^{33}$-substituted iso-butyl. In embodiments, $R^2$ is $R^{33}$-substituted n-butyl. In embodiments, $R^2$ is $R^{33}$-substituted n-propyl. In embodiments, $R^2$ is $R^{33}$-substituted n-pentyl. In embodiments, $R^2$ is unsubstituted methyl. In embodiments, $R^2$ is unsubstituted ethyl. In embodiments, $R^2$ is unsubstituted propyl. In embodiments, $R^2$ is unsubstituted isopropyl. In embodiments, $R^2$ is unsubstituted butyl. In embodiments, $R^2$ is unsubstituted pentyl. In embodiments, $R^2$ is unsubstituted tert-butyl. In embodiments, $R^2$ is unsubstituted isopropyl. In embodiments, $R^2$ is unsubstituted isopentyl. In embodiments, $R^2$ is unsubstituted iso-butyl. In embodiments, $R^2$ is unsubstituted n-butyl. In embodiments, $R^2$ is unsubstituted n-propyl. In embodiments, $R^2$ is unsubstituted n-pentyl.

In embodiments, $R^{33}$ is independently halogen. In embodiments, $R^{33}$ is independently —F. In embodiments, $R^{33}$ is independently —Cl. In embodiments, $R^{33}$ is independently —I. In embodiments, $R^{33}$ is independently —Br. In embodiments, $R^{33}$ is independently 4-halogen. In embodiments, $R^{33}$ is independently 4-Cl. In embodiments, $R^{33}$ is independently substituted or unsubstituted 5 to 6 membered heteroaryl. In embodiments, $R^{33}$ is independently substituted 5 to 6 membered heteroaryl. In embodiments, $R^{33}$ is independently unsubstituted 5 to 6 membered heteroaryl. In embodiments, $R^{33}$ is independently substituted or unsubstituted 5 membered heteroaryl. In embodiments, $R^{33}$ is independently substituted 5 membered heteroaryl. In embodiments, $R^{33}$ is independently unsubstituted 5 membered heteroaryl. In embodiments, $R^{33}$ is independently substituted or unsubstituted thienyl. In embodiments, $R^{33}$ is independently substituted thienyl. In embodiments, $R^{33}$ is independently unsubstituted thienyl. In embodiments, $R^{33}$ is independently —$CF_3$. In embodiments, $R^{33}$ is independently —$CCl_3$. In embodiments, $R^{33}$ is independently —$CBr_3$. In embodiments, $R^{33}$ is independently —$CI_3$. In embodiments, $R^{33}$ is independently unsubstituted methyl. In embodiments, $R^{33}$ is independently unsubstituted ethyl. In embodiments, $R^{33}$ is independently unsubstituted propyl. In embodiments, $R^{33}$ is independently unsubstituted isopropyl. In embodiments, $R^{33}$ is independently substituted or unsubstituted heteroaryl. In embodiments, $R^{33}$ is independently substituted or unsubstituted 5 to 6 membered heteroaryl. In embodiments, $R^{33}$ is independently unsubstituted 5 to 6 membered heteroaryl. In embodiments, $R^{33}$ is independently substituted 5 to 6 membered heteroaryl. In embodiments, $R^{33}$ is independently substituted or unsubstituted pyrrolyl. In embodiments, $R^{33}$ is independently unsubstituted pyrrolyl. In embodiments, $R^{33}$ is independently substituted pyrrolyl. In embodiments, $R^{33}$ is independently substituted or unsubstituted thienyl. In embodiments, $R^{33}$ is independently unsubstituted thienyl. In embodiments, $R^{33}$ is independently substituted thienyl. In embodiments, $R^{33}$ is independently substituted or unsubstituted furanyl. In embodiments, $R^{33}$ is independently unsubstituted furanyl. In embodiments, $R^{33}$ is independently substituted furanyl. In embodiments, $R^{33}$ is independently substituted or unsubstituted pyrazolyl. In embodiments, $R^{33}$ is independently unsubstituted pyrazolyl. In embodiments, $R^{33}$ is independently substituted pyrazolyl. In embodiments, $R^{33}$ is independently unsubstituted pyridyl. In embodiments, $R^{33}$ is independently substituted pyridyl. In embodiments, $R^{33}$ is independently unsubstituted phenyl. In embodiments, $R^{33}$ is independently substituted phenyl. In embodiments, $R^{33}$ is independently unsubstituted imidazolyl. In embodiments, $R^{33}$ is independently substituted imidazolyl. In embodiments, $R^{33}$ is independently unsubstituted oxazolyl. In embodiments, $R^{33}$ is independently substituted oxazolyl. In embodiments, $R^{33}$ is independently unsubstituted isoxazolyl. In embodiments, $R^{33}$ is independently substituted isoxazolyl. In embodiments, $R^{33}$ is independently unsubstituted thiazolyl. In embodiments, $R^{33}$ is independently substituted thiazolyl. In embodiments, $R^{33}$ is independently unsubstituted triazolyl. In embodiments, $R^{33}$ is independently substituted triazolyl. In embodiments, $R^{33}$ is independently unsubstituted pyridyl. In embodiments, $R^{33}$ is independently substituted pyridyl. In embodiments, $R^{33}$ is independently unsubstituted phenyl. In embodiments, $R^{33}$ is independently substituted phenyl.

$R^2$ may independently be —C(O)$R^{13}$. In embodiments, $R^{13}$ is independently substituted or unsubstituted 5 to 6 membered heteroaryl. In embodiments, $R^{13}$ is independently substituted 5 to 6 membered heteroaryl. In embodiments, $R^{13}$ is independently unsubstituted 5 to 6 membered heteroaryl. In embodiments, $R^{13}$ is independently substituted or unsubstituted 5 membered heteroaryl. In embodiments, $R^{13}$ is independently substituted 5 membered heteroaryl. In embodiments, $R^{13}$ is independently unsubstituted 5 membered heteroaryl. In embodiments, $R^{13}$ is independently substituted or unsubstituted thienyl. In embodiments, $R^{13}$ is independently substituted thienyl. In embodiments, $R^{13}$ is independently unsubstituted thienyl. In embodiments, $R^{13}$ is independently substituted or unsubstituted heteroaryl. In embodiments, $R^{13}$ is independently substituted or unsubstituted 5 to 6 membered heteroaryl. In embodiments, $R^{13}$ is independently unsubstituted 5 to 6 membered heteroaryl. In embodiments, $R^{13}$ is independently substituted 5 to 6 membered heteroaryl. In embodiments, $R^{13}$ independently $R^{13A}$-substituted 5 to 6 membered heteroaryl. In embodiments, $R^{13}$ is independently substituted or unsubstituted pyrrolyl. In embodiments, $R^{13}$ is independently unsubstituted pyrrolyl. In embodiments, $R^{13}$ is independently substituted pyrrolyl. In embodiments, $R^{13}$ is independently $R^{13A}$-substituted pyrrolyl. In embodiments, $R^{13}$ is independently substituted or unsubstituted thienyl. In embodiments, $R^{13}$ is independently unsubstituted thienyl. In embodiments, $R^{13}$ is independently substituted thienyl. In embodiments, $R^{13}$ is independently $R^{13A}$-substituted thienyl. In embodiments, $R^{13}$ is independently substituted or unsubstituted furanyl. In embodiments, $R^{13}$ is independently unsubstituted furanyl. In embodiments, $R^{13}$ is independently substituted furanyl. In embodiments, $R^{13}$ is independently $R^{13A}$-substituted furanyl. In embodiments, $R^{13}$ is independently substituted or unsubstituted pyrazolyl. In embodiments, $R^{13}$ is independently unsubstituted pyrazolyl. In embodiments, $R^{13}$ is independently substituted pyrazolyl. In embodiments, $R^{13}$ is independently $R^{13A}$-substituted pyrazolyl. In embodiments, $R^{13}$ is independently unsubstituted pyridyl. In embodiments, $R^{13}$ is independently substituted pyridyl. In embodiments, $R^{13}$ is independently $R^{13A}$-substituted pyridyl. In embodiments, $R^{13}$ is independently unsubstituted phenyl. In embodiments, $R^{13}$ is independently substituted phenyl. In embodiments, $R^{13}$ is independently $R^{13A}$-substituted phenyl. In embodiments, $R^{13}$ is independently unsubstituted imidazolyl. In embodiments, $R^{13}$ is independently substituted imidazolyl. In embodiments, $R^{13}$ is independently $R^{13A}$-substituted imidazolyl. In embodiments, $R^{13}$ is independently unsubstituted oxazolyl. In embodiments, $R^{13}$ is independently substituted oxazolyl. In embodiments, $R^{13}$ is independently $R^{13A}$-substituted oxazolyl. In embodiments, $R^{13}$ is independently unsubstituted isoxazolyl. In embodiments, $R^{13}$ is independently substituted isoxazolyl. In embodiments, $R^{13}$ is independently $R^{13A}$-substituted isoxazolyl. In embodiments, $R^{13}$ is independently unsubstituted thiazolyl. In embodiments, $R^{13}$ is independently substituted thiazolyl. In embodiments, $R^{13}$ is independently $R^{13A}$-substituted thiazolyl. In embodiments, $R^{13}$ is independently unsubstituted triazolyl. In embodiments, $R^{13}$ is independently substituted triazolyl. In embodiments, $R^{13}$ is independently $R^{13A}$-substituted triazolyl. In embodiments, $R^{13}$ is independently unsubstituted pyridyl. In embodiments, $R^{13}$ is independently substituted pyridyl. In embodiments, $R^{13}$ is independently $R^{13A}$-substituted pyridyl. In embodiments, $R^{13}$ is independently unsubstituted phenyl. In embodiments, $R^{13}$ is independently substituted phenyl. In embodiments, $R^{13}$ is independently $R^{13A}$-substituted phenyl. In embodiments, $R^{13}$ is independently hydrogen.

$R^2$ may independently be —$SO_2NR^{11}R^{12}$. In embodiments, $R^{11}$ is independently substituted propyl. In embodiments, $R^{11}$ is independently substituted butyl. In embodiments, $R^{11}$ is independently substituted pentyl. In embodiments, $R^{11}$ is independently substituted tert-butyl. In embodiments, $R^{11}$ is independently substituted isopropyl. In embodiments, $R^{11}$ is independently substituted isopentyl. In embodiments, $R^{11}$ is independently substituted iso-butyl. In embodiments, $R^{11}$ is independently substituted n-butyl. In embodiments, $R^{11}$ is independently substituted n-propyl. In embodiments, $R^{11}$ is independently substituted n-pentyl. In embodiments, $R^{11}$ is independently substituted ethyl. In embodiments, $R^{11}$ is independently substituted methyl. In embodiments, $R^{11}$ is independently hydrogen. In embodiments, $R^{11}$ is independently unsubstituted propyl. In embodiments, $R^{11}$ is independently unsubstituted butyl. In embodiments, $R^{11}$ is independently unsubstituted pentyl. In embodiments, $R^{11}$ is independently unsubstituted tert-butyl. In embodiments, $R^{11}$ is independently unsubstituted isopropyl. In embodiments, $R^{11}$ is independently unsubstituted isopentyl. In embodiments, $R^{11}$ is independently unsubstituted iso-butyl. In embodiments, $R^{11}$ is independently unsubstituted n-butyl. In embodiments, $R^{11}$ is independently unsubstituted n-propyl. In embodiments, $R^{11}$ is independently unsubstituted n-pentyl. In embodiments, $R^{11}$ is independently unsubstituted ethyl. In embodiments, $R^{11}$ is independently unsubstituted methyl. In embodiments, $R^{11}$ is independently substituted $C_1$-$C_6$ alkyl. In embodiments, $R^{11}$ is independently unsubstituted $C_1$-$C_6$ alkyl. In embodiments, $R^{11}$ is independently substituted $C_1$-$C_4$ alkyl. In embodiments, $R^{11}$ is independently unsubstituted $C_1$-$C_4$ alkyl. In embodiments, $R^{11}$ is independently substituted $C_1$-$C_8$ alkyl. In embodiments, $R^{11}$ is independently unsubstituted $C_1$-$C_8$ alkyl. In embodiments, $R^{11}$ is independently substituted heteroalkyl. In embodiments, $R^{11}$ is independently unsubstituted heteroalkyl. In embodiments, $R^{11}$ is independently substituted 2 to 8 membered heteroalkyl. In embodiments, $R^{11}$ is independently unsubstituted 2 to 8 membered heteroalkyl. In embodiments, $R^{11}$ is independently substituted 2 to 6 membered heteroalkyl. In embodiments, $R^{11}$ is independently unsubstituted 2 to 6 membered heteroalkyl. In embodiments, $R^{11}$ is independently substituted 2 to 4 membered heteroalkyl. In embodiments, $R^{11}$ is independently unsubstituted 2 to 4 membered heteroalkyl. In embodiments, $R^{12}$ is independently substituted propyl. In embodiments, $R^{12}$ is independently substituted butyl. In embodiments, $R^{12}$ is independently substituted pentyl. In embodiments, $R^{12}$ is independently substituted tert-butyl. In embodiments, $R^{12}$ is independently substituted isopropyl. In embodiments, $R^{12}$ is independently substituted isopentyl. In embodiments, $R^{12}$ is independently substituted iso-butyl. In embodiments, $R^{12}$ is independently substituted n-butyl. In embodiments, $R^{12}$ is independently substituted n-propyl. In embodiments, $R^{12}$ is independently substituted n-pentyl. In embodiments, $R^{12}$ is independently substituted ethyl. In embodiments, $R^{12}$ is independently substituted methyl. In embodiments, $R^{12}$ is independently hydrogen. In embodiments, $R^{12}$ is independently unsubstituted propyl. In embodiments, $R^{12}$ is independently unsubstituted butyl. In embodiments, $R^{12}$ is independently unsubstituted pentyl. In embodiments, $R^{12}$ is independently unsubstituted tert-butyl. In embodiments, $R^{12}$ is independently unsubstituted isopropyl. In embodiments, $R^{12}$ is independently unsubstituted isopentyl. In embodiments, $R^{12}$ is independently unsubstituted iso-butyl. In embodiments, $R^{12}$ is independently unsubstituted n-butyl. In embodiments, $R^{12}$ is independently unsubstituted n-propyl. In embodiments, $R^{12}$ is independently unsubstituted n-pentyl. In embodiments, $R^{12}$ is independently unsubstituted ethyl. In embodiments, $R^{12}$ is independently unsubstituted methyl. In embodiments, $R^{12}$ is independently substituted $C_1$-$C_6$ alkyl. In embodiments, $R^{12}$ is independently unsubstituted $C_1$-$C_6$ alkyl. In embodiments, $R^{12}$ is independently substituted $C_1$-$C_4$ alkyl. In embodiments, $R^{12}$ is independently unsubstituted $C_1$-$C_4$ alkyl. In embodiments, $R^{12}$ is independently substituted $C_1$-$C_5$ alkyl. In embodiments, $R^{12}$ is independently unsubstituted $C_1$-$C_8$ alkyl. In embodiments, $R^{12}$ is independently substituted heteroalkyl. In embodiments, $R^{12}$ is independently unsubstituted heteroalkyl. In embodiments, $R^{12}$ is independently substituted 2 to 8 membered heteroalkyl. In embodiments, $R^{12}$ is independently unsubstituted 2 to 8 membered heteroalkyl. In embodiments, $R^{12}$ is independently substituted 2 to 6 membered heteroalkyl. In embodiments, $R^{12}$ is independently unsubstituted 2 to 6 membered heteroalkyl. In embodiments, $R^{12}$ is independently substituted 2 to 4 membered heteroalkyl. In embodiments, $R^{12}$ is independently unsubstituted 2 to 4 membered heteroalkyl.

$R^2$ may independently be —$SO_2R^{14}$. In embodiments, $R^{14}$ is independently substituted propyl. In embodiments, $R^{14}$ is independently substituted butyl. In embodiments, $R^{14}$ is independently substituted pentyl. In embodiments, $R^{14}$ is independently substituted tert-butyl. In embodiments, $R^{14}$ is independently substituted isopropyl. In embodiments, $R^{14}$ is independently substituted isopentyl. In embodiments, $R^{14}$ is independently substituted iso-butyl. In embodiments, $R^{14}$ is independently substituted n-butyl. In embodiments, $R^{14}$ is independently substituted n-propyl. In embodiments, $R^{14}$ is independently substituted n-pentyl. In embodiments, $R^{14}$ is independently substituted ethyl. In embodiments, $R^{14}$ is independently substituted methyl. In embodiments, $R^{14}$ is independently hydrogen. In embodiments, $R^{14}$ is independently unsubstituted propyl. In embodiments, $R^{14}$ is independently unsubstituted butyl. In embodiments, $R^{14}$ is independently unsubstituted pentyl. In embodiments, $R^{14}$ is independently unsubstituted tert-butyl. In embodiments, $R^{14}$ is independently unsubstituted isopropyl. In embodiments, $R^{14}$ is independently unsubstituted isopentyl. In embodiments, $R^{14}$ is independently unsubstituted iso-butyl. In embodiments, $R^{14}$ is independently unsubstituted n-butyl. In embodiments, $R^{14}$ is independently unsubstituted n-propyl. In embodiments, $R^{14}$ is independently unsubstituted n-pentyl. In embodiments, $R^{14}$ is independently unsubstituted ethyl. In embodiments, $R^{14}$ is independently unsubstituted methyl. In embodiments, $R^{14}$ is independently substituted $C_1$-$C_6$ alkyl. In embodiments, $R^{14}$ is independently unsubstituted $C_1$-$C_6$ alkyl. In embodiments, $R^{14}$ is independently substituted $C_1$-$C_4$ alkyl. In embodiments, $R^{14}$ is independently unsubstituted $C_1$-$C_4$ alkyl. In embodiments, $R^{14}$ is independently substituted $C_1$-$C_8$ alkyl. In embodiments, $R^{14}$ is independently unsubstituted $C_1$-$C_5$ alkyl. In embodiments, $R^{14}$ is independently substituted heteroalkyl. In embodiments, $R^{14}$ is independently unsubstituted heteroalkyl. In embodiments, $R^{14}$ is independently substituted 2 to 8 membered heteroalkyl. In embodiments, $R^{14}$ is independently unsubstituted 2 to 8 membered heteroalkyl. In embodiments, $R^{14}$ is independently substituted 2 to 6 membered heteroalkyl. In embodiments, $R^{14}$ is independently unsubstituted 2 to 6 membered heteroalkyl. In embodiments, $R^{14}$ is independently substituted 2 to 4 membered heteroalkyl. In embodiments, $R^{14}$ is independently unsubstituted 2 to 4 membered heteroalkyl.

In embodiments, $R^3$ is independently a halogen, —$CX^3_3$, —$CHX^3_2$, —$CH_2X^3$, —$OCX^3_3$, —$OCH_2X$, —$OCHX^3_2$, —CN, —$SO_{n3}R^{18}$, —$SO_{v3}NR^{15}R^{16}$, —$NHNR^{15}R^{16}$, —$ONR^{15}R^{16}$, —NHC═(O)$NHNR^{15}R^{16}$, —NHC═(O)$NR^{15}R^{16}$, —NHC═($NR^{17}$)$NR^{15}R^{16}$, —$N(O)_{m3}$, —$NR^{15}R^{16}$, —C(O)$R^{17}$, —C(O)—$OR^{17}$, —C(O)$NR^{15}R^{16}$, —$OR^{18}$, —$NR^{15}SO_2R^{18}$, —$NR^{15}$C═(O)$R^{17}$, —$NR^{15}$C(O)—$OR^{17}$, —$NR^{15}OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently a halogen. In embodiments, $R^3$ is independently —$CX^3_3$. In embodiments, $R^3$ is independently —$CHX^3_2$. In embodiments, $R^3$ is independently —$CH_2X^3$. In embodiments, $R^3$ is independently —$OCX^3_3$. In embodiments, $R^3$ is independently —$OCH_2X^3$. In embodiments, $R^3$ is independently —$OCHX^3_2$. In embodiments, $R^3$ is independently —CN. In embodiments, $R^3$ is independently —$SO_{n3}R^{18}$. In embodiments, $R^3$ is independently —$SO_{v3}NR^{15}R^{16}$. In embodiments, $R^3$ is independently —$NHNR^{15}R^{16}$. In embodiments, $R^3$ is independently —$ONR^{15}R^{16}$. In embodiments, $R^3$ is independently —NHC═(O)$NHNR^{15}R^{16}$. In embodiments, $R^3$ is independently —NHC═(O)$NR^{15}R^{16}$. In embodiments, $R^3$ is independently —NHC═($NR^{17}$)$NR^{15}R^{16}$. In embodiments, $R^3$ is independently —$N(O)_{m3}$. In embodiments, $R^3$ is independently —$NR^{15}R^{16}$. In embodiments, $R^3$ is independently —C(O)$R^{17}$. In embodiments, $R^3$ is independently —C(O)—$OR^{17}$. In embodiments, $R^3$ is independently —C(O)$NR^{15}R^{16}$. In embodiments, $R^3$ is independently —$OR^{18}$. In embodiments, $R^3$ is independently —$NR^{15}SO_2R^{18}$. In embodiments, $R^3$ is independently —$NR^{15}$C═(O)$R^{17}$. In embodiments, $R^3$ is independently —$NR^{15}$C(O)—$OR^{17}$. In embodiments, $R^3$ is independently —$NR^{15}OR^{17}$. In embodiments, $R^3$ is independently —SH. In embodiments, $R^3$ is independently —$SO_2CH_3$. In embodiments, $R^3$ is independently —$SO_2NH_2$. In embodiments, $R^3$ is independently —$N(O)_2$. In embodiments, $R^3$ is independently —$NH_2$. In embodiments, $R^3$ is independently —C(O)$CH_3$. In embodiments, $R^3$ is independently —C(O)OH. In embodiments, $R^3$ is independently —C(O)$NH_2$. In embodiments, $R^3$ is independently —OH. In embodiments, $R^3$ is independently a halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —NHC═(NH)$NH_2$, —$NHSO_2H$, —NHC═(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently a halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —CO $NH_2$, —$NO_2$, —SH, —$NHNH_2$, —NHC═(NH)$NH_2$, —NHC(O)$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently —$CF_3$, —CN, —OH, —$NH_2$, —COOH, —$CONH_2$, —$NO_2$, —SH, —$NHNH_2$, —NHC═(NH)$NH_2$, —NHC(O)$NH_2$, —$OCF_3$, substituted or unsubstituted $C_1$-$C_4$ alkyl or substituted or unsubstituted 2 to 4 membered heteroalkyl. In embodiments, $R^3$ is independently —$CF_3$, —CN, —OH, —$NH_2$, —COOH, —$CONH_2$, —$NO_2$, —SH, —$NHNH_2$, —NHC═(NH)$NH_2$, —NHC(O)$NH_2$, —$OCF_3$, unsubstituted isopropyl, unsubstituted isobutyl, unsubstituted tert-butyl, unsubstituted propoxy, or unsubstituted butoxy. In embodiments, $R^3$ is independently unsubstituted isopropyl or unsubstituted tert-butyl. In embodiments, $R^3$ is independently unsubstituted isopropyl. In embodiments, $R^3$ is independently unsubstituted tert-butyl. In embodiments, $R^3$ is independently unsubstituted isobutyl. In embodiments, $R^3$ is independently substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^3$ is independently substituted or unsubstituted $C_1$-$C_8$ alkyl. In embodiments, $R^3$ is independently substituted or unsubstituted 2 to 8 membered heteroalkyl. In embodiments, $R^3$ is independently substituted or unsubstituted $C_3$-$C_8$ cycloalkyl. In embodiments, $R^3$ is independently substituted or unsubstituted 3 to 8 membered heterocycloalkyl. In embodiments, $R^3$ is independently substituted or unsubstituted $C_6$-$C_{10}$ aryl. In embodiments, $R^3$ is independently substituted or unsubstituted 5 to 10 membered heteroaryl. In embodiments, $R^3$ is independently unsubstituted $C_1$-$C_8$ alkyl. In embodiments, $R^3$ is independently unsubstituted 2 to 8 membered heteroalkyl. In embodiments, $R^3$ is independently unsubstituted $C_3$-$C_8$ cycloalkyl. In embodiments, $R^3$ is independently unsubstituted 3 to 8 membered heterocycloalkyl. In embodiments, $R^3$ is independently unsubstituted $C_6$-$C_{10}$ aryl. In embodiments, $R^3$ is independently unsubstituted 5 to 10 membered heteroaryl. In embodiments, $R^3$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently substituted or unsubstituted $C_1$-$C_6$ alkyl or substituted or unsubstituted 2 to 6 membered heteroalkyl. In embodiments, $R^3$ is independently substituted or unsubstituted $C_1$-$C_5$ alkyl, substituted or unsubstituted 2 to 5 membered alkoxy. In embodiments, $R^3$ is independently unsubstituted butyl, unsubstituted pentyl, unsubstituted hexyl, unsubstituted propoxy, unsubstituted butoxy, or unsubstituted pentoxy. In embodiments, $R^3$ is independently —NHC═(NH)$NH_2$. In embodiments, $R^3$ is independently hydrogen. In embodiments, $R^3$ is independently —$SO_2CH_3$, —$SO_2NH_2$, —C(O)$R^{17}$, $R^{36}$-substituted or unsubstituted methyl, $R^{36}$-substituted or unsubstituted tert-butyl, $R^{36}$-substituted or unsubstituted pyrazolyl, $R^{36}$-substituted or unsubstituted pyrrolyl, $R^{36}$-substituted or unsubstituted thienyl, $R^{36}$-substituted or unsubstituted phenyl, or $R^{36}$-substituted or unsubstituted pyridyl; and $R^{17}$ is unsubstituted thienyl; and $R^{36}$ is independently halogen, —$CF_3$, or unsubstituted thienyl. In embodiments, $R^3$ is independently —$SO_2R^{18}$, —$SO_2NR^{15}R^{16}$, —C(O)$R^{17}$, $R^{36}$-substituted or unsubstituted methyl, $R^{36}$-substituted or unsubstituted ethyl, $R^{36}$-substituted or unsubstituted isopropyl, $R^{36}$-substituted or unsubstituted tert-butyl, $R^{36}$-substituted or unsubstituted phenyl, or $R^{36}$-substituted or unsubstituted 5 to 6 membered heteroaryl; and $R^{15}$ and $R^{16}$ are independently hydrogen, —$CX_3$, —$CHX_2$, —$CH_2X$, or unsubstituted $C_1$-$C_4$ alkyl; $R^{17}$ is unsubstituted 5 to 6 membered heteroaryl; $R^{18}$ are independently —$CX_3$, —$CHX_2$, —$CH_2X$, or unsubstituted $C_1$-$C_4$ alkyl; and $R^{36}$ is independently halogen, —$CF_3$, —$CHF_2$, —$CH_2F$, or unsubstituted 5 to 6 membered heteroaryl.

In embodiments, $R^3$ is independently —$CX^3_3$. In embodiments, $R^3$ is independently —$CHX^3_2$. In embodiments, $R^3$ is independently —$CH_2X^3$. In embodiments, $R^3$ is independently —$OCX^3_3$. In embodiments, $R^3$ is independently —$OCH_2X^3$. In embodiments, $R^3$ is independently —$OCHX^3_2$. In embodiments, $R^3$ is independently —$CF_3$. In embodiments, $R^3$ is independently —$CCl_3$. In embodiments, $R^3$ is independently —$CBr_3$. In embodiments, $R^3$ is independently —$CI_3$. In embodiments, $R^3$ is independently —NHC═($NR^{17}$)$NR^{15}R^{16}$. In embodiments, $R^3$ is independently —NHC═(NH)$NH_2$. In embodiments, $R^3$ is independently —NHC═(O)$NH_2$. In embodiments, $R^3$ is independently —NHC═(O)$NR^{15}R^{16}$. In embodiments, $R^3$ is independently —C(O)$OR^{17}$. In embodiments, $R^3$ is independently —C(O)OH. In embodiments, $R^3$ is independently —C(O)$NR^{15}R^{16}$. In embodiments, $R^3$ is independently —C(O)$NH_2$. In embodiments, $R^3$ is independently —F. In embodiments, $R^3$ is independently —Cl. In embodiments, $R^3$ is independently —Br. In embodiments, $R^3$ is independently —I. In embodiments, $R^3$ is independently substituted or unsubstituted aryl or substituted or unsubstituted heteroaryl. In embodiments, $R^3$ is independently substituted or unsubstituted phenyl. In embodiments, $R^3$ is independently substituted or unsubstituted 5 to 6 membered heteroaryl. In embodiments, $R^3$ is independently unsubstituted phenyl. In embodiments, $R^3$ is independently unsubstituted 5 to 6 membered heteroaryl. In embodiments, $R^3$ is independently substituted or unsubstituted imidazolyl. In embodiments, $R^3$ is independently substituted or unsubstituted indolyl. In embodiments, $R^3$ is independently substituted or unsubstituted benzoxazolyl. In embodiments, $R^3$ is independently substituted or unsubstituted pyridyl. In embodiments, $R^3$ is independently substituted or unsubstituted thienyl. In embodiments, $R^3$ is independently substituted or unsubstituted heteroaryl. In embodiments, $R^3$ is independently substituted or unsubstituted 5 to 6 membered heteroaryl. In embodiments, $R^3$ is independently substituted or unsubstituted pyrrolyl. In embodiments, $R^3$ is independently substituted or unsubstituted thienyl. In embodiments, $R^3$ is independently substituted or unsubstituted furanyl. In embodiments, $R^3$ is independently substituted or unsubstituted pyrazolyl. In embodiments, $R^3$ is independently substituted or unsubstituted pyridyl. In embodiments, $R^3$ is independently substituted or unsubstituted phenyl. In embodiments, $R^3$ is independently substituted or unsubstituted imidazolyl. In embodiments, $R^3$ is independently substituted or unsubstituted oxazolyl. In embodiments, $R^3$ is independently substituted or unsubstituted isoxazolyl. In embodiments, $R^3$ is independently substituted or unsubstituted thiazolyl. In embodiments, $R^3$ is independently substituted or unsubstituted triazolyl. In embodiments, $R^3$ is independently substituted or unsubstituted pyridyl. In embodiments, $R^3$ is independently substituted or unsubstituted phenyl.

In embodiments, $R^3$ is substituted or unsubstituted phenyl. In embodiments, $R^3$ is $R^{36}$-substituted phenyl. In embodiments, $R^{36}$ is independently halogen. In embodiments, $R^{36}$ is independently 4-halogen. In embodiments, $R^{36}$ is independently 4-Cl. In embodiments, $R^3$ is independently unsubstituted tert-butyl.

In embodiments, $R^3$ is substituted or unsubstituted heteroaryl. In embodiments, $R^3$ is substituted or unsubstituted 5 to 6 membered heteroaryl. In embodiments, $R^3$ is unsubstituted 5 to 6 membered heteroaryl. In embodiments, $R^3$ is substituted 5 to 6 membered heteroaryl. In embodiments, $R^3$ is $R^{36}$-substituted 5 to 6 membered heteroaryl. In embodiments, $R^3$ is substituted or unsubstituted pyrrolyl. In embodiments, $R^3$ is unsubstituted pyrrolyl. In embodiments, $R^3$ is substituted pyrrolyl. In embodiments, $R^3$ is $R^{36}$-substituted pyrrolyl. In embodiments, $R^3$ is substituted or unsubstituted thienyl. In embodiments, $R^3$ is unsubstituted thienyl. In embodiments, $R^3$ is substituted thienyl. In embodiments, $R^3$ is $R^{36}$-substituted thienyl. In embodiments, $R^3$ is substituted or unsubstituted furanyl. In embodiments, $R^3$ is unsubstituted furanyl. In embodiments, $R^3$ is substituted furanyl. In embodiments, $R^3$ is $R^{36}$-substituted furanyl. In embodiments, $R^3$ is substituted or unsubstituted pyrazolyl. In embodiments, $R^3$ is unsubstituted pyrazolyl. In embodiments, $R^3$ is substituted pyrazolyl. In embodiments, $R^3$ is $R^{36}$-substituted pyrazolyl. In embodiments, $R^3$ is unsubstituted imidazolyl. In embodiments, $R^3$ is substituted imidazolyl. In embodiments, $R^3$ is $R^{36}$-substituted imidazolyl. In embodiments, $R^3$ is unsubstituted oxazolyl. In embodiments, $R^3$ is substituted oxazolyl. In embodiments, $R^3$ is $R^{36}$-substituted oxazolyl. In embodiments, $R^3$ is unsubstituted isoxazolyl. In embodiments, $R^3$ is substituted isoxazolyl. In embodiments, $R^3$ is $R^{36}$-substituted isoxazolyl. In embodiments, $R^3$ is unsubstituted thiazolyl. In embodiments, $R^3$ is substituted thiazolyl. In embodiments, $R^3$ is $R^{36}$-substituted thiazolyl. In embodiments, $R^3$ is unsubstituted triazolyl. In embodiments, $R^3$ is substituted triazolyl. In embodiments, $R^3$ is $R^{36}$-substituted triazolyl. In embodiments, $R^3$ is unsubstituted pyridyl. In embodiments, $R^3$ is substituted pyridyl. In embodiments, $R^3$ is $R^{36}$-substituted pyridyl. In embodiments, $R^3$ is unsubstituted phenyl. In embodiments, $R^3$ is substituted phenyl. In embodiments, $R^3$ is $R^{36}$-substituted phenyl.

In embodiments, $R^3$ is substituted or unsubstituted pyridyl. In embodiments, $R^3$ is unsubstituted pyridyl. In embodiments, $R^3$ is substituted or unsubstituted pyrid-2-yl. In embodiments, $R^3$ is substituted or unsubstituted pyrid-3-yl. In embodiments, $R^3$ is substituted or unsubstituted pyrid-4-yl. In embodiments, $R^3$ is substituted or unsubstituted pyridyl. In embodiments, $R^3$ is unsubstituted pyridin-2-yl. In embodiments, $R^3$ is unsubstituted pyridin-3-yl. In embodiments, $R^3$ is unsubstituted pyridin-4-yl. In embodiments, $R^3$ is unsubstituted pyridyl. In embodiments, $R^3$ is substituted or unsubstituted $C_1$-$C_6$ alkyl. In embodiments, $R^3$ is substituted $C_1$-$C_6$ alkyl. In embodiments, $R^3$ is unsubstituted $C_1$-$C_6$ alkyl. In embodiments, $R^3$ is $R^{36}$-substituted $C_1$-$C_6$ alkyl. In embodiments, $R^3$ is substituted or unsubstituted $C_1$-$C_4$ alkyl. In embodiments, $R^3$ is substituted $C_1$-$C_4$ alkyl. In embodiments, $R^3$ is unsubstituted $C_1$-$C_4$ alkyl. In embodiments, $R^3$ is $R^{36}$-substituted $C_1$-$C_4$ alkyl. In embodiments, $R^3$ is substituted or unsubstituted $C_3$-$C_5$ alkyl. In embodiments, $R^3$ is substituted $C_3$-$C_5$ alkyl. In embodiments, $R^3$ is unsubstituted $C_3$-$C_5$ alkyl. In embodiments, $R^3$ is $R^{36}$-substituted $C_3$-$C_5$ alkyl. In embodiments, $R^3$ is substituted propyl. In embodiments, $R^3$ is substituted methyl. In embodiments, $R^3$ is substituted ethyl. In embodiments, $R^3$ is substituted butyl. In embodiments, $R^3$ is substituted pentyl. In embodiments, $R^3$ is substituted tert-butyl. In embodiments, $R^3$ is substituted isopropyl. In embodiments, $R^3$ is substituted isopentyl. In embodiments, $R^3$ is substituted iso-butyl. In embodiments, $R^3$ is substituted n-butyl. In embodiments, $R^3$ is substituted n-propyl. In embodiments, $R^3$ is substituted n-pentyl. In embodiments, $R^3$ is $R^{36}$-substituted propyl. In embodiments, $R^3$ is $R^{36}$-substituted methyl. In embodiments, $R^3$ is $R^{36}$-substituted ethyl. In embodiments, $R^3$ is $R^{36}$-substituted butyl. In embodiments, $R^3$ is $R^{36}$-substituted pentyl. In embodiments, $R^3$ is $R^{36}$-substituted tert-butyl. In embodiments, $R^3$ is $R^{36}$-substituted isopropyl. In embodiments, $R^3$ is $R^{36}$-substituted isopentyl. In embodiments, $R^3$ is $R^{36}$-substituted iso-butyl. In embodiments, $R^3$ is $R^{36}$-substituted n-butyl. In embodiments, $R^3$ is $R^{36}$-substituted n-propyl. In embodiments, $R^3$ is $R^{36}$-substituted n-pentyl. In embodiments, $R^3$ is unsubstituted propyl. In embodiments, $R^3$ is unsubstituted methyl. In embodiments, $R^3$ is unsubstituted ethyl. In embodiments, $R^3$ is unsubstituted butyl. In embodiments, $R^3$ is unsubstituted pentyl. In embodiments, $R^3$ is unsubstituted tert-butyl. In embodiments, $R^3$ is unsubstituted isopropyl. In embodiments, $R^3$ is unsubstituted isopentyl. In embodiments, $R^3$ is unsubstituted iso-butyl. In embodiments, $R^3$ is unsubstituted n-butyl. In embodiments, $R^3$ is unsubstituted n-propyl. In embodiments, $R^3$ is unsubstituted n-pentyl.

In embodiments, $R^{36}$ is independently halogen. In embodiments, $R^{36}$ is independently —F. In embodiments, $R^{36}$ is independently —Cl. In embodiments, $R^{36}$ is independently —I. In embodiments, $R^{36}$ is independently —Br. In embodiments, $R^{36}$ is independently 4-halogen. In embodiments, $R^{36}$ is independently 4-Cl. In embodiments, $R^{36}$ is independently substituted or unsubstituted 5 to 6 membered heteroaryl. In embodiments, $R^{36}$ is independently substituted 5 to 6 membered heteroaryl. In embodiments, $R^{36}$ is independently unsubstituted 5 to 6 membered heteroaryl. In embodiments, $R^{36}$ is independently substituted or unsubstituted 5 membered heteroaryl. In embodiments, $R^{36}$ is independently substituted 5 membered heteroaryl. In embodiments, $R^{36}$ is independently unsubstituted 5 membered heteroaryl. In embodiments, $R^{36}$ is independently substituted or unsubstituted thienyl. In embodiments, $R^{36}$ is independently substituted thienyl. In embodiments, $R^{36}$ is independently unsubstituted thienyl. In embodiments, $R^{36}$ is independently $—CF_3$. In embodiments, $R^{36}$ is independently $—CCl_3$. In embodiments, $R^{36}$ is independently $—CBr_3$. In embodiments, $R^{36}$ is independently $—CI_3$. In embodiments, $R^{36}$ is independently unsubstituted methyl. In embodiments, $R^{36}$ is independently unsubstituted ethyl. In embodiments, $R^{36}$ is independently unsubstituted propyl. In embodiments, $R^{36}$ is independently unsubstituted isopropyl. In embodiments, $R^{36}$ is independently substituted or unsubstituted heteroaryl. In embodiments, $R^{36}$ is independently substituted or unsubstituted 5 to 6 membered heteroaryl. In embodiments, $R^{36}$ is independently unsubstituted 5 to 6 membered heteroaryl. In embodiments, $R^{36}$ is independently substituted 5 to 6 membered heteroaryl. In embodiments, $R^{36}$ is independently substituted or unsubstituted pyrrolyl. In embodiments, $R^{36}$ is independently unsubstituted pyrrolyl. In embodiments, $R^{36}$ is independently substituted pyrrolyl. In embodiments, $R^{36}$ is independently substituted or unsubstituted thienyl. In embodiments, $R^{36}$ is independently unsubstituted thienyl. In embodiments, $R^{36}$ is independently substituted thienyl. In embodiments, $R^{36}$ is independently substituted or unsubstituted furanyl. In embodiments, $R^{36}$ is independently unsubstituted furanyl. In embodiments, $R^{36}$ is independently substituted furanyl. In embodiments, $R^{36}$ is independently substituted or unsubstituted pyrazolyl. In embodiments, $R^{36}$ is independently unsubstituted pyrazolyl. In embodiments, $R^{36}$ is independently substituted pyrazolyl.

In embodiments, $R^{36}$ is independently unsubstituted pyridyl. In embodiments, $R^{36}$ is independently substituted pyridyl. In embodiments, $R^{36}$ is independently unsubstituted phenyl. In embodiments, $R^{36}$ is independently substituted phenyl. In embodiments, $R^{36}$ is independently unsubstituted imidazolyl. In embodiments, $R^{36}$ is independently substituted imidazolyl. In embodiments, $R^{36}$ is independently unsubstituted oxazolyl. In embodiments, $R^{36}$ is independently substituted oxazolyl. In embodiments, $R^{36}$ is independently unsubstituted isoxazolyl. In embodiments, $R^{36}$ is independently substituted isoxazolyl. In embodiments, $R^{36}$ is independently unsubstituted thiazolyl. In embodiments, $R^{36}$ is independently substituted thiazolyl. In embodiments, $R^{36}$ is independently unsubstituted triazolyl. In embodiments, $R^{36}$ is independently substituted triazolyl. In embodiments, $R^{36}$ is independently unsubstituted pyridyl. In embodiments, $R^{36}$ is independently substituted pyridyl. In embodiments, $R^{36}$ is independently unsubstituted phenyl. In embodiments, $R^{36}$ is independently substituted phenyl.

$R^3$ may independently be —C(O)$R^{17}$. In embodiments, $R^{17}$ is independently substituted or unsubstituted 5 to 6 membered heteroaryl. In embodiments, $R^{17}$ is independently substituted 5 to 6 membered heteroaryl. In embodiments, $R^{17}$ is independently unsubstituted 5 to 6 membered heteroaryl. In embodiments, $R^{17}$ is independently substituted or unsubstituted 5 membered heteroaryl. In embodiments, $R^{17}$ is independently substituted 5 membered heteroaryl. In embodiments, $R^{17}$ is independently unsubstituted 5 membered heteroaryl. In embodiments, $R^{17}$ is independently substituted or unsubstituted thienyl. In embodiments, $R^{17}$ is independently substituted thienyl. In embodiments, $R^{17}$ is independently unsubstituted thienyl. In embodiments, $R^{17}$ is independently substituted or unsubstituted heteroaryl. In embodiments, $R^7$ is independently substituted or unsubstituted 5 to 6 membered heteroaryl. In embodiments, $R^{17}$ is independently unsubstituted 5 to 6 membered heteroaryl. In embodiments, $R^{17}$ is independently substituted 5 to 6 membered heteroaryl. In embodiments, $R^{17}$ is independently $R^{17A}$-substituted 5 to 6 membered heteroaryl. In embodiments, $R^{17}$ is independently substituted or unsubstituted pyrrolyl. In embodiments, $R^7$ is independently unsubstituted pyrrolyl. In embodiments, $R^{17}$ is independently substituted pyrrolyl. In embodiments, $R^{17}$ is independently $R^{17A}$-substituted pyrrolyl. In embodiments, $R^{17}$ is independently substituted or unsubstituted thienyl. In embodiments, $R^{17}$ is independently unsubstituted thienyl. In embodiments, $R^{17}$ is independently substituted thienyl. In embodiments, $R^{17}$ is independently $R^{17A}$-substituted thienyl. In embodiments, $R^{17}$ is independently substituted or unsubstituted furanyl. In embodiments, $R^{17}$ is independently unsubstituted furanyl. In embodiments, $R^{17}$ is independently substituted furanyl. In embodiments, $R^{17}$ is independently $R^{17A}$-substituted furanyl. In embodiments, $R^{17}$ is independently substituted or unsubstituted pyrazolyl. In embodiments, $R^{17}$ is independently unsubstituted pyrazolyl. In embodiments, $R^{17}$ is independently substituted pyrazolyl. In embodiments, $R^{17}$ is independently $R^{17A}$-substituted pyrazolyl. In embodiments, $R^{17}$ is independently unsubstituted pyridyl. In embodiments, $R^{17}$ is independently substituted pyridyl. In embodiments, $R^{17}$ is independently $R^{17A}$-substituted pyridyl. In embodiments, $R^{17}$ is independently unsubstituted phenyl. In embodiments, $R^{17}$ is independently substituted phenyl. In embodiments, $R^{17}$ is independently $R^{17A}$-substituted phenyl. In embodiments, $R^{17}$ is independently unsubstituted imidazolyl. In embodiments, $R^{17}$ is independently substituted imidazolyl. In embodiments, $R^{17}$ is independently $R^{17A}$-substituted imidazolyl. In embodiments, $R^{17}$ is independently unsubstituted oxazolyl. In embodiments, $R^{17}$ is independently substituted oxazolyl. In embodiments, $R^{17}$ is independently $R^{17A}$-substituted oxazolyl. In embodiments, $R^{17}$ is independently unsubstituted isoxazolyl. In embodiments, $R^{17}$ is independently substituted isoxazolyl. In embodiments, $R^{17}$ is independently $R^{17A}$-substituted isoxazolyl. In embodiments, $R^{17}$ is independently unsubstituted thiazolyl. In embodiments, $R^{17}$ is independently substituted thiazolyl. In embodiments, $R^{17}$ is independently $R^{17A}$-substituted thiazolyl. In embodiments, $R^{17}$ is independently unsubstituted triazolyl. In embodiments, $R^{17}$ is independently substituted triazolyl. In embodiments, $R^{17}$ is independently $R^{17A}$-substituted triazolyl. In embodiments, $R^{17}$ is independently unsubstituted pyridyl. In embodiments, $R^{17}$ is independently substituted pyridyl. In embodiments, $R^{17}$ is independently $R^{17A}$-substituted pyridyl. In embodiments, $R^{17}$ is independently unsubstituted phenyl. In embodiments, $R^{17}$ is independently substituted phenyl. In embodiments, $R^{17}$ is independently $R^{17A}$-substituted phenyl. In embodiments, $R^{17}$ is independently hydrogen.

$R^3$ may independently be —$SO_2NR^{15}R^{16}$. In embodiments, $R^{15}$ is independently substituted propyl. In embodiments, $R^{15}$ is independently substituted butyl. In embodiments, $R^{15}$ is independently substituted pentyl. In embodiments, $R^{15}$ is independently substituted tert-butyl. In embodiments, $R^{15}$ is independently substituted isopropyl. In embodiments, $R^{15}$ is independently substituted isopentyl. In embodiments, $R^{15}$ is independently substituted iso-butyl. In embodiments, $R^{15}$ is independently substituted n-butyl. In embodiments, $R^{15}$ is independently substituted n-propyl. In embodiments, $R^{15}$ is independently substituted n-pentyl. In embodiments, $R^{15}$ is independently substituted ethyl. In embodiments, $R^{15}$ is independently substituted methyl. In embodiments, $R^{15}$ is independently hydrogen. In embodiments, $R^{15}$ is independently unsubstituted propyl. In embodiments, $R^{15}$ is independently unsubstituted butyl. In embodiments, $R^{15}$ is independently unsubstituted pentyl. In embodiments, $R^{15}$ is independently unsubstituted tert-butyl. In embodiments, $R^{15}$ is independently unsubstituted isopropyl. In embodiments, $R^{15}$ is independently unsubstituted isopentyl. In embodiments, $R^{15}$ is independently unsubstituted iso-butyl. In embodiments, $R^{15}$ is independently unsubstituted n-butyl. In embodiments, $R^{15}$ is independently unsubstituted n-propyl. In embodiments, $R^{15}$ is independently unsubstituted n-pentyl. In embodiments, $R^{15}$ is independently unsubstituted ethyl. In embodiments, $R^{15}$ is independently unsubstituted methyl. In embodiments, $R^{15}$ is independently substituted $C_1$-$C_6$ alkyl. In embodiments, $R^{15}$ is independently unsubstituted $C_1$-$C_6$ alkyl. In embodiments, $R^{15}$ is independently substituted $C_1$-$C_4$ alkyl. In embodiments, $R^{15}$ is independently unsubstituted $C_1$-$C_4$ alkyl. In embodiments, $R^{15}$ is independently substituted $C_1$-$C_8$ alkyl. In embodiments, $R^{15}$ is independently unsubstituted $C_1$-$C_8$ alkyl. In embodiments, $R^{15}$ is independently substituted heteroalkyl. In embodiments, $R^{15}$ is independently unsubstituted heteroalkyl. In embodiments, $R^{15}$ is independently substituted 2 to 8 membered heteroalkyl. In embodiments, $R^{15}$ is independently unsubstituted 2 to 8 membered heteroalkyl. In embodiments, $R^{15}$ is independently substituted 2 to 6 membered heteroalkyl. In embodiments, $R^{15}$ is independently unsubstituted 2 to 6 membered heteroalkyl. In embodiments, $R^{15}$ is independently substituted 2 to 4 membered heteroalkyl. In embodiments, $R^{15}$ is independently unsubstituted 2 to 4 membered heteroalkyl. In embodiments, $R^{16}$ is independently substituted propyl. In embodiments, $R^{16}$ is independently substituted butyl. In embodiments, $R^{16}$ is independently substituted pentyl. In embodiments, $R^{16}$ is independently substituted tert-butyl. In embodiments, $R^{16}$ is independently substituted isopropyl. In embodiments, $R^{16}$ is independently substituted isopentyl. In embodiments, $R^{16}$ is independently substituted iso-butyl. In embodiments, $R^{16}$ is independently substituted n-butyl. In embodiments, $R^{16}$ is independently substituted n-propyl. In embodiments, $R^{16}$ is independently substituted n-pentyl. In embodiments, $R^{16}$ is independently substituted ethyl. In embodiments, $R^{16}$ is independently substituted methyl. In embodiments, $R^{16}$ is independently hydrogen. In embodiments, $R^{16}$ is independently unsubstituted propyl. In embodiments, $R^{16}$ is independently unsubstituted butyl. In embodiments, $R^{16}$ is independently unsubstituted pentyl. In embodiments, $R^{16}$ is independently unsubstituted tert-butyl. In embodiments, $R^{16}$ is independently unsubstituted isopropyl. In embodiments, $R^{16}$ is independently unsubstituted isopentyl. In embodiments, $R^{16}$ is independently unsubstituted iso-butyl. In embodiments, $R^{16}$ is independently unsubstituted n-butyl. In embodiments, $R^{16}$ is independently unsubstituted n-propyl. In embodiments, $R^{16}$ is independently unsubstituted n-pentyl. In embodiments, $R^{16}$ is independently unsubstituted ethyl. In embodiments, $R^{16}$ is independently unsubstituted methyl. In embodiments, $R^{16}$ is independently substituted $C_1$-$C_6$ alkyl. In embodiments, $R^{16}$ is independently unsubstituted $C_1$-$C_6$ alkyl. In embodiments, $R^{16}$ is independently substituted $C_1$-$C_4$ alkyl. In embodiments, $R^{16}$ is independently unsubstituted $C_1$-$C_4$ alkyl. In embodiments, $R^{16}$ is independently substituted $C_1$-$C_8$ alkyl. In embodiments, $R^{16}$ is independently unsubstituted $C_1$-$C_8$ alkyl. In embodiments, $R^{16}$ is independently substituted heteroalkyl. In embodiments, $R^{16}$ is independently unsubstituted heteroalkyl. In embodiments, $R^{16}$ is independently substituted 2 to 8 membered heteroalkyl. In embodiments, $R^{16}$ is independently unsubstituted 2 to 8 membered heteroalkyl. In embodiments, $R^{16}$ is independently substituted 2 to 6 membered heteroalkyl. In embodiments, $R^{16}$ is independently unsubstituted 2 to 6 membered heteroalkyl. In embodiments, $R^{16}$ is independently substituted 2 to 4 membered heteroalkyl. In embodiments, $R^{16}$ is independently unsubstituted 2 to 4 membered heteroalkyl.

$R^3$ may independently be —$SO_2R^{18}$. In embodiments, $R^{18}$ is independently substituted propyl. In embodiments, $R^{18}$ is independently substituted butyl. In embodiments, $R^{18}$ is independently substituted pentyl. In embodiments, $R^{18}$ is independently substituted tert-butyl. In embodiments, $R^{18}$ is independently substituted isopropyl. In embodiments, $R^{18}$ is independently substituted isopentyl. In embodiments, $R^{18}$ is independently substituted iso-butyl. In embodiments, $R^{18}$ is independently substituted n-butyl. In embodiments, $R^{18}$ is independently substituted n-propyl. In embodiments, $R^{18}$ is independently substituted n-pentyl. In embodiments, $R^{18}$ is independently substituted ethyl. In embodiments, $R^{18}$ is independently substituted methyl. In embodiments, $R^{18}$ is independently hydrogen. In embodiments, $R^{18}$ is independently unsubstituted propyl. In embodiments, $R^{18}$ is independently unsubstituted butyl. In embodiments, $R^{18}$ is independently unsubstituted pentyl. In embodiments, $R^{18}$ is independently unsubstituted tert-butyl. In embodiments, $R^{18}$ is independently unsubstituted isopropyl. In embodiments, $R^{18}$ is independently unsubstituted isopentyl. In embodiments, $R^{18}$ is independently unsubstituted iso-butyl. In embodiments, $R^{18}$ is independently unsubstituted n-butyl. In embodiments, $R^{18}$ is independently unsubstituted n-propyl. In embodiments, $R^{18}$ is independently unsubstituted n-pentyl. In embodiments, $R^{18}$ is independently unsubstituted ethyl. In embodiments, $R^{18}$ is independently unsubstituted methyl. In embodiments, $R^{18}$ is independently substituted $C_1$-$C_6$ alkyl. In embodiments, $R^{18}$ is independently unsubstituted $C_1$-$C_6$ alkyl. In embodiments, $R^{18}$ is independently substituted $C_1$-$C_4$ alkyl. In embodiments, $R^{18}$ is independently unsubstituted $C_1$-$C_4$ alkyl. In embodiments, $R^{18}$ is independently substituted $C_1$-$C_8$ alkyl. In embodiments, $R^{18}$ is independently unsubstituted $C_1$-$C_8$ alkyl. In embodiments, $R^{18}$ is independently substituted heteroalkyl. In embodiments, $R^{18}$ is independently unsubstituted heteroalkyl. In embodiments, $R^{18}$ is independently substituted 2 to 8 membered heteroalkyl. In embodiments, $R^{18}$ is independently unsubstituted 2 to 8 membered heteroalkyl. In embodiments, $R^{18}$ is independently substituted 2 to 6 membered heteroalkyl. In embodiments, $R^{18}$ is independently unsubstituted 2 to 6 membered heteroalkyl. In embodiments, $R^{18}$ is independently substituted 2 to 4 membered heteroalkyl. In embodiments, $R^{18}$ is independently unsubstituted 2 to 4 membered heteroalkyl.

In embodiments, $R^4$ is independently halogen, —$CX^4_3$, —$CHX^4_2$, —$CH_2X^4$, —$OCX^4_3$, —$OCH_2X^4$, —$OCHX^4_2$, —CN, —$SO_{n4}R^{22}$, —$SO_{v4}NR^{19}R^{20}$, —$NHNR^{19}R^{20}$, —$ONR^{19}R^{20}$, —NHC=(O)$NHNR^{19}R^{20}$, —NHC=(O)$NR^{19}R^{20}$, —NHC=($NR^{21}$)$NR^{19}R^{20}$, —$N(O)_{m4}$, —$NR^{19}R^{20}$, —C(O)$R^{21}$, —C(O)$OR^{21}$, —C(O)$NR^{19}R^{20}$, —$OR^{22}$, —$NR^{19}SO_2R^{22}$, —$NR^{19}$C=(O)$R^{21}$, —$NR^{19}$C(O)$OR^{21}$, —$NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is independently halogen. In embodiments, $R^4$ is independently —$CX^4_3$. In embodiments, $R^4$ is independently —$CHX^4_2$. In embodiments, $R^4$ is independently —$CH_2X^4$. In embodiments, $R^4$ is independently —$OCX^4_3$. In embodiments, $R^4$ is independently —$OCH_2X^4$. In embodiments, $R^4$ is independently —$OCHX^4_2$. In embodiments, $R^4$ is independently —CN. In embodiments, $R^4$ is independently —$SO_{n4}R^{22}$. In embodiments, $R^4$ is independently —$SO_{v4}NR^{19}R^{20}$. In embodiments, $R^4$ is independently —$NHNR^{19}R^{20}$. In embodiments, $R^4$ is independently —$ONR^{19}R^{20}$. In embodiments, $R^4$ is independently —NHC=(O)$NHNR^{19}R^{20}$. In embodiments, $R^4$ is independently —NHC=(O)$NR^{19}R^{20}$. In embodiments, $R^4$ is independently —NHC=($NR^{21}$)$NR^{19}R^{20}$. In embodiments, $R^4$ is independently —$N(O)_{m4}$. In embodiments, $R^4$ is independently —$NR^{19}R^{20}$. In embodiments, $R^4$ is independently —C(O)$R^{21}$. In embodiments, $R^4$ is independently —C(O)$OR^{21}$. In embodiments, $R^4$ is independently —C(O)$NR^{19}R^{20}$. In embodiments, $R^4$ is independently —$OR^{22}$. In embodiments, $R^4$ is independently —$NR^{19}SO_2R^{22}$. In embodiments, $R^4$ is independently —$NR^{19}$C=(O)$R^{21}$. In embodiments, $R^4$ is independently —$NR^{19}$C(O)$OR^{21}$. In embodiments, $R^4$ is independently —$NR^{19}OR^{21}$. In embodiments, $R^4$ is independently —SH. In embodiments, $R^4$ is independently —$SO_2CH_3$. In embodiments, $R^4$ is independently —$SO_2NH_2$. In embodiments, $R^4$ is independently —$N(O)_2$. In embodiments, $R^4$ is independently —$NH_2$. In embodiments, $R^4$ is independently —C(O)$CH_3$. In embodiments, $R^4$ is independently —C(O)OH. In embodiments, $R^4$ is independently —C(O)$NH_2$. In embodiments, $R^4$ is independently —OH. In embodiments, $R^4$ is independently a hydrogen. In embodiments, $R^4$ is independently a hydrogen, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(NH)$NH_2$, —NHC=(O) $NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is independently a halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(NH)$NH_2$, —NHC═(O) $NH_2$, —$NHSO_2H$, —NHC═(O)H, —NHC (O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is independently a halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$NHNH_2$, —NHC═(NH)$NH_2$, —NHC(O)$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently —$CF_3$, —CN, —OH, —$NH_2$, —COOH, —$CONH_2$, —$NO_2$, —SH, —$NHNH_2$, —NHC═(NH)$NH_2$, —NHC(O)$NH_2$, —$OCF_3$, substituted or unsubstituted $C_1$-$C_4$ alkyl or substituted or unsubstituted 2 to 4 membered heteroalkyl. In embodiments, $R^4$ is independently —$CF_3$, —CN, —OH, —$NH_2$, —COOH, —$CONH_2$, —$NO_2$, —SH, —$NHNH_2$, —NHC═(NH)$NH_2$, —NHC(O)$NH_2$, —$OCF_3$, unsubstituted isopropyl, unsubstituted isobutyl, unsubstituted tert-butyl, unsubstituted propoxy, or unsubstituted butoxy. In embodiments, $R^4$ is independently unsubstituted isopropyl or unsubstituted tert-butyl. In embodiments, $R^4$ is independently unsubstituted isopropyl. In embodiments, $R^4$ is independently unsubstituted tert-butyl. In embodiments, $R^4$ is independently unsubstituted isobutyl. In embodiments, $R^4$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently substituted or unsubstituted $C_1$-$C_6$ alkyl or substituted or unsubstituted 2 to 6 membered heteroalkyl. In embodiments, $R^4$ is independently substituted or unsubstituted $C_1$-$C_5$ alkyl, substituted or unsubstituted 2 to 5 membered alkoxy. In embodiments, $R^4$ is independently halogen, —$CF_3$, —CN, —OH, —$NH_2$, —COOH, —$CONH_2$, —$NO_2$, —SH, or —$OCH_3$. In embodiments, $R^4$ is independently —OH, —$NH_2$, —COOH, —$CONH_2$, —SH, or —$OCH_3$. In embodiments, $R^4$ is independently —OH, —$NH_2$, or —COOH. In embodiments, $R^4$ is independently independently —OH. In embodiments, $R^4$ is independently halogen. In embodiments, $R^4$ is independently, —$CF_3$. In embodiments, $R^4$ is independently —CN. In embodiments, $R^4$ is independently —OH. In embodiments, $R^4$ is independently —$NH_2$. In embodiments, $R^4$ is independently —COOH. In embodiments, $R^4$ is independently —$CONH_2$. In embodiments, $R^4$ is independently —$NO_2$. In embodiments, $R^4$ is independently —SH. In embodiments, $R^4$ is independently —$OCH_3$. In embodiments, $R^4$ is independently —NHC═(NH)$NH_2$. In embodiments, $R^4$ is independently a hydrogen. In embodiments, $R^4$ is independently —$CX^4_3$. In embodiments, $R^4$ is independently —$CHX^4_2$. In embodiments, $R^4$ is independently —$CH_2X^4$. In embodiments, $R^4$ is independently —$OCX^4_3$. In embodiments, $R^4$ is independently —$OCH_2X^4$. In embodiments, $R^4$ is independently —$OCHX^4_2$.

$R^4$ may independently be substituted or unsubstituted cycloalkyl, substituted or unsubstituted heterocycloalkyl, substituted or unsubstituted aryl, or substituted or unsubstituted heteroaryl. $R^4$ may independently be substituted or unsubstituted aryl or substituted or unsubstituted heteroaryl. $R^4$ may independently be unsubstituted cycloalkyl, unsubstituted heterocycloalkyl, unsubstituted aryl, or unsubstituted heteroaryl. $R^4$ may independently be substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. $R^4$ may independently be unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. $R^4$ may independently be substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^4$ may independently be unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $R^4$ may independently be substituted or unsubstituted 5 to 6 membered heteroaryl. $R^4$ may independently be unsubstituted 5 to 6 membered heteroaryl. $R^4$ may independently be substituted or unsubstituted 5 membered heteroaryl. $R^4$ may independently be substituted or unsubstituted 6 membered heteroaryl. $R^4$ may independently be 5 to 6 membered heteroaryl substituted with halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^4$ may independently be 5 to 6 membered heteroaryl substituted with halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC (O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^4$ may independently be substituted or unsubstituted thienyl. $R^4$ may independently be thienyl substituted with halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^4$ may independently be thienyl substituted with halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O) $NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^4$ may independently be unsubstituted thienyl. In embodiments, $R^4$ is independently —OH, —$NH_2$, —COOH, —$CONH_2$, —SH, or —$OCH_3$. In embodiments, $R^4$ is independently —OH, —$NH_2$, or —COOH.

In embodiments, $R^4$ is independently —$OR^{22}$. In embodiments, $R^4$ is independently —$SR^{22}$. In embodiments, $R^{22}$ is independently hydrogen. $R^{22}$ may independently be hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{22}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{22}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^{22}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl $R^{22}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. $R^{22}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^{22}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $R^{22}$ may independently be unsubstituted $C_1$-$C_4$ alkyl. Each $R^{22}$ may independently be substituted $C_1$-$C_4$ alkyl. $R^{22}$ may independently be unsubstituted $C_1$-$C_3$ alkyl. $R^{22}$ may independently be substituted $C_1$-$C_4$ alkyl. $R^{22}$ may independently be unsubstituted methyl. $R^{22}$ may independently be unsubstituted ethyl.

$R^{22}$ may independently be substituted or unsubstituted benzyl. $R^{22}$ may independently be substituted benzyl. $R^{22}$ may independently be benzyl wherein the phenyl is substituted with one or more substituents independently selected from halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{22}$ may independently be benzyl wherein the phenyl is substituted with one or more substituents independently selected from halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, and substituted or unsubstituted 5 to 6 membered heteroaryl. $R^{22}$ may independently be benzyl wherein the phenyl is independently substituted with one halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O) $NHNH_2$, —NHC═(O) $NH_2$, —$NHSO_2H$, —NHC═(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^{22}$ may independently be methyl substituted with a substituted or unsubstituted phenyl or substituted or unsubstituted 5 to 6 membered heteroaryl. $R^{22}$ may independently be methyl substituted with a substituted or unsubstituted phenyl or substituted or unsubstituted 5 to 6 membered heteroaryl wherein the phenyl or heteroaryl is optionally substituted with halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O) $NHNH_2$, —NHC═(O) $NH_2$, —$NHSO_2H$, —NHC═(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl.

In embodiments, $R^4$ is independently —$NHR^{19}$. $R^{19}$ may independently be hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{19}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{19}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^{19}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl $R^{19}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. $R^{19}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^{19}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $R^{19}$ may independently be unsubstituted $C_1$-$C_4$ alkyl. Each $R^{19}$ may independently be substituted $C_1$-$C_4$ alkyl. $R^{19}$ may independently be unsubstituted $C_1$-$C_3$ alkyl. $R^{19}$ may independently be substituted $C_1$-$C_4$ alkyl. $R^{19}$ may independently be unsubstituted methyl. $R^{19}$ may independently be unsubstituted ethyl.

$R^{19}$ may independently be substituted or unsubstituted benzyl. $R^{19}$ may independently be substituted benzyl. $R^{19}$ may independently be benzyl wherein the phenyl is substituted with one or more substituents independently selected from halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{19}$ may independently be benzyl wherein the phenyl is substituted with one or more substituents independently selected from halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, and substituted or unsubstituted 5 to 6 membered heteroaryl. $R^{19}$ may independently be benzyl wherein the phenyl is independently substituted with one halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. $R^{19}$ may independently be methyl substituted with a substituted or unsubstituted phenyl or substituted or unsubstituted 5 to 6 membered heteroaryl. $R^{19}$ may independently be methyl substituted with a substituted or unsubstituted phenyl or substituted or unsubstituted 5 to 6 membered heteroaryl wherein the phenyl or heteroaryl is optionally substituted with halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl.

In embodiments, each $R^7$, $R^8$, $R^9$, $R^{10}$, $R^1$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ is independently hydrogen. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ may independently be hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O) $NHNH_2$, —NHC═(O) $NH_2$, —$NHSO_2H$, —NHC═(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^7$, $R^8$, $R^9$, $R^{10}$, $R^{11}$, $R^{12}$, $R^{13}$, $R^{14}$, $R^5$, $R^{16}$, $R^{17}$, $R^{18}$, $R^{19}$, $R^{20}$, $R^{21}$, and/or $R^{22}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. Each $R^7$, $R^8$, $R^9$, $R^{10}$, $R^{11}$, $R^{12}$, $R^{13}$, $R^{14}$, $R^1$, $R^{16}$, $R^{17}$, $R^{18}$, $R^{19}$, $R^{20}$, $R^{21}$, and/or $R^{22}$ may independently be unsubstituted $C_1$-$C_4$ alkyl. Each $R^7$, $R^8$, $R^9$, $R^{10}$, $R^{11}$, $R^{12}$, $R^{13}$, $R^{14}$, $R^5$, $R^{16}$, $R^{17}$, $R^{18}$, $R^{19}$, $R^{20}$, $R^{21}$, and/or $R^{22}$ may independently be substituted $C_1$-$C_4$ alkyl. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and/or $R^{22}$ may independently be unsubstituted $C_1$-$C_3$ alkyl. Each $R^7$, $R^8$, $R^9$, $R^{10}$, $R^{11}$, $R^{12}$, $R^{13}$, $R^{14}$, $R^5$, $R^{16}$, $R^{17}$, $R^{18}$, $R^{19}$, $R^{20}$, $R^{21}$, and/or $R^{22}$ may independently be substituted $C_1$-$C_4$ alkyl. Each $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and/or $R^{22}$ may independently be unsubstituted methyl.

Each $R^7$, $R^8$, $R^9$, $R^{10}$, $R^1$, $R^{12}$, $R^{13}$, $R^{14}$, $R^1$, $R^{16}$, $R^1$, $R^{18}$, $R^{19}$, $R^{20}$, $R^{21}$, and/or $R^{22}$ may independently be unsubstituted ethyl.

In embodiments, $R^7$ and $R^8$ substituents bonded to the same nitrogen atom may optionally be joined to form a substituted or unsubstituted heterocycloalkyl or substituted or unsubstituted heteroaryl. Each $R^7$ and $R^8$ substituents bonded to the same nitrogen atom may be joined to form a substituted or unsubstituted 4 to 6 membered heterocycloalkyl or 5 to 6 membered heteroaryl. Each $R^7$ and $R^8$ substituents bonded to the same nitrogen atom may be joined to form an unsubstituted 4 to 6 membered heterocycloalkyl or unsubstituted 5 to 6 membered heteroaryl. In embodiments, $R^{11}$ and $R^{12}$ substituents bonded to the same nitrogen atom may optionally be joined to form a substituted or unsubstituted heterocycloalkyl or substituted or unsubstituted heteroaryl. Each $R^{11}$ and $R^{12}$ substituents bonded to the same nitrogen atom may be joined to form a substituted or unsubstituted 4 to 6 membered heterocycloalkyl or 5 to 6 membered heteroaryl. Each $R^{11}$ and $R^{12}$ substituents bonded to the same nitrogen atom may be joined to form an unsubstituted 4 to 6 membered heterocycloalkyl or unsubstituted 5 to 6 membered heteroaryl. In embodiments, $R^{15}$ and $R^{16}$ substituents bonded to the same nitrogen atom may optionally be joined to form a substituted or unsubstituted heterocycloalkyl or substituted or unsubstituted heteroaryl. Each $R^{15}$ and $R^{16}$ substituents bonded to the same nitrogen atom may be joined to form a substituted or unsubstituted 4 to 6 membered heterocycloalkyl or 5 to 6 membered heteroaryl. Each $R^{15}$ and $R^{16}$ substituents bonded to the same nitrogen atom may be joined to form an unsubstituted 4 to 6 membered heterocycloalkyl or unsubstituted 5 to 6 membered heteroaryl. In embodiments, $R^{19}$ and $R^{20}$ substituents bonded to the same nitrogen atom may optionally be joined to form a substituted or unsubstituted heterocycloalkyl or substituted or unsubstituted heteroaryl. Each $R^{19}$ and $R^{20}$ substituents bonded to the same nitrogen atom may be joined to form a substituted or unsubstituted 4 to 6 membered heterocycloalkyl or 5 to 6 membered heteroaryl. Each $R^{19}$ and $R^{20}$ substituents bonded to the same nitrogen atom may be joined to form an unsubstituted 4 to 6 membered heterocycloalkyl or unsubstituted 5 to 6 membered heteroaryl.

X may independently be —F. X may independently be —Cl. X may independently be —Br. X may independently be —I. $X^1$ may independently be —F. $X^1$ may independently be —Cl. $X^1$ may independently be —Br. $X^1$ may independently be —I. $X^2$ may independently be —F. $X^2$ may independently be —Cl. $X^2$ may independently be —Br. $X^2$ may independently be —I. $X^3$ may independently be —F. $X^3$ may independently be —Cl. $X^3$ may independently be —Br. $X^3$ may independently be —I. $X^4$ may independently be —F. $X^4$ may independently be —Cl. $X^4$ may independently be —Br. $X^4$ may independently be —I. n1 may independently be 0. n1 may independently be 1. n1 may independently be 2. n1 may independently be 3. n1 may independently be 4. n2 may independently be 0. n2 may independently be 1. n2 may independently be 2. n2 may independently be 3. n2 may independently be 4. n3 may independently be 0. n3 may independently be 1. n3 may independently be 2. n3 may independently be 3. n3 may independently be 4. n4 may independently be 0. n4 may independently be 1. n4 may independently be 2. n4 may independently be 3. n4 may independently be 4. v1 may independently be 1. v1 may independently be 2. v2 may independently be 1. v2 may independently be 2. v3 may independently be 1. v3 may independently be 2. v4 may independently be 1. v4 may independently be 2. m1 may independently be 1. m1 may independently be 2. m2 may independently be 1. m2 may independently be 2. m3 may independently be 1. m3 may independently be 2. m4 may independently be 1. m4 may independently be 2.

In embodiments, the compound has the formula (II)

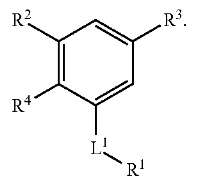

$R^1$, $R^2$, $R^3$, $R^4$, and $L^1$ are as described herein, including in embodiments.

In an aspect is provided a compound having the formula:

(IIa)

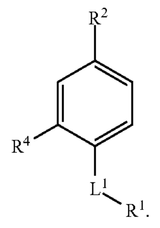

$R^1$, $R^2$, and $L^1$ are as described herein, including in embodiments. In embodiments, $L^1$-$R^1$ does not include a disulfide bond.

In an aspect is provided a compound having the formula:

(IIb)

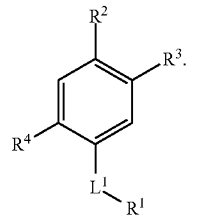

$R^1$, $R^2$, $R^3$, $R^4$, and $L^1$ are as described herein, including in embodiments. In embodiments, $L^1$-$R^1$ does not include a disulfide bond.

In an aspect is provided a compound having the formula:

(IIc)

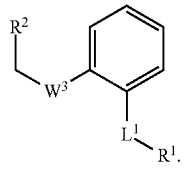

$R^1$, $R^2$, and $L^1$ are as described herein, including in embodiments. $W^3$ is O, NH, $CH_2$, or S. In embodiments, $W^3$ is O. In embodiments, $W^3$ is NH. In embodiments, $W^3$ is $CH_2$. In embodiments, $W^3$ is S. In embodiments, $L^1$-$R^1$ does not include a disulfide bond.

In an aspect is provided a compound having the formula:

(IId)

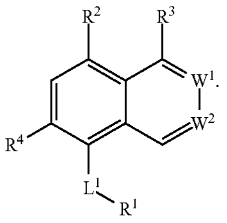

$W^1$, $W^2$, $R^1$, $R^2$, $R^3$, $R^4$, and $L^1$ are as described herein, including in embodiments. In embodiments, $L^1$-$R^1$ does not include a disulfide bond.

In an aspect is provided a compound having the formula:

(IIe)

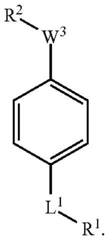

$W^3$, $R^1$, $R^2$, and $L^1$ are as described herein, including in embodiments. In embodiments, $L^1$-$R^1$ does not include a disulfide bond.

In an aspect is provided a compound having the formula:

(IIf)

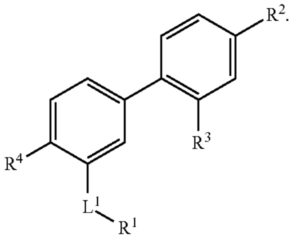

$R^2$, $R^3$, $R^4$, and $L^1$ are as described herein, including in embodiments. In embodiments, $L^1$-$R^1$ does not include a disulfide bond.

In an aspect is provided a compound having the formula:

(IIg)

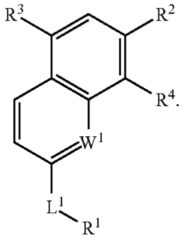

$W^1$, $R^1$, $R^2$, $R^3$, $R^4$, and $L^1$ are as described herein, including in embodiments. In embodiments, $L^1$-$R^1$ does not include a disulfide bond.

In embodiments, the compound has the formula:

(III)

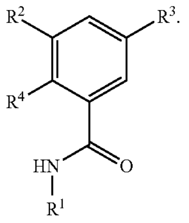

$R^1$, $R^2$, $R^3$, and $R^4$ are as described herein, including in embodiments. In embodiments, $R^1$ does not include a disulfide bond.

In embodiments, the compound has the formula:

(IIIa)

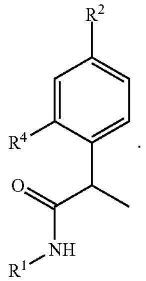

$R^1$, $R^2$, and $R^4$ are as described herein, including in embodiments. In embodiments, $R^1$ does not include a disulfide bond.

In embodiments, the compound has the formula:

(IIIaa)

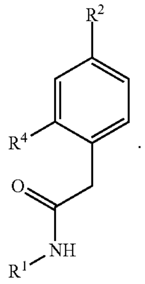

$R^1$, $R^2$, and $R^4$ are as described herein, including in embodiments. In embodiments, $R^1$ does not include a disulfide bond.

In embodiments, the compound has the formula:

(IIIb)

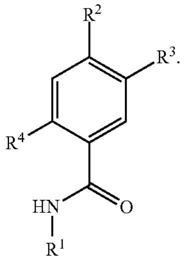

$R^1$, $R^2$, $R^3$, and $R^4$ are as described herein, including in embodiments. In embodiments, $R^1$ does not include a disulfide bond.

In embodiments, the compound has the formula:

(IIIc)

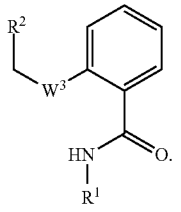

$W^3$, $R^1$, and $R^2$ are as described herein, including in embodiments. In embodiments, $R^1$ does not include a disulfide bond.

In embodiments, the compound has the formula:

(IIId)

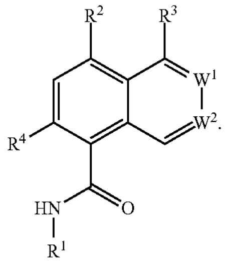

$W^1$, $W^2$, $R^1$, $R^2$, $R^3$, and $R^4$ are as described herein, including in embodiments. In embodiments, $R^1$ does not include a disulfide bond.

In embodiments, the compound has the formula:

(IIIe)

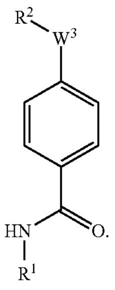

$W^3$, $R^1$, and $R^2$ are as described herein, including in embodiments. In embodiments, $R^1$ does not include a disulfide bond.

In embodiments, the compound has the formula:

(IIIf)

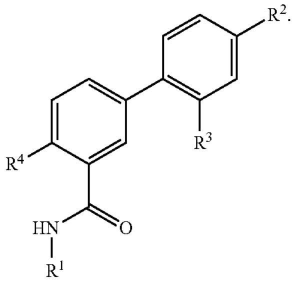

$R^1$, $R^2$, $R^3$, and $R^4$ are as described herein, including in embodiments. In embodiments, $R^1$ does not include a disulfide bond.

In embodiments, the compound has the formula:

(IIIg)

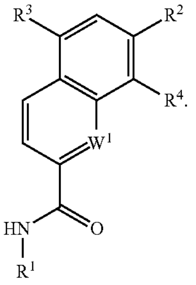

$W^1$, $R^1$, $R^2$, $R^3$, and $R^4$ are as described herein, including in embodiments. In embodiments, $R^1$ does not include a disulfide bond.

In embodiments, the compound has the formula:

(IIIh)

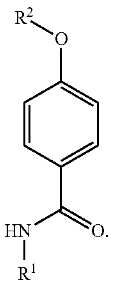

$R^1$ and $R^2$ are as described herein, including in embodiments. In embodiments, $R^1$ does not include a disulfide bond.

In embodiments, the compound has the formula:

(IIIi)

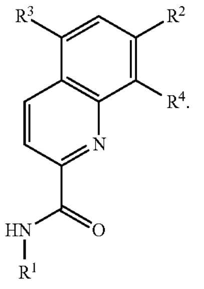

$R^1$, $R^2$, $R^3$, and $R^4$ are as described herein, including in embodiments. In embodiments, $R^1$ does not include a disulfide bond.

In embodiments, the compound has the formula:

(IIIj)

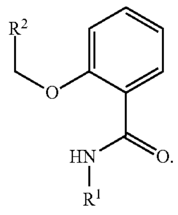

$R^1$ and $R^2$ are as described herein, including in embodiments. In embodiments, $R^1$ does not include a disulfide bond.

In embodiments, the compound has the formula:

(IIIk)

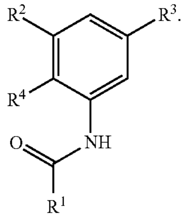

$R^1$, $R^2$, $R^3$, and $R^4$ are as described herein, including in embodiments. In embodiments, $R^1$ does not include a disulfide bond.

$R^1$ and $R^2$ are as described herein, including in embodiments.

In embodiments, the compound is

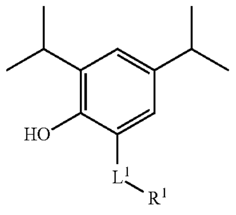

wherein $R^1$ and $L^1$ are as described herein, including in embodiments. In embodiments, the compound is

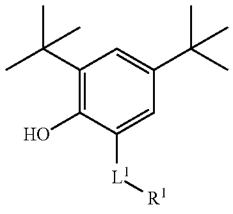

wherein $R^1$ and $L^1$ are as described herein, including in embodiments. In embodiments, the compound is

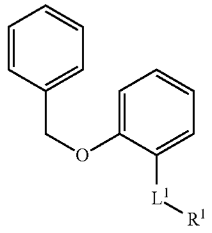

wherein $R^1$ and $L^1$ are as described herein, including in embodiments. In embodiments, the compound is

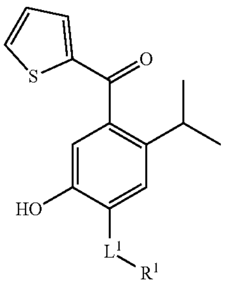

wherein $R^1$ and $L^1$ are as described herein, including in embodiments. In embodiments, the compound is

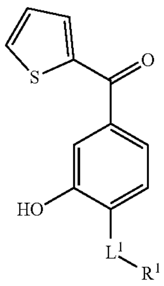

wherein $R^1$ and $L^1$ are as described herein, including in embodiments. In embodiments, the compound is

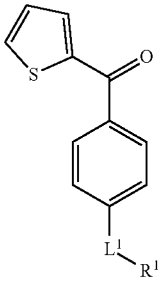

wherein $R^1$ and $L^1$ are as described herein, including in embodiments. In embodiments, the compound is

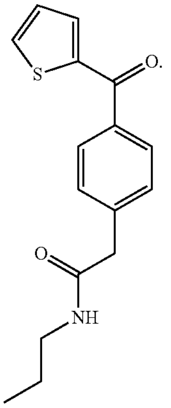 [SMILES: CCCNC(=O)Cc1ccc(C(=O)c2cccs2)cc1]

In embodiments, the compound is

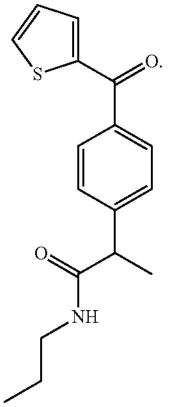 [SMILES: CCCNC(=O)C(C)c1ccc(C(=O)c2cccs2)cc1]

In embodiments, the compound is

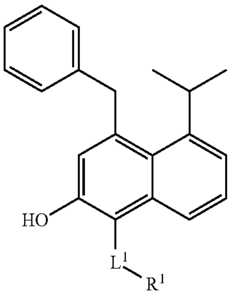

wherein $R^1$ and $L^1$ are as described herein, including in embodiments. In embodiments, the compound is

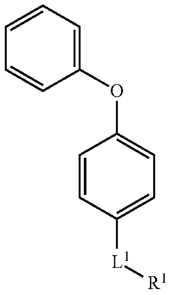

wherein $R^1$ and $L^1$ are as described herein, including in embodiments. In embodiments, the compound is

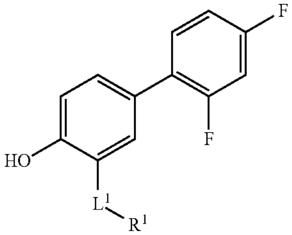

wherein $R^1$ and $L^1$ are as described herein, including in embodiments. In embodiments, the compound is

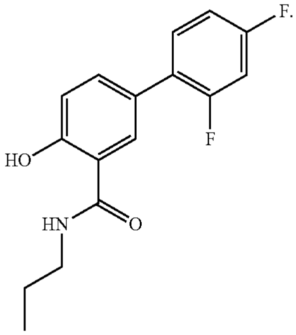 [SMILES: CCCNC(=O)c1cc(-c2ccc(F)cc2F)ccc1O]

In embodiments, the compound is

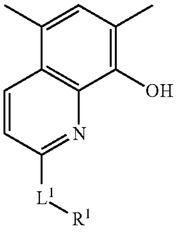

wherein $R^1$ and $L^1$ are as described herein, including in embodiments.

In embodiments, the compound has the formula:

(IV)

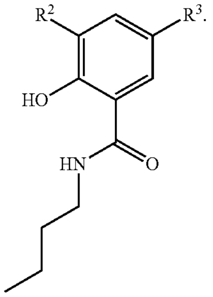

$R^2$ and $R^3$ are as described herein, including in embodiments. In embodiments, the compound has the formula:

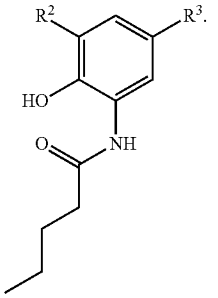

$R^2$ and $R^3$ are as described herein, including in embodiments. In embodiments, the compound has the formula:

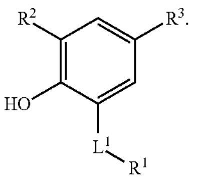

$L^1$, $R^1$, $R^2$, and $R^3$ are as described herein, including in embodiments.

In embodiments, $R^2$ is substituted or unsubstituted phenyl. In embodiments, $R^2$ is $R^{33}$-substituted phenyl. In embodiments, $R^{33}$ is independently halogen. In embodiments, $R^{33}$ is independently 4-halogen. In embodiments, $R^{33}$ is independently 4-Cl.

In embodiments, $R^2$ is substituted or unsubstituted heteroaryl. In embodiments, $R^2$ is substituted or unsubstituted 5 to 6 membered heteroaryl. In embodiments, $R^2$ is unsubstituted 5 to 6 membered heteroaryl. In embodiments, $R^2$ is substituted 5 to 6 membered heteroaryl. In embodiments, $R^2$ is $R^{33}$-substituted 5 to 6 membered heteroaryl. In embodiments, $R^2$ is substituted or unsubstituted pyrrolyl. In embodiments, $R^2$ is unsubstituted pyrrolyl. In embodiments, $R^2$ is substituted pyrrolyl. In embodiments, $R^2$ is $R^{33}$-substituted pyrrolyl. In embodiments, $R^2$ is substituted or unsubstituted thienyl. In embodiments, $R^2$ is unsubstituted thienyl. In embodiments, $R^2$ is substituted thienyl. In embodiments, $R^2$ is $R^{33}$-substituted thienyl. In embodiments, $R^2$ is substituted or unsubstituted furanyl. In embodiments, $R^2$ is unsubstituted furanyl. In embodiments, $R^2$ is substituted furanyl. In embodiments, $R^2$ is $R^{33}$-substituted furanyl. In embodiments, $R^2$ is substituted or unsubstituted pyrazolyl. In embodiments, $R^2$ is unsubstituted pyrazolyl. In embodiments, $R^2$ is substituted pyrazolyl. In embodiments, $R^2$ is $R^{33}$-substituted pyrazolyl.

In embodiments, $R^2$ is substituted or unsubstituted pyridyl. In embodiments, $R^2$ is unsubstituted pyridyl. In embodiments, $R^2$ is substituted or unsubstituted pyrid-2-yl. In embodiments, $R^2$ is substituted or unsubstituted pyrid-3-yl. In embodiments, $R^2$ is substituted or unsubstituted pyrid-4-yl. In embodiments, $R^2$ is substituted or unsubstituted pyridyl. In embodiments, $R^2$ is unsubstituted pyridin-2-yl. In embodiments, $R^2$ is unsubstituted pyridin-3-yl. In embodiments, $R^2$ is unsubstituted pyridin-4-yl. In embodiments, $R^2$ is unsubstituted pyridyl.

In embodiments, $R^2$ is substituted or unsubstituted $C_1$-$C_6$ alkyl. In embodiments, $R^2$ is substituted $C_1$-$C_6$ alkyl. In embodiments, $R^2$ is unsubstituted $C_1$-$C_6$ alkyl. In embodiments, $R^2$ is $R^{33}$-substituted $C_1$-$C_6$ alkyl. In embodiments, $R^2$ is substituted or unsubstituted $C_1$-$C_4$ alkyl. In embodiments, $R^2$ is substituted $C_1$-$C_4$ alkyl. In embodiments, $R^2$ is unsubstituted $C_1$-$C_4$ alkyl. In embodiments, $R^2$ is $R^{33}$-substituted $C_1$-$C_4$ alkyl. In embodiments, $R^2$ is substituted or unsubstituted $C_3$-$C_5$ alkyl. In embodiments, $R^2$ is substituted $C_3$-$C_5$ alkyl. In embodiments, $R^2$ is unsubstituted $C_3$-$C_5$ alkyl. In embodiments, $R^2$ is $R^{33}$-substituted $C_3$-$C_5$ alkyl. In embodiments, $R^2$ is substituted propyl. In embodiments, $R^2$ is substituted butyl. In embodiments, $R^2$ is substituted pentyl. In embodiments, $R^2$ is substituted tert-butyl. In embodiments, $R^2$ is substituted isopropyl. In embodiments, $R^2$ is substituted isopentyl. In embodiments, $R^2$ is substituted iso-butyl. In embodiments, $R^2$ is substituted n-butyl. In embodiments, $R^2$ is substituted n-propyl. In embodiments, $R^2$ is substituted n-pentyl. In embodiments, $R^2$ is substituted ethyl. In embodiments, $R^2$ is substituted methyl. In embodiments, $R^2$ is $R^{33}$-substituted propyl. In embodiments, $R^2$ is $R^{33}$-substituted butyl. In embodiments, $R^2$ is $R^{33}$-substituted pentyl. In embodiments, $R^2$ is $R^{33}$-substituted tert-butyl. In embodiments, $R^2$ is $R^{33}$-substituted isopropyl. In embodiments, $R^2$ is $R^{33}$-substituted isopentyl. In embodiments, $R^2$ is $R^{33}$-substituted iso-butyl. In embodiments, $R^2$ is $R^{33}$-substituted n-butyl. In embodiments, $R^2$ is $R^{33}$-substituted n-propyl. In embodiments, $R^2$ is $R^{33}$-substituted n-pentyl. In embodiments, $R^2$ is $R^{33}$-substituted ethyl. In embodiments, $R^2$ is $R^{33}$-substituted methyl. In embodiments, $R^2$ is unsubstituted propyl. In embodiments, $R^2$ is unsubstituted butyl. In embodiments, $R^2$ is unsubstituted pentyl. In embodiments, $R^2$ is unsubstituted tert-butyl. In embodiments, $R^2$ is unsubstituted isopropyl. In embodiments, $R^2$ is unsubstituted isopentyl. In embodiments, $R^2$ is unsubstituted iso-butyl. In embodiments, $R^2$ is unsubstituted n-butyl. In embodiments, $R^2$ is unsubstituted n-propyl. In embodiments, $R^2$ is unsubstituted n-pentyl. In embodiments, $R^2$ is unsubstituted ethyl. In embodiments, $R^2$ is unsubstituted methyl.

In embodiments, $R^{33}$ is independently halogen. In embodiments, $R^{33}$ is independently —F. In embodiments, $R^{33}$ is independently —Cl. In embodiments, $R^{33}$ is independently —I. In embodiments, $R^{33}$ is independently —Br. In embodiments, $R^{33}$ is independently 4-halogen. In embodiments, $R^{33}$ is independently 4-Cl. In embodiments, $R^{33}$ is substituted or unsubstituted 5 to 6 membered heteroaryl. In embodiments, $R^{33}$ is substituted 5 to 6 membered heteroaryl. In embodiments, $R^{33}$ is unsubstituted 5 to 6 membered heteroaryl. In embodiments, $R^{33}$ is substituted or unsubstituted 5 membered heteroaryl. In embodiments, $R^{33}$ is substituted 5 membered heteroaryl. In embodiments, $R^{33}$ is unsubstituted 5 membered heteroaryl. In embodiments, $R^{33}$ is substituted or unsubstituted thienyl. In embodiments, $R^{33}$ is substituted thienyl. In embodiments, $R^{33}$ is unsubstituted thienyl. In embodiments, $R^{33}$ is —$CF_3$. In embodiments, $R^{33}$ is —$CCl_3$. In embodiments, $R^{33}$ is —$CBr_3$. In embodiments, $R^{33}$ is —$CI_3$. In embodiments, $R^{33}$ is unsubstituted methyl. In embodiments, $R^{33}$ is unsubstituted ethyl. In embodiments, $R^{33}$ is unsubstituted propyl. In embodiments, $R^{33}$ is unsubstituted isopropyl.

$R^2$ may independently be —$C(O)R^{13}$. In embodiments, $R^{13}$ is substituted or unsubstituted 5 to 6 membered heteroaryl. In embodiments, $R^{13}$ is substituted 5 to 6 membered heteroaryl. In embodiments, $R^{13}$ is unsubstituted 5 to 6 membered heteroaryl. In embodiments, $R^{13}$ is substituted or unsubstituted 5 membered heteroaryl. In embodiments, $R^{13}$ is substituted 5 membered heteroaryl. In embodiments, $R^{13}$ is unsubstituted 5 membered heteroaryl. In embodiments, $R^{13}$ is substituted or unsubstituted thienyl. In embodiments, $R^{13}$ is substituted thienyl. In embodiments, $R^{13}$ is unsubstituted thienyl.

$R^2$ may independently be —$SO_2NR^{11}R^{12}$. In embodiments, $R^{11}$ is substituted propyl. In embodiments, $R^{11}$ is substituted butyl. In embodiments, $R^{11}$ is substituted pentyl. In embodiments, $R^{11}$ is substituted tert-butyl. In embodiments, $R^{11}$ is substituted isopropyl. In embodiments, $R^{11}$ is substituted isopentyl. In embodiments, $R^{11}$ is substituted iso-butyl. In embodiments, $R^{11}$ is substituted n-butyl. In embodiments, $R^{11}$ is substituted n-propyl. In embodiments, $R^{11}$ is substituted n-pentyl. In embodiments, $R^{11}$ is substituted ethyl. In embodiments, $R^{11}$ is substituted methyl. In embodiments, $R^{11}$ is hydrogen. In embodiments, $R^{11}$ is unsubstituted propyl. In embodiments, $R^{11}$ is unsubstituted butyl. In embodiments, $R^{11}$ is unsubstituted pentyl. In embodiments, $R^{11}$ is unsubstituted tert-butyl. In embodiments, $R^{11}$ is unsubstituted isopropyl. In embodiments, $R^{11}$ is unsubstituted isopentyl. In embodiments, $R^{11}$ is unsubstituted iso-butyl. In embodiments, $R^{11}$ is unsubstituted n-butyl. In embodiments, $R^{11}$ is unsubstituted n-propyl. In embodiments, $R^{11}$ is unsubstituted n-pentyl. In embodiments, $R^{11}$ is unsubstituted ethyl. In embodiments, $R^{11}$ is unsubstituted methyl. In embodiments, $R^{11}$ is substituted $C_1$-$C_6$ alkyl. In embodiments, $R^{11}$ is unsubstituted $C_1$-$C_6$ alkyl. In embodiments, $R^{11}$ is substituted $C_1$-$C_4$ alkyl. In embodiments, $R^{11}$ is unsubstituted $C_1$-$C_4$ alkyl. In embodiments, $R^{11}$ is substituted $C_1$-$C_8$ alkyl. In embodiments, $R^{11}$ is unsubstituted $C_1$-$C_8$ alkyl. In embodiments, $R^{11}$ is substituted heteroalkyl. In embodiments, $R^{11}$ is unsubstituted heteroalkyl. In embodiments, $R^{11}$ is substituted 2 to 8 membered heteroalkyl. In embodiments, $R^{11}$ is unsubstituted 2 to 8 membered heteroalkyl. In embodiments, $R^{11}$ is substituted 2 to 6 membered heteroalkyl. In embodiments, $R^{11}$ is unsubstituted 2 to 6 membered heteroalkyl. In embodiments, $R^{11}$ is substituted 2 to 4 membered heteroalkyl. In embodiments, $R^{11}$ is unsubstituted 2 to 4 membered heteroalkyl. In embodiments, $R^{12}$ is substituted propyl. In embodiments, $R^{12}$ is substituted butyl. In embodiments, $R^{12}$ is substituted pentyl. In embodiments, $R^{12}$ is substituted tert-butyl. In embodiments, $R^{12}$ is substituted isopropyl. In embodiments, $R^{12}$ is substituted isopentyl. In embodiments, $R^{12}$ is substituted iso-butyl. In embodiments, $R^{12}$ is substituted n-butyl. In embodiments, $R^{12}$ is substituted n-propyl. In embodiments, $R^{12}$ is substituted n-pentyl. In embodiments, $R^{12}$ is substituted ethyl. In embodiments, $R^{12}$ is substituted methyl. In embodiments, $R^{12}$ is hydrogen. In embodiments, $R^{12}$ is unsubstituted propyl. In embodiments, $R^{12}$ is unsubstituted butyl. In embodiments, $R^{12}$ is unsubstituted pentyl. In embodiments, $R^{12}$ is unsubstituted tert-butyl. In embodiments, $R^{12}$ is unsubstituted isopropyl. In embodiments, $R^{12}$ is unsubstituted isopentyl. In embodiments, $R^{12}$ is unsubstituted iso-butyl. In embodiments, $R^{12}$ is unsubstituted n-butyl. In embodiments, $R^{12}$ is unsubstituted n-propyl. In embodiments, $R^{12}$ is unsubstituted n-pentyl. In embodiments, $R^{12}$ is unsubstituted ethyl. In embodiments, $R^{12}$ is unsubstituted methyl. In embodiments, $R^{12}$ is substituted $C_1$-$C_6$ alkyl. In embodiments, $R^{12}$ is unsubstituted $C_1$-$C_6$ alkyl. In embodiments, $R^{12}$ is substituted $C_1$-$C_4$ alkyl. In embodiments, $R^{12}$ is unsubstituted $C_1$-$C_4$ alkyl. In embodiments, $R^{12}$ is substituted $C_1$-$C_8$ alkyl. In embodiments, $R^{12}$ is unsubstituted $C_1$-$C_8$ alkyl. In embodiments, $R^{12}$ is substituted heteroalkyl. In embodiments, $R^{12}$ is unsubstituted heteroalkyl. In embodiments, $R^{12}$ is substituted 2 to 8 membered heteroalkyl. In embodiments, $R^{12}$ is unsubstituted 2 to 8 membered heteroalkyl. In embodiments, $R^{12}$ is substituted 2 to 6 membered heteroalkyl. In embodiments, $R^{12}$ is unsubstituted 2 to 6 membered heteroalkyl. In embodiments, $R^{12}$ is substituted 2 to 4 membered heteroalkyl. In embodiments, $R^{12}$ is unsubstituted 2 to 4 membered heteroalkyl.

$R^2$ may independently be —$SO_2R^{14}$. In embodiments, $R^{14}$ is substituted propyl. In embodiments, $R^{14}$ is substituted butyl. In embodiments, $R^{14}$ is substituted pentyl. In embodiments, $R^{14}$ is substituted tert-butyl. In embodiments, $R^{14}$ is substituted isopropyl. In embodiments, $R^{14}$ is substituted isopentyl. In embodiments, $R^{14}$ is substituted iso-butyl. In embodiments, $R^{14}$ is substituted n-butyl. In embodiments, $R^{14}$ is substituted n-propyl. In embodiments, $R^{14}$ is substituted n-pentyl. In embodiments, $R^{14}$ is substituted ethyl. In embodiments, $R^{14}$ is substituted methyl. In embodiments, $R^{14}$ is hydrogen. In embodiments, $R^{14}$ is unsubstituted propyl. In embodiments, $R^{14}$ is unsubstituted butyl. In embodiments, $R^{14}$ is unsubstituted pentyl. In embodiments, $R^{14}$ is unsubstituted tert-butyl. In embodiments, $R^{14}$ is unsubstituted isopropyl. In embodiments, $R^{14}$ is unsubstituted isopentyl. In embodiments, $R^{14}$ is unsubstituted iso-butyl. In embodiments, $R^{14}$ is unsubstituted n-butyl. In embodiments, $R^{14}$ is unsubstituted n-propyl. In embodiments, $R^{14}$ is unsubstituted n-pentyl. In embodiments, $R^{14}$ is unsubstituted ethyl. In embodiments, $R^{14}$ is unsubstituted methyl. In embodiments, $R^{14}$ is substituted $C_1$-$C_6$ alkyl. In embodiments, $R^{14}$ is unsubstituted $C_1$-$C_6$ alkyl. In embodiments, $R^{14}$ is substituted $C_1$-$C_4$ alkyl. In embodiments, $R^{14}$ is unsubstituted $C_1$-$C_4$ alkyl. In embodiments, $R^{14}$ is substituted $C_1$-$C_8$ alkyl. In embodiments, $R^{14}$ is unsubstituted $C_1$-$C_8$ alkyl. In embodiments, $R^{14}$ is substituted heteroalkyl. In embodiments, $R^{14}$ is unsubstituted heteroalkyl. In embodiments, $R^{14}$ is substituted 2 to 8 membered heteroalkyl. In embodiments, $R^{14}$ is unsubstituted 2 to 8 membered heteroalkyl. In embodiments, $R^{14}$ is substituted 2 to 6 membered heteroalkyl. In embodiments, $R^{14}$ is unsubstituted 2 to 6 membered heteroalkyl. In embodiments, $R^{14}$ is substituted 2 to 4 membered heteroalkyl. In embodiments, $R^{14}$ is unsubstituted 2 to 4 membered heteroalkyl.

In embodiments, $R^3$ is substituted or unsubstituted phenyl. In embodiments, $R^3$ is $R^{36}$-substituted phenyl. In embodiments, $R^{36}$ is independently halogen. In embodiments, $R^{36}$ is independently 4-halogen. In embodiments, $R^{36}$ is independently 4-Cl.

In embodiments, $R^3$ is substituted or unsubstituted heteroaryl. In embodiments, $R^3$ is substituted or unsubstituted 5 to 6 membered heteroaryl. In embodiments, $R^3$ is unsubstituted 5 to 6 membered heteroaryl. In embodiments, $R^3$ is substituted 5 to 6 membered heteroaryl. In embodiments, $R^3$ is $R^{36}$-substituted 5 to 6 membered heteroaryl. In embodiments, $R^3$ is substituted or unsubstituted pyrrolyl. In embodiments, $R^3$ is unsubstituted pyrrolyl. In embodiments, $R^3$ is substituted pyrrolyl. In embodiments, $R^3$ is $R^{36}$—Substituted pyrrolyl. In embodiments, $R^3$ is substituted or unsubstituted thienyl. In embodiments, $R^3$ is unsubstituted thienyl. In embodiments, $R^3$ is substituted thienyl. In embodiments, $R^3$ is $R^{36}$-substituted thienyl. In embodiments, $R^3$ is substituted or unsubstituted furanyl. In embodiments, $R^3$ is unsubstituted furanyl. In embodiments, $R^3$ is substituted furanyl. In embodiments, $R^3$ is $R^{36}$-substituted furanyl. In embodiments, $R^3$ is substituted or unsubstituted pyrazolyl. In embodiments, $R^3$ is unsubstituted pyrazolyl. In embodiments, $R^3$ is substituted pyrazolyl. In embodiments, $R^3$ is $R^{36}$-substituted pyrazolyl.

In embodiments, $R^3$ is substituted or unsubstituted pyridyl. In embodiments, $R^3$ is unsubstituted pyridyl. In embodiments, $R^3$ is substituted or unsubstituted pyrid-2-yl. In embodiments, $R^3$ is substituted or unsubstituted pyrid-3-yl. In embodiments, $R^3$ is substituted or unsubstituted pyrid-4-yl. In embodiments, $R^3$ is substituted or unsubstituted pyridyl. In embodiments, $R^3$ is unsubstituted pyridin-2-yl. In embodiments, $R^3$ is unsubstituted pyridin-3-yl. In embodiments, $R^3$ is unsubstituted pyridin-4-yl. In embodiments, $R^3$ is unsubstituted pyridyl.

In embodiments, $R^3$ is substituted or unsubstituted $C_1$-$C_6$ alkyl. In embodiments, $R^3$ is substituted $C_1$-$C_6$ alkyl. In embodiments, $R^3$ is unsubstituted $C_1$-$C_6$ alkyl. In embodiments, $R^3$ is $R^{36}$-substituted $C_1$-$C_6$ alkyl. In embodiments, $R^3$ is substituted or unsubstituted $C_1$-$C_4$ alkyl. In embodiments, $R^3$ is substituted $C_1$-$C_4$ alkyl. In embodiments, $R^3$ is unsubstituted $C_1$-$C_4$ alkyl. In embodiments, $R^3$ is $R^{36}$-substituted $C_1$-$C_4$ alkyl. In embodiments, $R^3$ is substituted or unsubstituted $C_3$-$C_5$ alkyl. In embodiments, $R^3$ is substituted $C_3$-$C_5$ alkyl. In embodiments, $R^3$ is unsubstituted $C_3$-$C_5$ alkyl. In embodiments, $R^3$ is $R^{36}$-substituted $C_3$-$C_5$ alkyl. In embodiments, $R^3$ is substituted propyl. In embodiments, $R^3$ is substituted butyl. In embodiments, $R^3$ is substituted pentyl. In embodiments, $R^3$ is substituted tert-butyl. In embodiments, $R^3$ is substituted isopropyl. In embodiments, $R^3$ is substituted isopentyl. In embodiments, $R^3$ is substituted iso-butyl. In embodiments, $R^3$ is substituted n-butyl. In embodiments, $R^3$ is substituted n-propyl. In embodiments, $R^3$ is substituted n-pentyl. In embodiments, $R^3$ is substituted ethyl. In embodiments, $R^3$ is substituted methyl. In embodiments, $R^3$ is $R^{36}$-substituted propyl. In embodiments, $R^3$ is $R^{36}$-substituted butyl. In embodiments, $R^3$ is $R^{36}$-substituted pentyl. In embodiments, $R^3$ is $R^{36}$-substituted tert-butyl. In embodiments, $R^3$ is $R^{36}$-substituted isopropyl. In embodiments, $R^3$ is $R^{36}$-substituted isopentyl. In embodiments, $R^3$ is $R^{36}$-substituted iso-butyl. In embodiments, $R^3$ is $R^{36}$-substituted n-butyl. In embodiments, $R^3$ is $R^{36}$-substituted n-propyl. In embodiments, $R^3$ is $R^{36}$-substituted n-pentyl. In embodiments, $R^3$ is $R^{36}$-substituted ethyl. In embodiments, $R^3$ is $R^{36}$-substituted methyl. In embodiments, $R^3$ is unsubstituted propyl. In embodiments, $R^3$ is unsubstituted butyl. In embodiments, $R^3$ is unsubstituted pentyl. In embodiments, $R^3$ is unsubstituted tert-butyl. In embodiments, $R^3$ is unsubstituted isopropyl. In embodiments, $R^3$ is unsubstituted isopentyl. In embodiments, $R^3$ is unsubstituted iso-butyl. In embodiments, $R^3$ is unsubstituted n-butyl. In embodiments, $R^3$ is unsubstituted n-propyl. In embodiments, $R^3$ is unsubstituted n-pentyl. In embodiments, $R^3$ is unsubstituted ethyl. In embodiments, $R^3$ is unsubstituted methyl.

In embodiments, $R^{36}$ is independently halogen. In embodiments, $R^{36}$ is independently —F. In embodiments, $R^{36}$ is independently —Cl. In embodiments, $R^{36}$ is independently —I. In embodiments, $R^{36}$ is independently —Br. In embodiments, $R^{36}$ is independently 4-halogen. In embodiments, $R^{36}$ is independently 4-Cl. In embodiments, $R^{36}$ is substituted or unsubstituted 5 to 6 membered heteroaryl. In embodiments, $R^{36}$ is substituted 5 to 6 membered heteroaryl. In embodiments, $R^{36}$ is unsubstituted 5 to 6 membered heteroaryl. In embodiments, $R^{36}$ is substituted or unsubstituted 5 membered heteroaryl. In embodiments, $R^{36}$ is substituted 5 membered heteroaryl. In embodiments, $R^{36}$ is unsubstituted 5 membered heteroaryl. In embodiments, $R^{36}$ is substituted or unsubstituted thienyl. In embodiments, $R^{36}$ is substituted thienyl. In embodiments, $R^{36}$ is unsubstituted thienyl. In embodiments, $R^{36}$ is —$CF_3$. In embodiments, $R^{36}$ is —$CCl_3$. In embodiments, $R^{36}$ is —$CBr_3$. In embodiments, $R^{36}$ is —$CI_3$. In embodiments, $R^{36}$ is unsubstituted methyl. In embodiments, $R^{36}$ is unsubstituted ethyl. In embodiments, $R^{36}$ is unsubstituted propyl. In embodiments, $R^{36}$ is unsubstituted isopropyl.

$R^3$ may independently be —C(O)$R^{17}$. In embodiments, $R^{17}$ is substituted or unsubstituted 5 to 6 membered heteroaryl. In embodiments, $R^{17}$ is substituted 5 to 6 membered heteroaryl. In embodiments, $R^{17}$ is unsubstituted 5 to 6 membered heteroaryl. In embodiments, $R^{17}$ is substituted or unsubstituted 5 membered heteroaryl. In embodiments, $R^{17}$ is substituted 5 membered heteroaryl. In embodiments, $R^{17}$ is unsubstituted 5 membered heteroaryl. In embodiments, $R^{17}$ is substituted or unsubstituted thienyl. In embodiments, $R^{17}$ is substituted thienyl. In embodiments, $R^{17}$ is unsubstituted thienyl.

$R^3$ may independently be —$SO_2NR^{15}R^{16}$. In embodiments, $R^{15}$ is substituted propyl. In embodiments, $R^{15}$ is substituted butyl. In embodiments, $R^{15}$ is substituted pentyl. In embodiments, $R^{15}$ is substituted tert-butyl. In embodiments, $R^{15}$ is substituted isopropyl. In embodiments, $R^{15}$ is substituted isopentyl. In embodiments, $R^{15}$ is substituted iso-butyl. In embodiments, $R^{15}$ is substituted n-butyl. In embodiments, $R^{15}$ is substituted n-propyl. In embodiments, $R^{15}$ is substituted n-pentyl. In embodiments, $R^{15}$ is substituted ethyl. In embodiments, $R^{15}$ is substituted methyl. In embodiments, $R^{15}$ is hydrogen. In embodiments, $R^{15}$ is unsubstituted propyl. In embodiments, $R^{15}$ is unsubstituted butyl. In embodiments, $R^{15}$ is unsubstituted pentyl. In embodiments, $R^{15}$ is unsubstituted tert-butyl. In embodiments, $R^{15}$ is unsubstituted isopropyl. In embodiments, $R^{15}$ is unsubstituted isopentyl. In embodiments, $R^{15}$ is unsubstituted iso-butyl. In embodiments, $R^{15}$ is unsubstituted n-butyl. In embodiments, $R^{15}$ is unsubstituted n-propyl. In embodiments, $R^{15}$ is unsubstituted n-pentyl. In embodiments, $R^{15}$ is unsubstituted ethyl. In embodiments, $R^{15}$ is unsubstituted methyl. In embodiments, $R^{15}$ is substituted $C_1$-$C_6$ alkyl. In embodiments, $R^{15}$ is unsubstituted $C_1$-$C_6$ alkyl. In embodiments, $R^{15}$ is substituted $C_1$-$C_4$ alkyl. In embodiments, $R^{15}$ is unsubstituted $C_1$-$C_4$ alkyl. In embodiments, $R^{15}$ is substituted $C_1$-$C_8$ alkyl. In embodiments, $R^{15}$ is unsubstituted $C_1$-$C_8$ alkyl. In embodiments, $R^{15}$ is substituted heteroalkyl. In embodiments, $R^{15}$ is unsubstituted heteroalkyl. In embodiments, $R^{15}$ is substituted 2 to 8 membered heteroalkyl. In embodiments, $R^{15}$ is unsubstituted 2 to 8 membered heteroalkyl. In embodiments, $R^{15}$ is substituted 2 to 6 membered heteroalkyl. In embodiments, $R^{15}$ is unsubstituted 2 to 6 membered heteroalkyl. In embodiments, $R^{15}$ is substituted 2 to 4 membered heteroalkyl. In embodiments, $R^{15}$ is unsubstituted 2 to 4 membered heteroalkyl. In embodiments, $R^{16}$ is substituted propyl. In embodiments, $R^{16}$ is substituted butyl. In embodiments, $R^{16}$ is substituted pentyl. In embodiments, $R^{16}$ is substituted tert-butyl. In embodiments, $R^{16}$ is substituted isopropyl. In embodiments, $R^{16}$ is substituted isopentyl. In embodiments, $R^{16}$ is substituted iso-butyl. In embodiments, $R^{16}$ is substituted n-butyl. In embodiments, $R^{16}$ is substituted n-propyl. In embodiments, $R^{16}$ is substituted n-pentyl. In embodiments, $R^{16}$ is substituted ethyl. In embodiments, $R^{16}$ is substituted methyl. In embodiments, $R^{16}$ is hydrogen. In embodiments, $R^{16}$ is unsubstituted propyl. In embodiments, $R^{16}$ is unsubstituted butyl. In embodiments, $R^{16}$ is unsubstituted pentyl. In embodiments, $R^{16}$ is unsubstituted tert-butyl. In embodiments, $R^{16}$ is unsubstituted isopropyl. In embodiments, $R^{16}$ is unsubstituted isopentyl. In embodiments, $R^{16}$ is unsubstituted iso-butyl. In embodiments, $R^{16}$ is unsubstituted n-butyl. In embodiments, $R^{16}$ is unsubstituted n-propyl. In embodiments, $R^{16}$ is unsubstituted n-pentyl. In embodiments, $R^{16}$ is unsubstituted ethyl. In embodiments, $R^{16}$ is unsubstituted methyl. In embodiments, $R^{16}$ is substituted $C_1$-$C_6$ alkyl. In embodiments, $R^{16}$ is unsubstituted $C_1$-$C_6$ alkyl. In embodiments, $R^{16}$ is substituted $C_1$-$C_4$ alkyl. In embodiments, $R^{16}$ is unsubstituted $C_1$-$C_4$ alkyl. In embodiments, $R^{16}$ is substituted $C_1$-$C_8$ alkyl. In embodiments, $R^{16}$ is unsubstituted $C_1$-$C_8$ alkyl. In embodiments, $R^{16}$ is substituted heteroalkyl. In embodiments, $R^{16}$ is unsubstituted heteroalkyl. In embodiments, $R^{16}$ is substituted 2 to 8 membered heteroalkyl. In embodiments, $R^{16}$ is unsubstituted 2 to 8 membered heteroalkyl. In embodiments, $R^{16}$ is substituted 2 to 6 membered heteroalkyl. In embodiments, $R^{16}$ is unsubstituted 2 to 6 membered heteroalkyl. In embodiments, $R^{16}$ is substituted 2 to 4 membered heteroalkyl. In embodiments, $R^{16}$ is unsubstituted 2 to 4 membered heteroalkyl.

$R^3$ may independently be —$SO_2R^{18}$. In embodiments, $R^{18}$ is substituted propyl. In embodiments, $R^{18}$ is substituted butyl. In embodiments, $R^{18}$ is substituted pentyl. In embodiments, $R^{18}$ is substituted tert-butyl. In embodiments, $R^{18}$ is substituted isopropyl. In embodiments, $R^{18}$ is substituted isopentyl. In embodiments, $R^{18}$ is substituted iso-butyl. In embodiments, $R^{18}$ is substituted n-butyl. In embodiments, $R^{18}$ is substituted n-propyl. In embodiments, $R^{18}$ is substituted n-pentyl. In embodiments, $R^{18}$ is substituted ethyl. In embodiments, $R^{18}$ is substituted methyl. In embodiments, $R^{18}$ is hydrogen. In embodiments, $R^{18}$ is unsubstituted propyl. In embodiments, $R^{18}$ is unsubstituted butyl. In embodiments, $R^{18}$ is unsubstituted pentyl. In embodiments, $R^{18}$ is unsubstituted tert-butyl. In embodiments, $R^{18}$ is unsubstituted isopropyl. In embodiments, $R^{18}$ is unsubstituted isopentyl. In embodiments, $R^{18}$ is unsubstituted iso-butyl. In embodiments, $R^{18}$ is unsubstituted n-butyl. In embodiments, $R^{18}$ is unsubstituted n-propyl. In embodiments, $R^{18}$ is unsubstituted n-pentyl. In embodiments, $R^{18}$ is unsubstituted ethyl. In embodiments, $R^{18}$ is unsubstituted methyl. In embodiments, $R^{18}$ is substituted $C_1$-$C_6$ alkyl. In embodiments, $R^{18}$ is unsubstituted $C_1$-$C_6$ alkyl. In embodiments, $R^{18}$ is substituted $C_1$-$C_4$ alkyl. In embodiments, $R^{18}$ is unsubstituted $C_1$-$C_4$ alkyl. In embodiments, $R^{18}$ is substituted $C_1$-$C_5$ alkyl. In embodiments, $R^{18}$ is unsubstituted $C_1$-$C_8$ alkyl. In embodiments, $R^{18}$ is substituted heteroalkyl. In embodiments, $R^{18}$ is unsubstituted heteroalkyl. In embodiments, $R^{18}$ is substituted 2 to 8 membered heteroalkyl. In embodiments, $R^{18}$ is unsubstituted 2 to 8 membered heteroalkyl. In embodiments, $R^{18}$ is substituted 2 to 6 membered heteroalkyl. In embodiments, $R^{18}$ is unsubstituted 2 to 6 membered heteroalkyl. In embodiments, $R^{18}$ is substituted 2 to 4 membered heteroalkyl. In embodiments, $R^{18}$ is unsubstituted 2 to 4 membered heteroalkyl.

In embodiments, the compound has the formula:

(IVa)

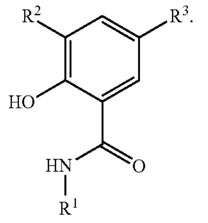

$R^1$, $R^2$, and $R^3$ are as described herein, including in embodiments. In embodiments, $R^1$ does not include a disulfide bond.

In embodiments, the compound is

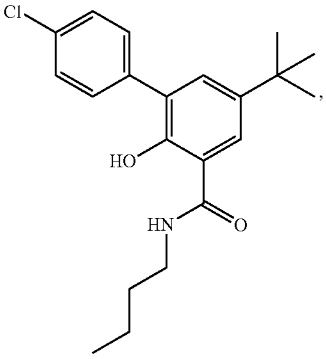
,

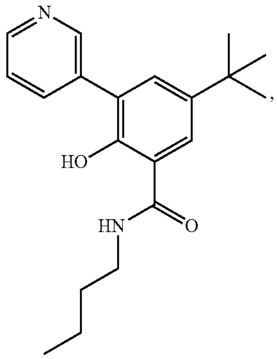
,

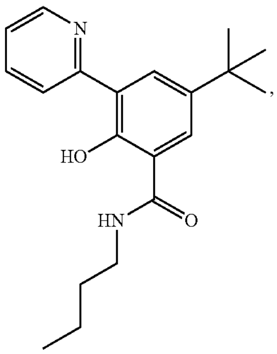
,

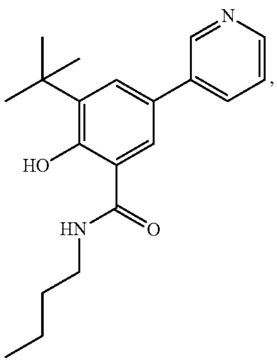
,

-continued
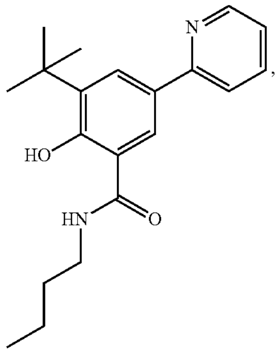
, or
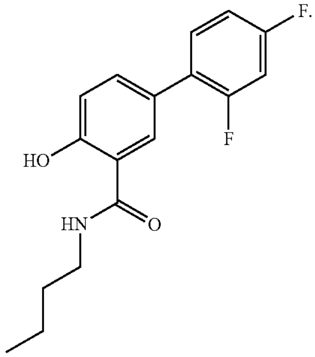
In embodiments, the compound is
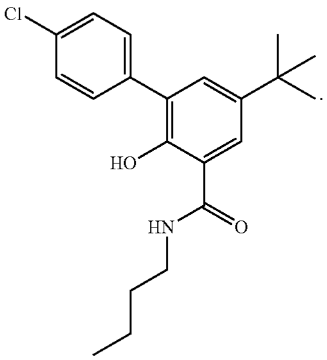 [SMILES: CCCCNC(=O)c1cc(C(C)(C)C)cc(-c2ccc(Cl)cc2)c1O]
In embodiments, the compound is
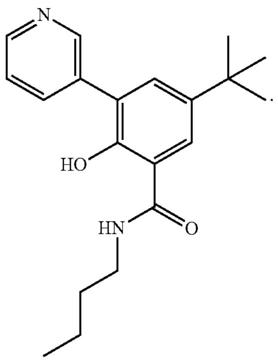 [SMILES: CCCCNC(=O)c1cc(C(C)(C)C)cc(-c2cccnc2)c1O]
In embodiments, the compound is
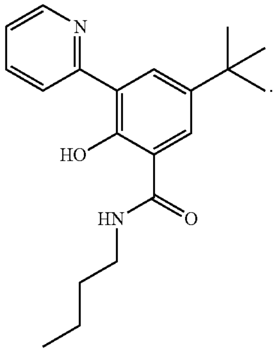 [SMILES: CCCCNC(=O)c1cc(C(C)(C)C)cc(-c2ccccn2)c1O]
In embodiments, the compound is
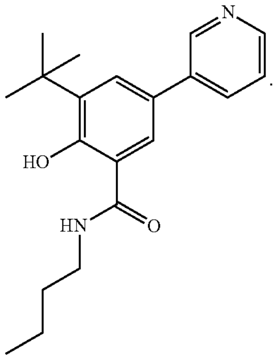 [SMILES: CCCCNC(=O)c1cc(-c2cccnc2)cc(C(C)(C)C)c1O]
In embodiments, the compound is
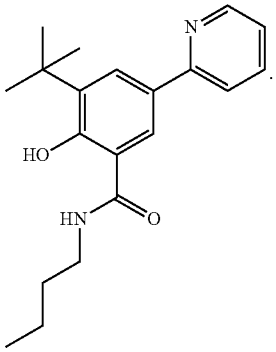 [SMILES: CCCCNC(=O)c1cc(-c2ccccn2)cc(C(C)(C)C)c1O]
In embodiments, the compound is
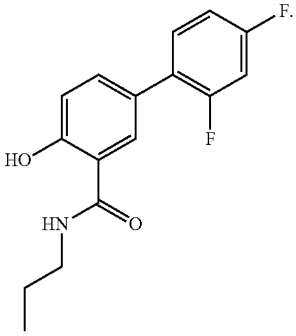 [SMILES: CCCNC(=O)c1cc(-c2ccc(F)cc2F)ccc1O]

In embodiments, the compound is
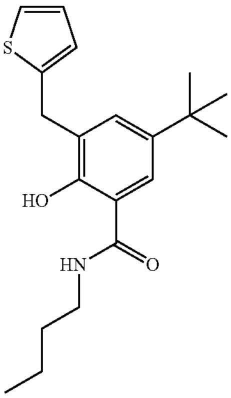
or
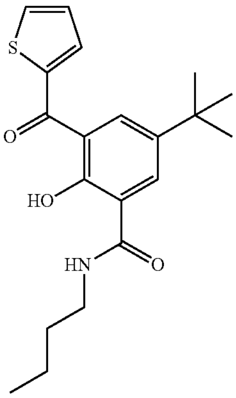
.
In embodiments, the compound is
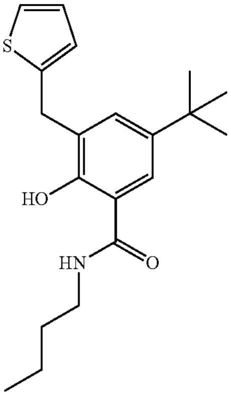
.
In embodiments, the compound is
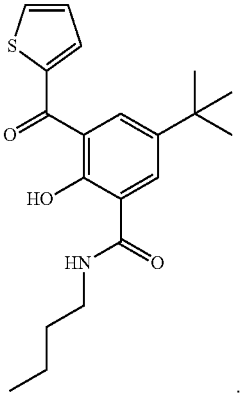 [SMILES: CCCCNC(=O)c1cc(C(C)(C)C)cc(C(=O)c2cccs2)c1O]
.
In embodiments, the compound is
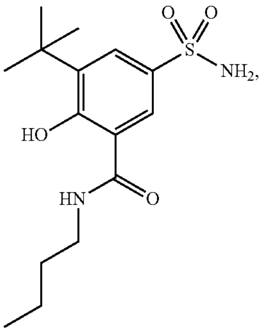 [SMILES: CCCCNC(=O)c1cc(S(N)(=O)=O)cc(C(C)(C)C)c1O]
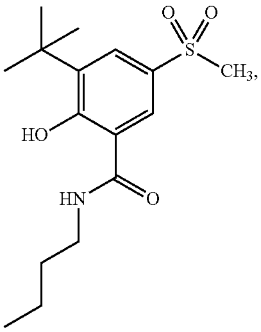 [SMILES: CCCCNC(=O)c1cc(S(C)(=O)=O)cc(C(C)(C)C)c1O]
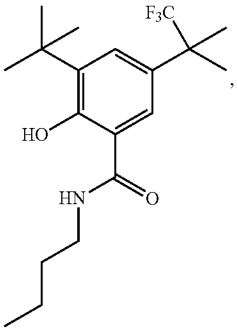
,
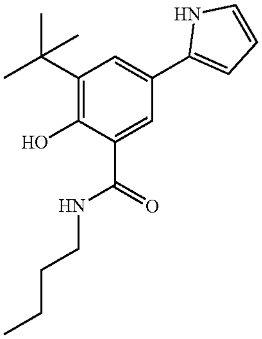
,
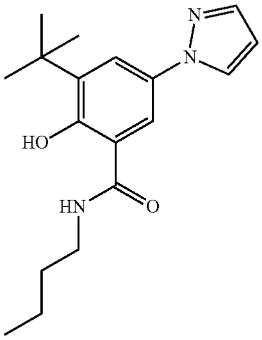
,
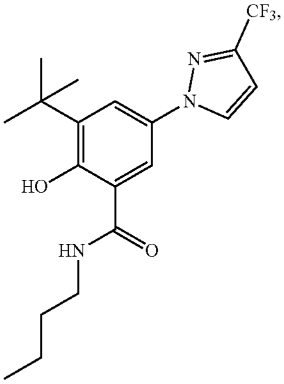

-continued
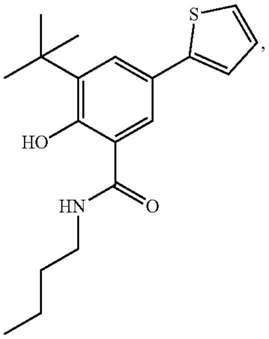
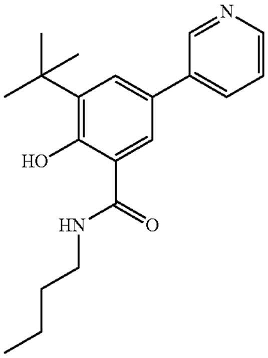
, or
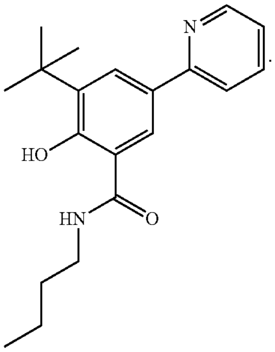
In embodiments, the compound is
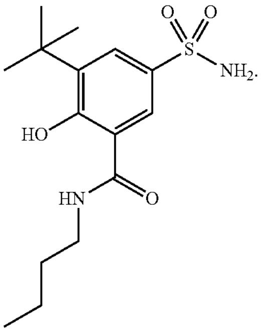
In embodiments, the compound is
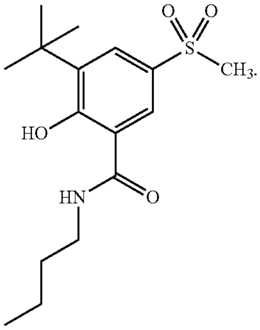
In embodiments, the compound is
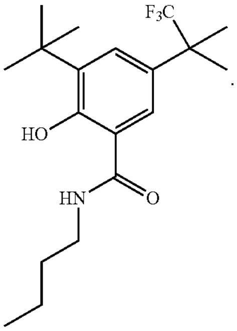 [SMILES: CCCCNC(=O)c1cc(C(C)(C)C(F)(F)F)cc(C(C)(C)C)c1O]
In embodiments, the compound is
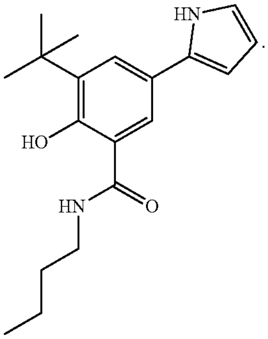 [SMILES: CCCCNC(=O)c1cc(-c2ccc[nH]2)cc(C(C)(C)C)c1O]
In embodiments, the compound is
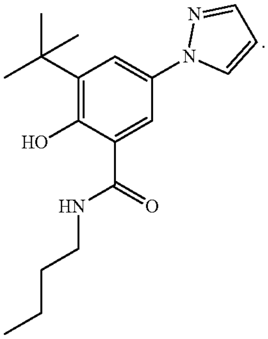 [SMILES: CCCCNC(=O)c1cc(-n2cccn2)cc(C(C)(C)C)c1O]

In embodiments, the compound is
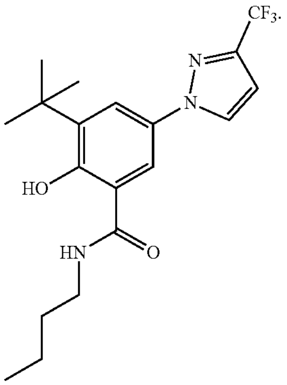 [SMILES: CCCCNC(=O)c1cc(-n2ccc(C(F)(F)F)n2)cc(C(C)(C)C)c1O]
In embodiments, the compound is
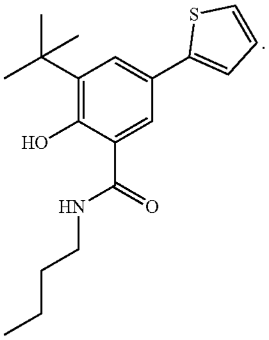 [SMILES: CCCCNC(=O)c1cc(-c2cccs2)cc(C(C)(C)C)c1O]
In embodiments, the compound is
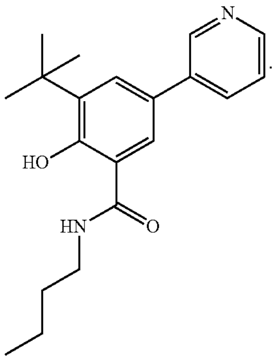 [SMILES: CCCCNC(=O)c1cc(-c2cccnc2)cc(C(C)(C)C)c1O]
In embodiments, the compound is
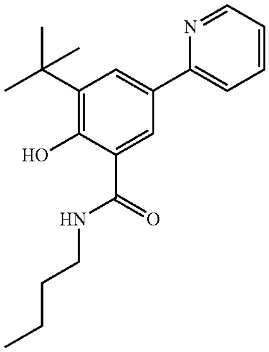
.
In embodiments, the compound is
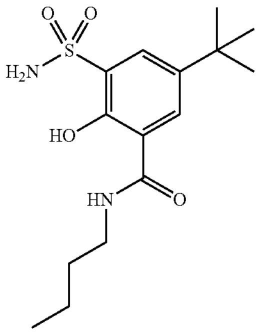
,
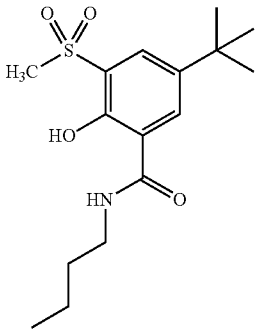
,
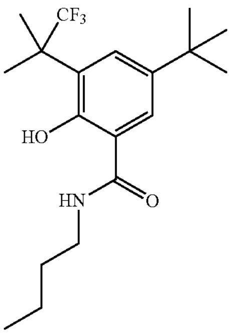
,
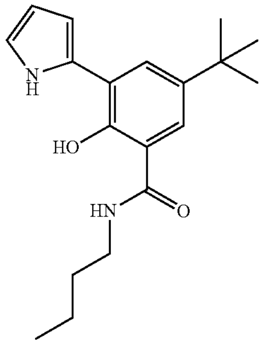
,
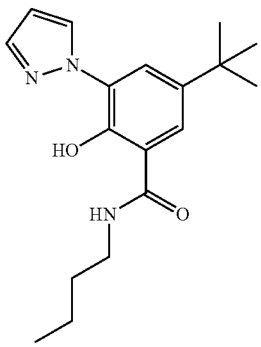
,
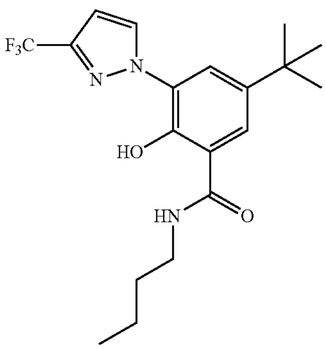
, -continued
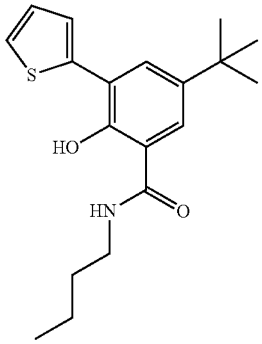
,
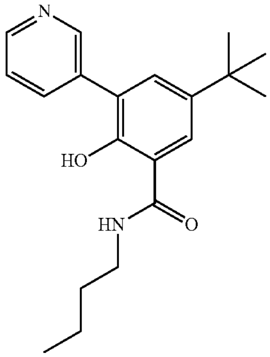
, or
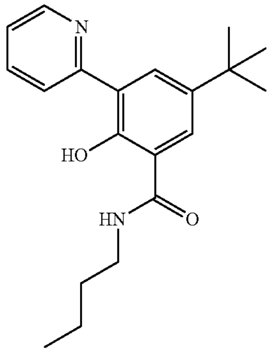
.
In embodiments, the compound is
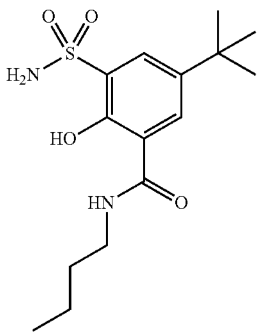
.
In embodiments, the compound is
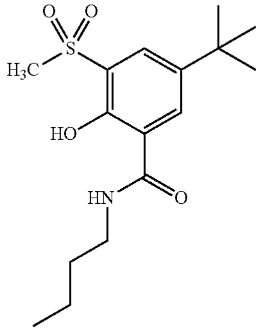
.
In embodiments, the compound is
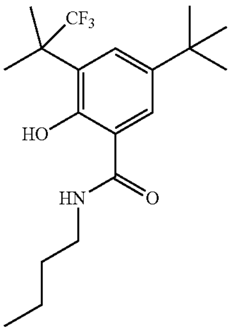
.
In embodiments, the compound is
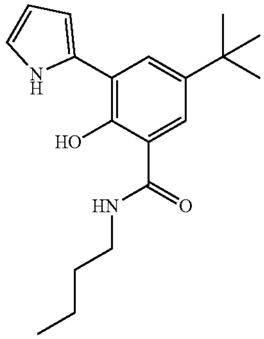
.
In embodiments, the compound is
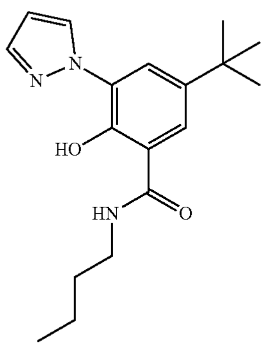
.

In embodiments, the compound is
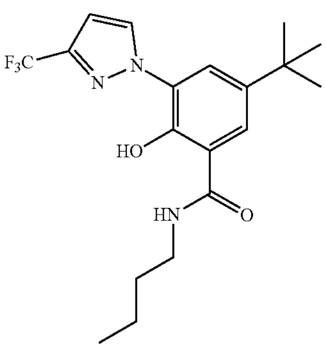
.
In embodiments, the compound is
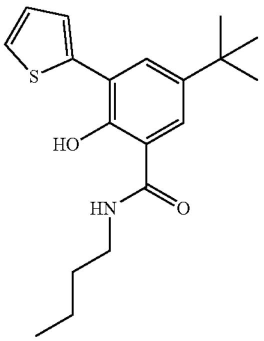
.
In embodiments, the compound is
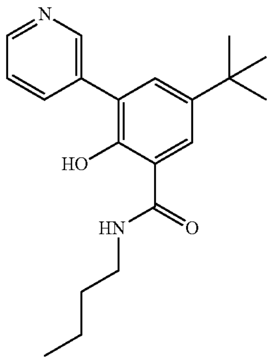
.
In embodiments, the compound is
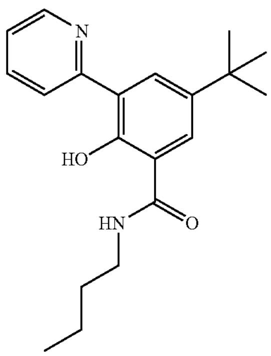
.
In embodiments, the compound is
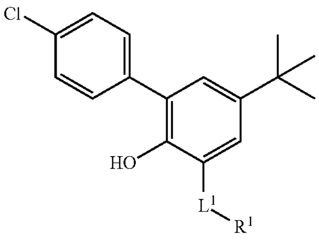
,
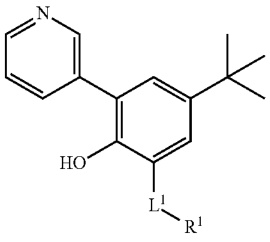
,
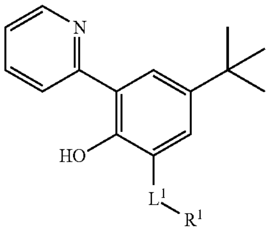
,
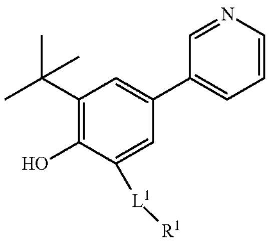
,
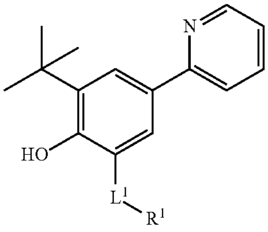
, or
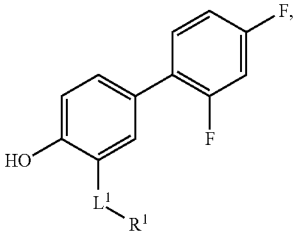
wherein $L^1$ and $R^1$ are as described herein.
In embodiments, the compound is
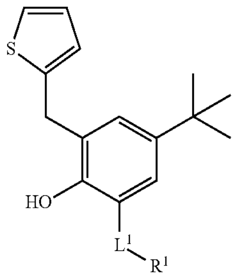
or
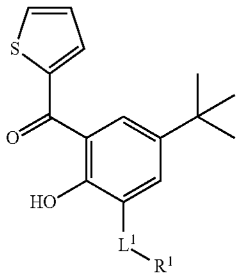
,
wherein $L^1$ and $R^1$ are as described herein.

In embodiments, the compound is
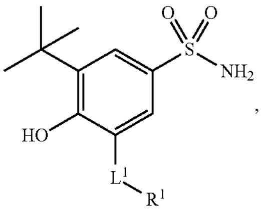
,
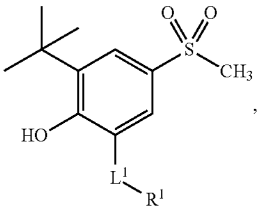
,
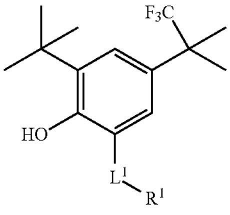
,
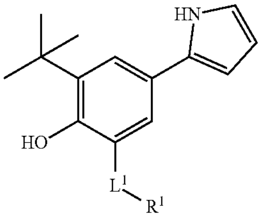
,
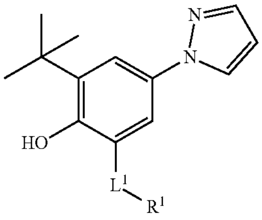
,
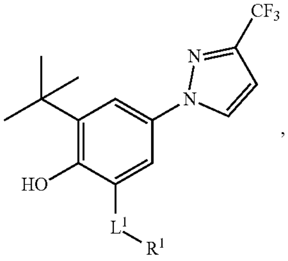
,
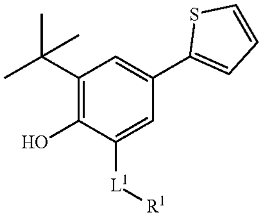
,
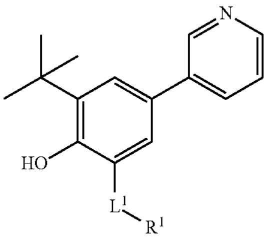
, or
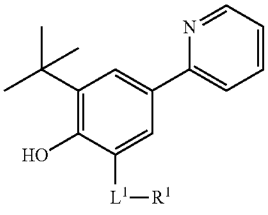
wherein $L^1$ and $R^1$ are as described herein.
In embodiments, the compound is
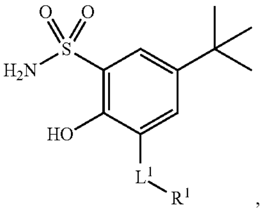
,
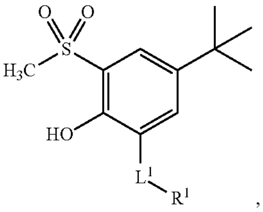
,
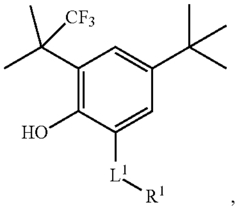
,
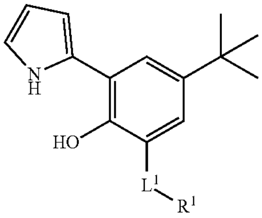
,
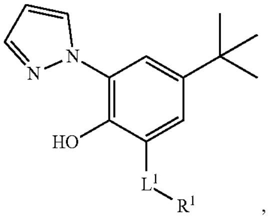
,
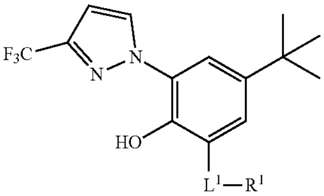
,
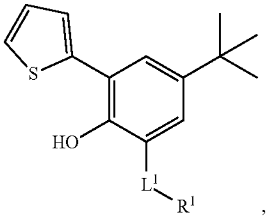
,
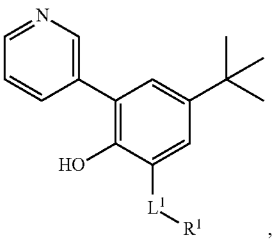
, or
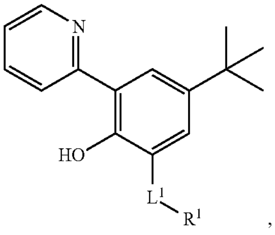
,
wherein $L^1$ and $R^1$ are as described herein.

In embodiments, the compound is
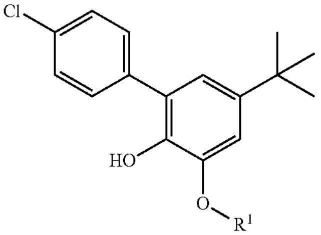
,
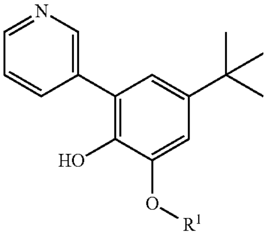
,
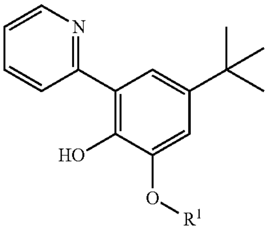
,
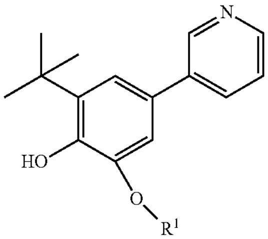
,
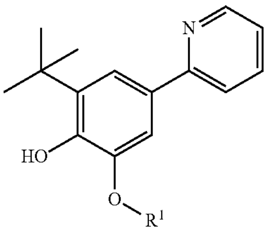
, or
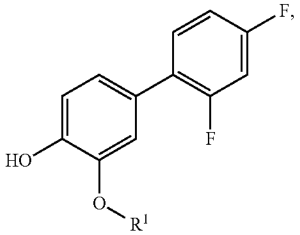
wherein $R^1$ is as described herein.
In embodiments, the compound is
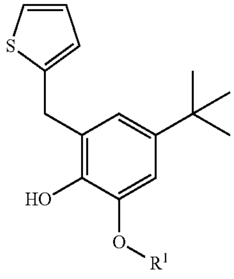
or
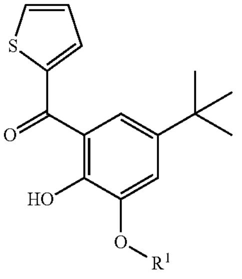
,
wherein $R^1$ is as described herein.
In embodiments, the compound is
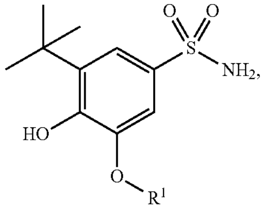
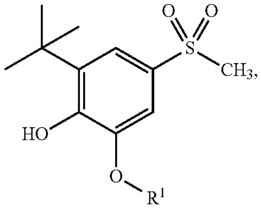
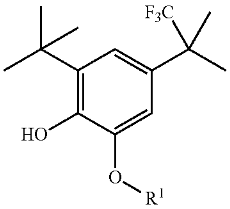
,
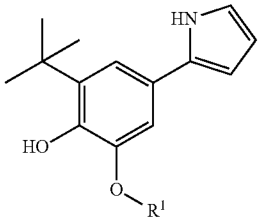
,
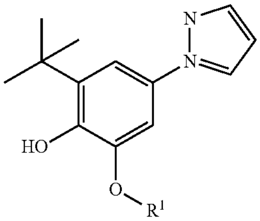
,
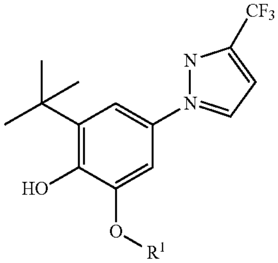
,
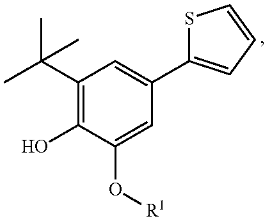
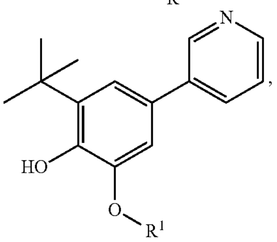
, or
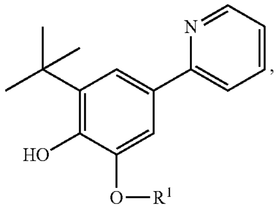
wherein $R^1$ is as described herein.
In embodiments, the compound is
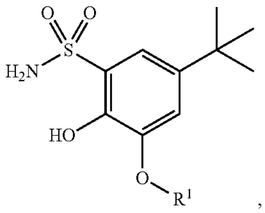
,
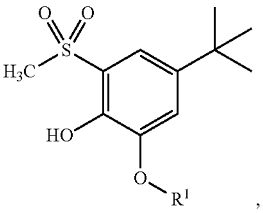
, -continued

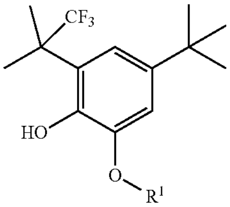

,

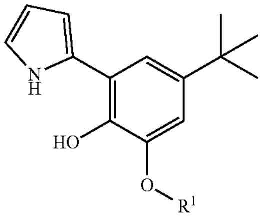

,

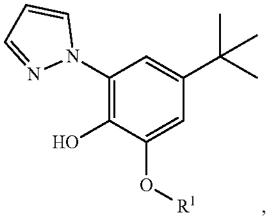

,

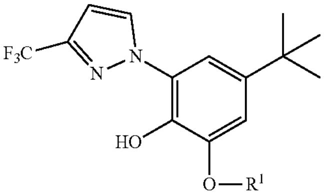

,

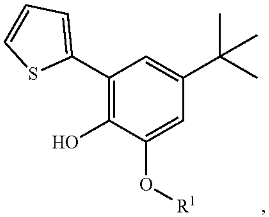

,

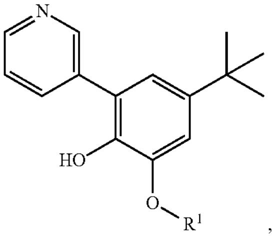

, or

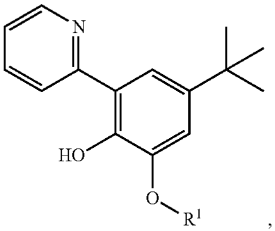

, wherein $R^1$ is as described herein.

In embodiments, the compound is

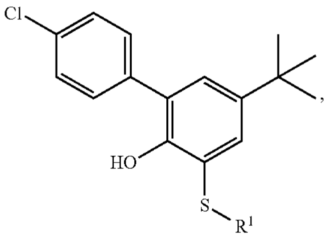

,

-continued

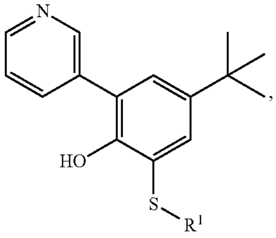

,

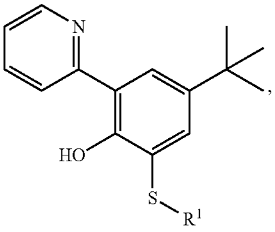

,

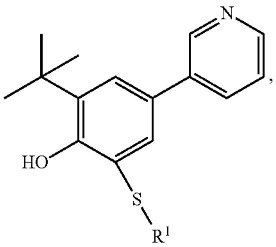

,

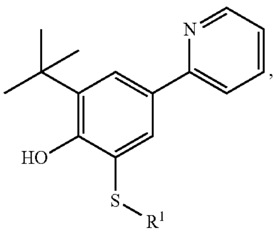

, or

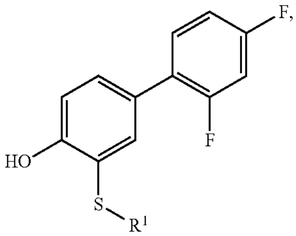

, wherein $R^1$ is as described herein. In embodiments, $R^1$ does not include a disulfide bond. In embodiments, $R^1$ does not include a thioether.

In embodiments, the compound is

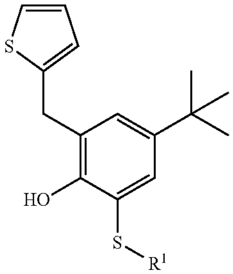

or

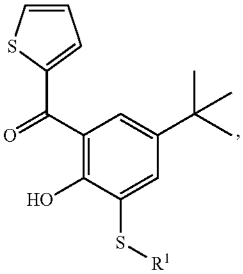

, wherein $R^1$ is as described herein. In embodiments, $R^1$ does not include a disulfide bond. In embodiments, $R^1$ does not include a thioether.

In embodiments, the compound is
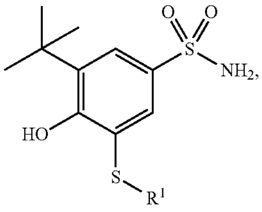
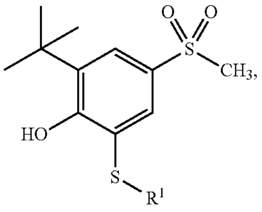
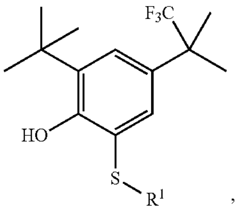
,
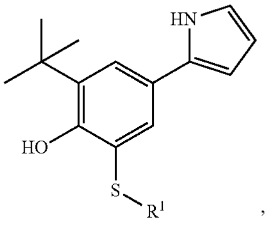
,
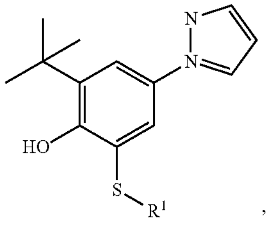
,
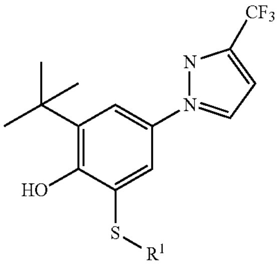
,
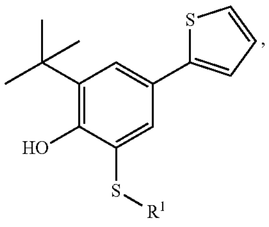
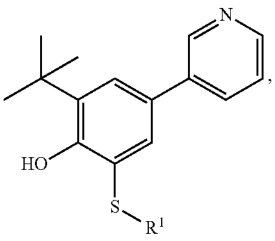
or
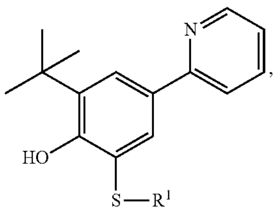
wherein $R^1$ is as described herein. In embodiments, $R^1$ does not include a disulfide bond. In embodiments, $R^1$ does not include a thioether.
In embodiments, the compound is
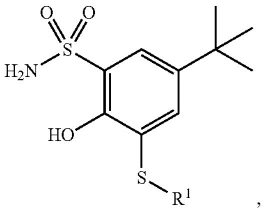
,
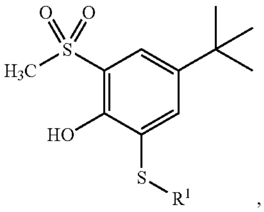
,
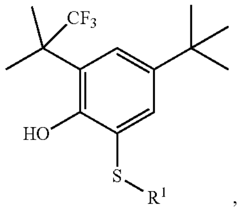
,
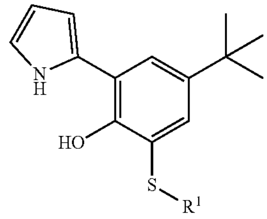
,
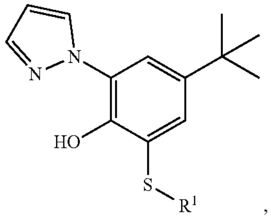
,
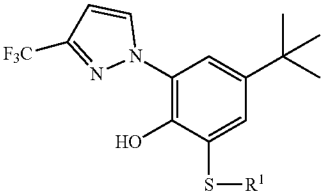
,
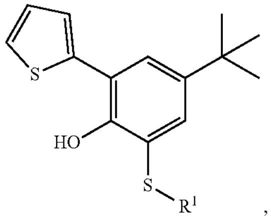
,
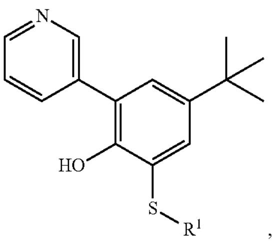
, or
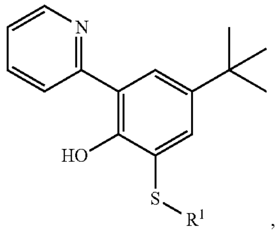
,
wherein $R^1$ is as described herein. In embodiments, $R^1$ does not include a disulfide bond. In embodiments, $R^1$ does not include a thioether.

In embodiments, the compound is
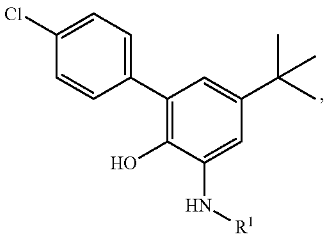
,
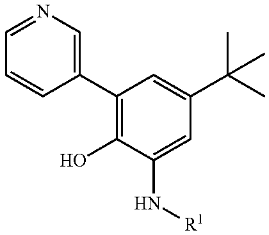
,
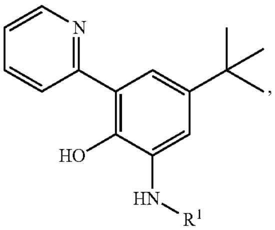
,
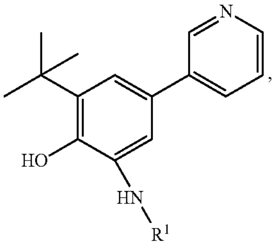
,
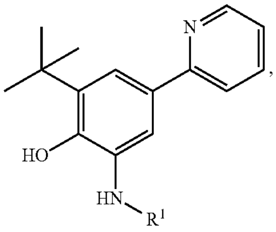
, or
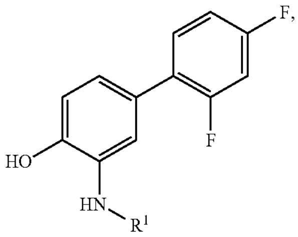
wherein $R^1$ is as described herein.
In embodiments, the compound is
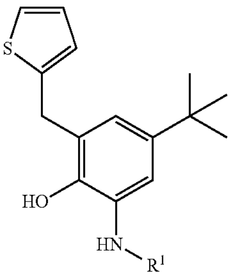
or
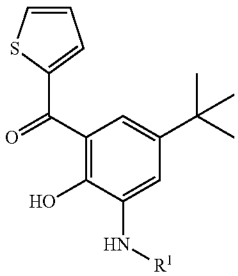
or wherein $R^1$ is as described herein.
In embodiments, the compound is
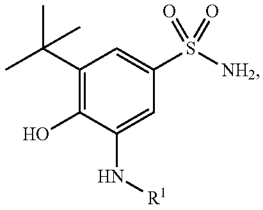
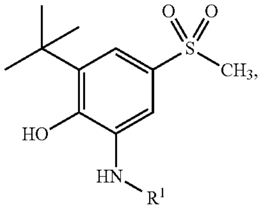
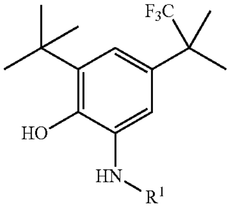
,
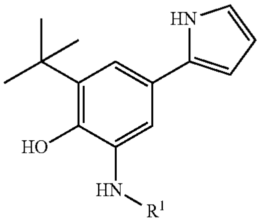
,
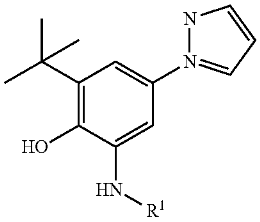
,
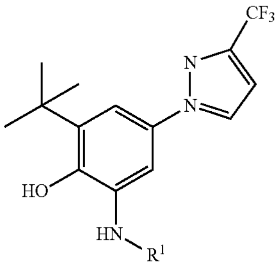
,
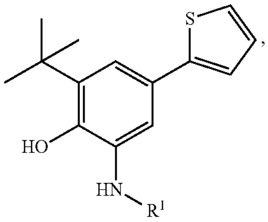
,
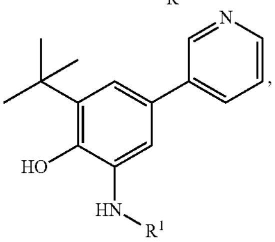
, or
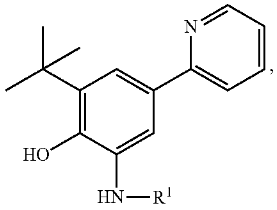
,
wherein $R^1$ is as described herein.
In embodiments, the compound is
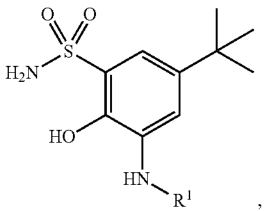
,
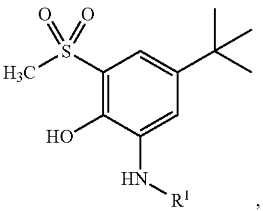
, -continued
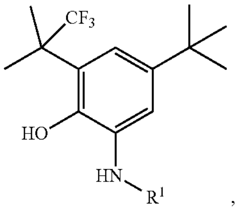 , 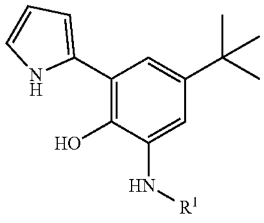 ,
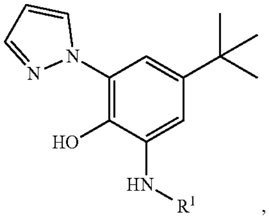 ,
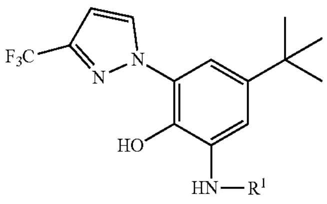 ,
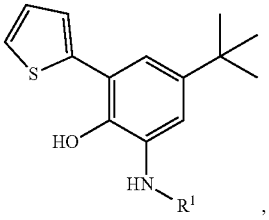 ,
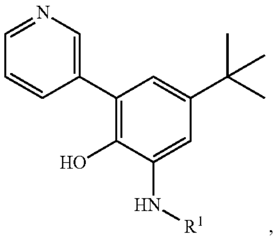 , or
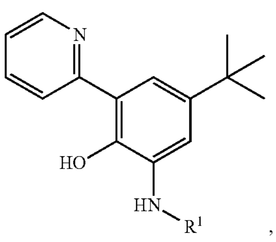 ,
wherein R[1] is as described herein.
In embodiments, the compound is
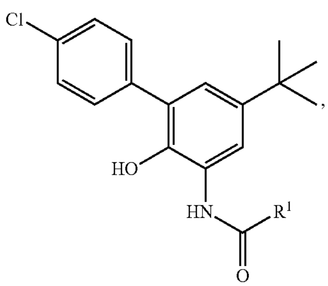 ,
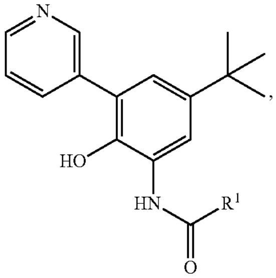 , 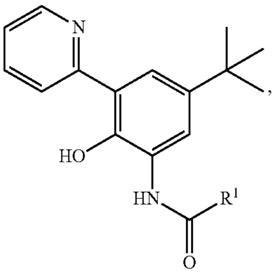 ,
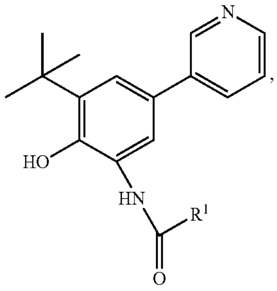 ,
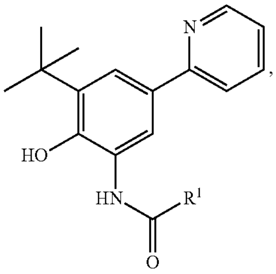 , or
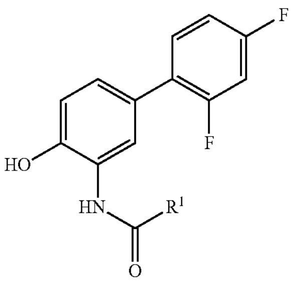
wherein R[1] is as described herein.

In embodiments, the compound is
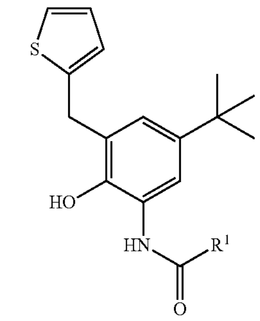
or
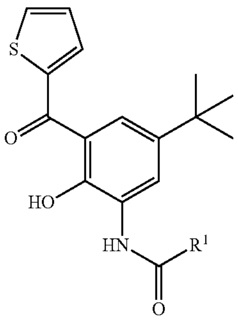
wherein $R^1$ is as described herein.
In embodiments, the compound is
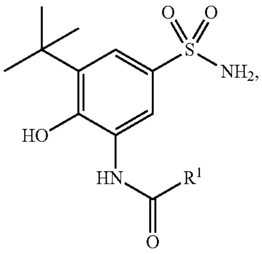
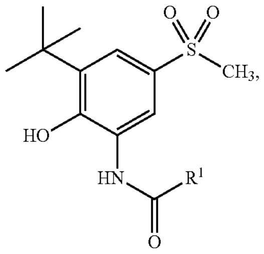
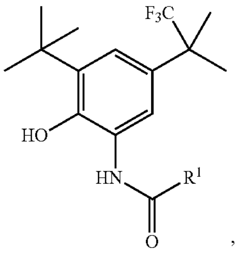
,
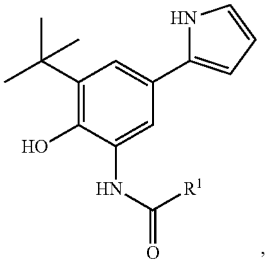
,
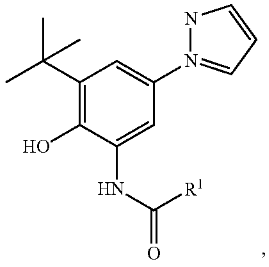
,
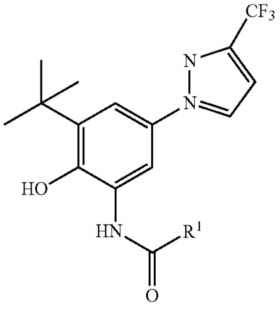
,
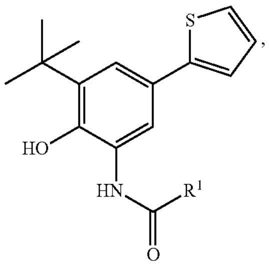
-continued
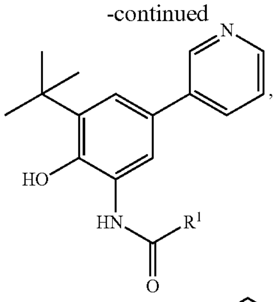
, or
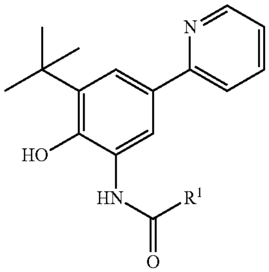
wherein $R^1$ is as described herein.
In embodiments, the compound is
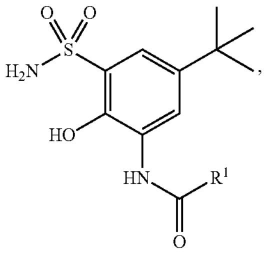
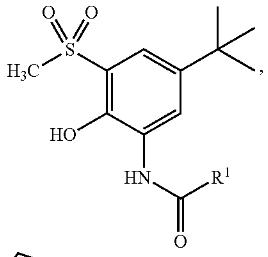
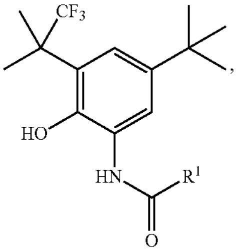
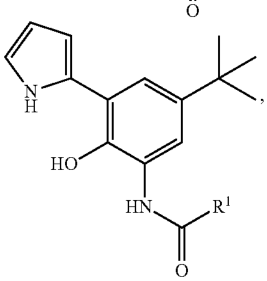
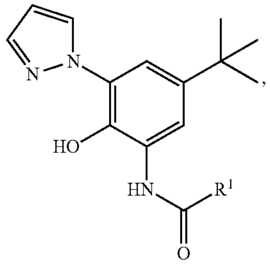
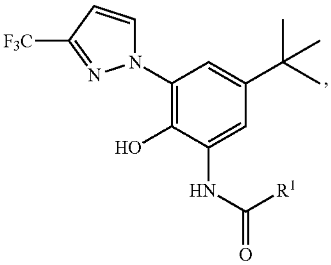

-continued

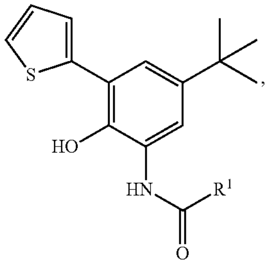
,

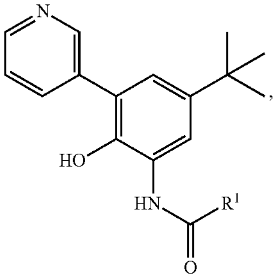
, or

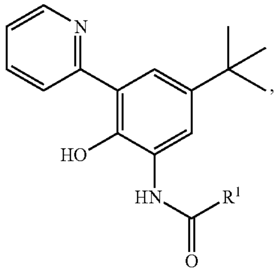
, wherein $R^1$ is as described herein.

In embodiments, the compound is

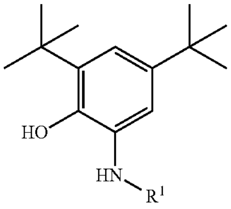

wherein $R^1$ is as described herein. In embodiments, the compound is

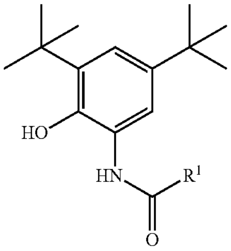

wherein $R^1$ is as described herein. In embodiments, the compound is

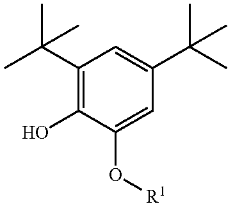

wherein $R^1$ is as described herein. In embodiments, the compound is

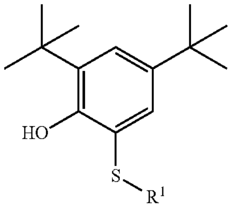
, wherein $R^1$ is as described herein. In embodiments, the compound is

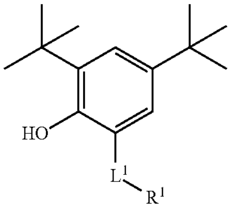
.

In embodiments, the compound is

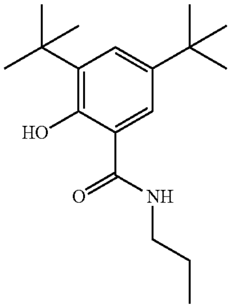
.

In embodiments, the compound is

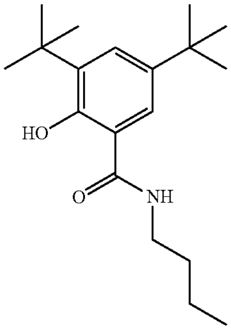
.

In embodiments, the compound is

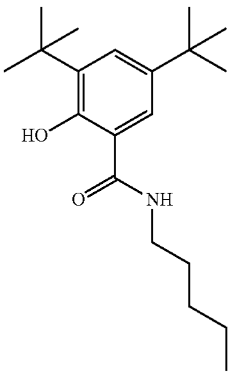

.

In embodiments, the compound is

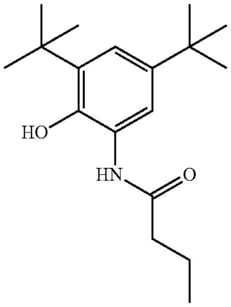

.

In embodiments, the compound is

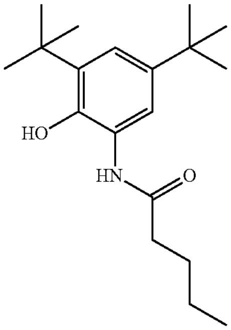

.

In embodiments, the compound is

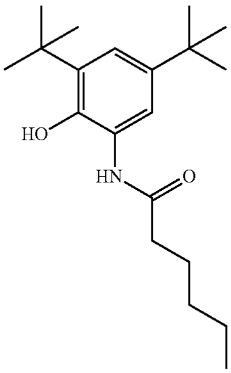

.

In embodiments, the compound is PME1. In embodiments, the compound is PME2. In embodiments, the compound is PME3. In embodiments, the compound is PME4. In embodiments, the compound is PME5. In embodiments, the compound is PME6. In embodiments, the compound is PME7. In embodiments, the compound is PME8. In embodiments, the compound is PME9. In embodiments, the compound is PME10. In embodiments, the compound is PME8, PME9, or PME 10. In embodiments, the compound is PME9 or PME 10.

In embodiments, the compound is not PME1. In embodiments, the compound is not PME2. In embodiments, the compound is not PME3. In embodiments, the compound is not PME4. In embodiments, the compound is not PME5. In embodiments, the compound is not PME6. In embodiments, the compound is not PME7. In embodiments, the compound is not PME8. In embodiments, the compound is not PME9. In embodiments, the compound is not PME10. In embodiments, the compound is not PME8, PME9, or PME 10. In embodiments, the compound is not PME8 or PME 9.

In embodiments, the compound is an agonist of a nuclear receptor. In embodiments, the compound is an agonist of LRH-1. In embodiments, the compound is an agonist of a human LRH-1. In embodiments, the compound is an agonist of wildtype human LRH-1. In embodiments, the compound is an agonist of a mutant human LRH-1. In embodiments, the compound is an antagonist of a nuclear receptor. In embodiments, the compound is an antagonist of an LRH-1. In embodiments, the compound is an antagonist of a human LRH-1. In embodiments, the compound is an antagonist of wildtype human LRH-1. In embodiments, the compound is an antagonist of a mutant human LRH-1. In embodiments, the compound is an antagonist of a drug-resistant human LRH-1. In embodiments, the compound forms a covalent bond with a nuclear receptor. In embodiments, the compound forms a covalent bond with an LRH-1. In embodiments, the covalent bond is reversible. In embodiments, the covalent bond is irreversible. In embodiments, the compound covalently (e.g., reversibly or irreversibly) bonds to Cys346 of human LRH-1. In embodiments, the compound covalently (e.g., reversibly or irreversibly) bonds to the residue corresponding to Cys346 of human LRH-1. In embodiments, the compound covalently (e.g., reversibly or irreversibly) bonds to a Cys residue of a nuclear receptor. In embodiments, the compound covalently (e.g., reversibly or irreversibly) bonds to a Cys residue of an LRH-1. In embodiments, the compound is an activator of LRH-1. In embodiments, the compound is an inhibitor of LRH-1. In embodiments, the compound contacts His390 of LRH-1. In embodiments, the compound contacts the residue corresponding to His390 of LRH-1. In embodiments, the compound contacts Arg393 of LRH-1. In embodiments, the compound contacts the residue corresponding to Arg393 of LRH-1. In embodiments, the compound contacts Thr352 of LRH-1. In embodiments, the compound contacts the residue corresponding to Thr352 of LRH-1. In embodiments, the compound contacts Met345 of LRH-1. In embodiments, the compound contacts the residue corresponding to Met345 of LRH-1. In embodiments, the compound contacts a residue in helix3 of LRH-1. In embodiments, the compound contacts a residue corresponding to a residue in helix3 of LRH-1. In embodiments, the compound contacts a residue in helix 11 of LRH-1. In embodiments, the compound contacts a residue corresponding to a residue in helix 1 of LRH-1. In embodiments, the compound contacts a residue in helix5 of LRH-1. In embodiments, the compound contacts a residue corresponding to a residue in helix5 of LRH-1. In embodiments, the compound increases the level of CYP24A1. In embodiments, the compound increases the level of CYP24A1 relative to control. In embodiments, the compound increases the level of CYP24A1 relative to the absence of the compound.

In embodiments, $R^1$ is independently hydrogen, oxo, halogen, $—CX^1_3$, $—CHX^1_2$, $—CH_2X^1$, $—OCX^1_3$, $—OCH_2X^1$, $—OCHX^1_2$, —CN, —OH, $—NH_2$, —COOH, —CO $NH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 6 membered, 4 to 6 membered, 4 to 5 membered, or 5 to 6 membered), $R^{30}$-substituted or unsubstituted aryl (e.g., $C_6$-$C_{10}$ or phenyl), or $R^{30}$-substituted or unsubstituted heteroaryl (e.g., 5 to 10 membered, 5 to 9 membered, or 5 to 6 membered). In embodiments, $R^1$ is independently oxo, halogen, $—CX^1_3$, $—CHX^1_2$, $—CH_2X^1$, $—OCX^1_3$, $—OCH_2X^1$, $—OCHX^1_2$, —CN, —OH, $—NH_2$, —COOH, —CO $NH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 6 membered, 4 to 6 membered, 4 to 5 membered, or 5 to 6 membered), $R^{30}$-substituted or unsubstituted aryl (e.g., $C_6$-$C_{10}$ or phenyl), or $R^{30}$-substituted or unsubstituted heteroaryl (e.g., 5 to 10 membered, 5 to 9 membered, or 5 to 6 membered). $X^1$ is —F, —Cl, —Br, or —I. In embodiments, $R^1$ is independently hydrogen. In embodiments, $R^1$ is independently methyl. In embodiments, $R^1$ is independently ethyl. In embodiments, $R^1$ is independently hydrogen, oxo, halogen, $—CX^1_3$, $—CHX^1_2$, $—CH_2X^1$, $—OCX^1_3$, $—OCH_2X^1$, $—OCHX^1_2$, —CN, —OH, $—NH_2$, —COOH, —CO $NH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{30}$ is independently oxo, halogen, $—CX^{30}_3$, $—CHX^{30}_2$, $—CH_2X^{30}$, $—OCX^{30}_3$, $—OCH_2X^{30}$, $—OCHX^{30}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{31}$-substituted or unsubstituted alkyl (e.g., $C_1$-$C_8$, $C_1$-$C_6$, $C_1$-$C_4$, or $C_1$-$C_2$), $R^{31}$-substituted or unsubstituted heteroalkyl (e.g., 2 to 8 membered, 2 to 6 membered, 4 to 6 membered, 2 to 3 membered, or 4 to 5 membered), $R^{31}$-substituted or unsubstituted cycloalkyl (e.g., $C_3$-$C_8$, $C_3$-$C_6$, $C_4$-$C_6$, or $C_5$-$C_6$), $R^{31}$-substituted or unsubstituted heterocycloalkyl (e.g., 3 to 6 membered, 4 to 6 membered, 4 to 5 membered, or 5 to 6 membered), $R^{31}$-substituted or unsubstituted aryl (e.g., $C_6$-$C_{10}$ or phenyl), or $R^{31}$-substituted or unsubstituted heteroaryl (e.g., 5 to 10 membered, 5 to 9 membered, or 5 to 6 membered). $X^{30}$ is —F, —Cl, —Br, or —I. In embodiments, $R^{30}$ is independently oxo, halogen, $—CX^{30}_3$, $—CHX^{30}_2$, $—CH_2X^{30}$, $—OCX^{30}_3$, $—OCH_2X^{30}$, $—OCHX^{30}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{31}$ is independently oxo, halogen, $—CX^{31}_3$, $—CHX^{31}_2$, $—CH_2X^{31}$, $—OCX^{31}_3$, $—OCH_2X^{31}$, $—OCHX^{31}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, $R^{32}$-substituted or unsubstituted alkyl (e.g., $C_1$-$C_8$, $C_1$-$C_6$, $C_1$-$C_4$, or $C_1$-$C_2$), $R^{32}$-substituted or unsubstituted heteroalkyl (e.g., 2 to 8 membered, 2 to 6 membered, 4 to 6 membered, 2 to 3 membered, or 4 to 5 membered), $R^{32}$-substituted or unsubstituted cycloalkyl (e.g., $C_3$-$C_8$, $C_3$-$C_6$, $C_4$-$C_6$, or $C_5$-$C_6$), $R^{32}$-substituted or unsubstituted heterocycloalkyl (e.g., 3 to 6 membered, 4 to 6 membered, 4 to 5 membered, or 5 to 6 membered), $R^{32}$-substituted or unsubstituted aryl (e.g., $C_6$-$C_{10}$ or phenyl), or $R^{32}$-substituted or unsubstituted heteroaryl (e.g., 5 to 10 membered, 5 to 9 membered, or 5 to 6 membered). $X^{31}$ is —F, —Cl, —Br, or —I. In embodiments, $R^{31}$ is independently oxo, halogen, $—CX^{31}_3$, $—CHX^{31}_2$, $—CH_2X^{31}$, $—OCX^{31}_3$, $—OCH_2X^{31}$, $—OCHX^{31}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{32}$ is independently oxo, halogen, $—CX^{32}_3$, $—CHX^{32}_2$, $—CH_2X^{32}$, $—OCX^{32}_3$, $—OCH_2X^{32}$, $—OCHX^{32}_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{32}$ is —F, —Cl, —Br, or —I.

In embodiments, $R^2$ is independently hydrogen, oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, 2 to 3 membered, or 4 to 5 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered). In embodiments, $R^2$ is independently oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, 2 to 3 membered, or 4 to 5 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered). $X^2$ is —F, —Cl, —Br, or —I. In embodiments, $R^2$ is independently hydrogen. In embodiments, $R^2$ is independently methyl. In embodiments, $R^2$ is independently ethyl. In embodiments, $R^2$ is independently hydrogen, oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{33}$ is independently oxo, halogen, —$CX^{33}_3$, —$CHX^{33}_2$, —$CH_2X^{33}$, —$OCX^{33}_3$, —$OCH_{2X33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{34}$-substituted or unsubstituted alkyl (e.g., $C_1$-$C_8$, $C_1$-$C_6$, $C_1$-$C_4$, or $C_1$-$C_2$), $R^{34}$-substituted or unsubstituted heteroalkyl (e.g., 2 to 8 membered, 2 to 6 membered, 4 to 6 membered, 2 to 3 membered, or 4 to 5 membered), $R^{34}$-substituted or unsubstituted cycloalkyl (e.g., $C_3$-$C_8$, $C_3$-$C_6$, $C_4$-$C_6$, or $C_5$-$C_6$), $R^{34}$-substituted or unsubstituted heterocycloalkyl (e.g., 3 to 6 membered, 4 to 6 membered, 4 to 5 membered, or 5 to 6 membered), $R^{34}$-substituted or unsubstituted aryl (e.g., $C_6$-$C_{10}$ or phenyl), or $R^{34}$-substituted or unsubstituted heteroaryl (e.g., 5 to 10 membered, 5 to 9 membered, or 5 to 6 membered). $X^{33}$ is —F, —Cl, —Br, or —I. In embodiments, $R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{34}$ is independently oxo, halogen, —$CX^{34}_3$, —$CHX^{34}_2$, —$CH_2X^{34}$, —$OCX^{34}_3$, —$OCH_2X^{34}$, —$OCHX^{34}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{35}$-substituted or unsubstituted alkyl (e.g., $C_1$-$C_8$, $C_1$-$C_6$, $C_1$-$C_4$, or $C_1$-$C_2$), $R^{35}$-substituted or unsubstituted heteroalkyl (e.g., 2 to 8 membered, 2 to 6 membered, 4 to 6 membered, 2 to 3 membered, or 4 to 5 membered), $R^{35}$-substituted or unsubstituted cycloalkyl (e.g., $C_3$-$C_8$, $C_3$-$C_6$, $C_4$-$C_6$, or $C_5$-$C_6$), $R^{35}$-substituted or unsubstituted heterocycloalkyl (e.g., 3 to 6 membered, 4 to 6 membered, 4 to 5 membered, or 5 to 6 membered), $R^{35}$-substituted or unsubstituted aryl (e.g., $C_6$-$C_{10}$ or phenyl), or $R^{35}$-substituted or unsubstituted heteroaryl (e.g., 5 to 10 membered, 5 to 9 membered, or 5 to 6 membered). $X^{34}$ is —F, —Cl, —Br, or —I. In embodiments, $R^{34}$ is independently oxo, halogen, —$CX^{34}_3$, —$CHX^{34}_2$, —$CH_2X^{34}$, —$OCX^{34}_3$, —$OCH_2X^{34}$, —$OCHX^{34}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{35}$ is independently oxo, halogen, —$CX^{35}_3$, —$CHX^{35}_2$, —$CH_2X^{35}$, —$OCX^{35}_3$, —$OCH_2X^{35}$, —$OCHX^{35}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{35}$ is —F, —Cl, —Br, or —I.

In embodiments, $R^3$ is independently hydrogen, oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, 2 to 3 membered, or 4 to 5 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered). In embodiments, $R^3$ is independently oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, 2 to 3 membered, or 4 to 5 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered). $X^3$ is —F, —Cl, —Br, or —I. In embodiments, $R^3$ is independently hydrogen. In embodiments, $R^3$ is independently methyl. In embodiments, $R^3$ is independently ethyl. In embodiments, $R^3$ is independently hydrogen, oxo, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{36}$ is independently oxo, halogen, —$CX^{3}63$, —$CHX^{36}_2$, —$CH_2X^{36}$, —$OCX^{36}_3$, —$OCH_2X^{36}$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{37}$-substituted or unsubstituted alkyl (e.g., $C_1$-$C_8$, $C_1$-$C_6$, $C_1$-$C_4$, or $C_1$-$C_2$), $R^{37}$-substituted or unsubstituted heteroalkyl (e.g., 2 to 8 membered, 2 to 6 membered, 4 to 6 membered, 2 to 3 membered, or 4 to 5 membered), $R^{37}$-substituted or unsubstituted cycloalkyl (e.g., $C_3$-$C_8$, $C_3$-$C_6$, $C_4$-$C_6$, or $C_5$-$C_6$), $R^{37}$-substituted or unsubstituted heterocycloalkyl (e.g., 3 to 6 membered, 4 to 6 membered, 4 to 5 membered, or 5 to 6 membered), $R^{37}$-substituted or unsubstituted aryl (e.g., $C_6$-$C_{10}$ or phenyl), or $R^{37}$-substituted or unsubstituted heteroaryl (e.g., 5 to 10 membered, 5 to 9 membered, or 5 to 6 membered). $X^{36}$ is —F, —Cl, —Br, or —I. In embodiments, $R^{36}$ is independently oxo, halogen, —$CX^{36}_3$, —$CHX^{36}2$, —$CH_2X^{36}$, —$OCX^{36}_3$, —$OCH_2X^{36}$, —$OCHX^{36}2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{37}$ is independently oxo, halogen, —$CX^{37}_3$, —$CHX^{37}_2$, —$CH_2X^{37}$, —$OCX^{37}_3$, —$OCH_2X^{37}$, —$OCHX^{37}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{38}$-substituted or unsubstituted alkyl (e.g., $C_1$-$C_8$, $C_1$-$C_6$, $C_1$-$C_4$, or $C_1$-$C_2$), $R^{38}$-substituted or unsubstituted heteroalkyl (e.g., 2 to 8 membered, 2 to 6 membered, 4 to 6 membered, 2 to 3 membered, or 4 to 5 membered), $R^{38}$-substituted or unsubstituted cycloalkyl (e.g., $C_3$-$C_8$, $C_3$-$C_6$, $C_4$-$C_6$, or $C_5$-$C_6$), $R^{38}$-substituted or unsubstituted heterocycloalkyl (e.g., 3 to 6 membered, 4 to 6 membered, 4 to 5 membered, or 5 to 6 membered), $R^{38}$-substituted or unsubstituted aryl (e.g., $C_6$-$C_{10}$ or phenyl), or $R^{38}$-substituted or unsubstituted heteroaryl (e.g., 5 to 10 membered, 5 to 9 membered, or 5 to 6 membered). $X^{37}$ is —F, —Cl, —Br, or —I. In embodiments, $R^{37}$ is independently oxo, halogen, —$CX^{37}_3$, —$CHX^{37}_2$, —$CH_2X^{37}$, —$OCX^{37}_3$, —$OCH_2X^{37}$, —$OCHX^{37}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{38}$ is independently oxo, halogen, —$CX^{38}_3$, —$CHX^{38}_2$, —$CH_2X^{38}$, —$OCX^{38}_3$, —$OCH_2X^{38}$, —$OCHX^{38}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{38}$ is —F, —Cl, —Br, or —I.

In embodiments, $R^4$ is independently hydrogen, oxo, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered). In embodiments, $R^4$ is independently oxo, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, 2 to 3 membered, or 4 to 5 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered). $X^4$ is —F, —Cl, —Br, or —I. In embodiments, $R^4$ is independently hydrogen. In embodiments, $R^4$ is independently methyl. In embodiments, $R^4$ is independently ethyl. In embodiments, $R^4$ is independently hydrogen, oxo, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{39}$ is independently oxo, halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered). $X^{39}$ is —F, —Cl, —Br, or —I. In embodiments, $R^{39}$ is independently oxo, halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{41}$-substituted or unsubstituted alkyl (e.g., $C_1$-$C_8$, $C_1$-$C_6$, $C_1$-$C_4$, or $C_1$-$C_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., $C_3$-$C_8$, $C_3$-$C_6$, $C_4$-$C_6$, or $C_5$-$C_6$), $R^{41}$-substituted or unsubstituted heterocycloalkyl (e.g., 3 to 6 membered, 4 to 6 membered, 4 to 5 membered, or 5 to 6 membered), $R^{41}$-substituted or unsubstituted aryl (e.g., $C_6$-$C_{10}$ or phenyl), or $R^{41}$-substituted or unsubstituted heteroaryl (e.g., 5 to 10 membered, 5 to 9 membered, or 5 to 6 membered). $X^{40}$ is —F, —Cl, —Br, or —I. In embodiments, $R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{41}$ is independently oxo, halogen, —$CX^{41}_3$, —$CHX^{41}2$, —$CH_2X^{41}$, —$OCX^{41}_3$, —$OCH_2X^{41}$, —$OCHX^{41}2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{41}$ is —F, —Cl, —Br, or —I.

In embodiments, $R^7$ is independently hydrogen, —$CX^{73}$, —CN, —COOH, —$CONH_2$, —$CHX^{72}$, —$CH_2X^7$, $R^{7A}$-substituted or unsubstituted alkyl (e.g., $C_1$-$C_5$, $C_1$-$C_6$, $C_1$-$C_4$, or $C_1$-$C_2$), $R^{7A}$-substituted or unsubstituted heteroalkyl (e.g., 2 to 8 membered, 2 to 6 membered, 4 to 6 membered, 2 to 3 membered, or 4 to 5 membered), $R^{7A}$-substituted or unsubstituted cycloalkyl (e.g., $C_3$-$C_8$, $C_3$-$C_6$, $C_4$-$C_6$, or $C_5$-$C_6$), $R^{7A}$-substituted or unsubstituted heterocycloalkyl (e.g., 3 to 6 membered, 4 to 6 membered, 4 to 5 membered, or 5 to 6 membered), $R^{7A}$-substituted or unsubstituted aryl (e.g., $C_6$-$C_{10}$ or phenyl), or $R^{7A}$-substituted or unsubstituted heteroaryl (e.g., 5 to 10 membered, 5 to 9 membered, or 5 to 6 membered). $X^7$ is —F, —Cl, —Br, or —I. In embodiments, $R^7$ is independently hydrogen. In embodiments, $R^7$ is independently methyl. In embodiments, $R^7$ is independently ethyl. In embodiments, $R^7$ is independently hydrogen, $—CX^7_3$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^7$ and $R^8$ substituents bonded to the same nitrogen atom may optionally be joined to form a $R^{7A}$-substituted or unsubstituted heterocycloalkyl or $R^{7A}$-substituted or unsubstituted heteroaryl. In embodiments, $R^7$ and $R^8$ substituents bonded to the same nitrogen atom may optionally be joined to form a $R^{7A}$-substituted or unsubstituted 3 to 6 membered heterocycloalkyl or $R^{7A}$-substituted or unsubstituted 5 to 6 membered heteroaryl. In embodiments, $R^7$ and $R^8$ substituents bonded to the same nitrogen atom may optionally be joined to form an unsubstituted 3 to 6 membered heterocycloalkyl or unsubstituted 5 to 6 membered heteroaryl. In embodiments, $R^7$ and $R^8$ substituents bonded to the same nitrogen atom may optionally be joined to form a $R^{7A}$-substituted or unsubstituted piperazinyl. In embodiments, $R^7$ and $R^8$ substituents bonded to the same nitrogen atom may optionally be joined to form a $R^{7A}$-substituted or unsubstituted piperidinyl. In embodiments, $R^7$ and $R^8$ substituents bonded to the same nitrogen atom may optionally be joined to form a $R^{7A}$-substituted or unsubstituted pyrrolidinyl. In embodiments, $R^7$ and $R^8$ substituents bonded to the same nitrogen atom may optionally be joined to form a $R^{7A}$-substituted or unsubstituted azetidinyl. In embodiments, $R^7$ and $R^8$ substituents bonded to the same nitrogen atom may optionally be joined to form a $R^{7A}$-substituted or unsubstituted morpholinyl. In embodiments, $R^7$ and $R^8$ substituents bonded to the same nitrogen atom may optionally be joined to form a $R^{7A}$-substituted or unsubstituted azeridinyl.

$R^{7A}$ is independently oxo, halogen, $—CX^{7A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{7A}_2$, $—CH_2X^{7A}$, $—OCX^{7A}_3$, $—OCH_2X^{7A}$, $—OCHX^{7A}_2$, $R^B$-substituted or unsubstituted alkyl (e.g., $C_1$-$C_5$, $C_1$-$C_6$, $C_1$-$C_4$, or $C_1$-$C_2$), $R^{7B}$-substituted or unsubstituted heteroalkyl (e.g., 2 to 8 membered, 2 to 6 membered, 4 to 6 membered, 2 to 3 membered, or 4 to 5 membered), $R^B$-substituted or unsubstituted cycloalkyl (e.g., $C_3$-$C_8$, $C_3$-$C_6$, $C_4$-$C_6$, or $C_5$-$C_6$), $R^B$-substituted or unsubstituted heterocycloalkyl (e.g., 3 to 6 membered, 4 to 6 membered, 4 to 5 membered, or 5 to 6 membered), $R^{7B}$-substituted or unsubstituted aryl (e.g., $C_6$-$C_{10}$ or phenyl), or $R^{7B}$-substituted or unsubstituted heteroaryl (e.g., 5 to 10 membered, 5 to 9 membered, or 5 to 6 membered). $X^{7A}$ is —F, —Cl, —Br, or —I. In embodiments, $R^{7A}$ is independently oxo, halogen, $—CX^{7A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{7A}_2$, $—CH_2X^{7A}$, $—OCX^{7A}_3$, $—OCH_2X^{7A}$, $—OCHX^{7A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{7B}$ is independently oxo, halogen, $—CX^{7B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{7B}_2$, $—CH_2X^{7B}$, $—OCX^{7B}_3$, $—OCH_2X^{7B}$, $—OCHX^{7B}_2$, $R^{7C}$-substituted or unsubstituted alkyl (e.g., $C_1$-$C_8$, $C_1$-$C_6$, $C_1$-$C_4$, or $C_1$-$C_2$), $R^{7C}$-substituted or unsubstituted heteroalkyl (e.g., 2 to 8 membered, 2 to 6 membered, 4 to 6 membered, 2 to 3 membered, or 4 to 5 membered), $R^{7C}$-substituted or unsubstituted cycloalkyl (e.g., $C_3$-$C_8$, $C_3$-$C_6$, $C_4$-$C_6$, or $C_5$-$C_6$), $R^{7C}$-substituted or unsubstituted heterocycloalkyl (e.g., 3 to 6 membered, 4 to 6 membered, 4 to 5 membered, or 5 to 6 membered), $R^{7C}$-substituted or unsubstituted aryl (e.g., $C_6$-$C_{10}$ or phenyl), or $R^{7C}$-substituted or unsubstituted heteroaryl (e.g., 5 to 10 membered, 5 to 9 membered, or 5 to 6 membered). $X^{7B}$ is —F, —Cl, —Br, or —I. In embodiments, $R^{7B}$ is independently oxo, halogen, $—CX^{7B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{7B}_2$, $—CH_2X^{7B}$, $—OCX^{7B}_3$, $—OCH_2X^{7B}$, $—OCHX^{7B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{7C}$ is independently oxo, halogen, $—CX^{7C}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{7C}_2$, $—CH_2X^{7C}$, $—OCX^{7C}_3$, $—OCH_2X^{7C}$, $—OCHX^{7C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7c}$ is —F, —Cl, —Br, or —I.

In embodiments, $R^8$ is independently hydrogen, $—CX^{83}$, —CN, —COOH, $—CONH_2$, $—CHX^{82}$, $—CH_2X^8$, $R^{8A}$-substituted or unsubstituted alkyl (e.g., $C_1$-$C_8$, $C_1$-$C_6$, $C_1$-$C_4$, or $C_1$-$C_2$), $R^{8A}$-substituted or unsubstituted heteroalkyl (e.g., 2 to 8 membered, 2 to 6 membered, 4 to 6 membered, 2 to 3 membered, or 4 to 5 membered), $R^{8A}$-substituted or unsubstituted cycloalkyl (e.g., $C_3$-$C_8$, $C_3$-$C_6$, $C_4$-$C_6$, or $C_5$-$C_6$), $R^{8A}$-substituted or unsubstituted heterocycloalkyl (e.g., 3 to 6 membered, 4 to 6 membered, 4 to 5 membered, or 5 to 6 membered), $R^{8A}$-substituted or unsubstituted aryl (e.g., $C_6$-$C_{10}$ or phenyl), or $R^{8A}$-substituted or unsubstituted heteroaryl (e.g., 5 to 10 membered, 5 to 9 membered, or 5 to 6 membered). $X^8$ is —F, —Cl, —Br, or —I. In embodiments, $R^8$ is independently hydrogen. In embodiments, $R^8$ is independently methyl. In embodiments, $R^8$ is independently ethyl. In embodiments, $R^8$ is independently hydrogen, $—CX^8$ 3, —CN, —COOH, $—CONH_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^8$ and $R^7$ substituents bonded to the same nitrogen atom may optionally be joined to form a $R^{8A}$-substituted or unsubstituted heterocycloalkyl or $R^{8A}$-substituted or unsubstituted heteroaryl. In embodiments, $R^8$ and $R^7$ substituents bonded to the same nitrogen atom may optionally be joined to form a $R^{8A}$-substituted or unsubstituted 3 to 6 membered heterocycloalkyl or $R^{8A}$-substituted or unsubstituted 5 to 6 membered heteroaryl. In embodiments, $R^8$ and $R^7$ substituents bonded to the same nitrogen atom may optionally be joined to form an unsubstituted 3 to 6 membered heterocycloalkyl or unsubstituted 5 to 6 membered heteroaryl. In embodiments, $R^8$ and $R^7$ substituents bonded to the same nitrogen atom may optionally be joined to form a $R^{8A}$-substituted or unsubstituted piperazinyl. In embodiments, $R^8$ and $R^7$ substituents bonded to the same nitrogen atom may optionally be joined to form a $R^{8A}$-substituted or unsubstituted piperidinyl. In embodiments, $R^8$ and $R^7$ substituents bonded to the same nitrogen atom may optionally be joined to form a $R^{8A}$-substituted or unsubstituted pyrrolidinyl. In embodiments, $R^8$ and $R^7$ substituents bonded to the same nitrogen atom may optionally be joined to form a $R^{8A}$-substituted or unsubstituted azetidinyl. In embodiments, $R^8$ and $R^7$ substituents bonded to the same nitrogen atom may optionally be joined to form a $R^{8A}$-substituted or unsubstituted morpholinyl. In embodiments, $R^8$ and $R^7$ substituents bonded to the same nitrogen atom may optionally be joined to form a $R^{8A}$-substituted or unsubstituted azeridinyl.

$R^{8A}$ is independently oxo, halogen, $-CX^{8A}_3$, —CN, —OH, $-NH_2$, —COOH, $-CONH_2$, —SH, $-NHNH_2$, $-ONH_2$, $-NHC(O)NHNH_2$, $-NHC(O)NH_2$, —NHC(O)H, —NHC(O)OH, —NHOH, $-CHX^{8A}_2$, $-CH_2X^{8A}$, $-OCX^{8A}_3$, $-OCH_2X^{8A}$, $-OCHX^{8A}_2$, $R^{8B}$-substituted or unsubstituted alkyl (e.g., $C_1$-$C_8$, $C_1$-$C_6$, $C_1$-$C_4$, or $C_1$-$C_2$), $R^{8B}$-substituted or unsubstituted heteroalkyl (e.g., 2 to 8 membered, 2 to 6 membered, 4 to 6 membered, 2 to 3 membered, or 4 to 5 membered), $R^{8B}$-substituted or unsubstituted cycloalkyl (e.g., $C_3$-$C_8$, $C_3$-$C_6$, $C_4$-$C_6$, or $C_5$-$C_6$), $R^{8B}$-substituted or unsubstituted heterocycloalkyl (e.g., 3 to 6 membered, 4 to 6 membered, 4 to 5 membered, or 5 to 6 membered), $R^{8B}$-substituted or unsubstituted aryl (e.g., $C_6$-$C_{10}$ or phenyl), or $R^{8B}$-substituted or unsubstituted heteroaryl (e.g., 5 to 10 membered, 5 to 9 membered, or 5 to 6 membered). $X^{8A}$ is —F, —Cl, —Br, or —I. In embodiments, $R^{8A}$ is independently oxo, halogen, $-CX^{8A}_3$, —CN, —OH, $-NH_2$, —COOH, $-CONH_2$, —SH, $-NHNH_2$, $-ONH_2$, $-NHC(O)NHNH_2$, $-NHC(O)NH_2$, —NHC(O)H, —NHC(O)OH, —NHOH, $-CHX^{8A}_2$, $-CH_2X^{8A}$, $-OCX^{8A}_3$, $-OCH_2X^{8A}$, $-OCHX^{8A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{8B}$ is independently oxo, halogen, $-CX^{8B}_3$, —CN, —OH, $-NH_2$, —COOH, $-CONH_2$, —SH, $-NHNH_2$, $-ONH_2$, $-NHC(O)NHNH_2$, $-NHC(O)NH_2$, —NHC(O)H, —NHC(O)OH, —NHOH, $-CHX^{8B}_2$, $-CH_2X^{8B}$, $-OCX^{8B}_3$, $-OCH_2X^{8B}$, $-OCHX^{8B}_2$, $R^{8C}$-substituted or unsubstituted alkyl (e.g., $C_1$-$C_8$, $C_1$-$C_6$, $C_1$-$C_4$, or $C_1$-$C_2$), $R^{8C}$-substituted or unsubstituted heteroalkyl (e.g., 2 to 8 membered, 2 to 6 membered, 4 to 6 membered, 2 to 3 membered, or 4 to 5 membered), $R^{8C}$-substituted or unsubstituted cycloalkyl (e.g., $C_3$-$C_8$, $C_3$-$C_6$, $C_4$-$C_6$, or $C_5$-$C_6$), $R^{8C}$-substituted or unsubstituted heterocycloalkyl (e.g., 3 to 6 membered, 4 to 6 membered, 4 to 5 membered, or 5 to 6 membered), $R^{8C}$-substituted or unsubstituted aryl (e.g., $C_6$-$C_{10}$ or phenyl), or $R^{8C}$-substituted or unsubstituted heteroaryl (e.g., 5 to 10 membered, 5 to 9 membered, or 5 to 6 membered). $X^{8B}$ is —F, —Cl, —Br, or —I. In embodiments, $R^{8B}$ is independently oxo, halogen, $-CX^{8B}_3$, —CN, —OH, $-NH_2$, —COOH, $-CONH_2$, —SH, $-NHNH_2$, $-ONH_2$, $-NHC(O)NHNH_2$, $-NHC(O)NH_2$, —NHC(O)H, —NHC(O)OH, —NHOH, $-CHX^{8B}_2$, $-CH_2X^{8B}$, $-OCX^{8B}_3$, $-OCH_2X^{8B}$, $-OCHX^{8B}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{8C}$ is independently oxo, halogen, $-CX^{8C}_3$, $-CHX^{8C}_2$, $-CH_2X^{8C}$, $-OCX^{8C}_3$, $-OCH_2X^{8C}$, $-OCHX^{8C}_2$, —CN, —OH, $-NH_2$, —COO H, $-CONH_2$, —SH, $-NHNH_2$, $-ONH_2$, $-NHC(O)NHNH_2$, $-NHC(O)NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{8C}$ is —F, —Cl, —Br, or —I.

In embodiments, $R^9$ is independently hydrogen, $-CX^{93}$, —CN, —COOH, $-CONH_2$, $-CHX^{92}$, $-CH_2X^9$, $R^{9A}$-substituted or unsubstituted alkyl (e.g., $C_1$-$C_8$, $C_1$-$C_6$, $C_1$-$C_4$, or $C_1$-$C_2$), $R^{9A}$-substituted or unsubstituted heteroalkyl (e.g., 2 to 8 membered, 2 to 6 membered, 4 to 6 membered, 2 to 3 membered, or 4 to 5 membered), $R^{9A}$-substituted or unsubstituted cycloalkyl (e.g., $C_3$-$C_8$, $C_3$-$C_6$, $C_4$-$C_6$, or $C_5$-$C_6$), $R^{9A}$-substituted or unsubstituted heterocycloalkyl (e.g., 3 to 6 membered, 4 to 6 membered, 4 to 5 membered, or 5 to 6 membered), $R^{9A}$-substituted or unsubstituted aryl (e.g., $C_6$-$C_{10}$ or phenyl), or $R^{9A}$-substituted or unsubstituted heteroaryl (e.g., 5 to 10 membered, 5 to 9 membered, or 5 to 6 membered). $X^9$ is —F, —Cl, —Br, or —I. In embodiments, $R^9$ is independently hydrogen. In embodiments, $R^9$ is independently methyl. In embodiments, $R^9$ is independently ethyl. In embodiments, $R^9$ is independently hydrogen, $-CX^9_3$, —CN, —COOH, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{9A}$ is independently oxo, halogen, $-CX^{9A}_3$, —CN, —OH, $-NH_2$, —COOH, $-CONH_2$, —SH, $-NHNH_2$, —ONH$_2$, —NHC(O)NHNH$_2$, —NHC(O)NH$_2$, —NHC(O)H, —NHC(O)OH, —NHOH, —CHX$^{9A}_2$, —CH$_2$X$^{9A}$, —OCX$^{9A}_3$, —OCH$_2$X$^{9A}$, —OCHX$^{9A}_2$, R$^{9B}$-substituted or unsubstituted alkyl (e.g., C$_1$-C$_8$, C$_1$-C$_6$, C$_1$-C$_4$, or C$_1$-C$_2$), R$^{9B}$-substituted or unsubstituted heteroalkyl (e.g., 2 to 8 membered, 2 to 6 membered, 4 to 6 membered, 2 to 3 membered, or 4 to 5 membered), R$^{9B}$-substituted or unsubstituted cycloalkyl (e.g., C$_3$-C$_8$, C$_3$-C$_6$, C$_4$-C$_6$, or C$_5$-C$_6$), R$^{9B}$-substituted or unsubstituted heterocycloalkyl (e.g., 3 to 6 membered, 4 to 6 membered, 4 to 5 membered, or 5 to 6 membered), R$^{9B}$-substituted or unsubstituted aryl (e.g., C$_6$-C$_{10}$ or phenyl), or R$^{9B}$-substituted or unsubstituted heteroaryl (e.g., 5 to 10 membered, 5 to 9 membered, or 5 to 6 membered). X$^{9A}$ is —F, —Cl, —Br, or —I. In embodiments, R$^{9A}$ is independently oxo, halogen, —CX$^{9A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{9A}_2$, —CH$_2$X$^{9A}$, —OCX$^{9A}_3$, —OCH$_2$X$^{9A}$, —OCHX$^9_{A2}$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{9B}$ is independently oxo, halogen, —CX$^{9B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{9B}_2$, —CH$_2$X$^{9B}$, —OCX$^{9B}_3$, —OCH$_2$X$^{9B}$, —OCHX$^{9B}_2$, R$^{9C}$-substituted or unsubstituted alkyl (e.g., C$_1$-C$_8$, C$_1$-C$_6$, C$_1$-C$_4$, Or C$_1$-C$_2$), R$^{9C}$-substituted or unsubstituted heteroalkyl (e.g., 2 to 8 membered, 2 to 6 membered, 4 to 6 membered, 2 to 3 membered, or 4 to 5 membered), R$^{9C}$-substituted or unsubstituted cycloalkyl (e.g., C$_3$-C$_8$, C$_3$-C$_6$, C$_4$-C$_6$, or C$_5$-C$_6$), R$^{9C}$-substituted or unsubstituted heterocycloalkyl (e.g., 3 to 6 membered, 4 to 6 membered, 4 to 5 membered, or 5 to 6 membered), R$^{9C}$-substituted or unsubstituted aryl (e.g., C$_6$-C$_{10}$ or phenyl), or R$^{9C}$-substituted or unsubstituted heteroaryl (e.g., 5 to 10 membered, 5 to 9 membered, or 5 to 6 membered). X$^{9B}$ is —F, —Cl, —Br, or —I. In embodiments, R$^{9B}$ is independently oxo, halogen, —CX$^{9B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —OCX$^{9B}_3$, —OCHX$^{9B}_2$, —CHX$^{9B}_2$, —CH$_2$X$^{9B}$, —OCX$^{9B}_3$, —OCH$_2$X$^{9B}$, —OCHX$^{9B}_2$, unsubstituted alkyl (e.g., C$_1$-C$_5$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{9C}$ is independently oxo, halogen, —CX$^{9C}_3$, —CHX$^{9C}_2$, —CH$_2$X$^{9C}$, —OCX$^{9C}_3$, —OCH$_2$X$^{9C}$, —OCHX$^{9C}_2$, —CN, —OH, —NH$_2$, —COO H, —CONH$_2$, —SH, —NHNH$_2$, —ONH$_2$, —NHC(O)NHNH$_2$, —NHC(O)NH$_2$, —NHC(O)H, —NHC(O)OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{9C}$ is —F, —Cl, —Br, or —I.

In embodiments, R$^{10}$ is independently hydrogen, —CX$^{10}_3$, —CN, —COOH, —CONH$_2$, —CHX$^{10}_2$, —CH$_2$X$^{10}$, R$^{10A}$-substituted or unsubstituted alkyl (e.g., C$_1$-C$_8$, C$_1$-C$_6$, C$_1$-C$_4$, or C$_1$-C$_2$), R$^{10A}$-substituted or unsubstituted heteroalkyl (e.g., 2 to 8 membered, 2 to 6 membered, 4 to 6 membered, 2 to 3 membered, or 4 to 5 membered), R$^{10A}$-substituted or unsubstituted cycloalkyl (e.g., C$_3$-C$_8$, C$_3$-C$_6$, C$_4$-C$_6$, or C$_5$-C$_6$), R$^{10A}$-substituted or unsubstituted heterocycloalkyl (e.g., 3 to 6 membered, 4 to 6 membered, 4 to 5 membered, or 5 to 6 membered), R$^{10A}$-substituted or unsubstituted aryl (e.g., C$_6$-C$_{10}$ or phenyl), or R$^{10A}$-substituted or unsubstituted heteroaryl (e.g., 5 to 10 membered, 5 to 9 membered, or 5 to 6 membered). X$^{10}$ is —F, —Cl, —Br, or —I. In embodiments, R$^{10}$ is independently hydrogen. In embodiments, R$^{10}$ is independently methyl. In embodiments, R$^{10}$ is independently ethyl. In embodiments, R$^{10}$ is independently hydrogen, —CX$^{10}_3$, —CN, —COOH, —CONH$_2$, unsubstituted alkyl (e.g., C$_1$-C$_5$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{10A}$ is independently oxo, halogen, —CX$^{A3}$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{10A}_2$, —CH$_2$X$^{10A}$, —OCX$^{10A}_3$, —OCH$_2$X$^{10A}$, —OCHX$^{10A}_2$, R$^{10B}$-substituted or unsubstituted alkyl (e.g., C$_1$-C$_8$, C$_1$-C$_6$, C$_1$-C$_4$, or C$_1$-C$_2$), R$^{10B}$-substituted or unsubstituted heteroalkyl (e.g., 2 to 8 membered, 2 to 6 membered, 4 to 6 membered, 2 to 3 membered, or 4 to 5 membered), R$^{10B}$-substituted or unsubstituted cycloalkyl (e.g., C$_3$-C$_8$, C$_3$-C$_6$, C$_4$-C$_6$, or C$_5$-C$_6$), R$^{10B}$-substituted or unsubstituted heterocycloalkyl (e.g., 3 to 6 membered, 4 to 6 membered, 4 to 5 membered, or 5 to 6 membered), R$^{10B}$-substituted or unsubstituted aryl (e.g., C$_6$-C$_{10}$ or phenyl), or R$^{10B}$-substituted or unsubstituted heteroaryl (e.g., 5 to 10 membered, 5 to 9 membered, or 5 to 6 membered). X$^{10A}$ is —F, —Cl, —Br, or —I. In embodiments, R$^{10A}$ is independently oxo, halogen, —CX$^{10A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{10A}_2$, —CH$_2$X$^{10A}$, —OCX$^{10A}_3$, —OCH$_2$X$^{10A}$, —OCHX$^{10A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{10B}$ is independently oxo, halogen, —CX$^{10B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{10B}_2$, —CH$_2$X$^{10B}$, —OCX$^{10B}_3$, —OCH$_2$X$^{10B}$, —OCHX$^{10B}_2$, R$^{10C}$-substituted or unsubstituted alkyl (e.g., C$_1$-C$_8$, C$_1$-C$_6$, C$_1$-C$_4$, or C$_1$-C$_2$), R$^{10C}$-substituted or unsubstituted heteroalkyl (e.g., 2 to 8 membered, 2 to 6 membered, 4 to 6 membered, 2 to 3 membered, or 4 to 5 membered), $R^{10C}$-substituted or unsubstituted cycloalkyl (e.g., $C_3$-$C_8$, $C_3$-$C_6$, $C_4$-$C_6$, or $C_5$-$C_6$), $R^{10C}$-substituted or unsubstituted heterocycloalkyl (e.g., 3 to 6 membered, 4 to 6 membered, 4 to 5 membered, or 5 to 6 membered), $R^{10C}$-substituted or unsubstituted aryl (e.g., $C_6$-$C_{10}$ or phenyl), or $R^{10C}$-substituted or unsubstituted heteroaryl (e.g., 5 to 10 membered, 5 to 9 membered, or 5 to 6 membered). $X^{10B}$ is —F, —Cl, —Br, or —I. In embodiments, $R^{10B}$ is independently oxo, halogen, $—CX^{10B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{10B}_2$, $—CH_2X^{10B}$, $—OCX^{10B}_3$, $—OCH_2X^{10B}$, $—OCHX^{10B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{10C}$ is independently oxo, halogen, $—CX^{10C}_3$, $—CHX^{10C}_2$, $—CH_2X^{10C}$, $—OCX^{10C}_3$, $—OCH_2X^{10C}$, $—OCHX^{10C}_2$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{10C}$ is —F, —Cl, —Br, or —I.

In embodiments, $R^{11}$ is independently hydrogen, $—CX^{11}_3$, —CN, —COOH, $—CONH_2$, $—CHX^{11}_2$, $—CH_2X^{11}$, $R^{11A}$-substituted or unsubstituted alkyl (e.g., $C_1$-$C_8$, $C_1$-$C_6$, $C_1$-$C_4$, or $C_1$-$C_2$), $R^{11A}$-substituted or unsubstituted heteroalkyl (e.g., 2 to 8 membered, 2 to 6 membered, 4 to 6 membered, 2 to 3 membered, or 4 to 5 membered), $R^{11A}$-substituted or unsubstituted cycloalkyl (e.g., $C_3$-$C_8$, $C_3$-$C_6$, $C_4$-$C_6$, or $C_5$-$C_6$), $R^{11A}$-substituted or unsubstituted heterocycloalkyl (e.g., 3 to 6 membered, 4 to 6 membered, 4 to 5 membered, or 5 to 6 membered), $R^{11A}$-substituted or unsubstituted aryl (e.g., $C_6$-$C_{10}$ or phenyl), or $R^{11A}$-substituted or unsubstituted heteroaryl (e.g., 5 to 10 membered, 5 to 9 membered, or 5 to 6 membered). $X^{11}$ is —F, —Cl, —Br, or —I. In embodiments, $R^{11}$ is independently hydrogen. In embodiments, $R^{11}$ is independently methyl. In embodiments, $R^{11}$ is independently ethyl. In embodiments, $R^{11}$ is independently hydrogen, $—CX^{11}_3$, —CN, —COOH, $—CONH_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{11}$ and $R^{12}$ substituents bonded to the same nitrogen atom may optionally be joined to form a $R^{11A}$-substituted or unsubstituted heterocycloalkyl or $R^{11A}$-substituted or unsubstituted heteroaryl. In embodiments, $R^{11}$ and $R^{12}$ substituents bonded to the same nitrogen atom may optionally be joined to form a $R^{11A}$-substituted or unsubstituted 3 to 6 membered heterocycloalkyl or $R^{11A}$-substituted or unsubstituted 5 to 6 membered heteroaryl. In embodiments, $R^{11}$ and $R^{12}$ substituents bonded to the same nitrogen atom may optionally be joined to form an unsubstituted 3 to 6 membered heterocycloalkyl or unsubstituted 5 to 6 membered heteroaryl. In embodiments, $R^{11}$ and $R^{12}$ substituents bonded to the same nitrogen atom may optionally be joined to form a $R^{11A}$-substituted or unsubstituted piperazinyl. In embodiments, $R^{11}$ and $R^{12}$ substituents bonded to the same nitrogen atom may optionally be joined to form a $R^{11A}$-substituted or unsubstituted piperidinyl. In embodiments, $R^{11}$ and $R^{12}$ substituents bonded to the same nitrogen atom may optionally be joined to form a $R^{11A}$-substituted or unsubstituted pyrrolidinyl. In embodiments, $R^{11}$ and $R^{12}$ substituents bonded to the same nitrogen atom may optionally be joined to form a $R^{11A}$-substituted or unsubstituted azetidinyl. In embodiments, $R^{11}$ and $R^{12}$ substituents bonded to the same nitrogen atom may optionally be joined to form a $R^{11A}$-substituted or unsubstituted morpholinyl. In embodiments, $R^{11}$ and $R^{12}$ substituents bonded to the same nitrogen atom may optionally be joined to form a $R^{11A}$-substituted or unsubstituted azeridinyl.

$R^{11A}$ is independently oxo, halogen, $—CX^{11A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{11A}_2$, $—CH_2X^{11A}$, $—OCX^{11}_3$, $—OCH_2X^{11A}$, $—OCHX^{11A}_2$, $R^{11B}$-substituted or unsubstituted alkyl (e.g., $C_1$-$C_8$, $C_1$-$C_6$, $C_1$-$C_4$, or $C_1$-$C_2$), $R^{11B}$-substituted or unsubstituted heteroalkyl (e.g., 2 to 8 membered, 2 to 6 membered, 4 to 6 membered, 2 to 3 membered, or 4 to 5 membered), $R^{11B}$-substituted or unsubstituted cycloalkyl (e.g., $C_3$-$C_8$, $C_3$-$C_6$, $C_4$-$C_6$, or $C_5$-$C_6$), $R^{11B}$-substituted or unsubstituted heterocycloalkyl (e.g., 3 to 6 membered, 4 to 6 membered, 4 to 5 membered, or 5 to 6 membered), $R^{11B}$-substituted or unsubstituted aryl (e.g., $C_6$-$C_{10}$ or phenyl), or $R^{11B}$-substituted or unsubstituted heteroaryl (e.g., 5 to 10 membered, 5 to 9 membered, or 5 to 6 membered). $X^{11A}$ is —F, —Cl, —Br, or —I. In embodiments, $R^{11A}$ is independently oxo, halogen, $—CX^{11A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{11A}_2$, $—CH_2X^{11}$, $—OCX^{11A}_3$, $—OCH_2X^{11A}$, $—OCHX^{A}2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{11B}$ is independently oxo, halogen, $—CX^{11B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{11B}_2$, $—CH_2X^{11B}$, $—OCX^{11B}_3$, $—OCH_2X^{11B}$, $—OCHX^{11B}_2$, $R^{11C}$-substituted or unsubstituted alkyl (e.g., $C_1$-$C_5$, $C_1$-$C_6$, $C_1$-$C_4$, or $C_1$-$C_2$), $R^{11C}$-substituted or unsubstituted heteroalkyl (e.g., 2 to 8 membered, 2 to 6 membered, 4 to 6 membered, 2 to 3 membered, or 4 to 5 membered), $R^{11C}$-substituted or unsubstituted cycloalkyl (e.g., $C_3$-$C_8$, $C_3$-$C_6$, $C_4$-$C_6$, or $C_5$-$C_6$), $R^{11C}$-substituted or unsubstituted heterocycloalkyl (e.g., 3 to 6 membered, 4 to 6 membered, 4 to 5 membered, or 5 to 6 membered), $R^{11C}$-substituted or unsubstituted aryl (e.g., $C_6$-$C_{10}$ or phenyl), or $R^{11C}$-substituted or unsubstituted heteroaryl (e.g., 5 to 10 membered, 5 to 9 membered, or 5 to 6 membered). $X^{11B}$ is —F, —Cl, —Br, or —I. In embodiments, $R^{11B}$ is independently oxo, halogen, $—CX^{11B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{11B}_2$, $—CH_2X^{11B}$, $—OCX^{11B}_3$, $—OCH_2X^{11B}$, $—OCHX^{11B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{11C}$ is independently oxo, halogen, $—CX^{11C}_3$, $—CHX^{11C}_2$, $—CH_2X^{11C}$, $—OCX^{11C}_3$, $—OCH_2X^{11C}$, $—OCHX^{11C}_2$, —CN, —OH, $—NH_2$, —C OOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{11C}$ is —F, —Cl, —Br, or —I.

In embodiments, $R^{12}$ is independently hydrogen, $—CX^{12}_3$, —CN, —COOH, $—CONH_2$, $—CHX^{12}_2$, $—CH_2X^{12}$, $R^{12A}$-substituted or unsubstituted alkyl (e.g., $C_1$-$C_8$, $C_1$-$C_6$, $C_1$-$C_4$, or $C_1$-$C_2$), $R^{12A}$-substituted or unsubstituted heteroalkyl (e.g., 2 to 8 membered, 2 to 6 membered, 4 to 6 membered, 2 to 3 membered, or 4 to 5 membered), $R^{12A}$-substituted or unsubstituted cycloalkyl (e.g., $C_3$-$C_8$, $C_3$-$C_6$, $C_4$-$C_6$, or $C_5$-$C_6$), $R^{12A}$-substituted or unsubstituted heterocycloalkyl (e.g., 3 to 6 membered, 4 to 6 membered, 4 to 5 membered, or 5 to 6 membered), $R^{12A}$-substituted or unsubstituted aryl (e.g., $C_6$-$C_{10}$ or phenyl), or $R^{12A}$-substituted or unsubstituted heteroaryl (e.g., 5 to 10 membered, 5 to 9 membered, or 5 to 6 membered). $X^{12}$ is —F, —Cl, —Br, or —I. In embodiments, $R^{12}$ is independently hydrogen. In embodiments, $R^{12}$ is independently methyl. In embodiments, $R^{12}$ is independently ethyl. In embodiments, $R^{12}$ is independently hydrogen, $—CX^{12}$ 3, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{12}$ and $R^{11}$ substituents bonded to the same nitrogen atom may optionally be joined to form a $R^{12A}$-substituted or unsubstituted heterocycloalkyl or $R^{12A}$ substituted or unsubstituted heteroaryl. In embodiments, $R^{12}$ and $R^{11}$ substituents bonded to the same nitrogen atom may optionally be joined to form a $R^{12A}$-substituted or unsubstituted 3 to 6 membered heterocycloalkyl or $R^{12A}$-substituted or unsubstituted 5 to 6 membered heteroaryl. In embodiments, $R^{12}$ and $R^{11}$ substituents bonded to the same nitrogen atom may optionally be joined to form an unsubstituted 3 to 6 membered heterocycloalkyl or unsubstituted 5 to 6 membered heteroaryl. In embodiments, $R^{12}$ and $R^{11}$ substituents bonded to the same nitrogen atom may optionally be joined to form a $R^{12A}$-substituted or unsubstituted piperazinyl. In embodiments, $R^{12}$ and $R^{11}$ substituents bonded to the same nitrogen atom may optionally be joined to form a $R^{12A}$-substituted or unsubstituted piperidinyl. In embodiments, $R^{12}$ and $R^{11}$ substituents bonded to the same nitrogen atom may optionally be joined to form a $R^{12A}$-substituted or unsubstituted pyrrolidinyl. In embodiments, $R^{12}$ and $R^{11}$ substituents bonded to the same nitrogen atom may optionally be joined to form a $R^{12A}$-substituted or unsubstituted azetidinyl. In embodiments, $R^{12}$ and $R^{11}$ substituents bonded to the same nitrogen atom may optionally be joined to form a $R^{12A}$-substituted or unsubstituted morpholinyl. In embodiments, $R^{12}$ and $R^{11}$ substituents bonded to the same nitrogen atom may optionally be joined to form a $R^{12A}$-substituted or unsubstituted azeridinyl.

$R^{12A}$ is independently oxo, halogen, $—CX^{12A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{12A}_2$, $—CH_2X^{12A}$, $—OCX^{12A}_3$, $—OCH_2X^{12A}$, $—OCHX^{12A}_2$, $R^{12B}$-substituted or unsubstituted alkyl (e.g., $C_1$-$C_8$, $C_1$-$C_6$, $C_1$-$C_4$, or $C_1$-$C_2$), $R^{12B}$-substituted or unsubstituted heteroalkyl (e.g., 2 to 8 membered, 2 to 6 membered, 4 to 6 membered, 2 to 3 membered, or 4 to 5 membered), $R^{12B}$-substituted or unsubstituted cycloalkyl (e.g., $C_3$-$C_8$, $C_3$-$C_6$, $C_4$-$C_6$, or $C_5$-$C_6$), $R^{12B}$-substituted or unsubstituted heterocycloalkyl (e.g., 3 to 6 membered, 4 to 6 membered, 4 to 5 membered, or 5 to 6 membered), $R^{12B}$-substituted or unsubstituted aryl (e.g., $C_6$-$C_{10}$ or phenyl), or $R^{12B}$-substituted or unsubstituted heteroaryl (e.g., 5 to 10 membered, 5 to 9 membered, or 5 to 6 membered). $X^{12A}$ is —F, —Cl, —Br, or —I. In embodiments, $R^{12A}$ is independently oxo, halogen, $—CX^{12A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{12A}_2$, $—CH_2X^{12A}$, $—OCX^{12A}_3$, $—OCH_2X^{12A}$, $—OCHX^{12A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{12B}$ is independently oxo, halogen, $—CX^{12B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{12B}_2$, $—CH_2X^{12B}$, $—OCX^{12B}_3$, $—OCH_2X^{12B}$, $—OCHX^{12B}_2$, $R^{12C}$-substituted or unsubstituted alkyl (e.g., $C_1$-$C_8$, $C_1$-$C_6$, $C_1$-$C_4$, or $C_1$-$C_2$), $R^{12C}$-substituted or unsubstituted heteroalkyl (e.g., 2 to 8 membered, 2 to 6 membered, 4 to 6 membered, 2 to 3 membered, or 4 to 5 membered), $R^{12C}$-substituted or unsubstituted cycloalkyl (e.g., $C_3$-$C_8$, $C_3$-$C_6$, $C_4$-$C_6$, or $C_5$-$C_6$), $R^{12C}$-substituted or unsubstituted heterocycloalkyl (e.g., 3 to 6 membered, 4 to 6 membered, 4 to 5 membered, or 5 to 6 membered), $R^{12C}$-substituted or unsubstituted aryl (e.g., $C_6$-$C_{10}$ or phenyl), or $R^{12C}$-substituted or unsubstituted heteroaryl (e.g., 5 to 10 membered, 5 to 9 membered, or 5 to 6 membered). $X^{12B}$ is —F, —Cl, —Br, or —I. In embodiments, $R^{12B}$ is independently oxo, halogen, $—CX^{12B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{12B}_2$, —$CH_2X^{12B}$, —$OCX^{12B}_3$, —$OCH_2X^{12B}$, —$OCHX^{12B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{12C}$ is independently oxo, halogen, —$CX^{12C}_3$, —$CHX^{12C}_2$, —$CH_2X^{12C}$, —$OCX^{12C}_3$, —$OCH_2X^{12C}$, —$OCHX^{12C}_2$, —CN, —OH, —$NH_2$, —C OOH, —$CONH_2$, —SH, —$NHNH_2$, —$ONH_2$, —NHC(O)$NHNH_2$, —NHC (O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{12C}$ is —F, —Cl, —Br, or —I.

In embodiments, $R^{13}$ is independently hydrogen, —$CX^{13}_3$, —CN, —COOH, —$CONH_2$, —$CHX^{13}_2$, —$CH_2X^{13}$, $R^{13A}$-substituted or unsubstituted alkyl (e.g., $C_1$-$C_8$, $C_1$-$C_6$, $C_1$-$C_4$, or $C_1$-$C_2$), $R^{13A}$-substituted or unsubstituted heteroalkyl (e.g., 2 to 8 membered, 2 to 6 membered, 4 to 6 membered, 2 to 3 membered, or 4 to 5 membered), $R^{13A}$-substituted or unsubstituted cycloalkyl (e.g., $C_3$-$C_8$, $C_3$-$C_6$, $C_4$-$C_6$, or $C_5$-$C_6$), $R^{13A}$-substituted or unsubstituted heterocycloalkyl (e.g., 3 to 6 membered, 4 to 6 membered, 4 to 5 membered, or 5 to 6 membered), $R^{13A}$-substituted or unsubstituted aryl (e.g., $C_6$-$C_{10}$ or phenyl), or $R^{13A}$-substituted or unsubstituted heteroaryl (e.g., 5 to 10 membered, 5 to 9 membered, or 5 to 6 membered). $X^{13}$ is —F, —Cl, —Br, or —I. In embodiments, $R^{13}$ is independently hydrogen. In embodiments, $R^{13}$ is independently methyl. In embodiments, $R^{13}$ is independently ethyl. In embodiments, $R^{13}$ is independently hydrogen, —$CX^{13}_3$, —CN, —COOH, —$CONH_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{13A}$ is independently oxo, halogen, —$CX^{13}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O) H, —NHC(O)OH, —NHOH, —$CHX^{13A}_2$, —$CH_2X^{13A}$, —$OCX^{13A}_3$, —$OCH_2X^{13A}$, —$OCHX^{13A}$2, $R^{13B}$-substituted or unsubstituted alkyl (e.g., $C_1$-$C_8$, $C_1$-$C_6$, $C_1$-$C_4$, or $C_1$-$C_2$), $R^{13B}$-substituted or unsubstituted heteroalkyl (e.g., 2 to 8 membered, 2 to 6 membered, 4 to 6 membered, 2 to 3 membered, or 4 to 5 membered), $R^{13B}$-substituted or unsubstituted cycloalkyl (e.g., $C_3$-$C_8$, $C_3$-$C_6$, $C_4$-$C_6$, or $C_5$-$C_6$), $R^{13B}$-substituted or unsubstituted heterocycloalkyl (e.g., 3 to 6 membered, 4 to 6 membered, 4 to 5 membered, or 5 to 6 membered), $R^{13B}$-substituted or unsubstituted aryl (e.g., $C_6$-$C_{10}$ or phenyl), or $R^{13B}$-substituted or unsubstituted heteroaryl (e.g., 5 to 10 membered, 5 to 9 membered, or 5 to 6 membered). $X^{13A}$ is —F, —Cl, —Br, or —I. In embodiments, $R^{13A}$ is independently oxo, halogen, —$CX^{13A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{13A}_2$, —$CH_2X^{13A}$, —$OCX^{13A}_3$, —$OCH_2X^{13A}$, —$OCHX^{13A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{13B}$ is independently oxo, halogen, —$CX^{13B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O) H, —NHC(O)OH, —NHOH, —$CHX^{13B}_2$, —$CH_2X^{13B}$, —$OCX^{13B}_3$, —$OCH_2X^{13B}$, —$OCHX^{13B}_2$, $R^{13C}$-substituted or unsubstituted alkyl (e.g., $C_1$-$C_8$, $C_1$-$C_6$, $C_1$-$C_4$, or $C_1$-$C_2$), $R^{13C}$-substituted or unsubstituted heteroalkyl (e.g., 2 to 8 membered, 2 to 6 membered, 4 to 6 membered, 2 to 3 membered, or 4 to 5 membered), $R^{13C}$-substituted or unsubstituted cycloalkyl (e.g., $C_3$-$C_8$, $C_3$-$C_6$, $C_4$-$C_6$, or $C_5$-$C_6$), $R^{13C}$-substituted or unsubstituted heterocycloalkyl (e.g., 3 to 6 membered, 4 to 6 membered, 4 to 5 membered, or 5 to 6 membered), $R^{13C}$-substituted or unsubstituted aryl (e.g., $C_6$-$C_{10}$ or phenyl), or $R^{13C}$-substituted or unsubstituted heteroaryl (e.g., 5 to 10 membered, 5 to 9 membered, or 5 to 6 membered). $X^{13B}$ is —F, —Cl, —Br, or —I. In embodiments, $R^{13B}$ is independently oxo, halogen, —$CX^{13B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{13B}_2$, —$CH_2X^{13B}$, —$OCX^{13B}_3$, —$OCH_2X^{13B}$, —$OCHX^{13B}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{13C}$ is independently oxo, halogen, —$CX^{13C}_3$, —$CHX^{13}C_2$, —$CH_2X^{13C}$, —$OCX^{13C}_3$, —$OCH_2X^{13C}$, —$OCHX^{13C}_2$, —CN, —OH, —$NH_2$, —C OOH, —$CONH_2$, —SH, —$NHNH_2$, —$ONH_2$, —NHC(O)$NHNH_2$, —NHC (O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{13C}$ is —F, —Cl, —Br, or —I.

In embodiments, $R^{14}$ is independently hydrogen, —$CX^{14}_3$, —CN, —COOH, —$CONH_2$, —$CHX^{14}_2$, —$CH_2X^{14}$, $R^{14A}$-substituted or unsubstituted alkyl (e.g., $C_1$-$C_8$, $C_1$-$C_6$, $C_1$-$C_4$, or $C_1$-$C_2$), $R^{14A}$-substituted or unsubstituted heteroalkyl (e.g., 2 to 8 membered, 2 to 6 membered, 4 to 6 membered, 2 to 3 membered, or 4 to 5 membered), $R^{14A}$-substituted or unsubstituted cycloalkyl (e.g., $C_3$-$C_8$, $C_3$-$C_6$, $C_4$-$C_6$, or $C_5$-$C_6$), $R^{14A}$-substituted or unsubstituted heterocycloalkyl (e.g., 3 to 6 membered, 4 to 6 membered, 4 to 5 membered, or 5 to 6 membered), $R^{14A}$-substituted or unsubstituted aryl (e.g., $C_6$-$C_{10}$ or phenyl), or $R^{14A}$-substituted or unsubstituted heteroaryl (e.g., 5 to 10 membered, 5 to 9 membered, or 5 to 6 membered). $X^{14}$ is —F, —Cl, —Br, or —I. In embodiments, $R^{14}$ is independently hydrogen. In embodiments, $R^{14}$ is independently methyl. In embodiments, $R^{14}$ is independently ethyl. In embodiments, $R^{14}$ is independently hydrogen, —$CX^{14}$ 3, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{14A}$ is independently oxo, halogen, —$CX^{14A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{14A}_2$, —$CH_2X^{14A}$, —$OCX^{14A}_3$, —$OCH_2X^{14A}$, —$OCHX^{14A}$2, $R^{14B}$-substituted or unsubstituted alkyl (e.g., $C_1$-$C_8$, $C_1$-$C_6$, $C_1$-$C_4$, or $C_1$-$C_2$), $R^{14B}$-substituted or unsubstituted heteroalkyl (e.g., 2 to 8 membered, 2 to 6 membered, 4 to 6 membered, 2 to 3 membered, or 4 to 5 membered), $R^{14B}$-substituted or unsubstituted cycloalkyl (e.g., $C_3$-$C_8$, $C_3$-$C_6$, $C_4$-$C_6$, or $C_5$-$C_6$), $R^{14B}$-substituted or unsubstituted heterocycloalkyl (e.g., 3 to 6 membered, 4 to 6 membered, 4 to 5 membered, or 5 to 6 membered), $R^{14B}$-substituted or unsubstituted aryl (e.g., $C_6$-$C_{10}$ or phenyl), or $R^{14B}$-substituted or unsubstituted heteroaryl (e.g., 5 to 10 membered, 5 to 9 membered, or 5 to 6 membered). $X^{14A}$ is —F, —Cl, —Br, or —I. In embodiments, $R^{14A}$ is independently oxo, halogen, —$CX^{14A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{14A}_2$, —$CH_2X^{14A}$, —$OCX^{14A}_3$, —$OCH_2X^{14A}$, —$OCHX^{14A}$2, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{14B}$ is independently oxo, halogen, —$CX^{14B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{14B}_2$, —$CH_2X^{14B}$, —$OCX^{14B}_3$, —$OCH_2X^{14B}$, —$OCHX^{14B}$2, $R^{14C}$-substituted or unsubstituted alkyl (e.g., $C_1$-$C_8$, $C_1$-$C_6$, $C_1$-$C_4$, or $C_1$-$C_2$), $R^{14C}$-substituted or unsubstituted heteroalkyl (e.g., 2 to 8 membered, 2 to 6 membered, 4 to 6 membered, 2 to 3 membered, or 4 to 5 membered), $R^{14C}$-substituted or unsubstituted cycloalkyl (e.g., $C_3$-$C_8$, $C_3$-$C_6$, $C_4$-$C_6$, or $C_5$-$C_6$), $R^{14C}$-substituted or unsubstituted heterocycloalkyl (e.g., 3 to 6 membered, 4 to 6 membered, 4 to 5 membered, or 5 to 6 membered), $R^{14C}$-substituted or unsubstituted aryl (e.g., $C_6$-$C_{10}$ or phenyl), or $R^{14C}$-substituted or unsubstituted heteroaryl (e.g., 5 to 10 membered, 5 to 9 membered, or 5 to 6 membered). $X^{14B}$ is —F, —Cl, —Br, or —I. In embodiments, $R^{14B}$ is independently oxo, halogen, —$CX^{14B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{14B}_2$, —$CH_2X^{14B}$, —$OCX^{14B}_3$, —$OCH_2X^{14B}$, —$OCHX^{14B}$2, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{14C}$ is independently oxo, halogen, —$CX^{14C}_3$, —$CHX^{14}C_2$, —$CH_2X^{14C}$, —$OCX^{14C}_3$, —$OCH_2X^{14C}$, —$OCHX^{14C}_2$, —CN, —OH, —$NH_2$, —C OOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{14C}$ is —F, —Cl, —Br, or —I.

In embodiments, $R^{15}$ is independently hydrogen, —$CX^{15}_3$, —CN, —COOH, —$CONH_2$, —$CHX^{15}_2$, —$CH_2X^{15}$, $R^{15A}$-substituted or unsubstituted alkyl (e.g., $C_1$-$C_5$, $C_1$-$C_6$, $C_1$-$C_4$, or $C_1$-$C_2$), $R^{15A}$-substituted or unsubstituted heteroalkyl (e.g., 2 to 8 membered, 2 to 6 membered, 4 to 6 membered, 2 to 3 membered, or 4 to 5 membered), $R^{15A}$-substituted or unsubstituted cycloalkyl (e.g., $C_3$-$C_8$, $C_3$-$C_6$, $C_4$-$C_6$, or $C_5$-$C_6$), $R^{15A}$-substituted or unsubstituted heterocycloalkyl (e.g., 3 to 6 membered, 4 to 6 membered, 4 to 5 membered, or 5 to 6 membered), $R^{15A}$-substituted or unsubstituted aryl (e.g., $C_6$-$C_{10}$ or phenyl), or $R^{15A}$-substituted or unsubstituted heteroaryl (e.g., 5 to 10 membered, 5 to 9 membered, or 5 to 6 membered). $X^{15}$ is —F, —Cl, —Br, or —I. In embodiments, $R^{15}$ is independently hydrogen. In embodiments, $R^{15}$ is independently methyl. In embodiments, $R^{15}$ is independently ethyl. In embodiments, $R^{15}$ is independently hydrogen, —$CX^{15}$ 3, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{15}$ and $R^{16}$ substituents bonded to the same nitrogen atom may optionally be joined to form a $R^{15A}$-substituted or unsubstituted heterocycloalkyl or $R^{15A}$-substituted or unsubstituted heteroaryl. In embodiments, $R^{15}$ and $R^{16}$ substituents bonded to the same nitrogen atom may optionally be joined to form a $R^{15A}$-substituted or unsubstituted 3 to 6 membered heterocycloalkyl or $R^{15A}$-substituted or unsubstituted 5 to 6 membered heteroaryl. In embodiments, $R^{15}$ and $R^{16}$ substituents bonded to the same nitrogen atom may optionally be joined to form an unsubstituted 3 to 6 membered heterocycloalkyl or unsubstituted 5 to 6 membered heteroaryl. In embodiments, $R^{15}$ and $R^{16}$ substituents bonded to the same nitrogen atom may optionally be joined to form a $R^{15A}$-substituted or unsubstituted piperazinyl. In embodiments, $R^{15}$ and $R^{16}$ substituents bonded to the same nitrogen atom may optionally be joined to form a $R^{15A}$-substituted or unsubstituted piperidinyl. In embodiments, $R^{15}$ and $R^{16}$ substituents bonded to the same nitrogen atom may optionally be joined to form a $R^{15A}$-substituted or unsubstituted pyrrolidinyl. In embodiments, $R^{15}$ and $R^{16}$ substituents bonded to the same nitrogen atom may optionally be joined to form a $R^{15A}$-substituted or unsubstituted azetidinyl. In embodiments, $R^{15}$ and $R^{16}$ substituents bonded to the same nitrogen atom may optionally be joined to form a $R^{15A}$-substituted or unsubstituted morpholinyl. In embodiments, $R^{15}$ and $R^{16}$ substituents bonded to the same nitrogen atom may optionally be joined to form a $R^{15A}$-substituted or unsubstituted azeridinyl.

$R^{15A}$ is independently oxo, halogen, —$CX^{15A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{15A}_2$, —$CH_2X^{15A}$, —$OCX^{15A}_3$, —$OCH_2X^{15A}$, —$OCHX^{15A}_2$, $R^{15B}$-substituted or unsubstituted alkyl (e.g., $C_1$-$C_5$, $C_1$-$C_6$, $C_1$-$C_4$, or $C_1$-$C_2$), $R^{15B}$-substituted or unsubstituted heteroalkyl (e.g., 2 to 8 membered, 2 to 6 membered, 4 to 6 membered, 2 to 3 membered, or 4 to 5 membered), $R^{15B}$-substituted or unsubstituted cycloalkyl (e.g., $C_3$-$C_8$, $C_3$-$C_6$, $C_4$-$C_6$, or $C_5$-$C_6$), $R^{15B}$-substituted or unsubstituted heterocycloalkyl (e.g., 3 to 6 membered, 4 to 6 membered, 4 to 5 membered, or 5 to 6 membered), $R^{15B}$-substituted or unsubstituted aryl (e.g., $C_6$-$C_{10}$ or phenyl), or $R^{15B}$-substituted or unsubstituted heteroaryl (e.g., 5 to 10 membered, 5 to 9 membered, or 5 to 6 membered). $X^{15A}$ is —F, —Cl, —Br, or —I. In embodiments, $R^{15A}$ is independently oxo, halogen, —$CX^{15A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{15A}_2$, —$CH_2X^{15A}$, —$OCX^{15A}_3$, —$OCH_2X^{15A}$, —$OCHX^{15A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{15B}$ is independently oxo, halogen, —$CX^{15B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{15B}_2$, —$CH_2X^{15B}$, —$OCX^{15B}_3$, —$OCH_2X^{15B}$, —$OCHX^{15B}2$, $R^{15C}$-substituted or unsubstituted alkyl (e.g., $C_1$-$C_8$, $C_1$-$C_6$, $C_1$-$C_4$, or $C_1$-$C_2$), $R^{15C}$-substituted or unsubstituted heteroalkyl (e.g., 2 to 8 membered, 2 to 6 membered, 4 to 6 membered, 2 to 3 membered, or 4 to 5 membered), $R^{15C}$-substituted or unsubstituted cycloalkyl (e.g., $C_3$-$C_8$, $C_3$-$C_6$, $C_4$-$C_6$, or $C_5$-$C_6$), $R^1$SC-substituted or unsubstituted heterocycloalkyl (e.g., 3 to 6 membered, 4 to 6 membered, 4 to 5 membered, or 5 to 6 membered), $R^{15C}$-substituted or unsubstituted aryl (e.g., $C_6$-$C_{10}$ or phenyl), or $R^{15C}$-substituted or unsubstituted heteroaryl (e.g., 5 to 10 membered, 5 to 9 membered, or 5 to 6 membered). $X^{15B}$ is —F, —Cl, —Br, or —I. In embodiments, $R^{15B}$ is independently oxo, halogen, —$CX^{15B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{15B}_2$, —$CH_2X^{15B}$, —$OCX^{15B}_3$, —$OCH_2X^{15B}$, —$OCHX^{15B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{15C}$ is independently oxo, halogen, —$CX^{15C}_3$, —$CHX^{15}C_2$, —$CH_2X^{15c}$, —$OCX^{15C}_3$, —$OCH_2X^{15C}$, —$OCHX^{15C}_2$, —CN, —OH, —$NH_2$, —C OOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15C}$ is —F, —Cl, —Br, or —I.

In embodiments, $R^{16}$ is independently hydrogen, —$CX^{16}_3$, —CN, —COOH, —$CONH_2$, —$CHX^{16}_2$, —$CH_2X^{16}$, $R^{16A}$-substituted or unsubstituted alkyl (e.g., $C_1$-$C_8$, $C_1$-$C_6$, $C_1$-$C_4$, or $C_1$-$C_2$), $R^{16A}$-substituted or unsubstituted heteroalkyl (e.g., 2 to 8 membered, 2 to 6 membered, 4 to 6 membered, 2 to 3 membered, or 4 to 5 membered), $R^{16A}$-substituted or unsubstituted cycloalkyl (e.g., $C_3$-$C_8$, $C_3$-$C_6$, $C_4$-$C_6$, or $C_5$-$C_6$), $R^{16A}$-substituted or unsubstituted heterocycloalkyl (e.g., 3 to 6 membered, 4 to 6 membered, 4 to 5 membered, or 5 to 6 membered), $R^{16A}$-substituted or unsubstituted aryl (e.g., $C_6$-$C_{10}$ or phenyl), or $R^{16A}$-substituted or unsubstituted heteroaryl (e.g., 5 to 10 membered, 5 to 9 membered, or 5 to 6 membered). $X^{16}$ is —F, —Cl, —Br, or —I. In embodiments, $R^{16}$ is independently hydrogen. In embodiments, $R^{16}$ is independently methyl. In embodiments, $R^{16}$ is independently ethyl. In embodiments, $R^{16}$ is independently hydrogen, —$CX^{16}$ 3, —CN, —COOH, —$CONH_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{16}$ and $R^{15}$ substituents bonded to the same nitrogen atom may optionally be joined to form a $R^{16A}$-substituted or unsubstituted heterocycloalkyl or $R^{16A}$-substituted or unsubstituted heteroaryl. In embodiments, $R^{16}$ and $R^{15}$ substituents bonded to the same nitrogen atom may optionally be joined to form a $R^{16A}$-substituted or unsubstituted 3 to 6 membered heterocycloalkyl or $R^{16A}$-substituted or unsubstituted 5 to 6 membered heteroaryl. In embodiments, $R^{16}$ and $R^{15}$ substituents bonded to the same nitrogen atom may optionally be joined to form an unsubstituted 3 to 6 membered heterocycloalkyl or unsubstituted 5 to 6 membered heteroaryl. In embodiments, $R^{16}$ and $R^{15}$ substituents bonded to the same nitrogen atom may optionally be joined to form a $R^{16A}$-substituted or unsubstituted piperazinyl. In embodiments, $R^{16}$ and $R^{15}$ substituents bonded to the same nitrogen atom may optionally be joined to form a $R^{16A}$-substituted or unsubstituted piperidinyl. In embodiments, $R^{16}$ and $R^{15}$ substituents bonded to the same nitrogen atom may optionally be joined to form a $R^{16A}$-substituted or unsubstituted pyrrolidinyl. In embodiments, $R^{16}$ and $R^{15}$ substituents bonded to the same nitrogen atom may optionally be joined to form a $R^{16A}$-substituted or unsubstituted azetidinyl. In embodiments, $R^{16}$ and $R^{15}$ substituents bonded to the same nitrogen atom may optionally be joined to form a $R^{16A}$-substituted or unsubstituted morpholinyl. In embodiments, $R^{16}$ and $R^{15}$ substituents bonded to the same nitrogen atom may optionally be joined to form a $R^{16A}$-substituted or unsubstituted azeridinyl.

$R^{16A}$ is independently oxo, halogen, —$CX^{16}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{16A}_2$, —$CH_2X^{16A}$, —$OCX^{16A}_3$, —$OCH_2X^{16A}$, —$OCHX^{16A}_2$, $R^{16B}$-substituted or unsubstituted alkyl (e.g., $C_1$-$C_8$, $C_1$-$C_6$, $C_1$-$C_4$, or $C_1$-$C_2$), $R^{16B}$-substituted or unsubstituted heteroalkyl (e.g., 2 to 8 membered, 2 to 6 membered, 4 to 6 membered, 2 to 3 membered, or 4 to 5 membered), $R^{16B}$-substituted or unsubstituted cycloalkyl (e.g., $C_3$-$C_8$, $C_3$-$C_6$, $C_4$-$C_6$, or $C_5$-$C_6$), $R^{16B}$-substituted or unsubstituted heterocycloalkyl (e.g., 3 to 6 membered, 4 to 6 membered, 4 to 5 membered, or 5 to 6 membered), $R^{16B}$-substituted or unsubstituted aryl (e.g., $C_6$-$C_{10}$ or phenyl), or $R^{16B}$-substituted or unsubstituted heteroaryl (e.g., 5 to 10 membered, 5 to 9 membered, or 5 to 6 membered). $X^{16A}$ is —F, —Cl, —Br, or —I. In embodiments, $R^{16A}$ is independently oxo, halogen, —$CX^{16A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{16A}_2$, —$CH_2X^{16A}$, —$OCX^{16A}_3$, —$OCH_2X^{16A}$, —$OCHX^{16A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{16B}$ is independently oxo, halogen, —$CX^{16B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{16B}_2$, —$CH_2X^{16B}$, —$OCX^{16B}_3$, —$OCH_2X^{16B}$, —$OCHX^{16B}_2$, $R^{16C}$-substituted or unsubstituted alkyl (e.g., $C_1$-$C_8$, $C_1$-$C_6$, $C_1$-$C_4$, or $C_1$-$C_2$), $R^{16C}$-substituted or unsubstituted heteroalkyl (e.g., 2 to 8 membered, 2 to 6 membered, 4 to 6 membered, 2 to 3 membered, or 4 to 5 membered), $R^{16C}$-substituted or unsubstituted cycloalkyl (e.g., $C_3$-$C_8$, $C_3$-$C_6$, $C_4$-$C_6$, or $C_5$-$C_6$), $R^{16C}$-substituted or unsubstituted heterocycloalkyl (e.g., 3 to 6 membered, 4 to 6 membered, 4 to 5 membered, or 5 to 6 membered), $R^{16C}$-substituted or unsubstituted aryl (e.g., $C_6$-$C_{10}$ or phenyl), or $R^{16C}$-substituted or unsubstituted heteroaryl (e.g., 5 to 10 membered, 5 to 9 membered, or 5 to 6 membered). $X^{16B}$ is —F, —Cl, —Br, or —I. In embodiments, $R^{16B}$ is independently oxo, halogen, —$CX^{16B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{16B}_2$, —$CH_2X^{16B}$, —$OCX^{16B}_3$, —$OCH_2X^{16B}$, —$OCHX^{16B}2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{16C}$ is independently oxo, halogen, —$CX^{16C}_3$, —$CHX^{16C}_2$, —$CH_2X^{16}$, —$OCX^{16C}_3$, —$OCH_2X^{16C}$, —$OCHX^{16C}_2$, —CN, —OH, —$NH_2$, —C OOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{16C}$ is —F, —Cl, —Br, or —I.

In embodiments, $R^{17}$ is independently hydrogen, —$CX^{17}_3$, —CN, —COOH, —$CONH_2$, —$CHX^{17}_2$, —$CH_2X^{17}$, $R^{17A}$-substituted or unsubstituted alkyl (e.g., $C_1$-$C_8$, $C_1$-$C_6$, $C_1$-$C_4$, or $C_1$-$C_2$), $R^{17A}$-substituted or unsubstituted heteroalkyl (e.g., 2 to 8 membered, 2 to 6 membered, 4 to 6 membered, 2 to 3 membered, or 4 to 5 membered), $R^{17A}$-substituted or unsubstituted cycloalkyl (e.g., $C_3$-$C_8$, $C_3$-$C_6$, $C_4$-$C_6$, or $C_5$-$C_6$), $R^{17A}$-substituted or unsubstituted heterocycloalkyl (e.g., 3 to 6 membered, 4 to 6 membered, 4 to 5 membered, or 5 to 6 membered), $R^{17A}$-substituted or unsubstituted aryl (e.g., $C_6$-$C_{10}$ or phenyl), or $R^{17A}$-substituted or unsubstituted heteroaryl (e.g., 5 to 10 membered, 5 to 9 membered, or 5 to 6 membered). $X^{17}$ is —F, —Cl, —Br, or —I. In embodiments, $R^{17}$ is independently hydrogen. In embodiments, $R^{17}$ is independently methyl. In embodiments, $R^{17}$ is independently ethyl. In embodiments, $R^{17}$ is independently hydrogen, —$CX^{17}$ 3, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{17A}$ is independently oxo, halogen, —$CX^{17A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{17A}_2$, —$CH_2X^{17A}$, —$OCX^{17A}_3$, —$OCH_2X^{17A}$, —$OCHX^{17A}2$, $R^{17B}$-substituted or unsubstituted alkyl (e.g., $C_1$-$C_8$, $C_1$-$C_6$, $C_1$-$C_4$, or $C_1$-$C_2$), $R^{17B}$-substituted or unsubstituted heteroalkyl (e.g., 2 to 8 membered, 2 to 6 membered, 4 to 6 membered, 2 to 3 membered, or 4 to 5 membered), $R^{17B}$-substituted or unsubstituted cycloalkyl (e.g., $C_3$-$C_8$, $C_3$-$C_6$, $C_4$-$C_6$, or $C_5$-$C_6$), $R^{17B}$-substituted or unsubstituted heterocycloalkyl (e.g., 3 to 6 membered, 4 to 6 membered, 4 to 5 membered, or 5 to 6 membered), $R^{17B}$-substituted or unsubstituted aryl (e.g., $C_6$-$C_{10}$ or phenyl), or $R^{17B}$-substituted or unsubstituted heteroaryl (e.g., 5 to 10 membered, 5 to 9 membered, or 5 to 6 membered). $X^{17A}$ is —F, —Cl, —Br, or —I. In embodiments, $R^{17A}$ is independently oxo, halogen, —$CX^{17A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{17A}_2$, —$CH_2X^{17A}$, —$OCX^{17A}_3$, —$OCH_2X^{17A}$, —$OCHX^{17A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{17B}$ is independently oxo, halogen, —$CX^{17B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{17B}_2$, —$CH_2X^{17B}$, —$OCX^{17B}_3$, —$OCH_2X^{17B}$, —$OCHX^{17B}_2$, $R^{17C}$-substituted or unsubstituted alkyl (e.g., $C_1$-$C_8$, $C_1$-$C_6$, $C_1$-$C_4$, or $C_1$-$C_2$), $R^{17C}$-substituted or unsubstituted heteroalkyl (e.g., 2 to 8 membered, 2 to 6 membered, 4 to 6 membered, 2 to 3 membered, or 4 to 5 membered), $R^{17C}$-substituted or unsubstituted cycloalkyl (e.g., $C_3$-$C_8$, $C_3$-$C_6$, $C_4$-$C_6$, or $C_5$-$C_6$), $R^{17C}$-substituted or unsubstituted heterocycloalkyl (e.g., 3 to 6 membered, 4 to 6 membered, 4 to 5 membered, or 5 to 6 membered), $R^{17C}$-substituted or unsubstituted aryl (e.g., $C_6$-$C_{10}$ or phenyl), or $R^{17C}$-substituted or unsubstituted heteroaryl (e.g., 5 to 10 membered, 5 to 9 membered, or 5 to 6 membered). $X^{17B}$ is —F, —Cl, —Br, or —I. In embodiments, $R^{17B}$ is independently oxo, halogen, —$CX^{17B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{17B}_2$, —$CH_2X^{17B}$, —$OCX^{17B}_3$, —$OCH_2X^{17B}$, —$OCHX^{17B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{17C}$ is independently oxo, halogen, —$CX^{17C}_3$, —$CHX^{17C}_2$, —$CH_2X^{17C}$, —$OCX^{17C}_3$, —$OCH_2X^{17C}$, —$OCHX^{17C}_2$, —CN, —OH, —$NH_2$, —C OOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17c}$ is —F, —Cl, —Br, or —I.

In embodiments, $R^{18}$ is independently hydrogen, —$CX^{18}_3$, —CN, —COOH, —$CONH_2$, —$CHX^{18}_2$, —$CH_2X^{18}$, $R^{18A}$-substituted or unsubstituted alkyl (e.g., $C_1$-$C_8$, $C_1$-$C_6$, $C_1$-$C_4$, or $C_1$-$C_2$), $R^{18A}$-substituted or unsubstituted heteroalkyl (e.g., 2 to 8 membered, 2 to 6 membered, 4 to 6 membered, 2 to 3 membered, or 4 to 5 membered), $R^{18A}$-substituted or unsubstituted cycloalkyl (e.g., $C_3$-$C_8$, $C_3$-$C_6$, $C_4$-$C_6$, or $C_5$-$C_6$), $R^{18A}$-substituted or unsubstituted heterocycloalkyl (e.g., 3 to 6 membered, 4 to 6 membered, 4 to 5 membered, or 5 to 6 membered), $R^{18A}$-substituted or unsubstituted aryl (e.g., $C_6$-$C_{10}$ or phenyl), or $R^{18A}$-substituted or unsubstituted heteroaryl (e.g., 5 to 10 membered, 5 to 9 membered, or 5 to 6 membered). $X^{18}$ is —F, —Cl, —Br, or —I. In embodiments, $R^{18}$ is independently hydrogen. In embodiments, $R^{18}$ is independently methyl. In embodiments, $R^{18}$ is independently ethyl. In embodiments, $R^{18}$ is independently hydrogen, —$CX^{18}$ 3, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{18A}$ is independently oxo, halogen, —$CX^{18A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18A}_2$, —$CH_2X^{18A}$, —$OCX^{18A}_3$, —$OCH_2X^{18A}$, —$OCHX^{18A}$2, $R^{18B}$-substituted or unsubstituted alkyl (e.g., $C_1$-$C_8$, $C_1$-$C_6$, $C_1$-$C_4$, or $C_1$-$C_2$), $R^{18B}$-substituted or unsubstituted heteroalkyl (e.g., 2 to 8 membered, 2 to 6 membered, 4 to 6 membered, 2 to 3 membered, or 4 to 5 membered), $R^{18B}$-substituted or unsubstituted cycloalkyl (e.g., $C_3$-$C_8$, $C_3$-$C_6$, $C_4$-$C_6$, or $C_5$-$C_6$), $R^{18B}$-substituted or unsubstituted heterocycloalkyl (e.g., 3 to 6 membered, 4 to 6 membered, 4 to 5 membered, or 5 to 6 membered), $R^{18B}$-substituted or unsubstituted aryl (e.g., $C_6$-$C_{10}$ or phenyl), or $R^{18B}$-substituted or unsubstituted heteroaryl (e.g., 5 to 10 membered, 5 to 9 membered, or 5 to 6 membered). $X^{18A}$ is —F, —Cl, —Br, or —I. In embodiments, $R^{18A}$ is independently oxo, halogen, —$CX^{18A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18A}_2$, —$CH_2X^{18A}$, —$OCX^{18A}_3$, —$OCH_2X^{18A}$, —$OCHX^{18A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{18B}$ is independently oxo, halogen, —$CX^{18B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18B}_2$, —$CH_2X^{18B}$, —$OCX^{18B}_3$, —$OCH_2X^{18B}$, —$OCHX^{18B}_2$, $R^{18C}$-substituted or unsubstituted alkyl (e.g., $C_1$-$C_8$, $C_1$-$C_6$, $C_1$-$C_4$, or $C_1$-$C_2$), $R^{18C}$-substituted or unsubstituted heteroalkyl (e.g., 2 to 8 membered, 2 to 6 membered, 4 to 6 membered, 2 to 3 membered, or 4 to 5 membered), $R^{18C}$-substituted or unsubstituted cycloalkyl (e.g., $C_3$-$C_8$, $C_3$-$C_6$, $C_4$-$C_6$, or $C_5$-$C_6$), $R^{18C}$-substituted or unsubstituted heterocycloalkyl (e.g., 3 to 6 membered, 4 to 6 membered, 4 to 5 membered, or 5 to 6 membered), $R^{18C}$-substituted or unsubstituted aryl (e.g., $C_6$-$C_{10}$ or phenyl), or $R^{18C}$-substituted or unsubstituted heteroaryl (e.g., 5 to 10 membered, 5 to 9 membered, or 5 to 6 membered). $X^{18B}$ is —F, —Cl, —Br, or —I. In embodiments, $R^{18B}$ is independently oxo, halogen, —$CX^{18B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18B}_2$, —$CH_2X^{18B}$, —$OCX^{18B}_3$, —$OCH_2X^{18B}$, —$OCHX^{18B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{18C}$ is independently oxo, halogen, —$CX^{18C}_3$, —$CHX^{18C}_2$, —$CH_2X^{18C}$, —$OCX^{18}C_3$, —$OCH_2X^{18C}$, —$OCHX^{18C}_2$, —CN, —OH, —$NH_2$, —C OOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{18C}$ is —F, —Cl, —Br, or —I.

In embodiments, $R^{19}$ is independently hydrogen, —$CX^{19}_3$, —CN, —COOH, —$CONH_2$, —$CHX^{19}_2$, —$CH_2X^{19}$, $R^{19A}$-substituted or unsubstituted alkyl (e.g., $C_1$-$C_8$, $C_1$-$C_6$, $C_1$-$C_4$, or $C_1$-$C_2$), $R^{19A}$-substituted or unsubstituted heteroalkyl (e.g., 2 to 8 membered, 2 to 6 membered, 4 to 6 membered, 2 to 3 membered, or 4 to 5 membered), $R^{19A}$-substituted or unsubstituted cycloalkyl (e.g., $C_3$-$C_8$, $C_3$-$C_6$, $C_4$-$C_6$, or $C_5$-$C_6$), $R^{19A}$-substituted or unsubstituted heterocycloalkyl (e.g., 3 to 6 membered, 4 to 6 membered, 4 to 5 membered, or 5 to 6 membered), $R^{19A}$-substituted or unsubstituted aryl (e.g., $C_6$-$C_{10}$ or phenyl), or $R^{19A}$-substituted or unsubstituted heteroaryl (e.g., 5 to 10 membered, 5 to 9 membered, or 5 to 6 membered). $X^{19}$ is —F, —Cl, —Br, or —I. In embodiments, $R^{19}$ is independently hydrogen. In embodiments, $R^{19}$ is independently methyl. In embodiments, $R^{19}$ is independently ethyl. In embodiments, $R^{19}$ is independently hydrogen, —$CX^{19}$ 3, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{19}$ and $R^{20}$ substituents bonded to the same nitrogen atom may optionally be joined to form a $R^{19A}$-substituted or unsubstituted heterocycloalkyl or $R^{19A}$-substituted or unsubstituted heteroaryl. In embodiments, $R^{19}$ and $R^{20}$ substituents bonded to the same nitrogen atom may optionally be joined to form a $R^{19A}$-substituted or unsubstituted 3 to 6 membered heterocycloalkyl or $R^{19A}$-substituted or unsubstituted 5 to 6 membered heteroaryl. In embodiments, $R^{19}$ and $R^{20}$ substituents bonded to the same nitrogen atom may optionally be joined to form an unsubstituted 3 to 6 membered heterocycloalkyl or unsubstituted 5 to 6 membered heteroaryl. In embodiments, $R^{19}$ and $R^{20}$ substituents bonded to the same nitrogen atom may optionally be joined to form a $R^{19A}$-substituted or unsubstituted piperazinyl. In embodiments, $R^{19}$ and $R^{20}$ substituents bonded to the same nitrogen atom may optionally be joined to form a $R^{19A}$-substituted or unsubstituted piperidinyl. In embodiments, $R^{19}$ and $R^{20}$ substituents bonded to the same nitrogen atom may optionally be joined to form a $R^{19A}$-substituted or unsubstituted pyrrolidinyl. In embodiments, $R^{19}$ and $R^{20}$ substituents bonded to the same nitrogen atom may optionally be joined to form a $R^{19A}$-substituted or unsubstituted azetidinyl. In embodiments, $R^{19}$ and $R^{20}$ substituents bonded to the same nitrogen atom may optionally be joined to form a $R^{19A}$-substituted or unsubstituted morpholinyl. In embodiments, $R^{19}$ and $R^{20}$ substituents bonded to the same nitrogen atom may optionally be joined to form a $R^{19A}$-substituted or unsubstituted azeridinyl.

$R^{19A}$ is independently oxo, halogen, —$CX^{19A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{19A}_2$, —$CH_2X^{19A}$, —$OCX^{19A}_3$, —$OCH_2X^{19A}$, —$OCHX^{19A}2$, $R^{19B}$-substituted or unsubstituted alkyl (e.g., $C_1$-$C_5$, $C_1$-$C_6$, $C_1$-$C_4$, or $C_1$-$C_2$), $R^{19B}$-substituted or unsubstituted heteroalkyl (e.g., 2 to 8 membered, 2 to 6 membered, 4 to 6 membered, 2 to 3 membered, or 4 to 5 membered), $R^{19B}$-substituted or unsubstituted cycloalkyl (e.g., $C_3$-$C_8$, $C_3$-$C_6$, $C_4$-$C_6$, or $C_5$-$C_6$), $R^{19B}$-substituted or unsubstituted heterocycloalkyl (e.g., 3 to 6 membered, 4 to 6 membered, 4 to 5 membered, or 5 to 6 membered), $R^{19B}$-substituted or unsubstituted aryl (e.g., $C_6$-$C_{10}$ or phenyl), or $R^{19B}$-substituted or unsubstituted heteroaryl (e.g., 5 to 10 membered, 5 to 9 membered, or 5 to 6 membered). $X^{19A}$ is —F, —Cl, —Br, or —I. In embodiments, $R^{19A}$ is independently oxo, halogen, —$CX^{19A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{19A}_2$, —$CH_2X^{19A}$, —$OCX^{19A}_3$, —$OCH_2X^{19A}$, —$OCHX^{19A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{19B}$ is independently oxo, halogen, —$CX^{19B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{19B}_2$, —$CH_2X^{19B}$, —$OCX^{19B}_3$, —$OCH_2X^{19B}$, —$OCHX^{19B}2$, $R^{19C}$-substituted or unsubstituted alkyl (e.g., $C_1$-$C_8$, $C_1$-$C_6$, $C_1$-$C_4$, or $C_1$-$C_2$), $R^{19}$-substituted or unsubstituted heteroalkyl (e.g., 2 to 8 membered, 2 to 6 membered, 4 to 6 membered, 2 to 3 membered, or 4 to 5 membered), $R^{19C}$-substituted or unsubstituted cycloalkyl (e.g., $C_3$-$C_8$, $C_3$-$C_6$, $C_4$-$C_6$, or $C_5$-$C_6$), $R^{19C}$-substituted or unsubstituted heterocycloalkyl (e.g., 3 to 6 membered, 4 to 6 membered, 4 to 5 membered, or 5 to 6 membered), $R^{19C}$-substituted or unsubstituted aryl (e.g., $C_6$-$C_{10}$ or phenyl), or $R^{19C}$-substituted or unsubstituted heteroaryl (e.g., 5 to 10 membered, 5 to 9 membered, or 5 to 6 membered). $X^{19B}$ is —F, —Cl, —Br, or —I. In embodiments, $R^{19B}$ is independently oxo, halogen, —$CX^{19B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{19B}_2$, —$CH_2X^{19B}$, —$OCX^{19B}_3$, —$OCH_2X^{19B}$, —$OCHX^{19B}2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{19C}$ is independently oxo, halogen, $—CX^{19C}_3$, $—CHX^{19C}_2$, $—CH_2X^{19C}$, $—OCX^{19C}_3$, $—OCH_2X^{19C}$, $—OCHX^{19C}_2$, —CN, —OH, $—NH_2$, —C OOH, $—CONH_2$, —SH, $—NHNH_2$, $—ONH_2$, $—NHC(O)NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{19C}$ is —F, —Cl, —Br, or —I.

In embodiments, $R^{20}$ is independently hydrogen, $—CX^{20}_3$, —CN, —COOH, $—CONH_2$, $—CHX^{20}_2$, $—CH_2X^{20}$, $R^{20A}$-substituted or unsubstituted alkyl (e.g., $C_1$-$C_8$, $C_1$-$C_6$, $C_1$-$C_4$, or $C_1$-$C_2$), $R^{20A}$-substituted or unsubstituted heteroalkyl (e.g., 2 to 8 membered, 2 to 6 membered, 4 to 6 membered, 2 to 3 membered, or 4 to 5 membered), $R^{20A}$-substituted or unsubstituted cycloalkyl (e.g., $C_3$-$C_8$, $C_3$-$C_6$, $C_4$-$C_6$, or $C_5$-$C_6$), $R^{20A}$-substituted or unsubstituted heterocycloalkyl (e.g., 3 to 6 membered, 4 to 6 membered, 4 to 5 membered, or 5 to 6 membered), $R^{20A}$-substituted or unsubstituted aryl (e.g., $C_6$-$C_{10}$ or phenyl), or $R^{20A}$-substituted or unsubstituted heteroaryl (e.g., 5 to 10 membered, 5 to 9 membered, or 5 to 6 membered). $X^{20}$ is —F, —Cl, —Br, or —I. In embodiments, $R^{20}$ is independently hydrogen. In embodiments, $R^{20}$ is independently methyl. In embodiments, $R^{20}$ is independently ethyl. In embodiments, $R^{20}$ is independently hydrogen, $—CX^{20}_3$, —CN, —COOH, $—CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{20}$ and $R^{19}$ substituents bonded to the same nitrogen atom may optionally be joined to form a $R^{20A}$-substituted or unsubstituted heterocycloalkyl or $R^{20A}$-substituted or unsubstituted heteroaryl. In embodiments, $R^{20}$ and $R^{19}$ substituents bonded to the same nitrogen atom may optionally be joined to form a $R^{20A}$-substituted or unsubstituted 3 to 6 membered heterocycloalkyl or $R^{20A}$-substituted or unsubstituted 5 to 6 membered heteroaryl. In embodiments, $R^{20}$ and $R^{19}$ substituents bonded to the same nitrogen atom may optionally be joined to form an unsubstituted 3 to 6 membered heterocycloalkyl or unsubstituted 5 to 6 membered heteroaryl. In embodiments, $R^{20}$ and $R^{19}$ substituents bonded to the same nitrogen atom may optionally be joined to form a $R^{20A}$-substituted or unsubstituted piperazinyl. In embodiments, $R^{20}$ and $R^{19}$ substituents bonded to the same nitrogen atom may optionally be joined to form a $R^{20A}$-substituted or unsubstituted piperidinyl. In embodiments, $R^{20}$ and $R^{19}$ substituents bonded to the same nitrogen atom may optionally be joined to form a $R^{20A}$-substituted or unsubstituted pyrrolidinyl. In embodiments, $R^{20}$ and $R^{19}$ substituents bonded to the same nitrogen atom may optionally be joined to form a $R^{20A}$-substituted or unsubstituted azetidinyl. In embodiments, $R^{20}$ and $R^{19}$ substituents bonded to the same nitrogen atom may optionally be joined to form a $R^{20A}$-substituted or unsubstituted morpholinyl. In embodiments, $R^{20}$ and $R^{19}$ substituents bonded to the same nitrogen atom may optionally be joined to form a $R^{20A}$-substituted or unsubstituted azeridinyl.

$R^{20A}$ is independently oxo, halogen, $—CX^{20A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{20A}_2$, $—CH_2X^{20A}$, $—OCX^{20A}_3$, $—OCH_2X^{20A}$, $—OCHX^{20A}2$, $R^{20B}$-substituted or unsubstituted alkyl (e.g., $C_1$-$C_8$, $C_1$-$C_6$, $C_1$-$C_4$, or $C_1$-$C_2$), $R^{20B}$-substituted or unsubstituted heteroalkyl (e.g., 2 to 8 membered, 2 to 6 membered, 4 to 6 membered, 2 to 3 membered, or 4 to 5 membered), $R^{20B}$-substituted or unsubstituted cycloalkyl (e.g., $C_3$-$C_8$, $C_3$-$C_6$, $C_4$-$C_6$, or $C_5$-$C_6$), $R^{20B}$-substituted or unsubstituted heterocycloalkyl (e.g., 3 to 6 membered, 4 to 6 membered, 4 to 5 membered, or 5 to 6 membered), $R^{20B}$-substituted or unsubstituted aryl (e.g., $C_6$-$C_{10}$ or phenyl), or $R^{20B}$-substituted or unsubstituted heteroaryl (e.g., 5 to 10 membered, 5 to 9 membered, or 5 to 6 membered). $X^{20A}$ is —F, —Cl, —Br, or —I. In embodiments, $R^{20A}$ is independently oxo, halogen, $—CX^{20A}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{20A}_2$, $—CH_2X^{20A}$, $—OCX^{20A}_3$, $—OCH_2X^{20A}$, $—OCHX^{20A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{20B}$ is independently oxo, halogen, $—CX^{20B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{20B}_2$, $—CH_2X^{20B}$, $—OCX^{20B}_3$, $—OCH_2X^{20B}$, $—OCHX^{20B}_2$, $R^{20C}$-substituted or unsubstituted alkyl (e.g., $C_1$-$C_8$, $C_1$-$C_6$, $C_1$-$C_4$, or $C_1$-$C_2$), $R^{20C}$-substituted or unsubstituted heteroalkyl (e.g., 2 to 8 membered, 2 to 6 membered, 4 to 6 membered, 2 to 3 membered, or 4 to 5 membered), $R^{20C}$-substituted or unsubstituted cycloalkyl (e.g., $C_3$-$C_8$, $C_3$-$C_6$, $C_4$-$C_6$, or $C_5$-$C_6$), $R^{20C}$-substituted or unsubstituted heterocycloalkyl (e.g., 3 to 6 membered, 4 to 6 membered, 4 to 5 membered, or 5 to 6 membered), $R^{20C}$-substituted or unsubstituted aryl (e.g., $C_6$-$C_{10}$ or phenyl), or $R^{20C}$-substituted or unsubstituted heteroaryl (e.g., 5 to 10 membered, 5 to 9 membered, or 5 to 6 membered). $X^{20B}$ is —F, —Cl, —Br, or —I. In embodiments, $R^{20B}$ is independently oxo, halogen, $—CX^{20B}_3$, —CN, —OH, $—NH_2$, —COOH, $—CONH_2$, —SH, $—NHNH_2$, $—ONH_2$, $—NHC(O)NHNH_2$, $—NHC(O)NH_2$, —NHC(O)H, —NHC(O)OH, —NHOH, $—CHX^{20B}_2$, $—CH_2X^{20B}$, $—OCX^{20B}_3$, $—OCH_2X^{20B}$, $—OCHX^{20B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{20C}$ is independently oxo, halogen, $—CX^{20C}_3$, $—CHX^{20C}_2$, $—CH_2X^{20C}$, $—OCX^{20C}_3$, $—OCH_2X^{20C}$, $—OCHX^{20C}_2$, —CN, —OH, $—NH_2$, —C OOH, $—CONH_2$, —SH, $—NHNH_2$, $—ONH_2$, $—NHC(O)NHNH_2$, —NHC (O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20C}$ is —F, —Cl, —Br, or —I.

In embodiments, $R^{21}$ is independently hydrogen, —$CX^{21}_3$, —CN, —COOH, —$CONH_2$, —$CHX^{21}_2$, —$CH_2X^{21}$, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 to 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 6 membered, 4 to 6 membered, 4 to 5 membered, or 5 to 6 membered), $R^{21A}$-substituted or unsubstituted aryl (e.g., $C_6$-$C_{10}$ or phenyl), or $R^{21A}$-substituted or unsubstituted heteroaryl (e.g., 5 to 10 membered, 5 to 9 membered, or 5 to 6 membered). $X^{21}$ is —F, —Cl, —Br, or —I. In embodiments, $R^{21}$ is independently hydrogen. In embodiments, $R^{21}$ is independently methyl. In embodiments, $R^{21}$ is independently ethyl. In embodiments, $R^{21}$ is independently hydrogen, —$CX^{21}_3$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21A}$ is independently oxo, halogen, —$CX^{21A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21A}_2$, —$CH_2X^{21A}$, —$OCX^{21A}_3$, —$OCH_2X^{21A}$, —$OCHX^{21A}$2, $R^{21B}$-substituted or unsubstituted alkyl (e.g., $C_1$-$C_8$, $C_1$-$C_6$, $C_1$-$C_4$, or $C_1$-$C_2$), $R^{21B}$-substituted or unsubstituted heteroalkyl (e.g., 2 to 8 membered, 2 to 6 membered, 4 to 6 membered, 2 to 3 membered, or 4 to 5 membered), $R^{21B}$-substituted or unsubstituted cycloalkyl (e.g., $C_3$-$C_8$, $C_3$-$C_6$, $C_4$-$C_6$, or $C_5$-$C_6$), $R^{21B}$-substituted or unsubstituted heterocycloalkyl (e.g., 3 to 6 membered, 4 to 6 membered, 4 to 5 membered, or 5 to 6 membered), $R^{21B}$-substituted or unsubstituted aryl (e.g., $C_6$-$C_{10}$ or phenyl), or $R^{21B}$-substituted or unsubstituted heteroaryl (e.g., 5 to 10 membered, 5 to 9 membered, or 5 to 6 membered). $X^{21A}$ is —F, —Cl, —Br, or —I. In embodiments, $R^{21A}$ is independently oxo, halogen, —$CX^{21A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21A}_2$, —$CH_2X^{21A}$, —$OCX^{21A}_3$, —$OCH_2X^{21A}$, —$OCHX^{21A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21B}$ is independently oxo, halogen, —$CX^{21B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21B}_2$, —$CH_2X^{21B}$, —$OCX^{21B}_3$, —$OCH_2X^{21B}$, —$OCHX^{21B}_2$, $R^{21C}$-substituted or unsubstituted alkyl (e.g., $C_1$-$C_8$, $C_1$-$C_6$, $C_1$-$C_4$, or $C_1$-$C_2$), $R^{21C}$-substituted or unsubstituted heteroalkyl (e.g., 2 to 8 membered, 2 to 6 membered, 4 to 6 membered, 2 to 3 membered, or 4 to 5 membered), $R^{21C}$-substituted or unsubstituted cycloalkyl (e.g., $C_3$-$C_8$, $C_3$-$C_6$, $C_4$-$C_6$, or $C_5$-$C_6$), $R^{21C}$-substituted or unsubstituted heterocycloalkyl (e.g., 3 to 6 membered, 4 to 6 membered, 4 to 5 membered, or 5 to 6 membered), $R^{21C}$-substituted or unsubstituted aryl (e.g., $C_6$-$C_{10}$ or phenyl), or $R^{21C}$-substituted or unsubstituted heteroaryl (e.g., 5 to 10 membered, 5 to 9 membered, or 5 to 6 membered). $X^{21B}$ is —F, —Cl, —Br, or —I. In embodiments, $R^{21B}$ is independently oxo, halogen, —$CX^{21B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21B}_2$, —$CH_2X^{21B}$, —$OCX^{21B}_3$, —$OCH_2X^{21B}$, —$OCHX^{21B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21C}$ is independently oxo, halogen, —$CX^{21}C_3$, —$CHX^{21C}_2$, —$CH_2X^{21C}$, —$OCX^{21C}_3$, —$OCH_2X^{21C}$, —$OCHX^{21C}_2$, —CN, —OH, —$NH_2$, —C OOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21C}$ is —F, —Cl, —Br, or —I.

In embodiments, $R^{22}$ is independently hydrogen, —$CX^{22}_3$, —CN, —COOH, —$CONH_2$, —$CHX^{22}_2$, —$CH_2X^{22}$, $R^{22A}$-substituted or unsubstituted alkyl (e.g., $C_1$-$C_8$, $C_1$-$C_6$, $C_1$-$C_4$, or $C_1$-$C_2$), $R^{22A}$-substituted or unsubstituted heteroalkyl (e.g., 2 to 8 membered, 2 to 6 membered, 4 to 6 membered, 2 to 3 membered, or 4 to 5 membered), $R^{22A}$-substituted or unsubstituted cycloalkyl (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 6 membered, 4 to 6 membered, 4 to 5 membered, or 5 to 6 membered), $R^{22A}$-substituted or unsubstituted aryl (e.g., $C_6$-$C_{10}$ or phenyl), or $R^{22A}$-substituted or unsubstituted heteroaryl (e.g., 5 to 10 membered, 5 to 9 membered, or 5 to 6 membered). $X^{22}$ is —F, —Cl, —Br, or —I. In embodiments, $R^{22}$ is independently hydrogen. In embodiments, $R^{22}$ is independently methyl. In embodiments, $R^{22}$ is independently ethyl. In embodiments, $R^{22}$ is independently hydrogen, —$CX^{22}$ 3, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22A}$ is independently oxo, halogen, —$CX^{22A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{22A}_2$, —$CH_2X^{22A}$, —$OCX^{22A}_3$, —$OCH_2X^{22A}$, —$OCHX^{22A}_2$, $R^{22B}$-substituted or unsubstituted alkyl (e.g., $C_1$-$C_8$, $C_1$-$C_6$, $C_1$-$C_4$, or $C_1$-$C_2$), $R^{22B}$-substituted or unsubstituted heteroalkyl (e.g., 2 to 8 membered, 2 to 6 membered, 4 to 6 membered, 2 to 3 membered, or 4 to 5 membered), $R^{22B}$-substituted or unsubstituted cycloalkyl (e.g., $C_3$-$C_8$, $C_3$-$C_6$, $C_4$-$C_6$, or $C_5$-$C_6$), $R^{22B}$-substituted or unsubstituted heterocycloalkyl (e.g., 3 to 6 membered, 4 to 6 membered, 4 to 5 membered, or 5 to 6 membered), $R^{22B}$-substituted or unsubstituted aryl (e.g., $C_6$-$C_{10}$ or phenyl), or $R^{22B}$-substituted or unsubstituted heteroaryl (e.g., 5 to 10 membered, 5 to 9 membered, or 5 to 6 membered). $X^{22A}$ is —F, —Cl, —Br, or —I. In embodiments, $R^{22A}$ is independently oxo, halogen, —$CX^{22A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{22A}_2$, —$CH_2X^{22A}$, —$OCX^{22A}_3$, —$OCH_2X^{22A}$, —$OCHX^{22A}_2$, unsubstituted alkyl (e.g., $C_1$-$C_5$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22B}$ is independently oxo, halogen, —$CX^{22B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{22B}_2$, —$CH_2X^{22B}$, —$OCX^{22B}_3$, —$OCH_2X^{22B}$, —$OCHX^{22B}_2$, $R^{22C}$-substituted or unsubstituted alkyl (e.g., $C_1$-$C_8$, $C_1$-$C_6$, $C_1$-$C_4$, or $C_1$-$C_2$), $R^{22C}$-substituted or unsubstituted heteroalkyl (e.g., 2 to 8 membered, 2 to 6 membered, 4 to 6 membered, 2 to 3 membered, or 4 to 5 membered), $R^{22C}$-substituted or unsubstituted cycloalkyl (e.g., $C_3$-$C_8$, $C_3$-$C_6$, $C_4$-$C_6$, or $C_5$-$C_6$), $R^{22C}$-substituted or unsubstituted heterocycloalkyl (e.g., 3 to 6 membered, 4 to 6 membered, 4 to 5 membered, or 5 to 6 membered), $R^{22C}$-substituted or unsubstituted aryl (e.g., $C_6$-$C_{10}$ or phenyl), or $R^{22C}$-substituted or unsubstituted heteroaryl (e.g., 5 to 10 membered, 5 to 9 membered, or 5 to 6 membered). $X^{22B}$ is —F, —Cl, —Br, or —I. In embodiments, $R^{22B}$ is independently oxo, halogen, —$CX^{22B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{22B}_2$, —$CH_2X^{22B}$, —$OCX^{22B}_3$, —$OCH_2X^{22B}$, —$OCHX^{22B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22C}$ is independently oxo, halogen, —$CX^{22C}_3$, —$CHX^{22C}_2$, —$CH_2X^{22C}$, —$OCX^{22C}_3$, —$OCH_2X^{22C}$, —$OCHX^{22C}_2$, —CN, —OH, —$NH_2$, —C OOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22C}$ is —F, —Cl, —Br, or —I.

In embodiments, $L^1$ is independently a bond, —O—, —NH—, —C(O)—, —C(O)NH—, —NHC(O)—, —S—, —NHC(O)NH—, $R^{23}$-substituted or unsubstituted alkylene (e.g., $C_1$-$C_8$, $C_1$-$C_6$, $C_1$-$C_4$, or $C_1$-$C_2$), $R^{23}$-substituted or unsubstituted heteroalkylene (e.g., 2 to 8 membered, 2 to 6 membered, 4 to 6 membered, 2 to 3 membered, or 4 to 5 membered), $R^{23}$-substituted or unsubstituted cycloalkylene (e.g., $C_3$-$C_8$, $C_3$-$C_6$, $C_4$-$C_6$, or $C_5$-$C_6$), $R^{23}$-substituted or unsubstituted heterocycloalkylene (e.g., 3 to 6 membered, 4 to 6 membered, 4 to 5 membered, or 5 to 6 membered), $R^{23}$-substituted or unsubstituted arylene (e.g., $C_6$-$C_{10}$ or phenyl), or $R^{23}$-substituted or unsubstituted heteroarylene (e.g., 5 to 10 membered, 5 to 9 membered, or 5 to 6 membered). In embodiments, L is independently a bond, —O—, —NH—, —C(O)—, —C(O)NH—, —NHC(O)—, —S—, —NHC(O)NH—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, 2 to 3 membered, or 4 to 5 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{23}$ is independently oxo, halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered). $X^{23}$ is —F, —Cl, —Br, or —I. In embodiments, $R^{23}$ is independently oxo, halogen, —$CX^{23}_3$, —$CHX^{23}2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 to 3 membered, or 4 to 5 membered), $R^{25}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 6 membered, 4 to 6 membered, 4 to 5 membered, or 5 to 6 membered), $R^{25}$-substituted or unsubstituted aryl (e.g., $C_6$-$C_{10}$ or phenyl), or $R^{25}$-substituted or unsubstituted heteroaryl (e.g., 5 to 10 membered, 5 to 9 membered, or 5 to 6 membered). $X^{24}$ is —F, —Cl, —Br, or —I. In embodiments, $R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{25}$ is independently oxo, halogen, —$CX^{25}_3$, —$CHX^{25}_2$, —$CH_2X^{25}$, —$OCX^{25}_3$, —$OCH_2X^{25}$, —$OCHX^{25}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25}$ is —F, —Cl, —Br, or —I.

In embodiments, $L^2$ is independently a bond, —O—, —C(O)—, —S—, —SO—, —$S(O)_2$—, —N(H)—, —NHC(O)—, —C(O)NH—, —$SO_2NH$—, —$NHSO_2$—, —OC(O)NH—, —NHC(O)O—, —NHC(O)NH—, $R^{26}$-substituted or unsubstituted alkylene (e.g., $C_1$-$C_8$, $C_1$-$C_6$, $C_1$-$C_4$, or $C_1$-$C_2$), $R^{26}$-substituted or unsubstituted heteroalkylene (e.g., 2 to 8 membered, 2 to 6 membered, 4 to 6 membered, 2 to 3 membered, or 4 to 5 membered), $R^{26}$-substituted or unsubstituted cycloalkylene (e.g., $C_3$-$C_8$, $C_3$-$C_6$, $C_4$-$C_6$, or $C_5$-$C_6$), $R^{26}$-substituted or unsubstituted heterocycloalkylene (e.g., 3 to 6 membered, 4 to 6 membered, 4 to 5 membered, or 5 to 6 membered), $R^{26}$-substituted or unsubstituted arylene (e.g., $C_6$-$C_{10}$ or phenyl), or $R^{26}$-substituted or unsubstituted heteroarylene (e.g., 5 to 10 membered, 5 to 9 membered, or 5 to 6 membered). In embodiments, $L^2$ is independently a bond, —O—, —C(O)—, —S—, —SO—, —$S(O)_2$—, —N(H)—, —NHC(O)—, —C(O)NH—, —$SO_2NH$—, —$NHSO_2$—, —OC(O)NH—, —NHC(O)O—, —NHC(O)NH—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, 2 to 3 membered, or 4 to 5 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, 2 to 3 membered, or 4 to 5 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 6 membered, 4 to 6 membered, 4 to 5 membered, or 5 to 6 membered), $R^{27}$-substituted or unsubstituted aryl (e.g., $C_6$-$C_{10}$ or phenyl), or $R^{27}$-substituted or unsubstituted heteroaryl (e.g., 5 to 10 membered, 5 to 9 membered, or 5 to 6 membered). $X^{26}$ is —F, —Cl, —Br, or —I. In embodiments, $R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{27}$ is independently oxo, halogen, —$CX^{27}_3$, —$CHX^{27}_2$, —$CH_2X^{27}$, —$OCX^{27}_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, 2 to 3 membered, or 4 to 5 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 6 membered, 4 to 6 membered, 4 to 5 membered, or 5 to 6 membered), $R^{28}$-substituted or unsubstituted aryl (e.g., $C_6$-$C_{10}$ or phenyl), or $R^{28}$-substituted or unsubstituted heteroaryl (e.g., 5 to 10 membered, 5 to 9 membered, or 5 to 6 membered). $X^{27}$ is —F, —Cl, —Br, or —I. In embodiments, $R^{27}$ is independently oxo, halogen, —$CX^{27}_3$, —$CHX^{27}_2$, —$CH_2X^{27}$, —$OCX^{27}_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{28}$ is independently oxo, halogen, —$CX^{28}_3$, —$CHX^{28}_2$, —$CH_2X^{28}$, —$OCX^{28}_3$, —$OCH_2X^{28}$, —$OCHX^{28}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28}$ is —F, —Cl, —Br, or —I.

In some embodiments, the compound is not

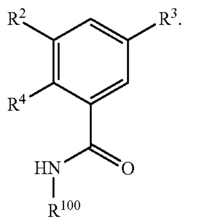

$R^2$, $R^3$, and $R^4$ are as described herein, including in embodiments.

In some embodiments, the compound is not

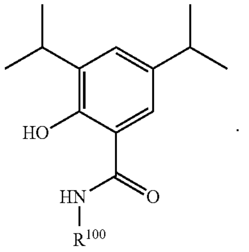

In some embodiments, the compound is not

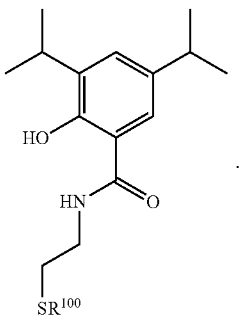

$R^{100}$ is hydrogen, halogen, —$CX^{100}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^{100}_3$, —$OCHX^{100}_2$, E, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^{100}$ is independently a halogen (e.g., —F, —Cl, —Br, and/or —I). In embodiments, $R^{100}$ is halogen, —$CX^{100}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$CHX^{100}_2$, —$CH_2X^{100}$, —$OCX^{100}_3$, —$OCH_2X^{100}$, —$OCHX^{100}_2$, E, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{100}$ is halogen, —$CX^{100}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$CHX^{100}_2$, —$CH_2X^{100}$, —$OCX^{100}_3$, —$OCH_2X^{100}$, or —$OCHX^{100}_2$. In embodiments, $R^{100}$ is E. In embodiments, $R^{100}$ is substituted or unsubstituted alkyl. In embodiments, $R^{100}$ is substituted or unsubstituted heteroalkyl. In embodiments, $R^{100}$ is substituted or unsubstituted cycloalkyl. In embodiments, $R^{100}$ is substituted or unsubstituted heterocycloalkyl. In embodiments, $R^{100}$ is substituted or unsubstituted aryl. In embodiments, $R^{100}$ is substituted or unsubstituted heteroaryl. In embodiments, $R^{100}$ is independently substituted or unsubstituted $C_1$-$C_8$ alkyl. In embodiments, $R^{100}$ is substituted or unsubstituted 2 to 8 membered heteroalkyl. In embodiments, $R^{100}$ is substituted or unsubstituted $C_3$-$C_8$ cycloalkyl. In embodiments, $R^{100}$ is substituted or unsubstituted 3 to 8 membered heterocycloalkyl. In embodiments, $R^{100}$ is substituted or unsubstituted $C_6$-$C_{10}$ aryl. In embodiments, $R^{100}$ is substituted or unsubstituted 5 to 10 membered heteroaryl. In embodiments, $R^{100}$ is independently unsubstituted $C_1$-$C_8$ alkyl. In embodiments, $R^{100}$ is independently unsubstituted 2 to 8 membered heteroalkyl. In embodiments, $R^{100}$ is independently unsubstituted $C_3$-$C_8$ cycloalkyl. In embodiments, $R^{100}$ is independently unsubstituted 3 to 8 membered heterocycloalkyl. In embodiments, $R^{100}$ is independently unsubstituted $C_6$-$C_{10}$ aryl. In embodiments, $R^{100}$ is independently unsubstituted 5 to 10 membered heteroaryl. In embodiments, $R^{100}$ is independently substituted or unsubstituted $C_1$-$C_6$ alkyl. In embodiments, $R^{100}$ is substituted or unsubstituted 2 to 6 membered heteroalkyl. In embodiments, $R^{100}$ is substituted or unsubstituted $C_3$-$C_6$ cycloalkyl. In embodiments, $R^{100}$ is substituted or unsubstituted 3 to 6 membered heterocycloalkyl. In embodiments, $R^{100}$ is substituted or unsubstituted phenyl. In embodiments, $R^{100}$ is substituted or unsubstituted 5 to 6 membered heteroaryl. In embodiments, $R^{100}$ is independently substituted or unsubstituted $C_1$-$C_3$ alkyl. In embodiments, $R^{100}$ is substituted or unsubstituted 2 to 3 membered heteroalkyl. In embodiments, $R^{100}$ is substituted or unsubstituted $C_3$-$C_4$ cycloalkyl. In embodiments, $R^{100}$ is substituted or unsubstituted 3 to 4 membered heterocycloalkyl. In embodiments, $R^{100}$ is substituted or unsubstituted phenyl. In embodiments, $R^{100}$ is substituted or unsubstituted 5 membered heteroaryl. In embodiments, $R^{100}$ is an embodiment of $R^1$.

In embodiments, the compound is not

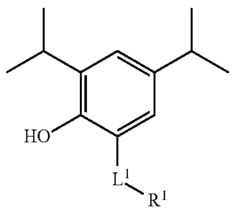

wherein $R^1$ and $L^1$ are as described herein, including in embodiments. In embodiments, the compound is not

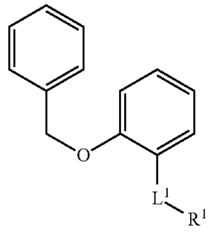

wherein $R^1$ and $L^1$ are as described herein, including in embodiments. In embodiments, the compound is not

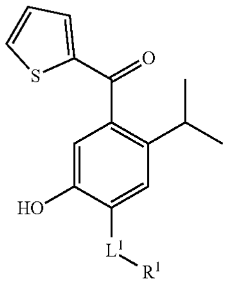

wherein $R^1$ and $L^1$ are as described herein, including in embodiments. In embodiments, the compound is not

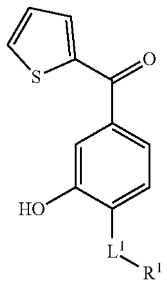

wherein $R^1$ and $L^1$ are as described herein, including in embodiments. In embodiments, the compound is not

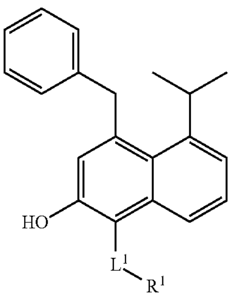

wherein $R^1$ and $L^1$ are as described herein, including in embodiments. In embodiments, the compound is not

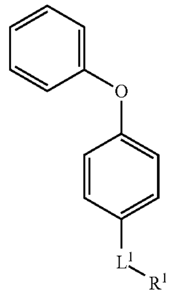

wherein $R^1$ and $L^1$ are as described herein, including in embodiments. In embodiments, the compound is not

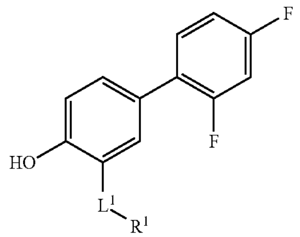

wherein $R^1$ and $L^1$ are as described herein, including in embodiments. In embodiments, the compound is not

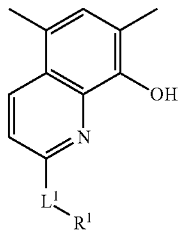

wherein $R^1$ and $L^1$ are as described herein, including in embodiments.

In embodiments, the compound is not a compound of formula (IIa). In embodiments, the compound is not a compound of formula (IIb). In embodiments, the compound is not a compound of formula (IIc). In embodiments, the compound is not a compound of formula (IId). In embodiments, the compound is not a compound of formula (IIe). In embodiments, the compound is not a compound of formula (IIf). In embodiments, the compound is not a compound of formula (IIg). In embodiments, the compound is not a compound of formula (IIIa). In embodiments, the compound is not a compound of formula (IIIb). In embodiments, the compound is not a compound of formula (IIIc). In embodiments, the compound is not a compound of formula (IIId). In embodiments, the compound is not a compound of formula (IIIe). In embodiments, the compound is not a compound of formula (IIIf). In embodiments, the compound is not a compound of formula (IIIg). In embodiments, the compound is not a compound of formula (IIIh). In embodiments, the compound is not a compound of formula (IIIi). In embodiments, the compound is not a compound of formula (IIIj).

In embodiments, the compound is not an embodiment of a compound of formula (IIa). In embodiments, the compound is not an embodiment of a compound of formula (IIb). In embodiments, the compound is not an embodiment of a compound of formula (IIc). In embodiments, the compound is not an embodiment of a compound of formula (IId). In embodiments, the compound is not an embodiment of a compound of formula (IIe). In embodiments, the compound is not an embodiment of a compound of formula (IIf). In embodiments, the compound is not an embodiment of a compound of formula (IIg). In embodiments, the compound is not an embodiment of a compound of formula (IIIa). In embodiments, the compound is not an embodiment of a compound of formula (IIIb). In embodiments, the compound is not an embodiment of a compound of formula (IIIc). In embodiments, the compound is not an embodiment of a compound of formula (IIId). In embodiments, the compound is not an embodiment of a compound of formula (IIIe). In embodiments, the compound is not an embodiment of a compound of formula (IIIf). In embodiments, the compound is not an embodiment of a compound of formula (IIIg). In embodiments, the compound is not an embodiment of a compound of formula (IIIh). In embodiments, the compound is not an embodiment of a compound of formula (IIIi). In embodiments, the compound is not an embodiment of a compound of formula (IIIj).

In some embodiments, the compound is not

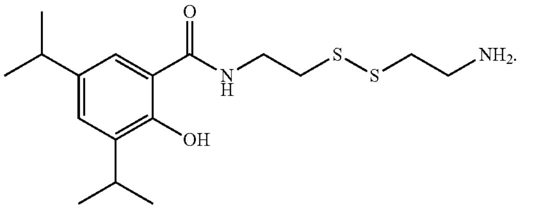 [SMILES: CC(C)c1cc(C(=O)NCCSSCCN)c(O)c(C(C)C)c1]

In some embodiments, the compound is not

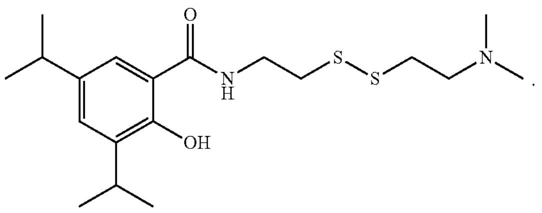 [SMILES: CC(C)c1cc(C(=O)NCCSSCCN(C)C)c(O)c(C(C)C)c1]

In some embodiments, the compound is not

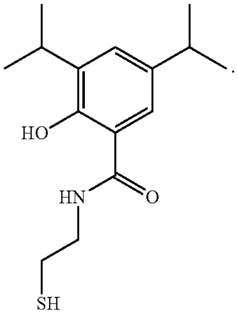 [SMILES: CC(C)c1cc(C(=O)NCCS)c(O)c(C(C)C)c1]

In some embodiments, the compound is not

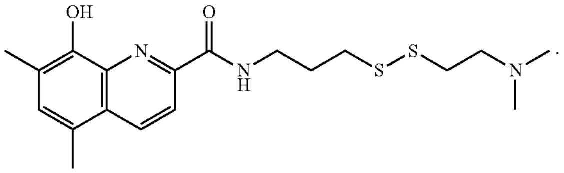

In some embodiments, the compound is not

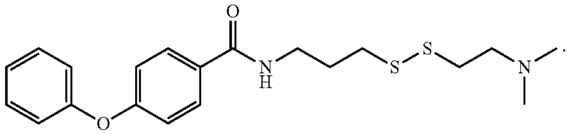 [SMILES: CN(C)CCSSCCCNC(=O)c1ccc(Oc2ccccc2)cc1]

In some embodiments, the compound is not

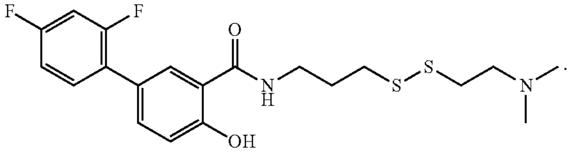 [SMILES: CN(C)CCSSCCCNC(=O)c1cc(-c2ccc(F)cc2F)ccc1O]

In embodiments, the compound is not

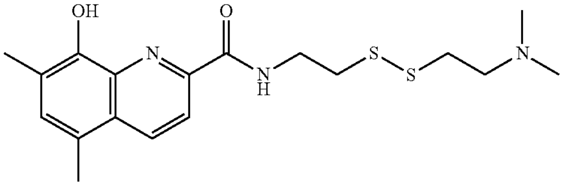

,

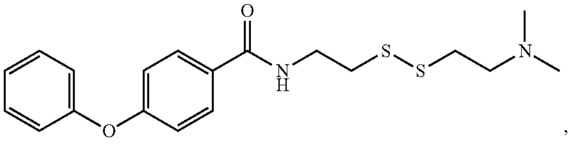

,

-continued
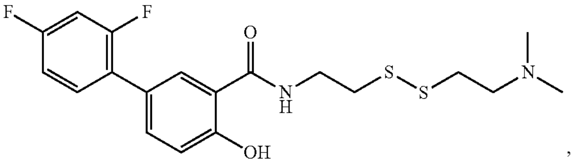
,
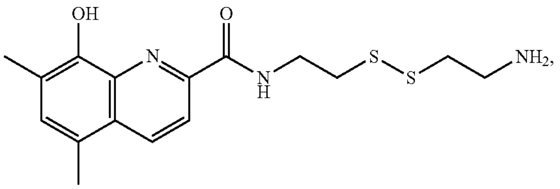
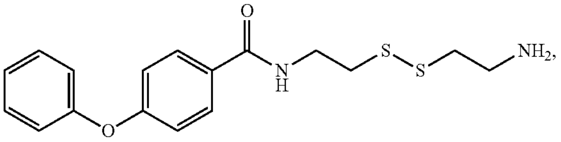
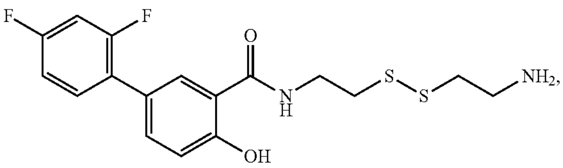
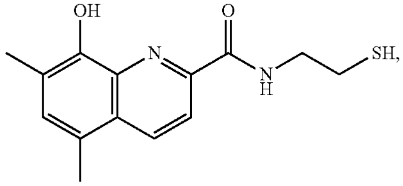
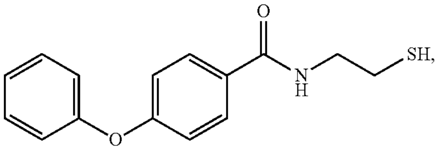
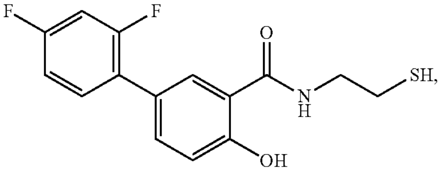
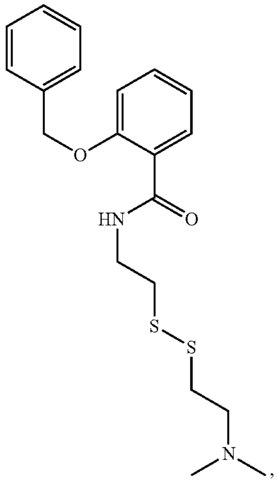
,
-continued
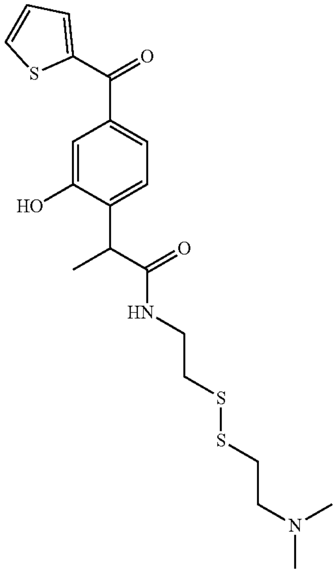
,
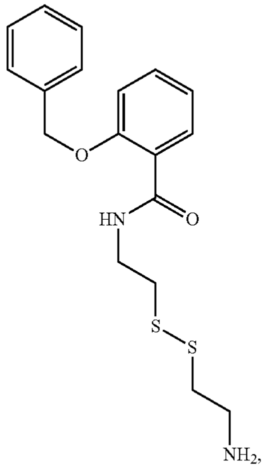
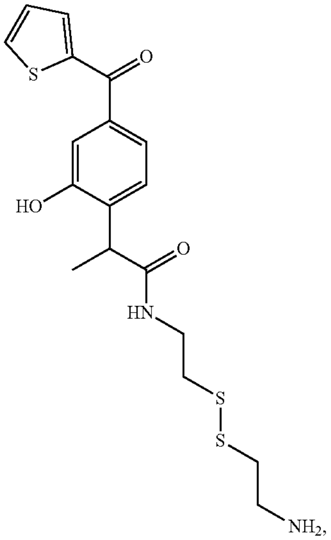
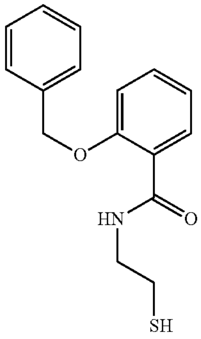
, -continued

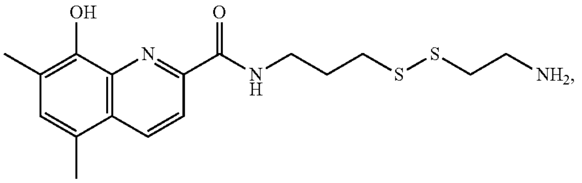

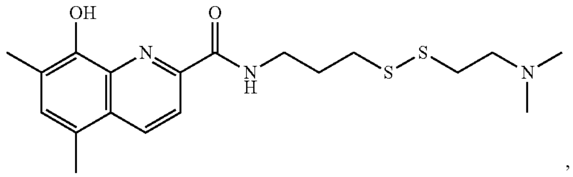

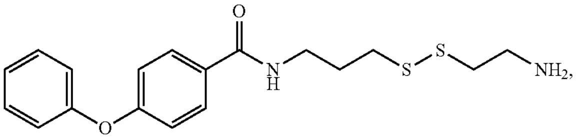

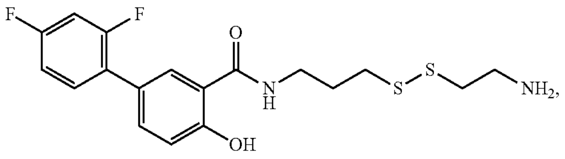

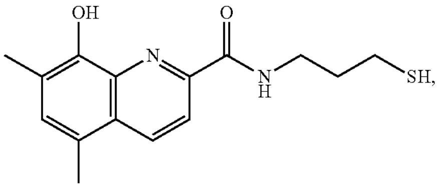

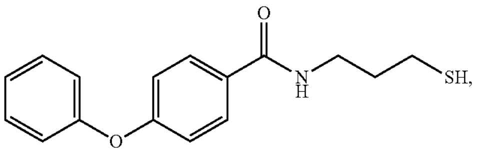

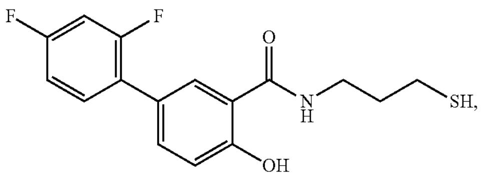

or

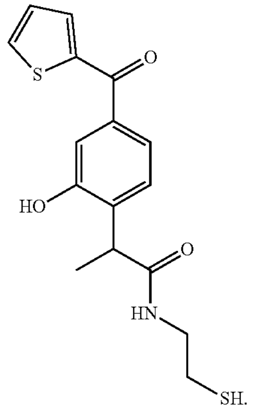

In embodiments, $R^1$ does not include a disulfide bond. In embodiments, $R^1$ does not include a thiol. In embodiments, $R^1$ is not a thiol.

In some embodiments, the compound is not

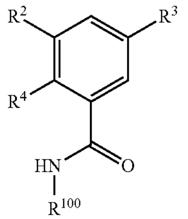

wherein $R^2$ is unsubstituted methyl, unsubstituted ethyl, unsubstituted isopropyl, unsubstituted tert-butyl, —COOH, —$CH(CH_3)(C(O)OH$, or —$CF_3$; $R^3$ is unsubstituted methyl, unsubstituted ethyl, unsubstituted isopropyl, unsubstituted tert-butyl, —$NHC(NH)NH_2$, —$CF_3$, or —CCH; $R^4$ is —OH, —$NH_2$, or —$NHC(NH)NH_2$; and $R^{100}$ is unsubstituted ethyl, unsubstituted n-propyl, or unsubstituted n-butyl. In embodiments, $R^2$ is unsubstituted methyl, unsubstituted ethyl, unsubstituted isopropyl, unsubstituted tert-butyl, —COOH, —$CH(CH_3)(C(O)OH$, or —$CF_3$. In embodiments, $R^3$ is unsubstituted methyl, unsubstituted ethyl, unsubstituted isopropyl, unsubstituted tert-butyl, —$NHC(NH)NH_2$, —$CF_3$, or —CCH. In embodiments, $R^4$ is —OH, —$NH_2$, or —$NHC(NH)NH_2$. In some embodiments, the compound is not

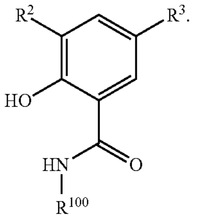

In embodiments, $R^{100}$ is unsubstituted ethyl, unsubstituted n-propyl, or unsubstituted n-butyl. In embodiments, the compound is not a compound described herein (e.g., in an aspect, embodiment, example, figures, table, or claim). In embodiments, the compound is not a compound wherein $R^1$ is —$CH_2CH_2SSCH_2CH_2NH_2$. In embodiments, the compound is not a compound wherein $R^1$ is —$CH_2CH_2SSCH_2CH_2N(CH_3)_2$. In embodiments, the compound is not a compound wherein $R^1$ is —$CH_2CH_2SH$. In embodiments, the compound is not a compound wherein $R^1$ is —$CH_2CH_2CH_2SSCH_2CH_2NH_2$. In embodiments, the compound is not a compound wherein $R^1$ is —$CH_2CH_2CH_2SSCH_2CH_2N(CH_3)_2$. In embodiments, the compound is not a compound wherein $R^1$ is —$CH_2CH_2CH_2SH$.

In an aspect is provided an LRH-1 agonist having the formula of any of the compounds described herein, including embodiments.

In an aspect is provided an LRH-1 agonist having the formula:

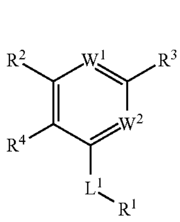

,

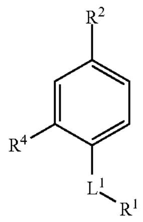

,

-continued

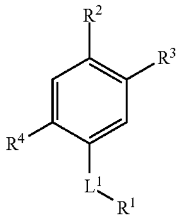
,
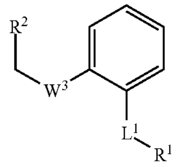
,
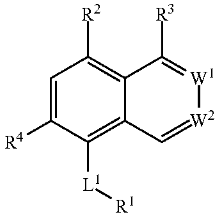
,
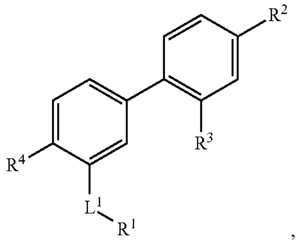
,
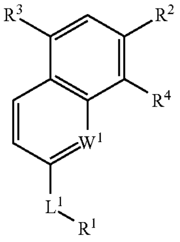
, or
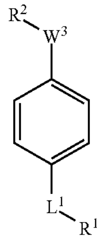
;

wherein $W^1$ and $W^2$ are independently CH or N;

$W^3$ is O, NH, $CH_2$, or S;

$L^1$ is independently a bond, —O—, —NH—, —C(O)—, —C(O)NH—, —NHC(O)—, —S—, —NHC(NH)NH—, —NHC(O)NH—, substituted or unsubstituted alkylene, substituted or unsubstituted heteroalkylene;

$R^1$ is independently a hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{10}$, —$SO_{v1}NR^7R^8$, —$NHNR^7R^8$, —$ONR^7R^8$, —NHC═(O)$NHNR^7R^8$, —NHC═(O)$NR^7R^8$, —$N(O)_{m1}$, —$NR^7R^8$, —C(O)$R^9$, —C(O)—$OR^9$, —C(O)$NR^7R^8$, —$OR^{10}$, —$NR^7SO_2R^{10}$, —$NR^7C$═(O)$R^9$, —$NR^7C$(O)—$OR^9$, —$NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

$R^2$ is independently a halogen, —$CX^2_3$, —$CHX^2_2$, —$CH_2X^2$, —$OCX^2_3$, —$OCH_2X^2$, —$OCHX^2_2$, —CN, —$SO_{n2}R^{14}$, —$SO_{v2}NR^{11}R^{12}$, —$NHNR^{11}R^{12}$, —$ONR^{11}R^{12}$, —NHC═(O)$NHNR^{11}R^{12}$, —NHC═(O)$NR^{11}R^{12}$, —$N(O)_{m2}$, —NR11$R^{12}$, —C(O)$R^{13}$, —C(O)—$OR^{13}$, —C(O)$NR^{11}R^{12}$, —$OR^{14}$, —$NR^{11}SO_2R^{14}$, —$NR^1C$═(O)$R^{13}$, —$NR^{11}C$(O)—$OR^{13}$, —$NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently a halogen, —$CX^3_3$, —$CHX^3_2$, —$CH_2X^3$, —$OCX^3_3$, —$OCH_2X^3$, —$OCHX^3_2$, —CN, —$SO_{n3}R^{18}$, —$SO_{v3}NR^{15}R^{16}$, —$NHNR^{15}R^{16}$, —$ONR^{15}R^{16}$, —NHC═(O)$NHNR^{15}R^{16}$, —NHC═(O)$NR^{15}R^{16}$, —$N(O)_{m3}$, —$NR^{15}R^{16}$, —C(O)$R^{17}$, —C(O)—$OR^{17}$, —C(O)$NR^{15}R^{16}$, —$OR^8$, —$NR^{15}SO_2R^{18}$, —$NR^{15}C$═(O)$R^{17}$, —$NR^{15}C$(O)—$OR^{17}$, —$NR^{15}OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{22}$, —$SO_{v4}NR^{19}R^{20}$, —$NHNR^{19}R^{20}$, —$ONR^{19}R^{20}$, —NHC═(O)$NHNR^{19}R^{20}$, —NHC═(O)$NR^{19}R^{20}$, —NHC═($NR^{21}$)$NR^{19}R^{20}$, —$N(O)_{m4}$, —$NR^{19}R^{20}$, —C(O)$R^{21}$, —C(O)$OR^{21}$, —C(O)$NR^{19}R^{20}$, —$OR^{22}$, —$NR^{19}SO_2R^{22}$, —$NR^{19}C$═(O)$R^{21}$, —$NR^{19}C$(O)$OR^{21}$, —$NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —$CHX_2$, —$CH_2X$, —$OCX_3$, —$OCH_2X$, —$OCHX_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl;

m1, m2, m3, m4, v1, v2, v3, and v4 are independently 1 or 2;

n1, n2, n3, and n4 are independently an integer from 0 to 4; X, $X^1$, $X^2$, $X^3$, and $X^4$ are independently —Cl, —Br, —I, or —F; and wherein $L^1$-$R^1$ does not include a disulfide bond.

In an aspect is provided a LRH-1 agonist having the formula:

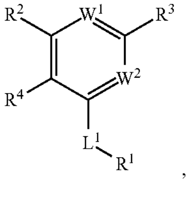
,
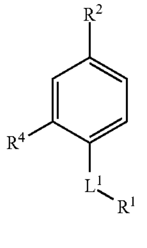
,

-continued

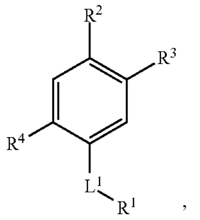

,

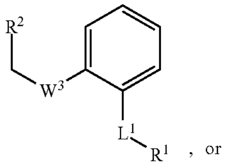

, or

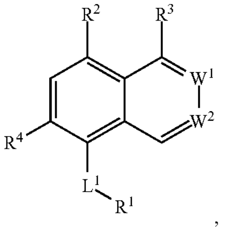

, wherein $W^1$ and $W^2$ are independently CH or N; $W^3$ is O, NH, $CH_2$, or S; $L^1$ is independently a bond, —O—, —NH—, —C(O)—, —C(O)NH—, —NHC(O)—, —S—, —NHC(NH)NH—, —NHC(O)NH—, substituted or unsubstituted $C_1$-$C_5$ alkylene, substituted or unsubstituted 2 to 5 membered heteroalkylene; $R^1$ is independently a hydrogen, halogen, $—CX^{13}$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, $—OCX^1_3$, $—OCHX^1_2$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; E is an electrophilic moiety; $R^2$ is independently a halogen, $—CX^2_3$, —CN, $—SO_2Cl$, $—SO_{n2}R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, $—OCX^2_3$, $—OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently a halogen, $—CX^3_3$, —CN, $—SO_2Cl$, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, $—OCX^3_3$, $—OCHX^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently hydrogen, halogen, $—CX^4_3$, —CN, $—SO_{n4}R^{22}$, $—SO_{v4}NR^{19}R^{20}$, $—NHNR^{19}R^{20}$, $—ONR^{19}R^{20}$, $—NHC{=}(O)NHNR^{19}R^{20}$, $—NHC{=}(O)NR^{19}R^{20}$, $—NHC{=}(NR^{21})NR^{19}R^{20}$, $—N(O)_{m4}$, $—NR^{19}R^{20}$, $—C(O)R^{21}$, $—C(O)OR^{21}$, $—C(O)NR^{19}R^{20}$, $—OR^{22}$, $—NR^{19}SO_2R^{22}$, $—NR^{19}C{=}(O)R^{21}$, $—NR^{19}C(O)OR^{21}$, $—NR^{19}OR^{21}$, $—OCX^4_3$, $—OCHX^4_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, —CN, —OH, $—NH_2$, —COOH, $—CONH_2$, $—NO_2$, —SH, $—SO_2Cl$, $—SO_3H$, $—SO_4H$, $—SO_2NH_2$, $—NHNH_2$, $—ONH_2$, $—NHC{=}(O)NHNH_2$, $—NHC{=}(O)\ NH_2$, $—NHSO_2H$, $—NHC{=}(O)H$, —NHC(O)—OH, —NHOH, $—OCX_3$, $—OCHX^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl; m1, m2, m3, m4, v1, v2, v3, and v4 are independently 1 or 2; n1, n2, n3, and n4 are independently an integer from 0 to 4; X, $X^1$, $X^2$, $X^3$, and $X^4$ are independently —Cl, —Br, —I, or —F.

In an aspect is provided an LRH-1 agonist having the formula:

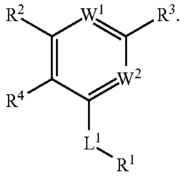

$W^1$ and $W^2$ are independently CH or N. $L^1$ is independently a bond, —O—, —NH—, —C(O)—, —C(O)NH—, —NHC(O)—, —S—, —NHC(O)NH—, substituted or unsubstituted alkylene, substituted or unsubstituted heteroalkylene. $R^1$ is independently a hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—NHC{=}(NR^9)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. E is an electrophilic moiety. $R^2$ is independently a hydrogen, halogen, $—CX^2_3$, $—CHX^2_2$, $—CH_2X^2$, $—OCX^2_3$, $—OCH_2X^2$, $—OCHX^2_2$, —CN, $—SO_{n2}R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—NHC{=}(NR^{13})NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $—CX^3_3$, $—CHX^3_2$, $—CH_2X^3$, $—OCX^3_3$, $—OCH_2X^3$, $—OCHX^3_2$, —CN, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—NHC{=}(NR^{17})NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{22}$, $—SO_{v4}NR^{19}R^{20}$, $—NHNR^{19}R^{20}$, $—ONR^{19}R^{20}$, $—NHC{=}(O)NHNR^{19}R^{20}$, $—NHC{=}(O)NR^{19}R^{20}$, $—NHC{=}(NR^{21})NR^{19}R^{20}$, $—N(O)_{m4}$, $—NR^{19}R^{20}$, $—C(O)R^{21}$, $—C(O)OR^{21}$, $—C(O)NR^{19}R^{20}$, $—OR^{22}$, $—NR^{19}SO_2R^{22}$, $—NR^{19}C{=}(O)R^{21}$, $—NR^{19}C(O)OR^{21}$, $—NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, $—CHX_2$, $—CH_2X$, $—OCX_3$, $—OCH_2X$, $—OCHX_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(NH)NH_2$, $—NHC{=}(O)NH_2$, $—NHSO_2H$, $—NHC{=}(O)H$, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl. The symbols m1, m2, m3, m4, v1, v2, v3, and v4 are independently 1 or 2. The symbols n1, n2, n3, and n4 are independently an integer from 0 to 4. X, $X^1$, $X^2$, $X^3$, and $X^4$ are independently —Cl, —Br, —I, or —F. In embodiments, $L^1$-$R^1$ does not include a disulfide bond. In embodiments, the LRH-1 agonist has the formula:

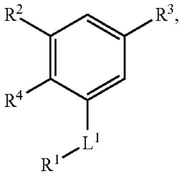

wherein $R^1$, $L^1$, $R^2$, $R^3$, and $R^4$ are as described herein.

In embodiments, the LRH-1 agonist is

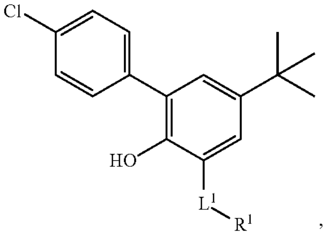

,

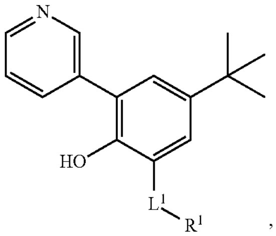

,

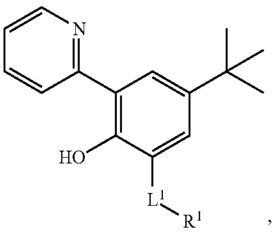

,

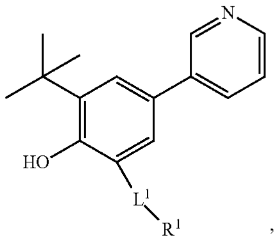

,

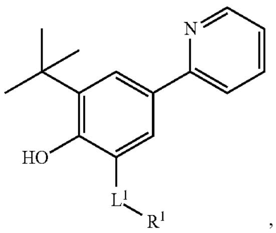

, or

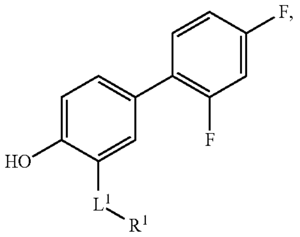

wherein $L^1$ and $R^1$ are as described herein.

In embodiments, the LRH-1 agonist is

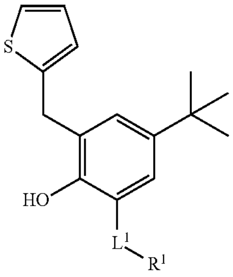

or

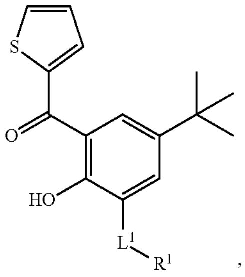

, wherein $L^1$ and $R^1$ are as described herein.

In embodiments, the LRH-1 agonist is
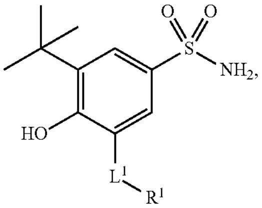
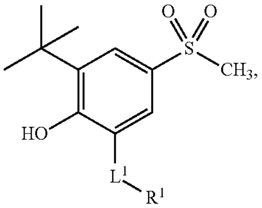
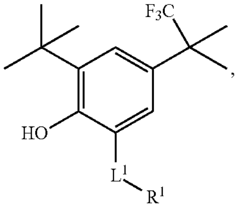
,
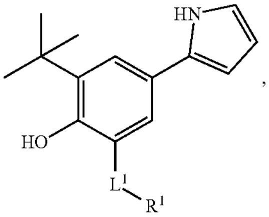
,
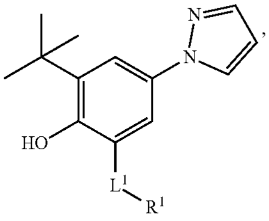
,
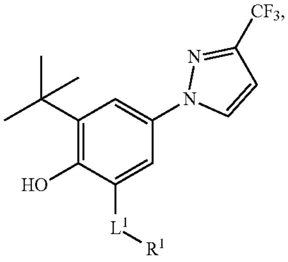
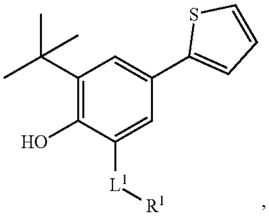
,
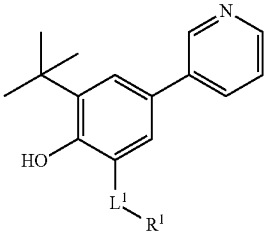
, or
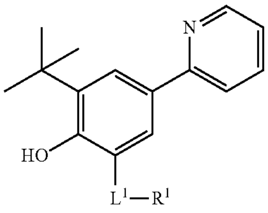
,
wherein $L^1$ and $R^1$ are as described herein.
In embodiments, the LRH-1 agonist is
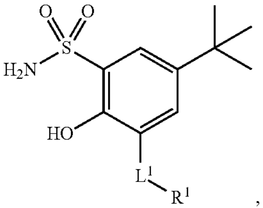
,
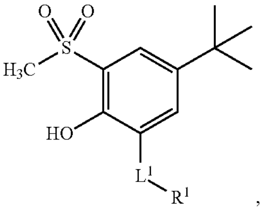
,
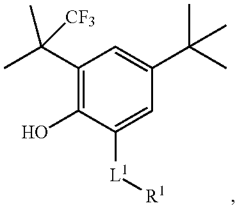
,
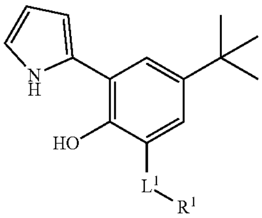
,
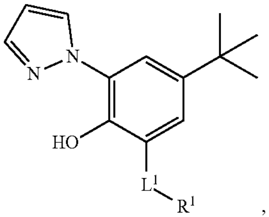
,
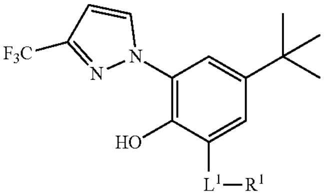
,
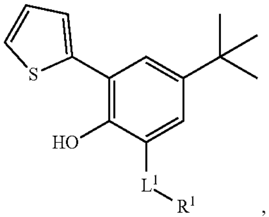
,
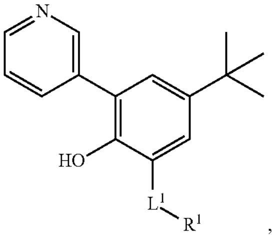
, or
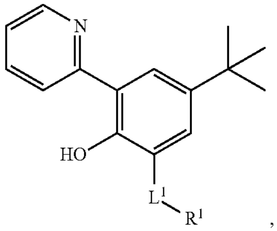
,
wherein $L^1$ and $R^1$ are as described herein.

In embodiments, the LRH-1 agonist is
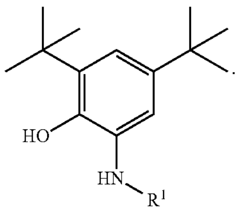
In embodiments, the LRH-1 agonist is
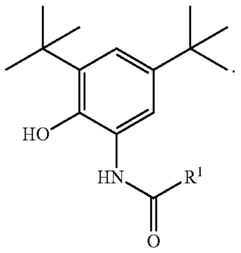
In embodiments, the LRH-1 agonist is
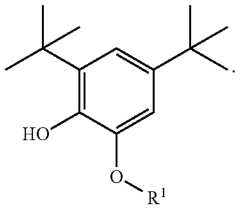
In embodiments, the LRH-1 agonist is
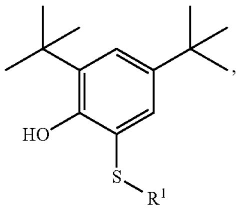
wherein $R^1$ does not include a disulfide bond. In embodiments, the LRH-1 agonist is
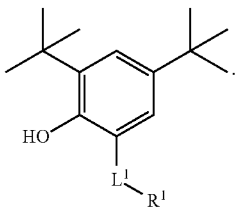
In embodiments, the LRH-1 agonist is
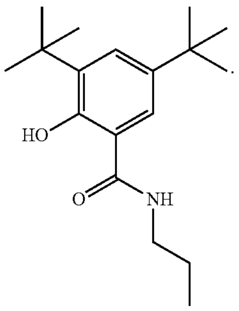 [SMILES: CCCNC(=O)c1cc(C(C)(C)C)cc(C(C)(C)C)c1O]
In embodiments, the LRH-1 agonist is
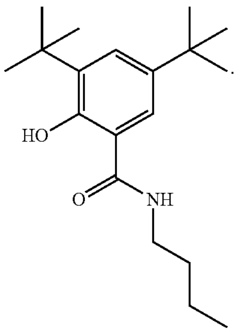 [SMILES: CCCCNC(=O)c1cc(C(C)(C)C)cc(C(C)(C)C)c1O]
In embodiments, the LRH-1 agonist is
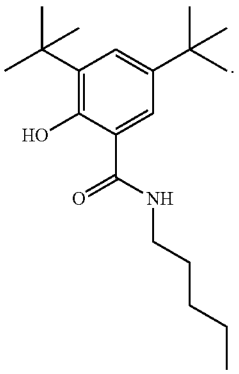 [SMILES: CCCCCNC(=O)c1cc(C(C)(C)C)cc(C(C)(C)C)c1O]
In embodiments, the LRH-1 agonist is
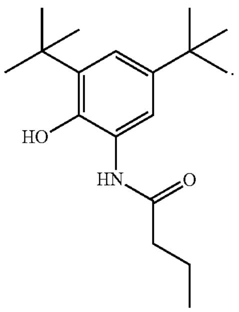 [SMILES: CCCC(=O)Nc1cc(C(C)(C)C)cc(C(C)(C)C)c1O]

In embodiments, the LRH-1 agonist is

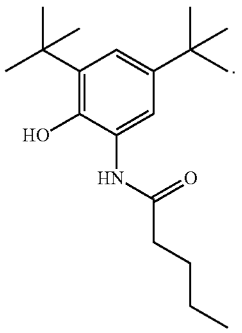 [SMILES: CCCCC(=O)Nc1cc(C(C)(C)C)cc(C(C)(C)C)c1O]

In embodiments, the LRH-1 agonist is

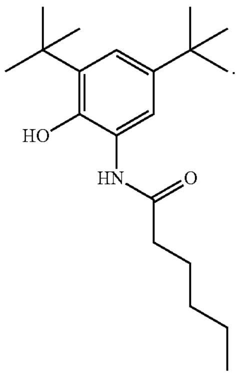 [SMILES: CCCCCC(=O)Nc1cc(C(C)(C)C)cc(C(C)(C)C)c1O]

In some embodiments, the LRH-1 agonist is not

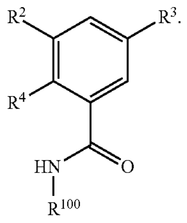

$R^2$, $R^3$, and $R^4$ are as described herein, including in embodiments.

In some embodiments, the LRH-1 agonist is not

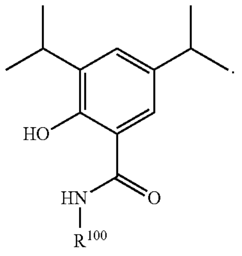

In some embodiments, the LRH-1 agonist is not

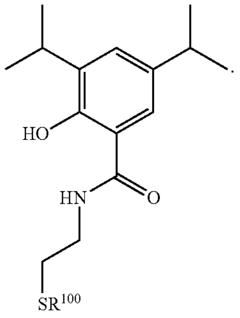

$R^{100}$ is hydrogen, halogen, $—CX^{100}_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—OCX^{100}_3$, $—OCHX^{100}_2$, E, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^{100}$ is independently a halogen (e.g., —F, —Cl, —Br, and/or —I). In embodiments, $R^{100}$ is halogen, $—CX^{100}_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—CHX^{100}_2$, $—CH_2X^{100}$, $—OCX^{100}_3$, $—OCH_2X^{100}$, $—OCHX^{100}_2$, E, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{100}$ is halogen, $—CX^{100}_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, $—CHX^{100}_2$, $—CH_2X^{100}$, $—OCX^{100}_3$, $—OCH_2X^{100}$, or $—OCHX^{100}_2$. In embodiments, $R^{100}$ is E. In embodiments, $R^{100}$ is substituted or unsubstituted alkyl. In embodiments, $R^{100}$ is substituted or unsubstituted heteroalkyl. In embodiments, $R^{100}$ is substituted or unsubstituted cycloalkyl. In embodiments, $R^{100}$ is substituted or unsubstituted heterocycloalkyl. In embodiments, $R^{100}$ is substituted or unsubstituted aryl. In embodiments, $R^{100}$ is substituted or unsubstituted heteroaryl. In embodiments, $R^{100}$ is independently substituted or unsubstituted $C_1$-$C_8$ alkyl. In embodiments, $R^{100}$ is substituted or unsubstituted 2 to 8 membered heteroalkyl. In embodiments, $R^{100}$ is substituted or unsubstituted $C_3$-$C_8$ cycloalkyl. In embodiments, $R^{100}$ is substituted or unsubstituted 3 to 8 membered heterocycloalkyl. In embodiments, $R^{100}$ is substituted or unsubstituted $C_6$-$C_{10}$ aryl. In embodiments, $R^{100}$ is substituted or unsubstituted 5 to 10 membered heteroaryl. In embodiments, $R^{100}$ is independently unsubstituted $C_1$-$C_8$ alkyl. In embodiments, $R^{100}$ is independently unsubstituted 2 to 8 membered heteroalkyl. In embodiments, $R^{100}$ is independently unsubstituted $C_3$-$C_8$ cycloalkyl. In embodiments, $R^{100}$ is independently unsubstituted 3 to 8 membered heterocycloalkyl. In embodiments, $R^{100}$ is independently unsubstituted $C_6$-$C_{10}$ aryl. In embodiments, $R^{100}$ is independently unsubstituted 5 to 10 membered heteroaryl. In embodiments, $R^{100}$ is independently substituted or unsubstituted $C_1$-$C_6$ alkyl. In embodiments, $R^{100}$ is substituted or unsubstituted 2 to 6 membered heteroalkyl. In embodiments, $R^{100}$ is substituted or unsubstituted $C_3$-$C_6$ cycloalkyl. In embodiments, $R^{100}$ is substituted or unsubstituted 3 to 6 membered heterocycloalkyl. In embodiments, $R^{100}$ is substituted or unsubstituted phenyl. In embodiments, $R^{100}$ is substituted or unsubstituted 5 to 6 membered heteroaryl. In embodiments, $R^{100}$ is independently substituted or unsubstituted $C_1$-$C_3$ alkyl. In embodiments, $R^{100}$ is substituted or unsubstituted 2 to 3 membered heteroalkyl. In embodiments, $R^{100}$ is substituted or unsubstituted $C_3$-$C_4$ cycloalkyl. In embodiments, $R^{100}$ is substituted or unsubstituted 3 to 4 membered heterocycloalkyl. In embodiments, $R^{100}$ is substituted or unsubstituted phenyl. In embodiments, $R^{100}$ is substituted or unsubstituted 5 membered heteroaryl. In embodiments, $R^{100}$ is an embodiment of $R^1$.

In embodiments, the LRH-1 agonist is not

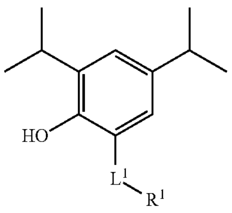

wherein $R^1$ and $L^1$ are as described herein, including in embodiments. In embodiments, the LRH-1 agonist is not

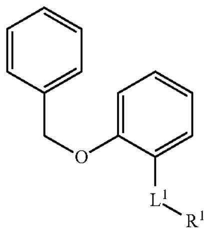

wherein $R^1$ and $L^1$ are as described herein, including in embodiments. In embodiments, the LRH-1 agonist is not

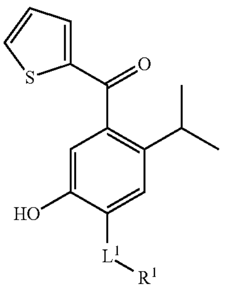

wherein $R^1$ and $L^1$ are as described herein, including in embodiments. In embodiments, the LRH-1 agonist is not

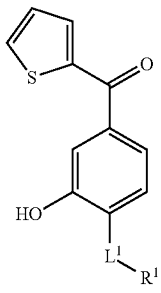

wherein $R^1$ and $L^1$ are as described herein, including in embodiments. In embodiments, the LRH-1 agonist is not

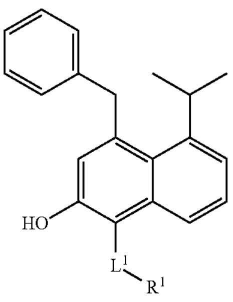

wherein $R^1$ and $L^1$ are as described herein, including in embodiments. In embodiments, the LRH-1 agonist is not

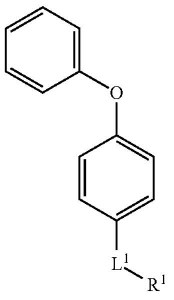

wherein $R^1$ and $L^1$ are as described herein, including in embodiments. In embodiments, the LRH-1 agonist is not

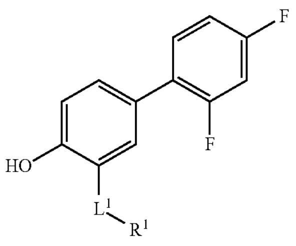

wherein $R^1$ and $L^1$ are as described herein, including in embodiments. In embodiments, the LRH-1 agonist is not

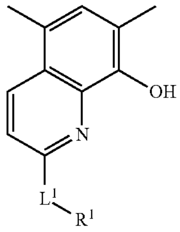

wherein $R^1$ and $L^1$ are as described herein, including in embodiments.

In embodiments, the LRH-1 agonist is not a LRH-1 agonist of formula (IIa). In embodiments, the LRH-1 agonist is not a LRH-1 agonist of formula (IIb). In embodiments, the LRH-1 agonist is not a LRH-1 agonist of formula (IIc). In embodiments, the LRH-1 agonist is not a LRH-1 agonist of formula (IId). In embodiments, the LRH-1 agonist is not a LRH-1 agonist of formula (IIe). In embodiments, the LRH-1 agonist is not a LRH-1 agonist of formula (IIf). In embodiments, the LRH-1 agonist is not a LRH-1 agonist of formula (IIg). In embodiments, the LRH-1 agonist is not a LRH-1 agonist of formula (IIIa). In embodiments, the LRH-1 agonist is not a LRH-1 agonist of formula (IIIb). In embodiments, the LRH-1 agonist is not a LRH-1 agonist of formula (IIIc). In embodiments, the LRH-1 agonist is not a LRH-1 agonist of formula (IIId). In embodiments, the LRH-1 agonist is not a LRH-1 agonist of formula (IIIe). In embodiments, the LRH-1 agonist is not a LRH-1 agonist of formula (IIIf). In embodiments, the LRH-1 agonist is not a LRH-1 agonist of formula (IIIg). In embodiments, the LRH-1 agonist is not a LRH-1 agonist of formula (IIIh). In embodiments, the LRH-1 agonist is not a LRH-1 agonist of formula (IIIi). In embodiments, the LRH-1 agonist is not a LRH-1 agonist of formula (IIIj).

In embodiments, the LRH-1 agonist is not an embodiment of a LRH-1 agonist of formula (IIa). In embodiments, the LRH-1 agonist is not an embodiment of a LRH-1 agonist of formula (IIb). In embodiments, the LRH-1 agonist is not an embodiment of a LRH-1 agonist of formula (IIc). In embodiments, the LRH-1 agonist is not an embodiment of a LRH-1 agonist of formula (IId). In embodiments, the LRH-1 agonist is not an embodiment of a LRH-1 agonist of formula (IIe). In embodiments, the LRH-1 agonist is not an embodiment of a LRH-1 agonist of formula (IIf). In embodiments, the LRH-1 agonist is not an embodiment of a LRH-1 agonist of formula (IIg). In embodiments, the LRH-1 agonist is not an embodiment of a LRH-1 agonist of formula (IIIa). In embodiments, the LRH-1 agonist is not an embodiment of a LRH-1 agonist of formula (IIIb). In embodiments, the LRH-1 agonist is not an embodiment of a LRH-1 agonist of formula (IIIc). In embodiments, the LRH-1 agonist is not an embodiment of a LRH-1 agonist of formula (IIId). In embodiments, the LRH-1 agonist is not an embodiment of a LRH-1 agonist of formula (IIIe). In embodiments, the LRH-1 agonist is not an embodiment of a LRH-1 agonist of formula (IIIf). In embodiments, the LRH-1 agonist is not an embodiment of a LRH-1 agonist of formula (IIIg). In embodiments, the LRH-1 agonist is not an embodiment of a LRH-1 agonist of formula (IIIh). In embodiments, the LRH-1 agonist is not an embodiment of a LRH-1 agonist of formula (IIIi). In embodiments, the LRH-1 agonist is not an embodiment of a LRH-1 agonist of formula (IIIj).

In some embodiments, the LRH-1 agonist is not

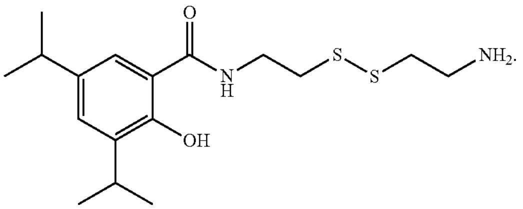 [SMILES: CC(C)c1cc(C(=O)NCCSSCCN)c(O)c(C(C)C)c1]

In some embodiments, the LRH-1 agonist is not

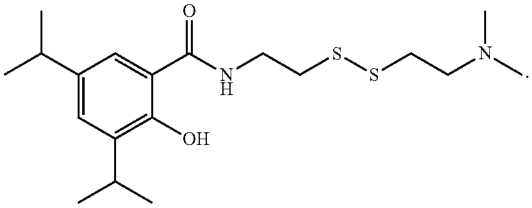 [SMILES: CC(C)c1cc(C(=O)NCCSSCCN(C)C)c(O)c(C(C)C)c1]

In some embodiments, the LRH-1 agonist is not

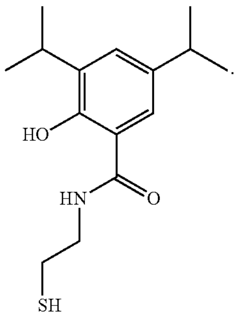 [SMILES: CC(C)c1cc(C(=O)NCCS)c(O)c(C(C)C)c1]

In some embodiments, the LRH-1 agonist is not

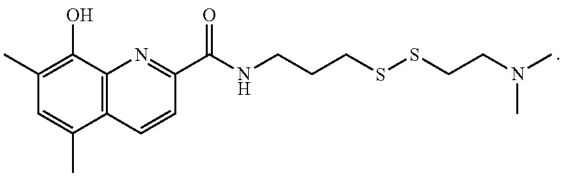

In some embodiments, the LRH-1 agonist is

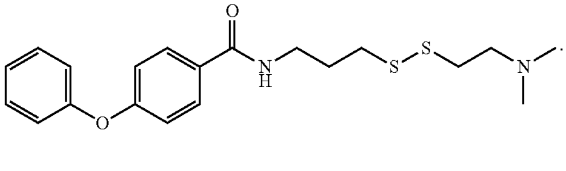 [SMILES: CN(C)CCSSCCCNC(=O)c1ccc(Oc2ccccc2)cc1]

In some embodiments, the LRH-1 agonist is not
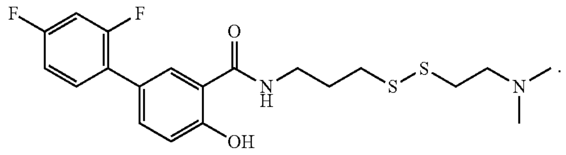 [SMILES: CN(C)CCSSCCCNC(=O)c1cc(-c2ccc(F)cc2F)ccc1O]
In embodiments, the LRH-1 agonist is not
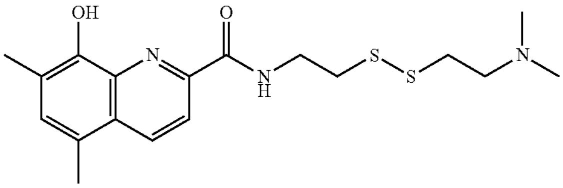
,
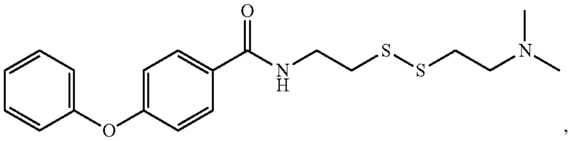
,
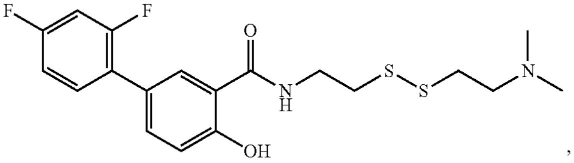
,
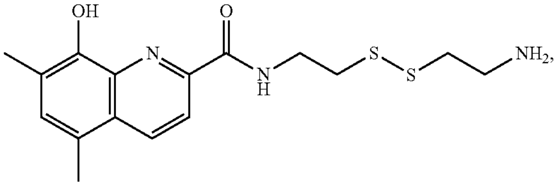
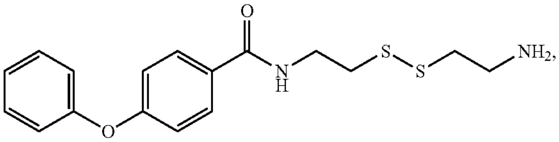
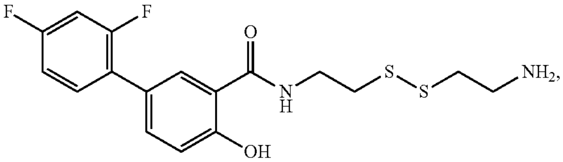
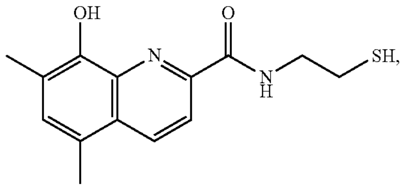
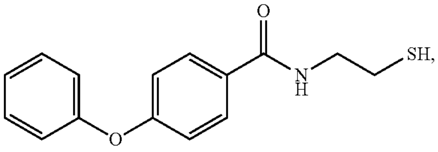
-continued
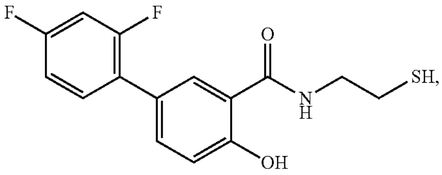
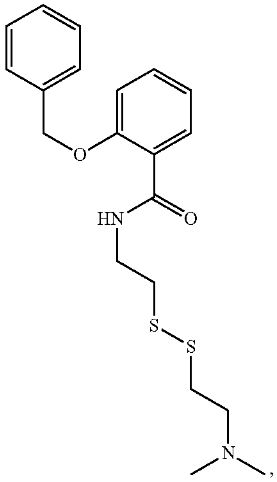
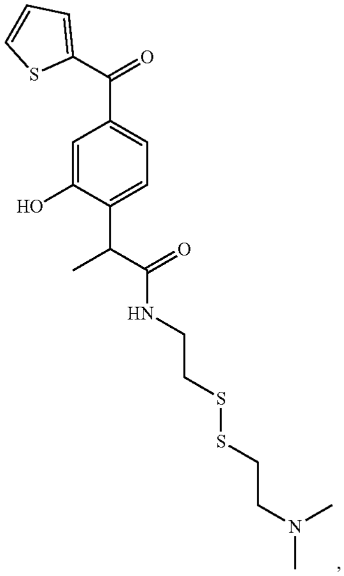
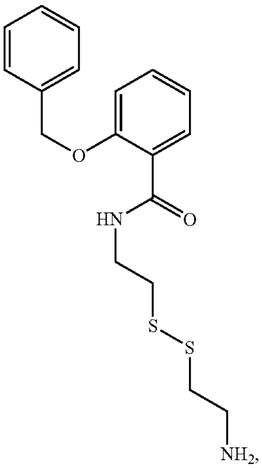

-continued

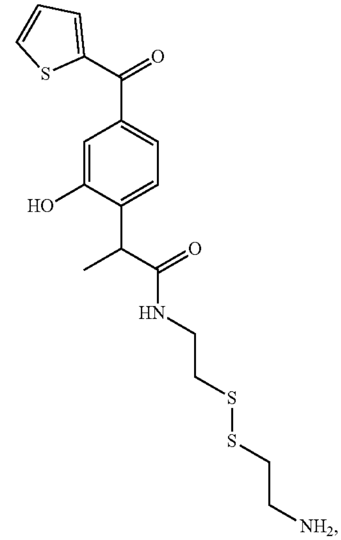

,

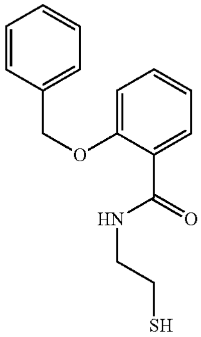

,

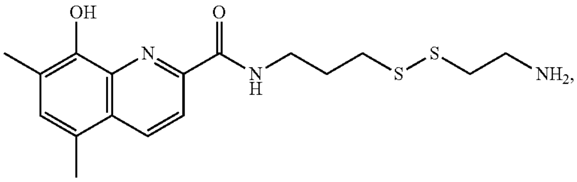

,

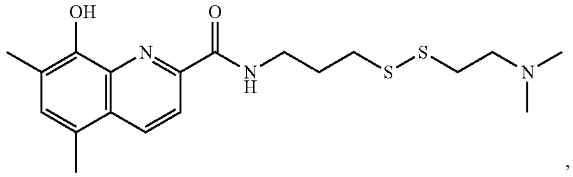

,

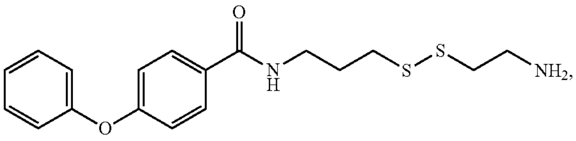

,

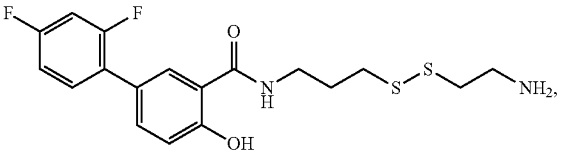

,

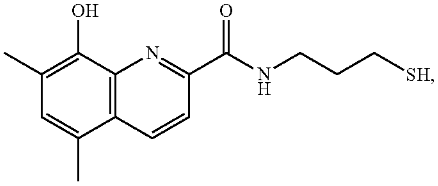

,

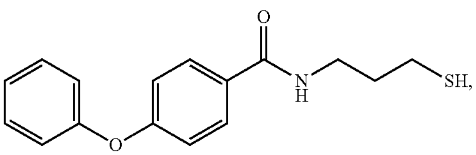

,

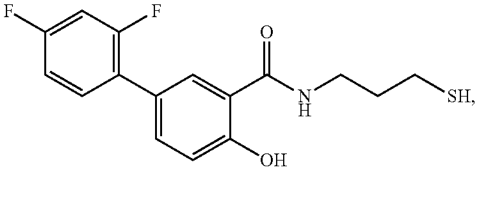

or

-continued

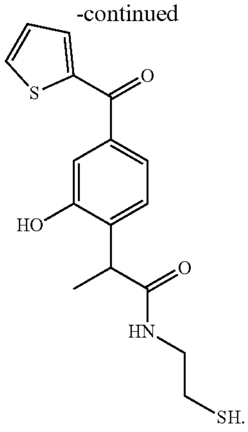

.

In embodiments, $R^1$ does not include a disulfide bond. In embodiments, $R^1$ does not include a thiol. In embodiments, $R^1$ is not a thiol.

In some embodiments, the LRH-1 agonist is not

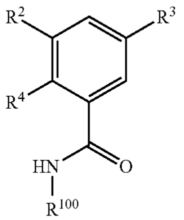

wherein $R^2$ is unsubstituted methyl, unsubstituted ethyl, unsubstituted isopropyl, unsubstituted tert-butyl, —COOH, —CH($CH_3$)(C(O)OH, or —$CF_3$; $R^3$ is unsubstituted methyl, unsubstituted ethyl, unsubstituted isopropyl, unsubstituted tert-butyl, —NHC(NH)$NH_2$, —$CF_3$, or —CCH; $R^4$ is —OH, —$NH_2$, or —NHC(NH)$NH_2$; and $R^{100}$ is unsubstituted ethyl, unsubstituted n-propyl, or unsubstituted n-butyl. In embodiments, $R^2$ is unsubstituted methyl, unsubstituted ethyl, unsubstituted isopropyl, unsubstituted tert-butyl, —COOH, —CH($CH_3$)(C(O)OH, or —$CF_3$. In embodiments, $R^3$ is unsubstituted methyl, unsubstituted ethyl, unsubstituted isopropyl, unsubstituted tert-butyl, —NHC(NH)$NH_2$, —$CF_3$, or —CCH. In embodiments, $R^4$ is —OH, —$NH_2$, or —NHC(NH)$NH_2$. In some embodiments, the LRH-1 agonist is not

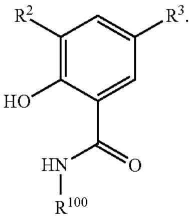

.

In embodiments, $R^{100}$ is unsubstituted ethyl, unsubstituted n-propyl, or unsubstituted n-butyl. In embodiments, the LRH-1 agonist is not a LRH-1 agonist described herein (e.g., in an aspect, embodiment, example, figures, table, or claim). In embodiments, the LRH-1 agonist is not a LRH-1 agonist wherein $R^1$ is —$CH_2CH_2SSCH_2CH_2NH_2$. In embodiments, the LRH-1 agonist is not a LRH-1 agonist wherein $R^1$ is $-CH_2CH_2SSCH_2CH_2N(CH_3)_2$. In embodiments, the LRH-1 agonist is not a LRH-1 agonist wherein $R^1$ is $-CH_2CH_2SH$. In embodiments, the LRH-1 agonist is not a LRH-1 agonist wherein $R^1$ is $-CH_2CH_2CH_2SSCH_2CH_2NH_2$. In embodiments, the LRH-1 agonist is not a LRH-1 agonist wherein $R^1$ is $-CH_2CH_2CH_2SSCH_2CH_2N(CH_3)_2$. In embodiments, the LRH-1 agonist is not a LRH-1 agonist wherein $R^1$ is $-CH_2CH_2CH_2SH$.

In embodiments, the agonist increases the expression or activity of CYP24A1 10%, 20%, 30%, 40%, 50%, 60%, 70%, 80%, 90% or more in comparison to a control. In embodiments, the agonist increases the expression or activity of CYP24A1 about 1%, 2%, 3%, 4%, 5%, 6%, 7%, 8%, 9%, 10%, 11%, 12%, 13%, 14%, 15%, 16%, 17%, 18%, 19%, 20%, 21% 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% more in comparison to a control.

In some embodiments, the compound is any one of the compounds described herein (e.g., in an aspect, embodiment, claim, figure, table, or example).

C. Pharmaceutical Compositions

In another aspect is provided a pharmaceutical composition including a pharmaceutically acceptable excipient and a compound or LRH-1 agonist, or a pharmaceutically acceptable salt thereof, as described herein, including embodiments. In embodiments, the pharmaceutical composition includes a compound, or a pharmaceutically acceptable salt thereof. In embodiments, the pharmaceutical composition includes an LRH-1 agonist, or a pharmaceutically acceptable salt thereof.

In embodiments of the pharmaceutical compositions, the compound or LRH-1 agonist, or a pharmaceutically acceptable salt thereof, as described herein, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments of the pharmaceutical compositions, the second agent is an agent for treating a disease associated with LRH-1 activity. In embodiments, the second agent is an anti-cancer agent. In embodiments, the second agent is a chemotherapeutic. In embodiments of the pharmaceutical compositions, the pharmaceutical composition does not include a second agent (e.g. therapeutic agent).

D. Methods of Treatment

In another aspect is provided a method of treating a nuclear receptor activity-associated disease in a subject in need of such treatment, the method including administering a compound or LRH-1 agonist, or a pharmaceutically acceptable salt thereof, as described herein, including embodiments (e.g., in an aspect, embodiment, example, table, figure, or claim).

In another aspect is provided a method of treating a disease associated with LRH-1 activity in a subject in need of the treatment, the method including administering an effective amount of a compound or LRH-1 agonist, or a pharmaceutically acceptable salt thereof, as described herein.

In another aspect is provided a method of treating a disease associated with aberrant LRH-1 activity in a subject in need of the treatment, the method including administering an effective amount of a compound or LRH-1 agonist, or a pharmaceutically acceptable salt thereof, as described herein.

In embodiments of the method, the compound or LRH-1 agonist, or a pharmaceutically acceptable salt thereof, as described herein, is included in an effective amount. In embodiments of the method, the compound or LRH-1 agonist, or a pharmaceutically acceptable salt thereof, as described herein, is included in a therapeutically effective amount. In embodiments of the method, the compound or LRH-1 agonist, or a pharmaceutically acceptable salt thereof, as described herein, is included in a prophylactically effective amount.

In embodiments, methods described herein do not include administering a second agent (e.g. pharmaceutical agent, therapeutic agent).

In embodiments, the method includes administering a second agent (e.g. therapeutic agent). In embodiments, the method includes administering a second agent (e.g. therapeutic agent) in a therapeutically effective amount. In embodiments of the methods, the second agent is an agent for treating cancer. In embodiments of the methods, the second agent is an agent for treating a disease associated with LRH-1 receptor activity. In embodiments, the second agent is an anti-cancer agent. In embodiments, the second agent is a chemotherapeutic.

In embodiments, the disease is inflammatory bowel disease. In embodiments, the disease is diabetes. In embodiments, the disease is type I diabetes. In embodiments, the disease is type II diabetes. In embodiments, the disease is cancer. In embodiments, the disease is prostate cancer. In embodiments, the disease is pancreatic cancer. In embodiments, the disease is breast cancer. In embodiments, the disease is triple negative breast cancer. In embodiments, the disease is colon cancer. In embodiments, the disease is liver cancer. In embodiments, the disease is bladder cancer. In embodiments, the disease is intestinal cancer. In embodiments, the disease is gall bladder cancer. In embodiments, the disease is gastrointestinal cancer. In embodiments, the disease is ovarian cancer. In embodiments, the disease is arteriosclerosis. In embodiments, the disease is an inflammatory disease. In embodiments, the disease is a cardiovascular disease. In embodiments, the disease is a metabolic disease. In embodiments, the disease is fatty liver disease.

In another aspect is provided a method of treating a inflammatory bowel disease in a subject in need of the treatment, the method including administering an effective amount of a compound or LRH-1 agonist, or a pharmaceutically acceptable salt thereof, as described herein. In embodiments, the disease is Crohn's disease, microscopic colitis, diversion colitis, indeterminate colitis, Behçet's disease, ulcerative colitis.

In another aspect is provided a method of treating diabetes (e.g., type II) in a subject in need of the treatment, the method including administering an effective amount of a compound or LRH-1 agonist, or a pharmaceutically acceptable salt thereof, as described herein. In embodiments, the diabetes is type I. In embodiments, the diabetes is type II.

In another aspect is provided a method of treating cancer in a subject in need of the treatment, the method including administering an effective amount of a compound described herein. In embodiments, the cancer is prostate cancer, pancreatic cancer, breast cancer, colon cancer, liver cancer, bladder cancer, stomach cancer, esophageal cancer, rectal cancer, gastrointestinal cancer, ovarian cancer, or intestinal cancer. In embodiments, the cancer is liver cancer. In embodiments, the cancer is pancreatic cancer. In embodiments, the cancer is ovarian cancer. In embodiments, the cancer is intestinal cancer.

In another aspect is provided a method of treating an inflammatory disease in a subject in need of the treatment, the method including administering an effective amount of a compound or LRH-1 agonist, or a pharmaceutically acceptable salt thereof, as described herein.

In another aspect is provided a method of treating a metabolic disease in a subject in need of the treatment, the method including administering an effective amount of a compound or LRH-1 agonist, or a pharmaceutically acceptable salt thereof, as described herein. In embodiments the metabolic disease is juvenile onset diabetes, diabetes mellitus type 1, or diabetes mellitus type 2.

In another aspect is provided a method of treating a cardiovascular disease in a subject in need of the treatment, the method including administering an effective amount of a compound or LRH-1 agonist, or a pharmaceutically acceptable salt thereof, as described herein.

In embodiments, the method of treatment is a method of prevention. In embodiments, the compounds set forth herein are provided as pharmaceutical compositions including the compound or LRH-1 agonist, or a pharmaceutically acceptable salt thereof, as described herein and a pharmaceutically acceptable excipient.

In another aspect is provided a method of treating arteriosclerosis in a subject in need of the treatment, the method including administering an effective amount of a compound or LRH-1 agonist, or a pharmaceutically acceptable salt thereof, as described herein.

In an aspect is provided a method of treating fatty liver disease in a subject in need of said treatment, said method comprising administering an effective amount of a compound or LRH-1 agonist, or a pharmaceutically acceptable salt thereof, as described herein. In embodiments, the fatty liver disease is alcoholic liver disease. In embodiments, the fatty liver disease is non-alcoholic liver disease. In embodiments, the fatty liver disease is non-alcoholic steatohepatitis.

E. Methods of Modulating a Nuclear Receptor

In another aspect is provided a method of inhibiting LRH-1 activity in a subject in need thereof, including administering to the subject an effective amount of a compound or LRH-1 agonist, or a pharmaceutically acceptable salt thereof, as described herein.

In another aspect is provided a method of activating LRH-1 activity in a subject in need thereof, including administering to the subject an effective amount of a compound or LRH-1 agonist, or a pharmaceutically acceptable salt thereof, as described herein.

In another aspect is provided a method of increasing the level of activity of LRH-1 (e.g., relative to the level of activity in the absence of the compound) in a subject in need thereof, including administering to the subject an effective amount of a compound or LRH-1 agonist, or a pharmaceutically acceptable salt thereof, as described herein.

In another aspect is provided a method of modulating LRH-1 activity, including contacting a cell with a compound or LRH-1 agonist, or a pharmaceutically acceptable salt thereof, as described herein.

In embodiments, the LRH-1 is a human LRH-1.

F. Further Embodiments

Embodiment P1

A compound having the formula:

(I)

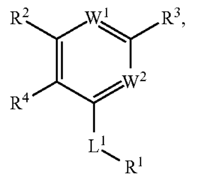

(IIa)

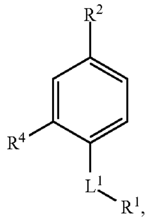

(IIb)

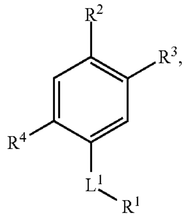

(IIc)

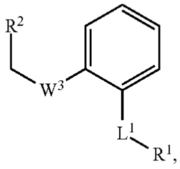

or (IId)

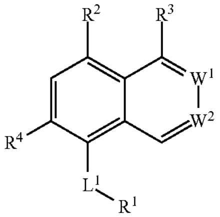

wherein $W^1$ and $W^2$ are independently CH or N; $W^3$ is O, NH, $CH_2$, or S; $L^1$ is independently a bond, —O—, —NH—, —C(O)—, —C(O)NH—, —NHC(O)—, —S—, —NHC(NH)NH—, —NHC(O)NH—, substituted or unsubstituted $C_1$-$C_5$ alkylene, substituted or unsubstituted 2 to 5 membered heteroalkylene; $R^1$ is independently a hydrogen, halogen, $—CX^1_3$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, —$OCX^1{}_3$, —$OCHX^{12}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; E is an electrophilic moiety; $R^2$ is independently a halogen, —$CX^2{}_3$, —CN, —$SO_2Cl$, —$SO_{n2}R^{14}$, —$SO_{v2}NR^{11}R^{12}$, —$NHNR^{11}R^{12}$, —$ONR^{11}R^{12}$, —NHC═(O)$NHNR^{11}R^{12}$, —NHC═(O) $NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}$C═(O)$R^{13}$, —$NR^{11}$C(O)—$OR^{13}$, —$NR^{11}OR^{13}$, —$OCX^2{}_3$, —$OCHX^2{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently a halogen, —$CX^3{}_3$, —CN, —$SO_2Cl$, —$SO_{n3}R^{18}$, —$SO_{v3}NR^{15}R^{16}$, —$NHNR^{15}R^{16}$, —$ONR^{15}R^{16}$, —NHC═(O)$NHNR^{15}R^{16}$, —NHC═(O)$NR^{15}R^{16}$, —$N(O)_{m3}$, —$NR^{15}R^{16}$, —C(O)$R^{17}$, —C(O)—$OR^{17}$, —C(O)$NR^{15}R^{16}$, —$OR^8$, —$NR^{15}SO_2R^8$, —$NR^{15}$C═(O)$R^{17}$, —$NR^{15}$C(O)—$OR^{17}$, —$NR^{15}OR^{17}$, —$OCX^3{}_3$, —$OCHX^3{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is independently hydrogen, halogen, —$CX^4{}_3$, —CN, —$SO_{n4}R^{22}$, —$SO_{v4}NR^{19}R^{20}$, —$NHNR^{19}R^{20}$, —$ONR^{19}R^{20}$, —NHC═(O)$NHNR^{19}R^{20}$, —NHC═(O)$NR^{19}R^{20}$, —NHC═($NR^{21}$)$NR^{19}R^{20}$, —$N(O)_{m4}$, —$NR^{19}R^{20}$, —C(O)$R^{21}$, —C(O)$OR^{21}$, —C(O)$NR^{19}R^{20}$, —$OR^{22}$, —$NR^{19}SO_2R^{22}$, —$NR^{19}$C═(O)$R^{21}$, —$NR^{19}$C(O)$OR^{21}$, —$NR^{19}OR^{21}$, —$OCX^4{}_3$, —$OCHX^4{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCX_3$, —$OCHX^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl; m1, m2, m3, m4, v1, v2, v3, and v4 are independently 1 or 2; n1, n2, n3, and n4 are independently an integer from 0 to 4; X, $X^1$, $X^2$, $X^3$, and $X^4$ are independently —Cl, —Br, —I, or —F.

Embodiment P2

The compound of embodiment P1, wherein $L^1$ is independently a bond, —O—, —NH—, —C(O)—, —C(O)NH—, —NHC(O)—, —S—, —NHC(O)NH—, —NHC(NH)NH—, substituted or unsubstituted $C_1$-$C_3$ alkylene, substituted or unsubstituted 2 to 3 membered heteroalkylene; $R^1$ is independently E, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; $R^2$ is independently a halogen, —$CX^2{}_3$, —CN, —OH, —$NH_2$, —C(O)$R^{13}$, —COOH, —$CONH_2$, —$NO_2$, —SH, —$NHNH_2$, —NHC(O)$NH_2$, —NHC(NH)$NH_2$, —$OCX^2{}_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^3$ is independently a halogen, —$CX^3{}_3$, —CN, —OH, —$NH_2$, —COOH, —$CONH_2$, —$NO_2$, —SH, —$NHNH_2$, —NHC(O)$NH_2$, —NHC(NH)$NH_2$, —$OCX^3{}_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^4$ is independently halogen, —$CF_3$, —CN, —OH, —$NH_2$, —COOH, —$CONH_2$, —$NO_2$, —SH, or —$OCH_3$.

Embodiment P3

The compound of one of embodiments P1 to P2, wherein $L^1$ is independently a bond or —C(O)NH—.

Embodiment P4

The compound of one of embodiments P1 to P2, having the formula:

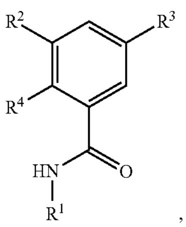
,
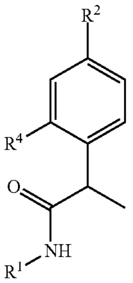
,
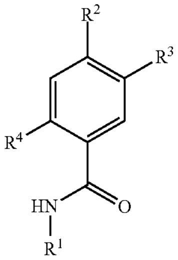
,
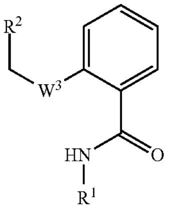
,
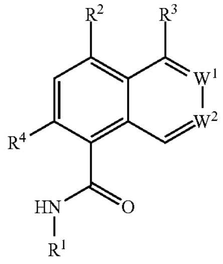
,
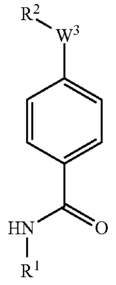
, -continued

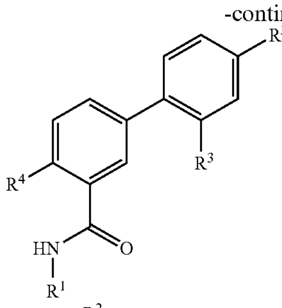

,

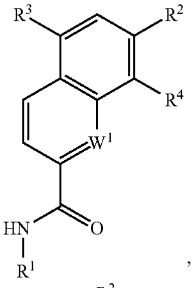

,

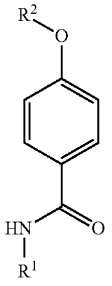

, or

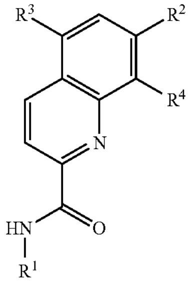

.

Embodiment P5

The compound of one of embodiments P1 to P4, wherein $R^1$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P6

The compound of one of embodiments P1 to P4, wherein $R^1$ is independently substituted or unsubstituted $C_1$-$C_6$ alkyl or substituted or unsubstituted 2 to 6 membered heteroalkyl.

Embodiment P7

The compound of one of embodiments P1 to P4, wherein $R^1$ is independently substituted or unsubstituted $C_1$-$C_5$ alkyl, substituted or unsubstituted 2 to 5 membered alkoxy.

Embodiment P8

The compound of one of embodiments P1 to P4, wherein $R^1$ is independently unsubstituted butyl, unsubstituted pentyl, unsubstituted hexyl, unsubstituted propoxy, unsubstituted butoxy, or unsubstituted pentoxy.

Embodiment P9

The compound of one of embodiments P1 to P4, wherein $R^1$ is independently E; and E is

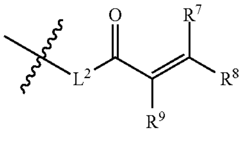

,

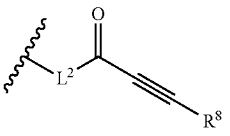

,

-continued

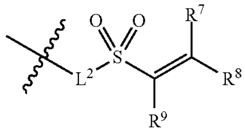

,

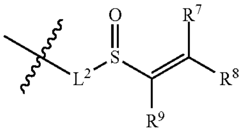

,

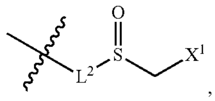

, or

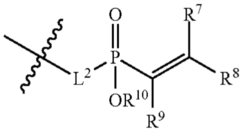

;

$L^2$ is a bond, —O—, —C(O)—, —S—, —SO—, —$S(O)_2$—, —N(H)—, —NHC(O)—, —C(O)NH—, —$SO_2NH$—, —$NHSO_2$—, —OC(O)NH—, —NHC(O)O—, —NHC(O)NH—, —NHC(NH)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P10

The compound of one of embodiments P1 to P9, wherein $R^2$ is independently —$CF_3$, —CN, —OH, —$NH_2$, —COOH, —$CONH_2$, —$NO_2$, —SH, —$NHNH_2$, —NHC(O)$NH_2$, —$OCF_3$, —C(O)$R^{13}$, substituted or unsubstituted $C_1$-$C_4$ alkyl, substituted or unsubstituted 2 to 4 membered heteroalkyl, substituted or unsubstituted phenyl, or substituted or unsubstituted 5 to 6 membered heteroaryl; and $R^{13}$ is unsubstituted phenyl or unsubstituted 5 to 6 membered heteroaryl.

Embodiment P11

The compound of one of embodiments P1 to P9, wherein $R^2$ is independently —$CF_3$, —CN, —OH, —$NH_2$, —COOH, —$CONH_2$, —$NO_2$, —SH, —$NHNH_2$, —NHC(O)$NH_2$, —$OCF_3$, —C(O)$R^{13}$, unsubstituted isopropyl, unsubstituted isobutyl, unsubstituted tert-butyl, unsubstituted propoxy, unsubstituted butoxy, or unsubstituted phenyl; and $R^{13}$ is unsubstituted phenyl or unsubstituted 5 to 6 membered heteroaryl.

Embodiment P12

The compound of one of embodiments P1 to P9, wherein $R^2$ is independently —C(O)$R^{13}$, unsubstituted isopropyl, unsubstituted tert-butyl, or unsubstituted phenyl; and $R^{13}$ is unsubstituted thienyl.

Embodiment P13

The compound of one of embodiments P1 to P12, wherein $R^3$ is independently —$CF_3$, —CN, —OH, —$NH_2$, —COOH, —$CONH_2$, —$NO_2$, —SH, —$NHNH_2$, —NHC(O)$NH_2$, —NHC(NH)$NH_2$, —$OCF_3$, substituted or unsubstituted $C_1$-$C_4$ alkyl or substituted or unsubstituted 2 to 4 membered heteroalkyl.

Embodiment P14

The compound of one of embodiments P1 to P12, wherein $R^3$ is independently —$CF_3$, —CN, —OH, —$NH_2$, —COOH, —$CONH_2$, —$NO_2$, —SH, —$NHNH_2$, —NHC(O)$NH_2$, —NHC(NH)$NH_2$, —$OCF_3$, unsubstituted isopropyl, unsubstituted isobutyl, unsubstituted tert-butyl, unsubstituted propoxy, or unsubstituted butoxy.

Embodiment P15

The compound of one of embodiments P1 to P12, wherein $R^3$ is independently unsubstituted isopropyl or unsubstituted tert-butyl.

Embodiment P16

The compound of one of embodiments P1 to P15, wherein $R^4$ is independently —OH, —$NH_2$, —COOH, —$CONH_2$, —SH, or —$OCH_3$.

Embodiment P17

The compound of one of embodiments P1 to P15, wherein $R^4$ is independently —OH, —$NH_2$, or —COOH.

Embodiment P18

The compound of one of embodiments P1 to P15, wherein $R^4$ is independently —OH.

Embodiment P19

The compound of one of embodiments P1 to P18, wherein said compound is an agonist of a nuclear receptor.

Embodiment P20

The compound of one of embodiments P1 to P18, wherein said compound is an agonist of an LRH-1 receptor.

Embodiment P21

The compound of one of embodiments P1 to P18, wherein said compound is an antagonist of a nuclear receptor.

Embodiment P22

The compound of one of embodiments P1 to P18, wherein said compound is an antagonist of an LRH-1 receptor.

Embodiment P23

A pharmaceutical composition comprising a compound of one of embodiments P1 to P22, or a pharmaceutically acceptable salt thereof, and a pharmaceutically acceptable excipient.

Embodiment P24

The pharmaceutical composition of embodiment P23, comprising a therapeutically effective amount of said compound.

Embodiment P25

A method of treating a disease associated with aberrant LRH-1 activity in a subject in need of said treatment, said method comprising administering an effective amount of a compound of one of embodiments P1 to P22, to said subject.

Embodiment P26

A method of treating an inflammatory disease in a subject in need of said treatment, said method comprising administering an effective amount of a compound of one of embodiments P1 to P22, to said subject.

Embodiment P27

A method of treating inflammatory bowel disease in a subject in need of said treatment, said method comprising administering an effective amount of a compound of one of embodiments P1 to P22, to said subject.

Embodiment P28

A method of treating diabetes in a subject in need of said treatment, said method comprising administering an effective amount of a compound of one of embodiments P1 to P22, to said subject.

Embodiment P29

A method of treating a cardiovascular disease in a subject in need of said treatment, said method comprising administering an effective amount of a compound of one of embodiments P1 to P22, to said subject.

Embodiment P30

A method of treating arteriosclerosis in a subject in need of said treatment, said method comprising administering an effective amount of a compound of one of embodiments P1 to P22, to said subject.

Embodiment P31

A method of treating cancer in a subject in need of said treatment, said method comprising administering an effective amount of a compound of one of embodiments P1 to P22, to said subject.

Embodiment P32

The method of embodiment P31, wherein the cancer is prostate cancer, pancreatic cancer, breast cancer, colon cancer, liver cancer, bladder cancer, ovarian cancer, or intestinal cancer.

G. Additional Embodiments

Embodiment 1

A compound having the formula:

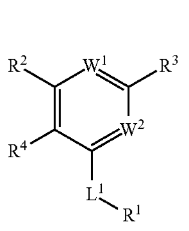

,

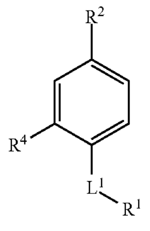

,

-continued

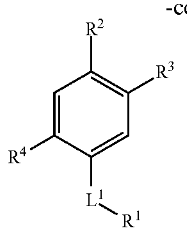

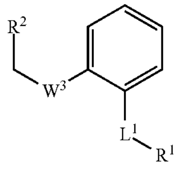

,

,

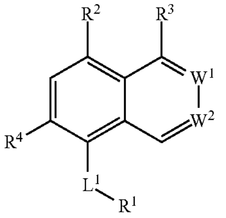

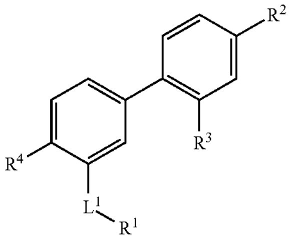

,

,

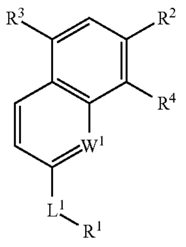

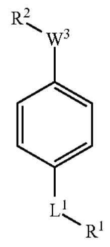

, or

;

wherein $W^1$ and $W^2$ are independently CH or N;

$W^3$ is O, NH, $CH_2$, Or S;

$L^1$ is independently a bond, —O—, —NH—, —C(O)—, —C(O)NH—, —NHC(O)—, —S—, —NHC(NH)NH—, —NHC(O)NH—, substituted or unsubstituted alkylene, substituted or unsubstituted heteroalkylene;

$R^1$ is independently a hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

$R^2$ is independently a halogen, $—CX^2_3$, $—CHX^2_2$, $—CH_{2X2}$, $—OCX^2_3$, $—OCH_{2X2}$, $—OCHX^2_2$, —CN, $—SO_{n2}R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently a halogen, $—CX^3_3$, $—CHX^3_2$, $—CH_2X^3$, $—OCX^3_3$, $—OCH_2X^3$, $—OCHX^3_2$, —CN, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, $—CX^4_3$, $—CHX^4_2$, $—CH_2X^4$, $—OCX^4_3$, $—OCH_2X^4$, $—OCHX^4_2$, —CN, $—SO_{n4}R^{22}$, $—SO_{v4}NR^{19}R^{20}$, $—NHNR^{19}R^{20}$, $—ONR^{19}R^{20}$, $—NHC{=}(O)NHNR^{19}R^{20}$, $—NHC{=}(O)NR^{19}R^{20}$, $—NHC{=}(NR^{21})NR^{19}R^{20}$, $—N(O)_{m4}$, $—NR^{19}R^{20}$, $—C(O)R^{21}$, $—C(O)OR^{21}$, $—C(O)NR^{19}R^{20}$, $—OR^{22}$, $—NR^{19}SO_2R^{22}$, $—NR^{19}C{=}(O)R^{21}$, $—NR^{19}C(O)OR^{21}$, $—NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, $—CHX_2$, $—CH_2X$, $—OCX_3$, $—OCH_2X$, $—OCHX_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)NH_2$, $—NHSO_2H$, $—NHC{=}(O)H$, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl;

m1, m2, m3, m4, v1, v2, v3, and v4 are independently 1 or 2;

n1, n2, n3, and n4 are independently an integer from 0 to 4;

X, $X^1$, $X^2$, $X^3$, and $X^4$ are independently —Cl, —Br, —I, or —F; and wherein $L^1$-R does not include a disulfide bond.

Embodiment 2

The compound of embodiment 1, wherein $L^1$ is independently a bond, —O—, —NH—, —C(O)—, —C(O)NH—, —NHC(O)—, —S—, —NHC(O)NH—, —NHC(NH)NH—, substituted or unsubstituted $C_1$-$C_4$ alkylene, substituted or unsubstituted 2 to 4 membered heteroalkylene; $R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, E, substituted or unsubstituted $C_1$-$C_5$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; $R^2$ is independently a halogen, $—CX^2_3$, $—CHX^2_2$, $—CH_2X^2$, $—OCX^2_3$, $—OCH_2X^2$, $—OCHX^2_2$, —CN, $—SO_{n2}R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^3$ is independently a halogen, $—CX^3_3$, $—CHX^3_2$, $—CH_2X^3$, $—OCX^3_3$, $—OCH_2X^3$, $—OCHX^3_2$, —CN, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^4$ is independently halogen, $—CF_3$, —CN, —OH, $—NH_2$, —COOH, $—CONH_2$, $—NO_2$, —SH, or $—OCH_3$.

Embodiment 3

The compound of embodiment 1, wherein $L^1$ is independently a bond, —O—, —NH—, —C(O)—, —C(O)NH—, —NHC(O)—, —S—, —NHC(O)NH—, —NHC(NH)NH—, substituted or unsubstituted $C_1$-$C_4$ alkylene, substituted or unsubstituted 2 to 4 membered heteroalkylene; $R^1$ is independently hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, substituted or unsubstituted $C_1$-$C_5$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; $R^2$ is independently a halogen, $—CX^2_3$, $—CHX^2_2$, $—CH_2X^2$, $—OCX^2_3$, $—OCH_2X^2$, $—OCHX^2_2$, —CN, $—SO_{n2}R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^3$ is independently a halogen, $—CX^3_3$, $—CHX^3_2$, $—CH_2X^3$, $—OCX^3_3$, $—OCH_2X^3$, $—OCHX^3_2$, —CN, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^4$ is independently halogen, $—CF_3$, —CN, —OH, $—NH_2$, —COOH, $—CONH_2$, $—NO_2$, —SH, or $—OCH_3$.

Embodiment 4

The compound of one of embodiments 1 to 2, wherein $L^1$ is independently a bond.

Embodiment 5

The compound of one of embodiments 1 to 2, wherein $L^1$ is independently —O—.

Embodiment 6

The compound of one of embodiments 1 to 2, wherein $L^1$ is independently —NH—.

Embodiment 7

The compound of one of embodiments 1 to 2, wherein $L^1$ is independently —C(O)—.

Embodiment 8

The compound of one of embodiments 1 to 2, wherein $L^1$ is independently —C(O)NH—.

Embodiment 9

The compound of one of embodiments 1 to 2, wherein $L^1$ is independently —NHC(O)—.

Embodiment 10

The compound of one of embodiments 1 to 2, wherein $L^1$ is independently —S—.

Embodiment 11

The compound of embodiment 1, having the formula:

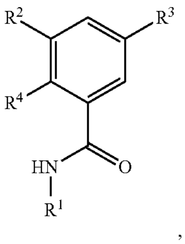
,
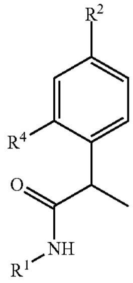
,

-continued

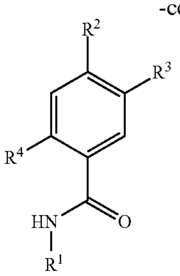

,

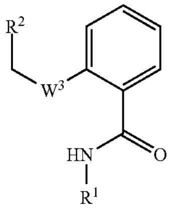

,

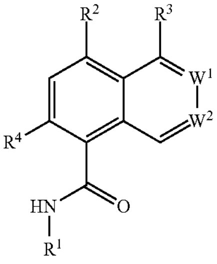

,

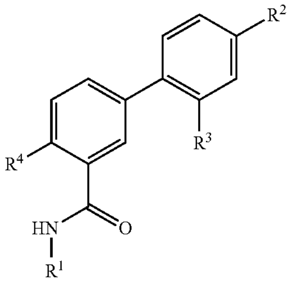

,

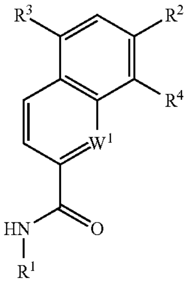

, or

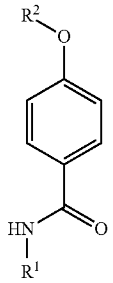

.

Embodiment 12

The compound of one of embodiments 1 to 10, having the formula:

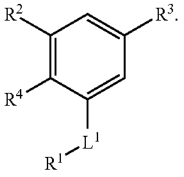

Embodiment 13

The compound of embodiment 1, having the formula:

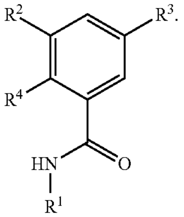

Embodiment 14

The compound of one of embodiments 1 to 13, wherein $R^1$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 15

The compound of one of embodiments 1 to 13, wherein $R^1$ is independently substituted or unsubstituted $C_1$-$C_6$ alkyl or substituted or unsubstituted 2 to 6 membered heteroalkyl.

Embodiment 16

The compound of one of embodiments 1 to 13, wherein $R^1$ is independently substituted or unsubstituted $C_1$-$C_5$ alkyl, substituted or unsubstituted 2 to 5 membered alkoxy.

Embodiment 17

The compound of one of embodiments 1 to 13, wherein $R^1$ is independently unsubstituted butyl, unsubstituted pentyl, unsubstituted hexyl, unsubstituted propoxy, unsubstituted butoxy, or unsubstituted pentoxy.

Embodiment 18

The compound of one of embodiments 1, 2, 4 to 13, wherein $R^1$ is independently E; wherein E is

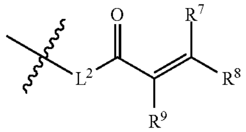

,

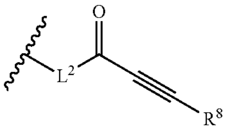

,

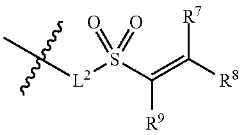

,

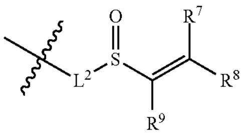

,

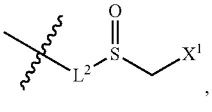

, or

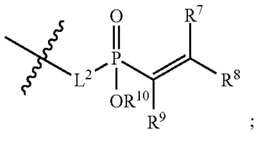

;

and $L^2$ is a bond, —O—, —C(O)—, —S—, —SO—, —$S(O)_2$—, —N(H)—, —NHC(O)—, —C(O)NH—, —$SO_2$NH—, —NH$SO_2$—, —OC(O)NH—, —NHC(O)O—, —NHC(O)NH—, —NHC(NH)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 19

The compound of embodiment 18, wherein $L^2$ is —N(H)—.

Embodiment 20

The compound of embodiment 18, wherein $L^2$ is substituted or unsubstituted 5 to 7 membered heterocycloalkylene.

Embodiment 21

The compound of embodiment 18, wherein $L^2$ is substituted or unsubstituted pyrrolidinyl, substituted or unsubstituted imidazolidinyl, substituted or unsubstituted pyrazolidinyl, substituted or unsubstituted piperidinyl, or substituted or unsubstituted piperazinyl.

Embodiment 22

The compound of one of embodiments 1 to 13, wherein $R^1$ is independently unsubstituted $C_3$-$C_5$ alkyl.

Embodiment 23

The compound of one of embodiments 1 to 13, wherein $R^1$ is independently unsubstituted n-butyl.

Embodiment 24

The compound of one of embodiments 1 to 23, wherein $R^2$ is independently —$CX^2_3$, —$CHX^2_2$, —$CH_2X^2$, —$OCX^2_3$, —$OCH_2X^2$, —$OCHX^2_2$, —CN, —$SO_2R^{14}$, —$SR^{14}$, —$SO_2NR^{11}R^{12}$, —$NR^{11}R^{12}$, —$C(O)R^{13}$, —C(O)$OR^{13}$, —$C(O)NR^{11}R^{12}$, —$OR^{14}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^{11}$, $R^{12}$, $R^{13}$, and $R^{14}$ are independently hydrogen, —$CX_3$, —$CHX_2$, —$CH_2X$, —CN, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 25

The compound of one of embodiments 1 to 23, wherein $R^2$ is independently —$SO_2R^{14}$, —$SO_2NR^{11}R^{12}$, —$C(O)R^{13}$, $R^{33}$-substituted or unsubstituted $C_1$-$C_5$ alkyl, $R^{33}$-substituted or unsubstituted 2 to 5 membered heteroalkyl, $R^{33}$-substituted or unsubstituted $C_3$-$C_6$ cycloalkyl, $R^{33}$-substituted or unsubstituted 3 to 6 membered heterocycloalkyl, $R^{33}$-substituted or unsubstituted phenyl, or $R^{33}$-substituted or unsubstituted 5 to 6 membered heteroaryl; and $R^{11}$, $R^{12}$, $R^{13}$, and $R^{14}$ are independently hydrogen, —$CX_3$, —$CHX_2$, —$CH_2X$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $R^{33}$ is independently halogen, —$CF_3$, —$CHF_2$, —$CH_2F$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 26

The compound of one of embodiments 1 to 23, wherein $R^2$ is independently —$SO_2R^{14}$, —$SO_2NR^{11}R^{12}$, —$C(O)R^{13}$, $R^{33}$-substituted or unsubstituted methyl, $R^{33}$-substituted or unsubstituted ethyl, $R^{33}$-substituted or unsubstituted isopropyl, $R^{33}$-substituted or unsubstituted tert-butyl, $R^{33}$-substituted or unsubstituted phenyl, or $R^{33}$-substituted or unsubstituted 5 to 6 membered heteroaryl; and $R^{11}$ and $R^{12}$ are independently hydrogen, —$CX_3$, —$CHX_2$, —$CH_2X$, or unsubstituted $C_1$-$C_4$ alkyl; $R^{13}$ is unsubstituted 5 to 6 membered heteroaryl; $R^{14}$ are independently —$CX_3$, —$CHX_2$, —$CH_2X$, or unsubstituted $C_1$-$C_4$ alkyl; and $R^{33}$ is independently halogen, —$CF_3$, —$CHF_2$, —$CH_2F$, or unsubstituted 5 to 6 membered heteroaryl.

Embodiment 27

The compound of one of embodiments 1 to 23, wherein $R^2$ is independently —$SO_2CH_3$, —$SO_2NH_2$, —$C(O)R^{13}$, $R^{33}$-substituted or unsubstituted methyl, $R^{33}$-substituted or unsubstituted tert-butyl, $R^{33}$-substituted or unsubstituted pyrazolyl, $R^{33}$-substituted or unsubstituted pyrrolyl, $R^{33}$-substituted or unsubstituted thienyl, $R^{33}$-substituted or unsubstituted phenyl, or $R^{33}$-substituted or unsubstituted pyridyl; and $R^{13}$ is unsubstituted thienyl; and $R^{33}$ is independently halogen, —$CF_3$, or unsubstituted thienyl.

Embodiment 28

The compound of one of embodiments 1 to 23, wherein $R^2$ is independently unsubstituted tert-butyl.

Embodiment 29

The compound of one of embodiments 1 to 28, wherein $R^3$ is independently —$CX^3_3$, —$CHX^3_2$, —$CH_2X^3$, —$OCX^3_3$, —$OCH_2X^3$, —$OCHX^3_2$, —CN, —$SO_2R^{18}$, —$SR^{18}$, —$SO_2NR^{15}R^{16}$, —$NR^{15}R^{16}$, —$C(O)R^{17}$, —C(O)—$OR^{17}$, —$C(O)NR^{15}R^{16}$, —$OR^{18}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^{15}$, $R^{16}$, $R^{17}$, and $R^{18}$ are independently hydrogen, —$CX_3$, —$CHX_2$, —$CH_2X$, —CN, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 30

The compound of one of embodiments 1 to 28, wherein $R^3$ is independently —$SO_2R^{18}$, —$SO_2NR^{15}R^{16}$, —$C(O)R^{17}$, $R^{36}$-substituted or unsubstituted $C_1$-$C_5$ alkyl, $R^{36}$-substituted or unsubstituted 2 to 5 membered heteroalkyl, $R^{36}$-substituted or unsubstituted $C_3$-$C_6$ cycloalkyl, $R^{36}$-substituted or unsubstituted 3 to 6 membered heterocycloalkyl, $R^{36}$-substituted or unsubstituted phenyl, or $R^{36}$-substituted or unsubstituted 5 to 6 membered heteroaryl; and $R^{15}$, $R^{16}$, $R^{17}$, and $R^{18}$ are independently hydrogen, —$CX_3$, —$CHX_2$, —$CH_2X$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $R^{36}$ is independently halogen, —$CF_3$, —$CHF_2$, —$CH_2F$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 31

The compound of one of embodiments 1 to 28, wherein $R^3$ is independently $—SO_2R^{18}$, $—SO_2NR^{15}R^{16}$, $—C(O)R^{17}$, $R^{36}$-substituted or unsubstituted methyl, $R^{36}$-substituted or unsubstituted ethyl, $R^{36}$-substituted or unsubstituted isopropyl, $R^{36}$-substituted or unsubstituted tert-butyl, $R^{36}$-substituted or unsubstituted phenyl, or $R^{36}$-substituted or unsubstituted 5 to 6 membered heteroaryl; and $R^{15}$ and $R^{16}$ are independently hydrogen, $—CX_3$, $—CHX_2$, $—CH_2X$, or unsubstituted $C_1$-$C_4$ alkyl; $R^{17}$ is unsubstituted 5 to 6 membered heteroaryl; $R^{18}$ are independently $—CX_3$, $—CHX_2$, $—CH_2X$, or unsubstituted $C_1$-$C_4$ alkyl; and $R^{36}$ is independently halogen, $—CF_3$, $—CHF_2$, $—CH_2F$, or unsubstituted 5 to 6 membered heteroaryl.

Embodiment 32

The compound of one of embodiments 1 to 28, wherein $R^3$ is independently $—SO_2CH_3$, $—SO_2NH_2$, $—C(O)R^{17}$, $R^{36}$-substituted or unsubstituted methyl, $R^{36}$-substituted or unsubstituted tert-butyl, $R^{36}$-substituted or unsubstituted pyrazolyl, $R^{36}$-substituted or unsubstituted pyrrolyl, $R^{36}$-substituted or unsubstituted thienyl, $R^{36}$-substituted or unsubstituted phenyl, or $R^{36}$-substituted or unsubstituted pyridyl; and $R^{17}$ is unsubstituted thienyl; and $R^{36}$ is independently halogen, $—CF_3$, or unsubstituted thienyl.

Embodiment 33

The compound of one of embodiments 1 to 28, wherein $R^3$ is independently unsubstituted tert-butyl.

Embodiment 34

The compound of one of embodiments 1 to 33, wherein $R^4$ is independently —OH, $—NH_2$, —COOH, $—CONH_2$, —SH, or $—OCH_3$.

Embodiment 35

The compound of one of embodiments 1 to 33, wherein $R^4$ is independently —OH, $—NH_2$, or —COOH.

Embodiment 36

The compound of one of embodiments 1 to 33, wherein $R^4$ is independently —OH.

Embodiment 37

The compound of one of embodiments 1 to 33, wherein $R^4$ is independently $—NH_2$.

Embodiment 38

The compound of one of embodiments 1 to 33, wherein $R^4$ is independently —COOH.

Embodiment 39

The compound of one of embodiments 1 to 33, wherein $R^4$ is independently —SH.

Embodiment 40

The compound of one of embodiments 1 to 33, wherein $R^4$ is independently $—CONH_2$.

Embodiment 41

The compound of one of embodiments 1 to 33, wherein $R^4$ is independently $—OCH_3$.

Embodiment 42

The compound of one of embodiments 1 to 41, wherein said compound is an agonist of a nuclear receptor.

Embodiment 43

The compound of one of embodiments 1 to 41, wherein said compound is an agonist of a LRH-1 receptor.

Embodiment 44

The compound of one of embodiments 1 to 41, wherein said compound is an agonist of a human LRH-1 receptor.

Embodiment 45

The compound of one of embodiments 1 to 41, wherein said compound is an antagonist of a nuclear receptor.

Embodiment 46

The compound of one of embodiments 1 to 41, wherein said compound is an antagonist of a LRH-1 receptor.

Embodiment 47

The compound of one of embodiments 1 to 41, wherein said compound is an antagonist of a human LRH-1 receptor.

Embodiment 48

A pharmaceutical composition comprising a compound of one of embodiments 1 to 47, or a pharmaceutically acceptable salt thereof, and a pharmaceutically acceptable excipient.

Embodiment 49

The pharmaceutical composition of embodiment 48, comprising a therapeutically effective amount of said compound.

Embodiment 50

A method of treating a disease associated with aberrant LRH-1 activity in a subject in need of said treatment, said method comprising administering an effective amount of a compound of one of embodiments 1 to 47, to said subject.

Embodiment 51

A method of treating an inflammatory disease in a subject in need of said treatment, said method comprising administering an effective amount of a compound of one of embodiments 1 to 47, to said subject.

Embodiment 52

A method of treating inflammatory bowel disease in a subject in need of said treatment, said method comprising administering an effective amount of a compound of one of embodiments 1 to 47, to said subject.

Embodiment 53

A method of treating diabetes in a subject in need of said treatment, said method comprising administering an effective amount of a compound of one of embodiments 1 to 47, to said subject.

Embodiment 54

A method of treating a cardiovascular disease in a subject in need of said treatment, said method comprising administering an effective amount of a compound of one of embodiments 1 to 47, to said subject.

Embodiment 55

A method of treating arteriosclerosis in a subject in need of said treatment, said method comprising administering an effective amount of a compound of one of embodiments 1 to 47, to said subject.

Embodiment 56

A method of treating cancer in a subject in need of said treatment, said method comprising administering an effective amount of a compound of one of embodiments 1 to 47, to said subject.

Embodiment 57

The method of embodiment 56, wherein the cancer is prostate cancer, pancreatic cancer, breast cancer, colon cancer, liver cancer, bladder cancer, ovarian cancer, or intestinal cancer.

Embodiment 58

A method of treating fatty liver disease in a subject in need of said treatment, said method comprising administering an effective amount of a compound of one of embodiments 1 to 47, to said subject.

Embodiment 59

The method of embodiment 58, wherein the fatty liver disease is alcoholic liver disease.

Embodiment 60

The method of embodiment 58, wherein the fatty liver disease is non-alcoholic liver disease.

Embodiment 61

The method of embodiment 60, wherein the non-alcoholic fatty liver disease is non-alcoholic steatohepatitis.

Embodiment A1

A LRH-1 agonist having the formula:

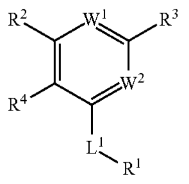

,

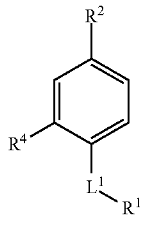

,

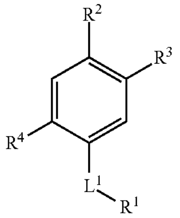

,

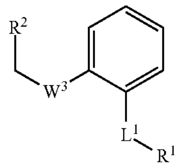

,

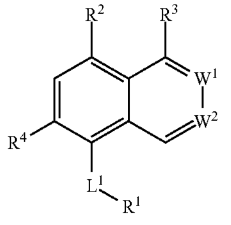

,

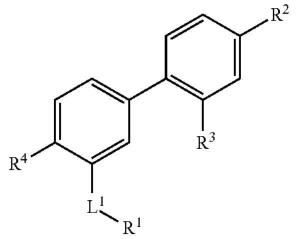

,

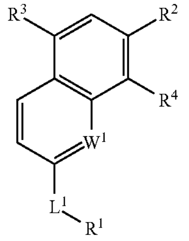

, or

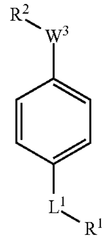

;

wherein $W^1$ and $W^2$ are independently CH or N;

$W^3$ is O, NH, $CH_2$, or S;

$L^1$ is independently a bond, —O—, —NH—, —C(O)—, —C(O)NH—, —NHC(O)—, —S—, —NHC(NH)NH—, —NHC(O)NH—, substituted or unsubstituted alkylene, substituted or unsubstituted heteroalkylene;

$R^1$ is independently a hydrogen, halogen, $—CX^1_3$, $—CHX^1_2$, $—CH_2X^1$, $—OCX^1_3$, $—OCH_2X^1$, $—OCHX^1_2$, —CN, $—SO_{n1}R^{10}$, $—SO_{v1}NR^7R^8$, $—NHNR^7R^8$, $—ONR^7R^8$, $—NHC{=}(O)NHNR^7R^8$, $—NHC{=}(O)NR^7R^8$, $—N(O)_{m1}$, $—NR^7R^8$, $—C(O)R^9$, $—C(O)—OR^9$, $—C(O)NR^7R^8$, $—OR^{10}$, $—NR^7SO_2R^{10}$, $—NR^7C{=}(O)R^9$, $—NR^7C(O)—OR^9$, $—NR^7OR^9$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

$R^2$ is independently a halogen, —$CX^2_3$, —$CHX^2_2$, —$CH_2X^2$, —$OCX^2_3$, —$OCH_2X^2$, —$OCHX^2_2$, —CN, —$SO_{n2}R^{14}$, —$SO_{v2}NR^{11}R^{12}$, —$NHNR^{11}R^{12}$, —$ONR^{11}R^{12}$, —NHC═(O)$NHNR^{11}R^{12}$, —NHC═(O)$NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}C$═(O)$R^{13}$, —$NR^{11}C$(O)—$OR^{13}$, —$NR^{11}OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently a halogen, —$CX^3_3$, —$CHX^3_2$, —$CH_2X^3$, —$OCX^3_3$, —$OCH_2X^3$, —$OCHX^3_2$, —CN, —$SO_{n3}R^{18}$, —$SO_{v3}NR^{15}R^{16}$, —$NHNR^{15}R^{16}$, —$ONR^{15}R^{16}$, —NHC═(O)$NHNR^{15}R^{16}$, —NHC═(O)$NR^{15}R^{16}$, —$N(O)_{m3}$, —$NR^{15}R^{16}$, —C(O)$R^{17}$, —C(O)—$OR^{17}$, —C(O)$NR^{15}R^{16}$, —$OR^{18}$, —$NR^{15}SO_2R^{18}$, —$NR^{15}C$═(O)$R^{17}$, —$NR^{15}C$(O)—$OR^{17}$, —$NR^5OR^{17}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{22}$, —$SO_{v4}NR^{19}R^{20}$, —$NHNR^{19}R^{20}$, —$ONR^{19}R^{20}$, —NHC═(O)$NHNR^{19}R^{20}$, —NHC═(O)$NR^{19}R^{20}$, —NHC═($NR^{21}$)$NR^{19}R^{20}$, —$N(O)_{m4}$, —$NR^{19}R^{20}$, —C(O)$R^{21}$, —C(O)$OR^{21}$, —C(O)$NR^{19}R^{20}$, —$OR^{22}$, —$NR^{19}SO_2R^{22}$, —$NR^{19}C$═(O)$R^{21}$, —$NR^{19}C$(O)$OR^{21}$, —$NR^{19}OR^{21}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —$CHX_2$, —$CH_2X$, —$OCX_3$, —$OCH_2X$, —$OCHX_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl;

m1, m2, m3, m4, v1, v2, v3, and v4 are independently 1 or 2;

n1, n2, n3, and n4 are independently an integer from 0 to 4;

X, $X^1$, $X^2$, $X^3$, and $X^4$ are independently —Cl, —Br, —I, or —F; and wherein $L^1$-$R^1$ does not include a disulfide bond.

Embodiment A2

The LRH-1 agonist of Embodiment A1, wherein $L^1$ is independently a bond, —O—, —NH—, —C(O)—, —C(O)NH—, —NHC(O)—, —S—, —NHC(O)NH—, —NHC(NH)NH—, substituted or unsubstituted $C_1$-$C_4$ alkylene, substituted or unsubstituted 2 to 4 membered heteroalkylene; $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{10}$, —$SO_{v1}NR^7R^8$, —$NHNR^7R^8$, —$ONR^7R^8$, —NHC═(O)$NHNR^7R^8$, —NHC═(O)$NR^7R^8$, —$N(O)_{m1}$, —$NR^7R^8$, —C(O)$R^9$, —C(O)—$OR^9$, —C(O)$NR^7R^8$, —$OR^{10}$, —$NR^7SO_2R^{10}$, —$NR^7C$═(O)$R^9$, —$NR^7C$(O)—$OR^9$, —$NR^7OR^9$, E, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; $R^2$ is independently a halogen, —$CX^2_3$, —$CHX^2_2$, —$CH_2X^2$, —$OCX^2_3$, —$OCH_2X^2$, —$OCHX^2_2$, —CN, —$SO_{n2}R^{14}$, —$SO_{v2}NR^{11}R^{12}$, —$NHNR^{11}R^{12}$, —$ONR^{11}R^{12}$, —NHC═(O)$NHNR^{11}R^{12}$, —NHC═(O)$NR^{11}R^{12}$, —$N(O)_{m2}$, —$NR^{11}R^{12}$, —C(O)$R^{13}$, —C(O)—$OR^{13}$, —C(O)$NR^{11}R^{12}$, —$OR^{14}$, —$NR^{11}SO_2R^{14}$, —$NR^{11}C$═(O)$R^{13}$, —$NR^{11}C$(O)—$OR^{13}$, —$NR^{11}OR^{13}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^3$ is independently a halogen, —$CX^3_3$, —$CHX^3_2$, —$CH_2X^3$, —$OCX^3_3$, —$OCH_2X^3$, —$OCHX^3_2$, —CN, —$SO_{n3}R^{18}$, —$SO_{v3}NR^{15}R^{16}$, —$NHNR^{15}R^{16}$, —$ONR^{15}R^{16}$, —NHC═(O)$NHNR^{15}R^{16}$, —NHC═(O)$NR^{15}R^{16}$, —$N(O)_{m3}$, —$NR^{15}R^{16}$, —C(O)$R^{17}$, —C(O)—$OR^{17}$, —C(O)$NR^{15}R^{16}$, —$OR^{18}$, —$NR^{15}SO_2R^{18}$, —$NR^{15}C$═(O)$R^{17}$, —$NR^{15}C$(O)—$OR^{17}$, —$NR^{15}OR^{17}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^4$ is independently halogen, —$CF_3$, —CN, —OH, —$NH_2$, —COOH, —$CONH_2$, —$NO_2$, —SH, or —$OCH_3$.

Embodiment A3

The LRH-1 agonist of Embodiment A1, wherein $L^1$ is independently a bond, —O—, —NH—, —C(O)—, —C(O)NH—, —NHC(O)—, —S—, —NHC(O)NH—, —NHC(NH)NH—, substituted or unsubstituted $C_1$-$C_4$ alkylene, substituted or unsubstituted 2 to 4 membered heteroalkylene; $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{10}$, —$SO_{v1}NR^7R^8$, —$NHNR^7R^8$, —$ONR^7R^8$, —NHC═(O)$NHNR^7R^8$, —NHC═(O)$NR^7R^8$, —$N(O)_{m1}$, —$NR^7R^8$, —C(O)$R^9$, —C(O)—$OR^9$, —C(O)

$NR^7R^8$, $—OR^{10}$, $—NR^7SO_2R^{10}$, $—NR^7C{=}(O)R^9$, $—NR^7C(O)—OR^9$, $—NR^7OR^9$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; $R^2$ is independently a halogen, $—CX^2_3$, $—CHX^2_2$, $—CH_2X^2$, $—OCX^2_3$, $—OCH_2X$, $—OCHX^2_2$, —CN, $—SO_{n2}R^{14}$, $—SO_{v2}NR^{11}R^{12}$, $—NHNR^{11}R^{12}$, $—ONR^{11}R^{12}$, $—NHC{=}(O)NHNR^{11}R^{12}$, $—NHC{=}(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C{=}(O)R^{13}$, $—NR^{11}C(O)—OR^{13}$, $—NR^{11}OR^{13}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^3$ is independently a halogen, $—CX^3_3$, $—CHX^3_2$, $—CH_2X^3$, $—OCX^3_3$, $—OCH_2X^3$, $—OCHX^3_2$, —CN, $—SO_{n3}R^{18}$, $—SO_{v3}NR^{15}R^{16}$, $—NHNR^{15}R^{16}$, $—ONR^{15}R^{16}$, $—NHC{=}(O)NHNR^{15}R^{16}$, $—NHC{=}(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C{=}(O)R^{17}$, $—NR^{15}C(O)—OR^{17}$, $—NR^{15}OR^{17}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^4$ is independently halogen, $—CF_3$, —CN, —OH, $—NH_2$, —COOH, $—CONH_2$, $—NO_2$, —SH, or $—OCH_3$.

Embodiment A4

The LRH-1 agonist of one of Embodiments A1 to A2, wherein $L^1$ is independently a bond.

Embodiment A5

The LRH-1 agonist of one of Embodiments A1 to A2, wherein $L^1$ is independently —O—.

Embodiment A6

The LRH-1 agonist of one of Embodiments A1 to A2, wherein $L^1$ is independently —NH—.

Embodiment A7

The LRH-1 agonist of one of Embodiments A1 to A2, wherein $L^1$ is independently —C(O)—.

Embodiment A8

The LRH-1 agonist of one of Embodiments A1 to A2, wherein $L^1$ is independently —C(O)NH—.

Embodiment A9

The LRH-1 agonist of one of Embodiments A1 to A2, wherein $L^1$ is independently —NHC(O)—.

Embodiment A10

The LRH-1 agonist of one of Embodiments A1 to A2, wherein $L^1$ is independently —S—.

Embodiment A11

The LRH-1 agonist of Embodiment A1, having the formula:

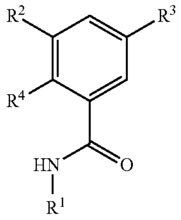
,
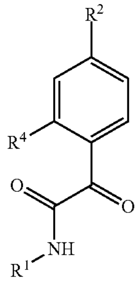
,
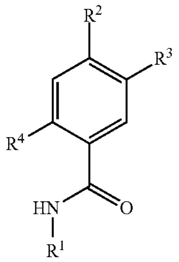
,
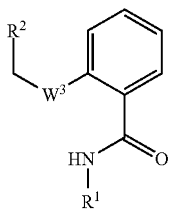
,
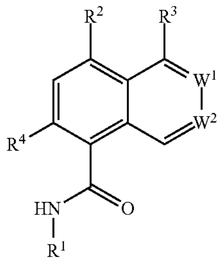
,
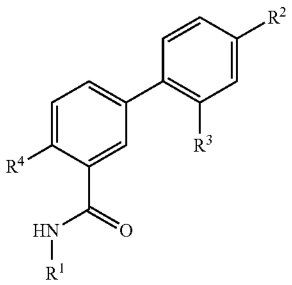
,
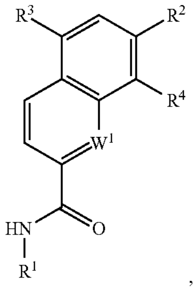
, or
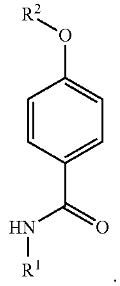
.

Embodiment A12

The LRH-1 agonist of one of Embodiments A1 to A10, having the formula:

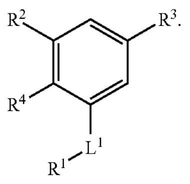

Embodiment A13

The LRH-1 agonist of Embodiment A1, having the formula:

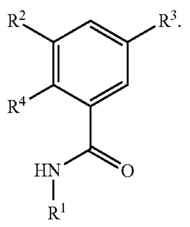

Embodiment A14

The LRH-1 agonist of one of Embodiments A1 to A13, wherein $R^1$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment A15

The LRH-1 agonist of one of Embodiments A1 to A13, wherein $R^1$ is independently substituted or unsubstituted $C_1$-$C_6$ alkyl or substituted or unsubstituted 2 to 6 membered heteroalkyl.

Embodiment A16

The LRH-1 agonist of one of Embodiments A1 to A13, wherein $R^1$ is independently substituted or unsubstituted $C_1$-$C_5$ alkyl, substituted or unsubstituted 2 to 5 membered alkoxy.

Embodiment A17

The LRH-1 agonist of one of Embodiments A1 to A13, wherein $R^1$ is independently unsubstituted butyl, unsubstituted pentyl, unsubstituted hexyl, unsubstituted propoxy, unsubstituted butoxy, or unsubstituted pentoxy.

Embodiment A18

The LRH-1 agonist of one of Embodiments A1, A2, A4 to A13, wherein $R^1$ is independently E; wherein E is

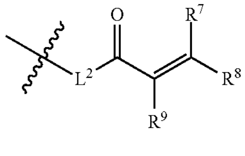

,

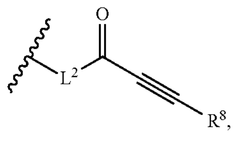

-continued

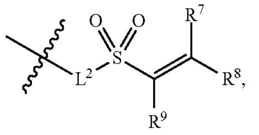

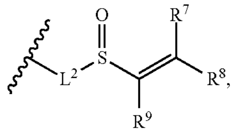

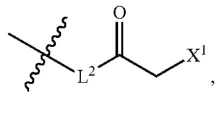

, or

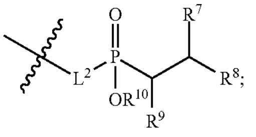

and $L^2$ is a bond, —O—, —C(O)—, —S—, —SO—, —$S(O)_2$—, —N(H)—, —NHC(O)—, —C(O)NH—, —$SO_2$NH—, —NH$SO_2$—, —OC(O)NH—, —NHC(O)O—, —NHC(O)NH—, —NHC(NH)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment A19

The LRH-1 agonist of Embodiment A18, wherein $L^2$ is —N(H)—.

Embodiment A20

The LRH-1 agonist of Embodiment A18, wherein $L^2$ is substituted or unsubstituted 5 to 7 membered heterocycloalkylene.

Embodiment A21

The LRH-1 agonist of Embodiment A18, wherein $L^2$ is substituted or unsubstituted pyrrolidinyl, substituted or unsubstituted imidazolidinyl, substituted or unsubstituted pyrazolidinyl, substituted or unsubstituted piperidinyl, or substituted or unsubstituted piperazinyl.

Embodiment A22

The LRH-1 agonist of one of Embodiments A1 to A13, wherein $R^1$ is independently unsubstituted $C_3$-$C_5$ alkyl.

Embodiment A23

The LRH-1 agonist of one of Embodiments A1 to A13, wherein $R^1$ is independently unsubstituted n-butyl.

Embodiment A24

The LRH-1 agonist of one of Embodiments A1 to A23, wherein $R^2$ is independently —$CX^2_3$, —$CHX^2_2$, —$CH_2X^2$, —$OCX^2_3$, —$OCH_2X^2$, —$OCHX^2_2$, —CN, —$SO_2R^{14}$, —$SR^{14}$, —$SO_2NR^{11}R^{12}$, —$NR^{11}R^{12}$, —C(O)$R^{13}$, —C(O)$OR^{13}$, —C(O)$NR^{11}R^{12}$, —$OR^{14}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^{11}$, $R^{12}$, $R^{13}$, and $R^{14}$ are independently hydrogen, —$CX_3$, —$CHX_2$, —$CH_2X$, —CN, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment A25

The LRH-1 agonist of one of Embodiments A1 to A23, wherein $R^2$ is independently —$SO_2R^{14}$, —$SO_2NR^{11}R^{12}$, —$C(O)R^{13}$, $R^{33}$-substituted or unsubstituted $C_1$-$C_5$ alkyl, $R^{33}$-substituted or unsubstituted 2 to 5 membered heteroalkyl, $R^{33}$-substituted or unsubstituted $C_3$-$C_6$ cycloalkyl, $R^{33}$-substituted or unsubstituted 3 to 6 membered heterocycloalkyl, $R^{33}$-substituted or unsubstituted phenyl, or $R^{33}$-substituted or unsubstituted 5 to 6 membered heteroaryl; and $R^{11}$, $R^{12}$, $R^{13}$, and $R^{14}$ are independently hydrogen, —$CX_3$, —$CHX_2$, —$CH_2X$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $R^{33}$ is independently halogen, —$CF_3$, —$CHF_2$, —$CH_2F$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment A26

The LRH-1 agonist of one of Embodiments A1 to A23, wherein $R^2$ is independently —$SO_2R^{14}$, —$SO_2NR^{11}R^{12}$, —$C(O)R^{13}$, $R^{33}$-substituted or unsubstituted methyl, $R^{33}$-substituted or unsubstituted ethyl, $R^{33}$-substituted or unsubstituted isopropyl, $R^{33}$-substituted or unsubstituted tert-butyl, $R^{33}$-substituted or unsubstituted phenyl, or $R^{33}$-substituted or unsubstituted 5 to 6 membered heteroaryl; and $R^{11}$ and $R^{12}$ are independently hydrogen, —$CX_3$, —$CHX_2$, —$CH_2X$, or unsubstituted $C_1$-$C_4$ alkyl; $R^{13}$ is unsubstituted 5 to 6 membered heteroaryl; $R^{14}$ are independently —$CX_3$, —$CHX_2$, —$CH_2X$, or unsubstituted $C_1$-$C_4$ alkyl; and $R^{33}$ is independently halogen, —$CF_3$, —$CHF_2$, —$CH_2F$, or unsubstituted 5 to 6 membered heteroaryl.

Embodiment A27

The LRH-1 agonist of one of Embodiments A1 to A23, wherein $R^2$ is independently —$SO_2CH_3$, —$SO_2NH_2$, —$C(O)R^{13}$, $R^{33}$-substituted or unsubstituted methyl, $R^{33}$-substituted or unsubstituted tert-butyl, $R^{33}$-substituted or unsubstituted pyrazolyl, $R^{33}$-substituted or unsubstituted pyrrolyl, $R^{33}$-substituted or unsubstituted thienyl, $R^{33}$-substituted or unsubstituted phenyl, or $R^{33}$-substituted or unsubstituted pyridyl; and $R^{13}$ is unsubstituted thienyl; and $R^{33}$ is independently halogen, —$CF_3$, or unsubstituted thienyl.

Embodiment A28

The LRH-1 agonist of one of Embodiments A1 to A23, wherein $R^2$ is independently unsubstituted tert-butyl.

Embodiment A29

The LRH-1 agonist of one of Embodiments A1 to A28, wherein $R^3$ is independently —$CX^3_3$, —$CHX^3_2$, —$CH_2X^3$, —$OCX^3_3$, —$OCH_2X^3$, —$OCHX^3_2$, —CN, —$SO_2R^{18}$, —$SR^{18}$, —$SO_2NR^{15}R^{16}$, —$NR^{15}R^{16}$, —$C(O)R^{17}$, —C(O)—$OR^{17}$, —$C(O)NR^{15}R^{16}$, —$OR^{18}$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $R^{15}$, $R^{16}$, $R^{17}$, and $R^{18}$ are independently hydrogen, —$CX_3$, —$CHX_2$, —$CH_2X$, —CN, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment A30

The LRH-1 agonist of one of Embodiments A1 to A28, wherein $R^3$ is independently —$SO_2R^{18}$, —$SO_2NR^{15}R^{16}$, —$C(O)R^{17}$, $R^{36}$-substituted or unsubstituted $C_1$-$C_5$ alkyl, $R^{36}$-substituted or unsubstituted 2 to 5 membered heteroalkyl, $R^{36}$-substituted or unsubstituted $C_3$-$C_6$ cycloalkyl, $R^{36}$-substituted or unsubstituted 3 to 6 membered heterocycloalkyl, $R^{36}$-substituted or unsubstituted phenyl, or $R^{36}$-substituted or unsubstituted 5 to 6 membered heteroaryl; and $R^{15}$, $R^{16}$, $R^{17}$, and $R^{18}$ are independently hydrogen, —$CX_3$, —$CHX_2$, —$CH_2X$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; and $R^{36}$ is independently halogen, —$CF_3$, —$CHF_2$, —$CH_2F$, unsubstituted $C_1$-$C_4$ alkyl, unsubstituted 2 to 4 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment A31

The LRH-1 agonist of one of Embodiments A1 to A28, wherein $R^3$ is independently —$SO_2R^{18}$, —$SO_2NR^{15}R^{16}$, —$C(O)R^{17}$, $R^{36}$-substituted or unsubstituted methyl, $R^{36}$-substituted or unsubstituted ethyl, $R^{36}$-substituted or unsubstituted isopropyl, $R^{36}$-substituted or unsubstituted tert-butyl, $R^{36}$-substituted or unsubstituted phenyl, or $R^{36}$-substituted or unsubstituted 5 to 6 membered heteroaryl; and $R^{15}$ and $R^{16}$ are independently hydrogen, —$CX_3$, —$CHX_2$, —$CH_2X$, or unsubstituted $C_1$-$C_4$ alkyl; $R^{17}$ is unsubstituted 5 to 6 membered heteroaryl; $R^{18}$ are independently —$CX_3$, —$CHX_2$, —$CH_2X$, or unsubstituted $C_1$-$C_4$ alkyl; and $R^{36}$ is independently halogen, —$CF_3$, —$CHF_2$, —$CH_2F$, or unsubstituted 5 to 6 membered heteroaryl.

Embodiment A32

The LRH-1 agonist of one of Embodiments A1 to A28, wherein $R^3$ is independently —$SO_2CH_3$, —$SO_2NH_2$, —$C(O)R^{17}$, $R^{36}$-substituted or unsubstituted methyl, $R^{36}$-substituted or unsubstituted tert-butyl, $R^{36}$-substituted or unsubstituted pyrazolyl, $R^{36}$-substituted or unsubstituted pyrrolyl, $R^{36}$-substituted or unsubstituted thienyl, $R^{36}$-substituted or unsubstituted phenyl, or $R^{36}$-substituted or unsubstituted pyridyl; and $R^{17}$ is unsubstituted thienyl; and $R^{36}$ is independently halogen, —$CF_3$, or unsubstituted thienyl.

Embodiment A33

The LRH-1 agonist of one of Embodiments A1 to A28, wherein $R^3$ is independently unsubstituted tert-butyl.

Embodiment A34

The LRH-1 agonist of one of Embodiments A1 to A33, wherein $R^4$ is independently —OH, —$NH_2$, —COOH, —$CONH_2$, —SH, or —$OCH_3$.

Embodiment A35

The LRH-1 agonist of one of Embodiments A1 to A33, wherein $R^4$ is independently —OH, —$NH_2$, or —COOH.

Embodiment A36

The LRH-1 agonist of one of Embodiments A1 to A33, wherein $R^4$ is independently —OH.

Embodiment A37

The LRH-1 agonist of one of Embodiments A1 to A33, wherein $R^4$ is independently —$NH_2$.

Embodiment A38

The LRH-1 agonist of one of Embodiments A1 to A33, wherein $R^4$ is independently —COOH.

Embodiment A39

The LRH-1 agonist of one of Embodiments A1 to A33, wherein $R^4$ is independently —SH.

Embodiment A40

The LRH-1 agonist of one of Embodiments A1 to A33, wherein $R^4$ is independently —$CONH_2$.

Embodiment A41

The LRH-1 agonist of one of Embodiments A1 to A33, wherein $R^4$ is independently —$OCH_3$.

Embodiment 42

The LRH-1 agonist of one of Embodiments A1 to A41, wherein said LRH-1 agonist is an agonist of a nuclear receptor.

Embodiment A43

The LRH-1 agonist of one of Embodiments A1 to A41, wherein said LRH-1 agonist is an agonist of a LRH-1 receptor.

Embodiment A44

The LRH-1 agonist of one of Embodiments A1 to A41, wherein said LRH-1 agonist is an agonist of a human LRH-1 receptor.

Embodiment 45

The LRH-1 agonist of one of Embodiments A1 to A41, wherein said LRH-1 agonist is an antagonist of a nuclear receptor.

Embodiment A46

The LRH-1 agonist of one of Embodiments A1 to A41, wherein said LRH-1 agonist is an antagonist of a LRH-1 receptor.

Embodiment A47

The LRH-1 agonist of one of Embodiments A1 to A41, wherein said LRH-1 agonist is an antagonist of a human LRH-1 receptor.

Embodiment A48

A pharmaceutical composition comprising a LRH-1 agonist of one of Embodiments A1 to A47, or a pharmaceutically acceptable salt thereof, and a pharmaceutically acceptable excipient.

Embodiment A49

The pharmaceutical composition of Embodiment A48, comprising a therapeutically effective amount of said LRH-1 agonist.

Embodiment A50

A method of treating a disease associated with aberrant LRH-1 activity in a subject in need of said treatment, said method comprising administering an effective amount of a LRH-1 agonist of one of Embodiments A1 to A47, to said subject.

Embodiment A51

A method of treating an inflammatory disease in a subject in need of said treatment, said method comprising administering an effective amount of a LRH-1 agonist of one of Embodiments A1 to A47, to said subject.

Embodiment A52

A method of treating inflammatory bowel disease in a subject in need of said treatment, said method comprising administering an effective amount of a LRH-1 agonist of one of Embodiments A1 to A47, to said subject.

Embodiment A53

A method of treating diabetes in a subject in need of said treatment, said method comprising administering an effective amount of a LRH-1 agonist of one of Embodiments A1 to A47, to said subject.

Embodiment A54

A method of treating a cardiovascular disease in a subject in need of said treatment, said method comprising administering an effective amount of a LRH-1 agonist of one of Embodiments A1 to A47, to said subject.

Embodiment A55

A method of treating arteriosclerosis in a subject in need of said treatment, said method comprising administering an effective amount of a LRH-1 agonist of one of Embodiments A1 to A47, to said subject.

Embodiment A56

A method of treating cancer in a subject in need of said treatment, said method comprising administering an effective amount of a LRH-1 agonist of one of Embodiments A1 to A47, to said subject.

Embodiment A57

The method of Embodiment A56, wherein the cancer is prostate cancer, pancreatic cancer, breast cancer, colon cancer, liver cancer, bladder cancer, ovarian cancer, or intestinal cancer.

Embodiment A58

A method of treating fatty liver disease in a subject in need of said treatment, said method comprising administering an effective amount of a LRH-1 agonist of one of Embodiments A1 to A47, to said subject.

Embodiment A59

The method of Embodiment A58, wherein the fatty liver disease is alcoholic liver disease.

Embodiment A60

The method of Embodiment A58, wherein the fatty liver disease is non-alcoholic liver disease.

Embodiment A61

The method of Embodiment A60, wherein the non-alcoholic fatty liver disease is non-alcoholic steatohepatitis.

H. EXAMPLES

Example 1. Disulfide-Trapping Screen

Described herein is a strategy that identified lead compounds based on their ability to form covalent adducts (disulfide bonds) with a target cysteine residue lining the ligand binding pocket. Importantly, adduct formation is governed by the intrinsic affinity of the compounds for the pocket as the screen is carried out in the presence of saturating concentrations of 3-mercaptoethanol (BME). Computational docking was used to visualize compound orientations within the LRH-1 LBD and guide the development of higher affinity ligands. Because the fragments are modeled as disulfide-linked (covalently bound) to the receptor at a specific site in the pocket (Cys346), the modeled poses were expected to be very accurate.

Library compounds are incubated with the target protein (LRH-1 LBD) under high reductant conditions (500 μM BME), where disulfide exchange is rapid. Compounds with high intrinsic affinity for a binding site near a cysteine residue ($Cys^{346}$ in LRH-1) have superior residence time and thus encourage the formation of a disulfide bond between the protein thiol and compound thiol.

Notably, the tethering screen was carried out against LRH-1 bound to a phospholipid (phosphatidylethanolamine) co-expressed with the receptor in bacteria. As was observed by Whitby et al. (J Med Chem 2006, 49, 6652), small non-polar molecules are clearly able to displace bound bacterial phospholipid ligands from the pocket.

A library of 1280 disulfide-linked low molecular weight (~300 Da) compounds was screened against the LRH-1 LBD. To specifically target the cysteine residue lining the ligand binding pocket ($Cys^{346}$), the two surface-exposed cysteine residues ($Cys^{311}$, $Cys^{487}$) were mutated to serine. Twenty-eight compounds conjugated with high efficiency (>2 standard deviations above the mean) to this site under stringent conditions (500 μM BME). One compound (15.31) conjugated with remarkably high efficiency (~85%) and was selected for further development.

A screen of 1280 disulfide-linked compounds against hLRH-1 identified 28 hits that were trapped within the ligand binding pocket through a disulfide exchange reaction with $Cys^{346}$. Computational modeling of these hits conjugated to $Cys^{346}$ suggested they bind within a similar region of the pocket, at the top of the hourglass with the alkyl amide pointing toward the middle of the pocket. An advantage of covalent docking is that modeled ligand-receptor interactions (poses) are expected to be particularly accurate as the possible ligand orientations (translations and rotations) are strongly constrained by the covalent link to the protein.

The top hit 15.31, a substituted benzamide, was selected for further study owing to its remarkable conjugation efficiency (85%) under stringent conditions (500 μM BME) and the ease with which a small, yet informative, structure activity relationship study could be carried out.

Increasing the size of both the R1 and R2 (of the structure indicated in FIG. 6) aryl ring substituents, from isopropyl to tert-butyl groups, to better fill the pocket provided compounds that were active in cells. The most active compound, 9 (PME9), was even more effective than RJW100, the highest affinity agonist described to date [Whitby R J et al. J Med Chem. 2011; 54(7):2266-81]. The alkyl chain length (R3 of the structure indicated in FIG. 6) also proved important, with N-butyl-benzamides being more active in cells than the corresponding N-propyl- or N-pentylbenzamide compounds. This pattern, which is observed among compounds 1-3 and 8-10 (PME8-10), may reflect an inability of amide-linked alkyl groups to traverse the pocket constriction. As phospholipid tails apparently bind the length of the pocket, replacing the amide with an alkyl or ether linkage may improve the activity of compounds with longer R3 substituents. The hydroxyl group also contributes to efficacy, as evidenced by the difference in activity between compounds 6 and 7, the latter forming a hydrogen bond with the backbone carbonyl of $Met^{345}$ according to the computational model.

Together, these data highlight PME9 as a strong starting point for further development of hLRH-1 ligands. Specific features of the ligand binding site yet to be exploited include polar interactions with arginine and histidine residues positioned 4.8 and 3.7 Å of the R1 and R2 substituents (of the structure indicated in FIG. 6). Moreover, the other 27 hits from the screen point to additional modifications of the benzamide scaffold expected to improve ligand efficacy, such as merging structures.

Collective data obtained from numerous in vitro and in vivo studies suggest that LRH-1 is a potential therapeutic target for several diseases including pancreatic cancer, breast cancer, colon cancer, inflammatory bowel disease and fatty liver disease. The dearth of effective synthetic probes for LRH-1 has hindered efforts to validate this nuclear receptor as a therapeutic target. Our success in developing new ligands for LRH-1 that effectively drive target gene expression is an important step and highlights the value of disulfide-trapping as a strategy for discovering lead compounds targeting nuclear receptors.

Example 2. Computational Modeling

Covalent docking was used to visualize conjugated compounds bound within the LRH-1 ligand binding pocket. The ligand binding pocket is an hourglass shaped structure with the bottom portion nearest to the solvent. Modeling of top hit 15.31 conjugated to $Cys^{346}$ indicated this compound occupies the top of the pocket, partially overlapping the binding side for RJW100 and suggested a clear avenue for improving binding (FIGS. 1A-1D). The two isopropyl groups inadequately fill the top of the pocket, suggesting that larger substituents would improve binding. The propyl amide bends to form the disulfide link with $Cys^{346}$; absent the disulfide the alkyl chain might be lengthened to better fill the middle of pocket. The hydroxyl group on 15.31 is located within 2.8 Å of a backbone carbonyl ($Met^{345}$), and is the only polar contact observed in the model.

A library of 1280 disulfide-linked compounds was covalently docked to the hLRH-1 LBD. Library compounds were initially represented by their SMILES strings and then converted to 3D structures using Maestro's LigPrep feature. In addition, LigPrep was used to identify and generate tautomers of each ligand, yielding a total of 1407 compounds for covalent docking. The library of compounds was covalently docked to $Cys^{346}$ in hLRH-1 using the PDB coordinate file 3PLZ, which shows the thiol sidechain oriented into the ligand binding pocket and accessible to docked ligands. PDB 3PLZ is missing the loop near $Cys^{346}$, which connects helix 2 and helix 3. To limit potential docking artifacts, the missing H2-H3 loop residues (330-337) were manually added to the hLRH-1 sequence and the loop orientation was optimized with Prime. The predicted positions of residues within the H2-H3 loop closely aligned with other previously reported hLRH-1 crystal structures. In addition, hydrogen atoms were added and the correct charges specified using the protein preparation wizard in Maestro. Before covalently docking the library, leaving groups for the ligands and receptor were defined. Prime was used to covalently dock the 1280 disulfide-linked compounds to $Cys^{346}$ of hLRH1. The covalent docking feature first docks each ligand to the receptor to generate a non-covalent pose. The covalent bond between the compound and the $Cys^{346}$ side chain is then formed and the ligand pose is refined. The free energy of each ligand and the leaving groups were determined using Prime. To determine the overall binding energy the following equation was used: $E=E_{complex}+E_{R,LG}+E_{L,LG}-E_{receptor}-E_{ligand}$, where $E_{R,LG}$ and $E_{L,LG}$ are the free energies of the receptor and the ligand leaving group, respectively.

Example 3. Ligand Development

Figure 2:
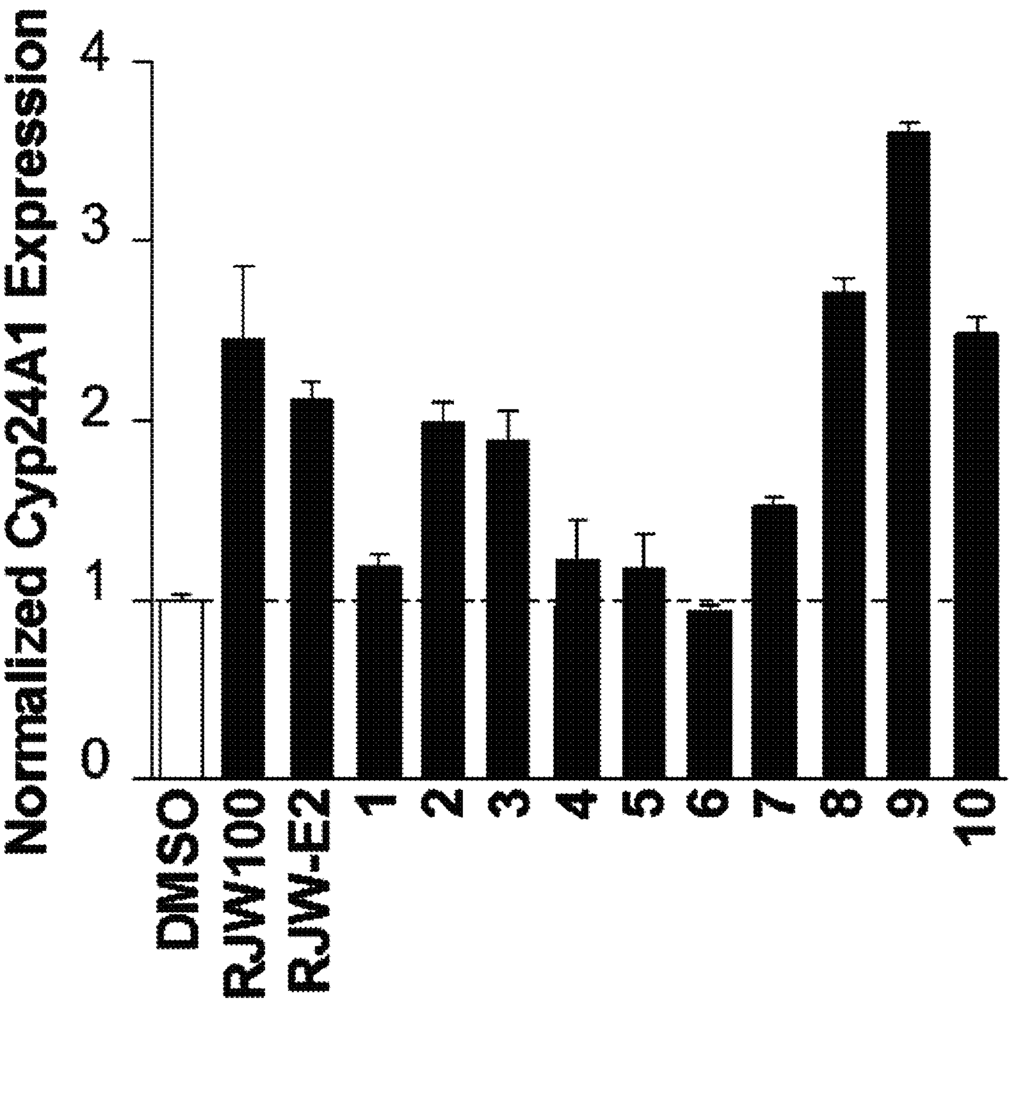
FIG. 2. Modulator (e.g., ligand) effects on CYP24A1 expression.

Based on computational models, analogs of 15.31 were designed and prepared to define the ligand-receptor pharmacophore at three positions (FIG. 2). In selected derivatives, the isopropyl groups were removed and/or replaced with t-butyl groups and the ethyl thiol substitution on the amide group was replaced with alkyl chains of varying lengths. Analogs 1-10 were prepared from commercially available scaffolds, by activating the carboxylic acid and subsequently coupling to alkyl amines with the indicated chain length.

TABLE 1

| Compound (corresponding to FIG. 2) | $R^1$ (corresponding to substitution on amide in c of FIG. 1B) | $R^2$ (corresponding to a of FIG. 1B) | $R^3$ (corresponding to b of FIG. 1B) |
|---|---|---|---|
| 1 | n-propyl | isopropyl | isopropyl |
| 2 | n-butyl | isopropyl | isopropyl |
| 3 | n-pentyl | isopropyl | isopropyl |
| 4 | n-propyl | isopropyl | hydrogen |
| 5 | n-propyl | hydrogen | isopropyl |
| 6 | n-propyl | Tert-butyl | hydrogen |
| 7 | n-propyl | hydrogen | Tert-butyl |
| 8 | n-propyl | Tert-butyl | Tert-butyl |
| 9 | n-butyl | Tert-butyl | Tert-butyl |
| 10 | n-pentyl | Tert-butyl | Tert-butyl |

Example 4. Synthesis

General Scheme for Selected LRH-1 Ligands:

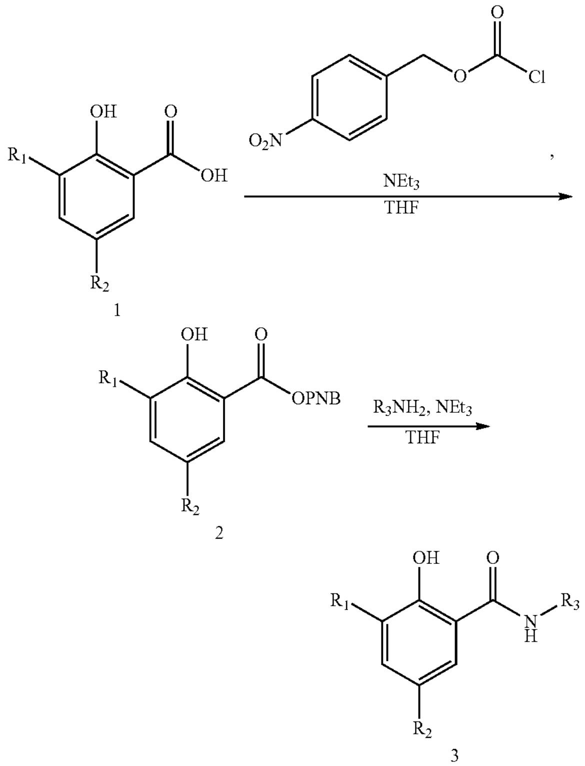

1

2

3

General Procedure for 2

To a flame dried flask was added carboxylic acid 1 (1 eq) in THF (0.2 M), followed by p-nitrobenzyl chloroformate (1.1 eq) and $NEt_3$ (1.2 eq). The reaction was allowed to stir for one hour, at which the product was extracted with EtOAc and $NaHCO_3$. The organic layer was dried and concentrated to give a crude product that underwent silica gel chromatography to isolate the product 2.

General Procedure for 3

To a flame dried flask was added p-nitrobenzyl ester 2 (1 eq) in THF (0.2 M). The corresponding amine (1.1 eq) and $NEt_3$ (1.2 eq) was the added at rt and the reaction was stirred overnight. The solvent was removed via rotary evaporation and product was purified via column chromatography to isolate the product 3. Lyophilization gave the product as a powder.

General Scheme for Carboxylic Acid Containing LRH-1 Ligands

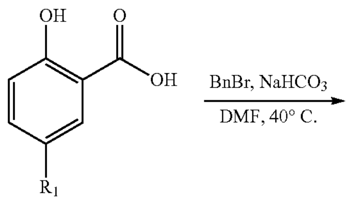

4a

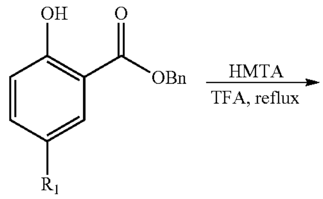

5a

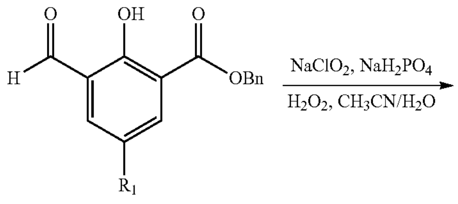

6a

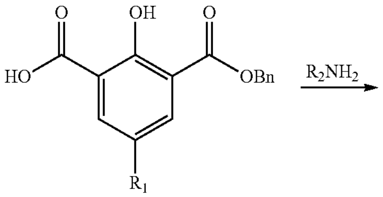

7a

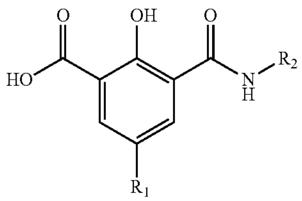

8a

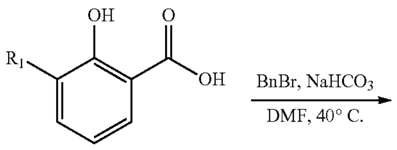

4b

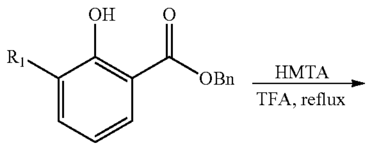

5b

-continued

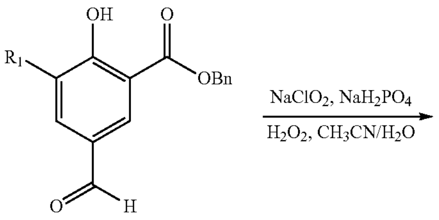

6b

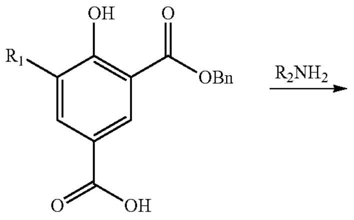

7b

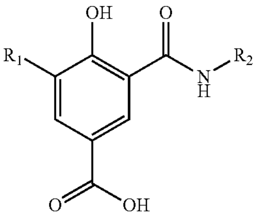

8b

General Procedure for 5a, 5b

To a flask was added carboxylic acid 4a or 4b (1 eq) in DMF (0.3 M), followed by benzyl bromide (1.5 eq) and $NaHCO_3$ (1.2 eq). The reaction was warmed to 40° C. and stirred overnight. The reaction was extracted with $Et_2O$ and water. The organic layer was dried and concentrated to give a crude product that underwent silica gel chromatography to isolate the product 5a or 5b.

General Procedure for 6a, 6b

To a flask was added 5a or 5b (1 eq) in TFA (0.3 M), followed by HMTA (1.0 eq). 1 M HCl was added to the reaction to dilute and the product was extracted with EtOAc. The organic layer was dried and concentrated to give a crude product that underwent silica gel chromatography to isolate the product 6a or 6b.

General Procedure for 7a, 7b

To a flask was added 6a or 6b (1 eq) in $CH_3CN:H_2O$ (0.05 M), followed by $NaClO_2$ (1.2 eq), $NaH_2PO_4$ (7 eq) and $H_2O_2$ (10 eq). The reaction was stirred for 30 min and extracted with EtOAc and water. The organic layer was dried and concentrated to give a crude product that underwent silica gel chromatography to isolate the product 7a or 7b.

General Procedure for 8a, 8b 7a or 7b (1 eq) was added to a flask, followed by the corresponding amine $R_2NH_2$ (0.2 M) as a neat solution. The reaction was stirred overnight. The solvent was removed via rotary evaporation and the crude material underwent silica gel chromatography to isolate the product 8a or 8b.

Characterization of Compounds

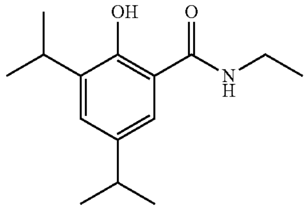 [SMILES: CCNC(=O)c1cc(C(C)C)cc(C(C)C)c1O]

$^{1}$H NMR (400 MHz, $CDCl_3$) δ 7.18 (s, 1H), 6.97 (s, 1H), 6.31 (s, 1H), 3.67-3.42 (m, 2H), 3.35 (hept, J=7.0 Hz, 1H), 2.82 (hept, J=7.5 Hz, 1H), 1.24-1.20 (m, 15H). $^{13}$C NMR (400 MHz, $CDCl_3$) δ 170.83, 157.46, 138.42, 137.82, 129.11, 119.87, 113.38, 34.83, 33.89, 26.88, 24.42, 22.64, 15.01.

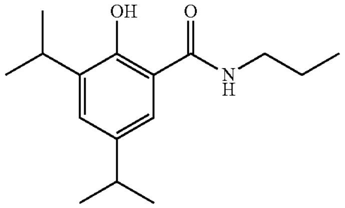 [SMILES: CCCNC(=O)c1cc(C(C)C)cc(C(C)C)c1O]

$^{1}$H NMR (400 MHz, $CDCl_3$) δ 7.18 (s, 1H), 6.96 (s, 1H), 6.29 (s, 1H), 3.44-3.38 (m, 2H), 3.37-3.31 (m, 1H), 2.83 (hept, J=7.7 Hz, 1H), 1.74-1.58 (m, 2H), 1.24-1.20 (m, 12H), 0.98 (t, J=7.4 Hz, 3H).

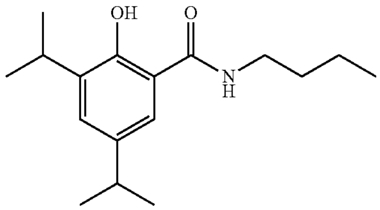 [SMILES: CCCCNC(=O)c1cc(C(C)C)cc(C(C)C)c1O]

$^{1}$H NMR (400 MHz, $CDCl_3$) δ 7.18 (d, J=2.1 Hz, 1H), 6.97 (d, J=2.1 Hz, 1H), 6.32 (s, 1H), 3.49-3.38 (m, 2H), 3.34 (hept, J=7.1 Hz, 1H), 2.82 (hept, J=7.1 Hz, 1H), 1.67-1.52 (m, 2H), 1.46-1.34 (m, 2H), 1.23 (d, J=2.2 Hz, 6H), 1.22 (d, J=2.2 Hz, 6H), 0.95 (t, J=7.3 Hz, 3H). $^{13}$C NMR (400 Mhz, $CDCl_3$) δ 170.86, 157.45, 138.42, 137.85, 129.06, 119.85, 113.43, 39.68, 33.89, 31.85, 26.88, 24.43, 22.65, 20.37, 13.98.

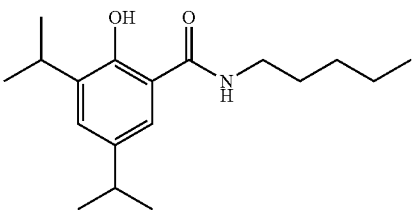 [SMILES: CCCCCNC(=O)c1cc(C(C)C)cc(C(C)C)c1O]

$^{1}$H NMR (400 MHz, $CDCl_3$) δ 12.50 (s, 1H), 7.19 (d, J=2.1 Hz, 1H), 6.97 (d, J=2.1 Hz, 1H), 6.32 (s, 1H), 3.45-3.39 (m, 2H), 3.35 (q, J=6.9 Hz, 1H), 2.83 (p, J=6.9 Hz, 1H), 1.68-1.55 (m, 2H), 1.39-1.32 (m, 4H), 1.24 (d, J=1.8 Hz, 6H), 1.22 (d, J=1.8 Hz, 6H), 0.97-0.87 (m, 3H). $^{13}$C NMR (400 Mhz, $CDCl_3$) δ 170.61, 157.23, 138.18, 137.62, 128.83, 119.62, 113.19, 39.72, 33.66, 29.26, 29.09, 26.64, 24.19, 22.41, 22.35, 13.95.

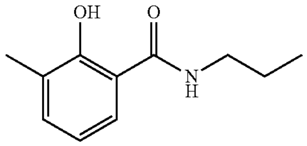

$^{1}$H NMR (400 MHz, $CDCl_3$) δ 7.23 (d, J=6.3 Hz, 1H), 7.21 (d, J=7.3 Hz, 1H), 6.71 (t, J=7.6 Hz, 1H), 6.54 (s, 1H), 3.44-3.33 (m, 2H), 2.25 (s, 3H), 1.63 (h, J=7.4 Hz, 2H), 0.97 (t, J=7.4 Hz, 3H).

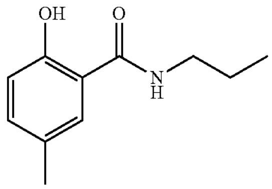

$^{1}$H NMR (400 MHz, $CDCl_3$) δ 7.17 (d, J=8.4 Hz, 2H), 7.11 (s, 1H), 6.87 (d, J=8.4 Hz, 2H), 6.32 (s, 1H), 3.44-3.34 (m, 2H), 2.26 (s, 3H), 1.64 (h, J=7.2 Hz, 2H), 0.98 (t, J=7.4 Hz, 3H). $^{13}$C NMR (400 Mhz, $CDCl_3$) δ 170.21, 159.55, 135.19, 127.88, 125.37, 118.58, 114.16, 41.56, 22.99, 20.74, 11.63.

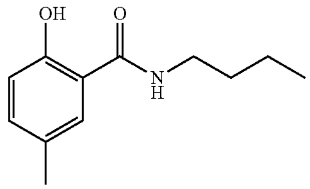

$^{1}$H NMR (400 MHz, $CDCl_3$) δ 12.19 (s, 1H), 7.16-7.11 (m, 2H), 6.83 (d, J=8.9, 1H), 6.58 (s, 1H), 3.39 (m, 2H), 2.22 (s, 3H), 1.64-1.51 (m, 2H), 1.42-1.32 (m, 2H), 0.92 (t, J=7.3, 3H). $^{13}$C NMR (400 Mhz, $CDCl_3$) δ 169.96, 159.19, 134.81, 127.58, 125.37, 118.16, 114.02, 60.36, 39.36, 31.49, 29.64, 20.96.

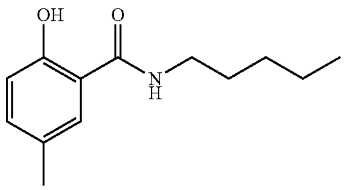 [SMILES: CCCCCNC(=O)c1cc(C)ccc1O]

$^{1}$H NMR (400 MHz, $CDCl_3$) δ 12.20 (d, J=1.0 Hz, 1H), 7.15 (d, J=6.9 Hz, 3H), 6.85 (dd, J=9.0, 1.0 Hz, 1H), 6.53 (s, 2H), 3.40 (tdd, J=7.0, 5.7, 1.0 Hz, 3H), 2.24 (s, 3H), 1.66-1.55 (m, 3H), 1.39-1.29 (m, 4H), 1.27-1.16 (m, 7H). $^{13}$C NMR (400 Mhz, $CDCl_3$) δ 169.95, 159.24, 134.85, 128.27, 125.33, 118.21, 114.01, 60.37, 39.65, 29.11, 22.32, 20.97, 13.91.

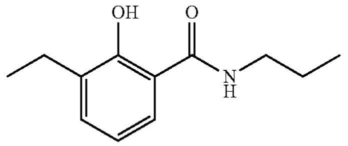

$^1$H NMR (400 MHz, $CDCl_3$) δ 7.27 (d, J=7.2 Hz, 1H), 7.19 (d, J=7.2 Hz, 1H), 6.77 (t, J=7.7 Hz, 1H), 6.30 (s, 1H), 3.48-3.35 (m, 2H), 2.68 (q, J=7.5 Hz, 2H), 1.65 (h, J=7.2 Hz, 2H), 1.22 (t, J=7.5 Hz, 3H), 0.99 (t, J=7.4 Hz, 3H). $^{13}$C NMR (400 Mhz, $CDCl_3$) δ 170.67, 159.88, 133.83, 133.35, 122.81, 118.20, 113.82, 41.61, 23.05, 23.00, 13.95, 11.61.

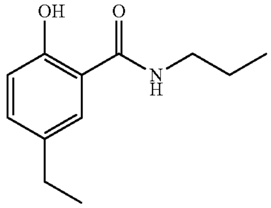

$^1$H NMR (400 MHz, $CDCl_3$) δ 7.23 (dd, J=8.5, 2.1 Hz, 1H), 7.12 (d, J=2.1 Hz, 1H), 6.91 (d, J=8.5 Hz, 1H), 6.33 (s, 1H), 3.46-3.34 (m, 2H), 2.58 (q, J=7.6 Hz, 2H), 1.66 (h, J=7.4 Hz, 2H), 1.21 (t, J=7.6 Hz, 3H), 1.00 (t, J=7.4 Hz, 3H). $^{13}$C NMR (400 Mhz, $CDCl_3$) δ 170.27, 159.78, 134.46, 134.07, 124.20, 118.71, 114.18, 41.58, 28.29, 23.03, 16.09, 11.65.

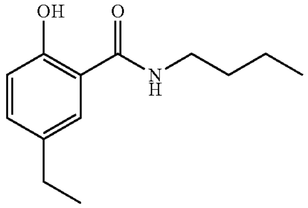 [SMILES: CCCCNC(=O)c1cc(CC)ccc1O]

$^1$H NMR (400 MHz, $CDCl_3$) δ 12.20 (s, 1H), 7.21 (dd, J=8.4, 2.2 Hz, 1H), 7.12 (d, J=2.2 Hz, 1H), 6.89 (d, J=8.5 Hz, 1H), 6.40 (s, 1H), 3.43 (m, 2H), 2.55 (q, J=7.6 Hz, 2H), 1.64-1.55 (m, 2H), 1.46-1.33 (m, 2H), 1.19 (t, J=7.6 Hz, 3H), 0.94 (t, J=7.4 Hz, 3H). $^{13}$C NMR (400 Mhz, $CDCl_3$) δ 170.00, 159.46, 134.25, 133.78, 124.06, 118.39, 113.97, 39.41, 31.55, 28.03, 20.12, 15.84, 13.72.

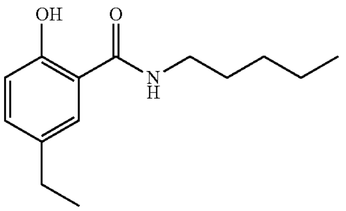 [SMILES: CCCCCNC(=O)c1cc(CC)ccc1O]

$^1$H NMR (400 MHz, $CDCl_3$) δ 12.20 (s, 1H), 7.21 (dd, J=8.5, 2.2 Hz, 1H), 7.12 (d, J=2.1 Hz, 1H), 6.89 (d, J=8.5 Hz, 1H), 6.38 (s, 1H), 3.54-3.33 (m, 2H), 2.56 (q, J=7.6 Hz, 2H), 1.70-1.54 (m, 4H), 1.35 (dq, J=7.2, 3.5 Hz, 2H), 1.19 (t, J=7.6 Hz, 3H), 0.97-0.83 (m, 3H). $^{13}$C NMR (400 Mhz, $CDCl_3$) δ 169.98, 159.48, 145.52, 133.78, 124.04, 118.40, 113.96, 39.68, 29.20, 29.08, 28.04, 22.34, 15.84, 13.94.

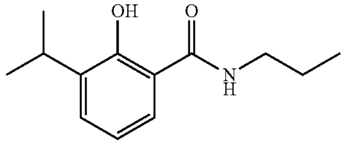 [SMILES: CCCNC(=O)c1cccc(C(C)C)c1O]

$^1$H NMR (400 MHz, $CDCl_3$) δ 7.31 (d, J=7.5 Hz, 1H), 7.18 (d, J=8.0 Hz, 1H), 6.90-6.72 (m, 1H), 6.3 (s, 1H), 3.77-3.20 (m, 3H), 1.63 (h, J=7.1 Hz, 6H), 1.22 (d, J=6.9 Hz, 6H), 0.97 (t, J=7.4 Hz, 3H). $^{13}$C NMR (400 Mhz, $CDCl_3$) δ 170.79, 159.35, 138.12, 130.61, 122.70, 118.29, 113.84, 41.62, 26.66, 22.98, 22.60, 11.60.

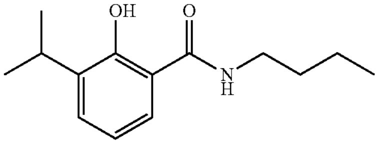 [SMILES: CCCCNC(=O)c1cccc(C(C)C)c1O]

$^1$H NMR (400 MHz, $CDCl_3$) δ 12.71 (s, 1H), 7.31 (d, J=7.5 Hz, 1H), 7.18 (d, J=8.0 Hz, 1H), 6.77 (t, J=7.7 Hz, 1H), 6.37 (s, 1H), 3.55-3.21 (m, 3H), 1.63-1.52 (m, 2H), 1.49-1.35 (m, 2H), 1.22 (d, J=7.1 Hz, 6H), 0.94 (t, J=7.4 Hz, 3H). $^{13}$C NMR (400 Mhz, $CDCl_3$) δ 170.52, 159.11, 130.33, 128.29, 122.49, 118.01, 113.61, 39.43, 31.51, 26.41, 22.34, 20.08, 13.70.

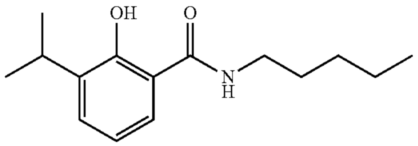 [SMILES: CCCCCNC(=O)c1cccc(C(C)C)c1O]

$^1$H NMR (400 MHz, $CDCl_3$) δ 12.75 (s, 1H), 7.30 (d, J=6.8 Hz, 1H), 7.20 (d, J=8.0 Hz, 1H), 6.77 (t, J=7.7 Hz, 1H), 3.62-3.03 (m, 2H), 1.68-1.51 (m, 2H), 1.34 (m, 4H), 1.22 (d, J=6.9 Hz, 6H), 0.95-0.83 (m, 3H). $^{13}$C NMR (400 Mhz, $CDCl_3$) δ 170.53, 159.12, 130.30, 128.28, 122.56, 118.00, 113.64, 60.37, 39.70, 29.10, 26.42, 22.34, 20.99, 14.03.

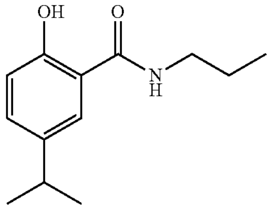 [SMILES: CCCNC(=O)c1cc(C(C)C)ccc1O]

$^1$H NMR (400 MHz, $CDCl_3$) δ 12.19 (s, 1H), 7.26 (d, J=8.6 Hz, 1H), 7.14 (s, 1H), 6.91 (d, J=8.5 Hz, 1H), 6.40 (s, 1H), 3.46-3.33 (m, 2H), 2.96-2.70 (m, 1H), 1.85-1.56 (m, 2H), 1.22 (d, J=7.0 Hz, 6H), 0.99 (t, J=7.4 Hz, 3H). $^{13}$C NMR (400 Mhz, $CDCl_3$) δ 170.33, 159.80, 139.17, 132.54, 122.85, 118.69, 114.12, 41.60, 33.66, 24.34, 23.04, 11.65.

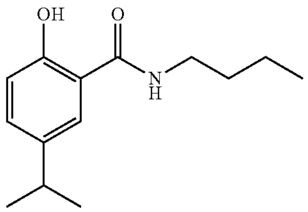 [SMILES: CCCCNC(=O)c1cc(C(C)C)ccc1O]

$^1$H NMR (400 MHz, $CDCl_3$) δ 12.18 (s, 1H), 7.26 (d, J=8.5 Hz, 1H), 7.11 (s, 1H), 6.91 (d, J=8.5 Hz, 1H), 6.32 (s, 1H), 3.50-3.31 (m, 2H), 2.83 (dp, J=13.2, 6.8 Hz, 1H), 1.68-1.53 (m, 2H), 1.49-1.34 (m, 2H), 1.21 (d, J=6.9 Hz, 6H), 0.96 (t, J=7.4 Hz, 3H). $^{13}$C NMR (400 Mhz, $CDCl_3$) δ 170.03, 159.58, 138.89, 133.29, 132.28, 122.55, 118.47, 113.87, 39.42, 33.42, 31.59, 24.11, 20.14, 13.74.

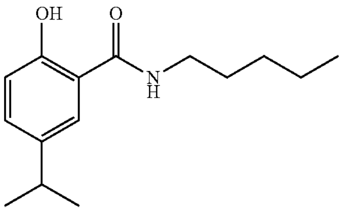 [SMILES: CCCCCNC(=O)c1cc(C(C)C)ccc1O]

$^1$H NMR (400 MHz, $CDCl_3$) δ 12.18 (s, 1H), 7.26 (d, J=8.7 Hz, 1H), 7.11 (s, 1H), 6.91 (d, J=8.6 Hz, 1H), 6.30 (s, 1H), 3.65-3.26 (m, 2H), 2.83 (p, J=6.9 Hz, 1H), 1.69-1.58 (m, 2H), 1.46-1.33 (m, 4H), 1.22 (d, J=6.9 Hz, 6H), 0.91 (t, J=6.5 Hz, 3H). $^{13}$C NMR (400 Mhz, $CDCl_3$) δ 170.01, 159.60, 138.88, 132.28, 122.53, 118.48, 109.99, 39.70, 33.42, 29.24, 29.09, 24.11, 22.34, 13.95.

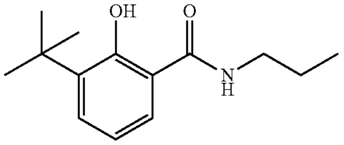 [SMILES: CCCNC(=O)c1cccc(C(C)(C)C)c1O]

$^1$H NMR (400 MHz, $CDCl_3$) δ 7.38 (d, J=7.8 Hz, 1H), 7.20 (d, J=8.1 Hz, 1H), 6.75 (t, J=7.8 Hz, 1H), 3.48-3.32 (m, 2H), 1.65 (td, J=14.7, 7.4 Hz, 2H), 1.42 (s, 9H), 0.99 (t, J=7.4 Hz, 3H).

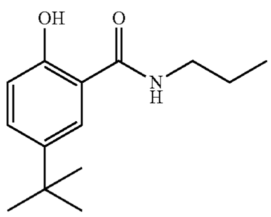 [SMILES: CCCNC(=O)c1cc(C(C)(C)C)ccc1O]

$^1$H NMR (400 MHz, $CDCl_3$) δ 12.20 (s, 1H), 7.42 (dd, J=8.7, 2.3 Hz, 1H), 7.28 (d, J=2.4 Hz, 1H), 6.90 (d, J=8.7 Hz, 1H), 6.47 (s, 1H), 3.49-3.34 (m, 2H), 1.72-1.58 (m, 2H), 1.28 (s, 9H), 0.97 (t, J=7.4 Hz, 3H). $^{13}$C NMR (400 Mhz, $CDCl_3$) δ 170.48, 159.41, 141.52, 131.86, 121.40, 118.34, 113.84, 41.62, 34.32, 31.61, 23.06, 11.63.

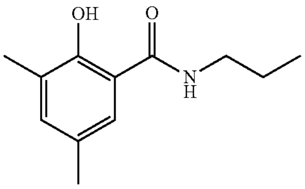

$^1$H NMR (400 MHz, $CDCl_3$) δ 12.40 (s, 1H), 7.07 (s, 1H), 6.96 (s, 1H), 6.33 (s, 1H), 3.44-3.34 (m, 2H), 2.24 (s, 3H), 2.22 (s, 3H), 1.79-1.51 (m, 2H), 0.98 (t, J=7.4 Hz, 3H). $^{13}$C NMR (400 Mhz, $CDCl_3$) δ 170.62, 157.96, 136.10, 127.57, 127.05, 122.78, 113.37, 41.59, 23.01, 20.74, 15.96, 11.63.

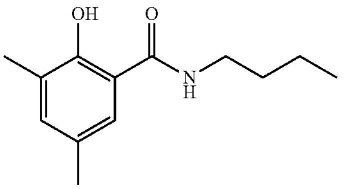 [SMILES: CCCCNC(=O)c1cc(C)cc(C)c1O]

$^1$H NMR (400 MHz, $CDCl_3$) δ 12.42 (s, 1H), 7.05 (s, 1H), 6.96 (s, 1H), 6.37 (s, 1H), 3.41 (td, J=7.2, 5.8 Hz, 2H), 2.22 (s, 3H), 2.21 (s, 3H), 1.68-1.51 (m, 2H), 1.47-1.31 (m, 2H), 0.94 (t, J=7.3 Hz, 3H). $^{13}$C NMR (400 Mhz, $CDCl_3$) δ 170.36, 157.70, 145.51, 135.83, 127.26, 122.58, 113.14, 39.40, 31.53, 20.47, 20.10, 15.70, 13.71.

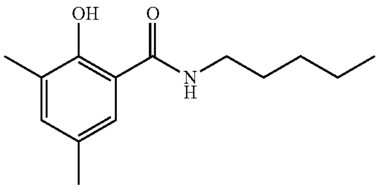 [SMILES: CCCCCNC(=O)c1cc(C)cc(C)c1O]

$^1$H NMR (400 MHz, $CDCl_3$) δ 12.43 (s, 1H), 7.06 (s, 1H), 6.97 (s, 1H), 6.38 (s, 1H), 3.59-3.25 (m, 2H), 2.22 (s, 3H), 2.21 (s, 3H), 1.68-1.54 (m, 2H), 1.43-1.29 (m, 4H), 0.90 (t, J=6.9 Hz, 3H). $^{13}$C NMR (400 Mhz, $CDCl_3$) δ 170.36, 157.71, 135.82, 133.29, 126.79, 122.60, 113.15, 39.68, 29.19, 29.07, 22.34, 20.47, 15.70, 13.93.

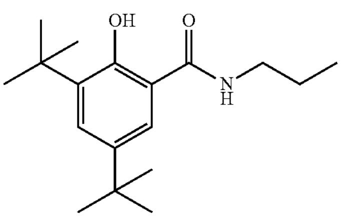 [SMILES: CCCNC(=O)c1cc(C(C)(C)C)cc(C(C)(C)C)c1O]

$^1$H NMR (400 MHz, $CDCl_3$) δ 7.45 (d, J=1.9 Hz, 1H), 7.13 (d, J=1.8 Hz, 1H), 6.34 (s, 1H), 3.49-3.33 (m, 2H), 1.65 (h, J=7.6 Hz, 2H), 1.42 (s, 9H), 1.30 (s, 9H), 0.98 (t, J=7.4 Hz, 3H). $^{13}$C NMR (400 Mhz, $CDCl_3$) δ 171.46, 158.91, 139.97, 138.38, 128.87, 119.07, 113.57, 41.66, 35.41, 34.48, 31.70, 29.59, 23.08, 11.63.

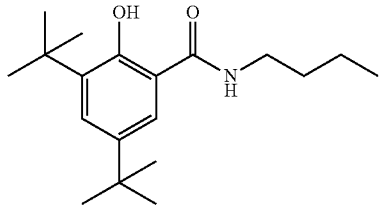 [SMILES: CCCCNC(=O)c1cc(C(C)(C)C)cc(C(C)(C)C)c1O]

$^1$H NMR (400 MHz, $CDCl_3$) δ 12.75 (s, 1H), 7.45 (s, 1H), 7.14 (s, 1H), 6.35 (s, 1H), 3.43 (m, 2H), 1.72-1.55 (m, 2H), 1.41-1.36 (m, 2H), 1.42 (s, 9H), 1.30 (s, 8H), 0.95 (t, J=7.3 Hz, 3H). $^{13}$C NMR (400 Mhz, $CDCl_3$) δ 171.19, 158.67, 139.73, 138.12, 128.61, 118.85, 113.33, 39.51, 35.17, 34.24, 31.64, 31.46, 29.35, 20.14, 13.76.

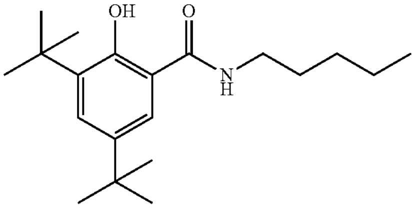 [SMILES: CCCCCNC(=O)c1cc(C(C)(C)C)cc(C(C)(C)C)c1O]

$^1$H NMR (400 MHz, $CDCl_3$) δ 12.76 (s, 1H), 7.45 (s, 1H), 7.14 (s, 1H), 6.36 (s, 1H), 3.90-2.71 (m, 2H), 1.77-1.50 (m, 32), 1.42 (s, 9H), 1.39-1.31 (m, 4H), 1.30 (s, 9H), 0.91 (t, J=6.5 Hz, 3H). $^{13}$C NMR (400 Mhz, $CDCl_3$) δ 171.18, 158.67, 139.73, 138.12, 128.61, 118.87, 113.34, 39.79, 35.17, 34.24, 31.46, 29.36, 29.27, 29.10, 22.36, 13.96.

All reagents were commercially available and used without further purification unless otherwise indicated. $^1$H NMR spectra were recorded using a 400 MHz Varian Inova NMR spectrometer. Chemical shifts (δ) are reported relative to the internal standard tetramethylsilane (TMS). Mass spectra were obtained at the University of California at Berkeley Mass Spectrometry Facility using electron spray ionization and an LTQ-FT instrument. Thin-layer chromatography was performed using silica gel 60 F254-coated plates (EM Science, Gibbstown, N.J.). Flash column chromatography was carried out using silica gel 60 (EMD Chemical, Inc., Cincinnati, Ohio). All reactions were carried out under an inert atmosphere of argon unless otherwise indicated.

Compounds 1-10 were synthesized from commercially available carboxylic acids according to the following general procedures, first activating the carboxylic acid as the para-nitrobenzyl ester and then coupling to the alkyl amine to form the desired amide.

General procedure for preparing the activated, para-nitrobenzyl esters. To a flame-dried round bottom flask was added commercially available carboxylic acid (1 eq) as a solution in anhydrous THF (0.2 M), followed by para-nitrobenzyl chloroformate (1.1 eq) and NEt3 (1.2 eq) at ambient temperature. After stirring for 1 h, the mixture was poured into a separatory funnel and extracted with EtOAc against NaHCO3. The organic layer was dried over MgSO4 and then concentrated to dryness to give the crude activated ester that was used without further purification.

General procedure for preparing the amides. To a flame-dried round bottom flask was added the para-nitrobenzyl ester (1 eq) as a solution in anhydrous THF (0.2 M), followed by the appropriate amine (1.1 eq) and NEt3 (1.2 eq) at ambient temperature. After stirring overnight, the solvent was removed via rotary evaporation and the amide was purified to homogeneity via flash silica gel chromatography and concentrated to dryness to give the desired final product in an overall yield of 49%-65% over two steps.

Analytical Data for Compounds 1-10. 2-hydroxy-3,5-diisopropyl-N-propylbenzamide (1): The title compound was synthesized in two steps from 2-hydroxy-3,5-diisopropylbenzoic acid with an overall yield of 50%; $^1$H NMR (400 MHz, CDCl3) 7.18 (s, 1H), 6.96 (s, 1H), 6.29 (s, 1H), 3.44-3.38 (m, 2H), 3.37-3.31 (m, 1H), 2.83 (hept, J=7.7 Hz, 1H), 1.74-1.58 (m, 2H), 1.24-1.20 (m, 12H), 0.98 (t, J=7.4 Hz, 3H); $^{13}$C NMR (400 Mhz, CDCl3) 170.67, 157.42, 138.20, 137.69, 128.89, 119.85, 113.22, 41.40, 33.68, 26.68, 24.22, 22.86, 22.43, 11.42. HRMS (ESI+) calcd for [M+H]+=m/z 264.1958, found 264.1955.

N-butyl-2-hydroxy-3,5-diisopropylbenzamide (2)

The title compound was synthesized from 2-hydroxy-3,5-diisopropylbenzoic acid in two steps with an overall yield of 50%; $^1$H NMR (400 MHz, CDCl3) δ 7.18 (s, 1H), 6.97 (s, 1H), 6.32 (s, 1H), 3.49-3.38 (m, 2H), 3.34 (hept, J=7.1 Hz, 1H), 2.82 (hept, J=7.1 Hz, 1H), 1.67-1.52 (m, 2H), 1.46-1.34 (m, 2H), 1.231.22 (m, 12H), 0.95 (t, J=7.3 Hz, 3H). $^{13}$C NMR (400 Mhz, CDCl3) 170.86, 157.45, 138.42, 137.85, 129.06, 119.85, 113.43, 39.68, 33.89, 31.85, 26.88, 24.43, 22.65, 20.37, 13.98. HRMS (ESI+) calcd for [M+H]+=m/z 278.2115, found 278.2111.

2-hydroxy-3,5-diisopropyl-N-pentylbenzamide (3)

The title compound was synthesized from 2-hydroxy-3,5-diisopropylbenzoic acid in two steps with an overall yield of 49%; $^1$H NMR (400 MHz, CDCl3) δ 12.50 (s, 1H), 7.19 (s, 1H), 6.97 (s, 1H), 6.32 (s, 1H), 3.45-3.39 (m, 2H), 3.35 (q, J=6.9 Hz, 1H), 2.83 (p, J=6.9 Hz, 1H), 1.68-1.55 (m, 2H), 1.39-1.32 (m, 4H), 1.24-1.22 (m 12H), 0.97-0.87 (m, 3H). $^{13}$C NMR (400 Mhz, CDCl3) 170.61, 157.23, 138.18, 137.62, 128.83, 119.62, 113.19, 39.72, 33.66, 29.26, 29.09, 26.64, 24.19, 22.41, 22.35, 13.95. HRMS (ESI+) calcd for [M+H]+=m/z 292.2271, found 292.2267.

2-hydroxy-3-isopropyl-N-propylbenzamide (4)

The title compound was synthesized from 2-hydroxy-3-isopropylbenzoic acid in two steps with an overall yield of 51%; $^1$H NMR (400 MHz, CDCl3) δ 7.31 (d, J=7.5 Hz, 1H), 7.18 (d, J=7.5 Hz, 1H), 6.90-6.72 (m, 1H), 6.3 (s, 1H), 3.77-3.20 (m, 3H), 1.63 (h, J=7.1 Hz, 2H), 1.22 (d, J=6.9 Hz, 6H), 0.97 (t, J=7.4 Hz, 3H). $^{13}$C NMR (400 Mhz, CDCl3) 170.79, 159.35, 138.12, 130.61, 122.70, 118.29, 113.84, 41.62, 26.66, 22.98, 22.60, 11.60. HRMS (ESI+) calcd for [M+H]+=m/z 222.1489, found 222.1486.

2-hydroxy-5-isopropyl-N-propylbenzamide (5)

The title compound was synthesized in two steps from 2-hydroxy-5-isopropylbenzoic acid with an overall yield of 50%; $^1$H NMR (400 MHz, CDCl3) δ 12.19 (s, 1H), 7.26 (d, J=8.6 Hz, 1H), 7.14 (s, 1H), 6.91 (d, J=8.5 Hz, 1H), 6.40 (s, 1H), 3.46-3.33 (m, 2H), 2.96-2.70 (m, 1H), 1.85-1.56 (m, 2H), 1.22 (d, J=7.0 Hz, 6H), 0.99 (t, J=7.4 Hz, 3H). $^{13}$C NMR (400 Mhz, CDCl3) 170.33, 159.80, 139.17, 132.54, 122.85, 118.69, 114.12, 41.60, 33.66, 24.34, 23.04, 11.65. HRMS (ESI+) calcd for [M+H]+=m/z 222.1489, found 222.1486.

3-(tert-butyl)-2-hydroxy-N-propylbenzamide (6)

The title compound was synthesized in two steps from 3-(tert-butyl)-2-hydroxybenzoic acid with an overall yield of 51%; $^1$H NMR (400 MHz, CDCl3) δ 7.38 (d, J=7.8 Hz, 1H), 7.20 (d, J=8.1 Hz, 1H), 6.75 (t, J=7.8 Hz, 1H), 3.48-3.32 (m, 2H), 1.65 (m, 2H), 1.42 (s, 9H), 0.99 (t, J=7.4 Hz, 3H). $^{13}$C NMR (400 Mhz, CDCl3) 170.78, 159.36, 138.52, 130.86, 122.40, 118.33, 113.85, 41.64, 30.25, 27.32, 22.62, 11.58. HRMS (ESI−) calcd for [M−H]+=m/z 234.1500, found 234.1500.

5-(tert-butyl)-2-hydroxy-N-propylbenzamide (7)

The title compound was synthesized in two steps from 5-(tert-butyl)-2-hydroxybenzoic acid with an overall yield of 55%; H NMR (400 MHz, CDCl3) δ 12.20 (s, 1H), 7.42 (dd, J=8.7, 2.3 Hz, 1H), 7.28 (d, J=2.4 Hz, 1H), 6.90 (d, J=8.7 Hz, 1H), 6.47 (s, 1H), 3.49-3.34 (m, 2H), 1.72-1.58 (m, 2H), 1.28 (s, 9H), 0.97 (t, J=7.4 Hz, 3H). $^{13}$C NMR (400 Mhz, CDCl3) 170.48, 159.41, 141.52, 131.86, 121.40, 118.34, 113.84, 41.62, 34.32, 31.61, 23.06, 11.63. HRMS (ESI+) calcd for [M+H]+=m/z 236.1645, found 236.1642.

3,5-di-tert-butyl-2-hydroxy-N-propylbenzamide (8)

The title compound was synthesized in two steps from 3,5-di-tert-butyl-2-hydroxybenzoic acid with an overall yield of 56%; $^{1H}$ NMR (400 MHz, CDCl3) δ 7.45 (d, J=1.9 Hz, 1H), 7.13 (d, J=1.8 Hz, 1H), 6.34 (s, 1H), 3.493.33 (m, 2H), 1.65 (h, J=7.6 Hz, 2H), 1.42 (s, 9H), 1.30 (s, 9H), 0.98 (t, J=7.4 Hz, 3H). 13C NMR (400 Mhz, CDCl3) 171.46, 158.91, 139.97, 138.38, 128.87, 119.07, 113.57, 41.66, 35.41, 34.48, 31.70, 29.59, 23.08, 11.63. HRMS (ESI+) calcd for [M+H]+=m/z 292.2271, found 292.2267.

3,5-di-tert-butyl-N-butyl-2-hydroxybenzamide (9)

The title compound was synthesized in two steps from 3,5-di-tert-butyl-2-hydroxybenzoic acid with an overall yield of 50%; $^1$HNMR (400 MHz, CDCl3) δ 12.75 (s, 1H), 7.45 (s, 1H), 7.14 (s, 1H), 6.35 (s, 1H), 3.43 (m, 2H), 1.72-1.55 (m, 2H), 1.41-1.36 (m, 2H), 1.42 (s, 9H), 1.30 (s, 8H), 0.95 (t, J=7.3 Hz, 3H). 13C NMR (400 Mhz, CDCl3) 171.19, 158.67, 139.73, 138.12, 128.61, 118.85, 113.33, 39.51, 35.17, 34.24, 31.64, 31.46, 29.35, 20.14, 13.76. HRMS (ESI+) calcd for [M+H]+=m/z 306.2428, found 306.2423.

3,5-di-tert-butyl-2-hydroxy-N-pentylbenzamide (10)

The title compound was synthesized from 3,5-di-tert-butyl-2-hydroxybenzoic acid in two steps with an overall yield of 65%; $^1$H NMR (400 MHz, CDCl3) δ 12.76 (s, 1H), 7.45 (s, 1H), 7.14 (s, 1H), 6.36 (s, 1H), 3.90-2.71 (m, 2H), 1.77-1.50 (m, 32), 1.42 (s, 9H), 1.39-1.31 (m, 4H), 1.30 (s, 9H), 0.91 (t, J=6.5 Hz, 3H). $^{13}$C NMR (400 Mhz, CDCl3) 171.18, 158.67, 139.73, 138.12, 128.61, 118.87, 113.34, 39.79, 35.17, 34.24, 31.46, 29.36, 29.27, 29.10, 22.36, 13.96. HRMS (ESI+) calcd for [M+H]+=m/z 320.2584, found 320.2580.

Example 5. Cellular Assays

Figure 3:
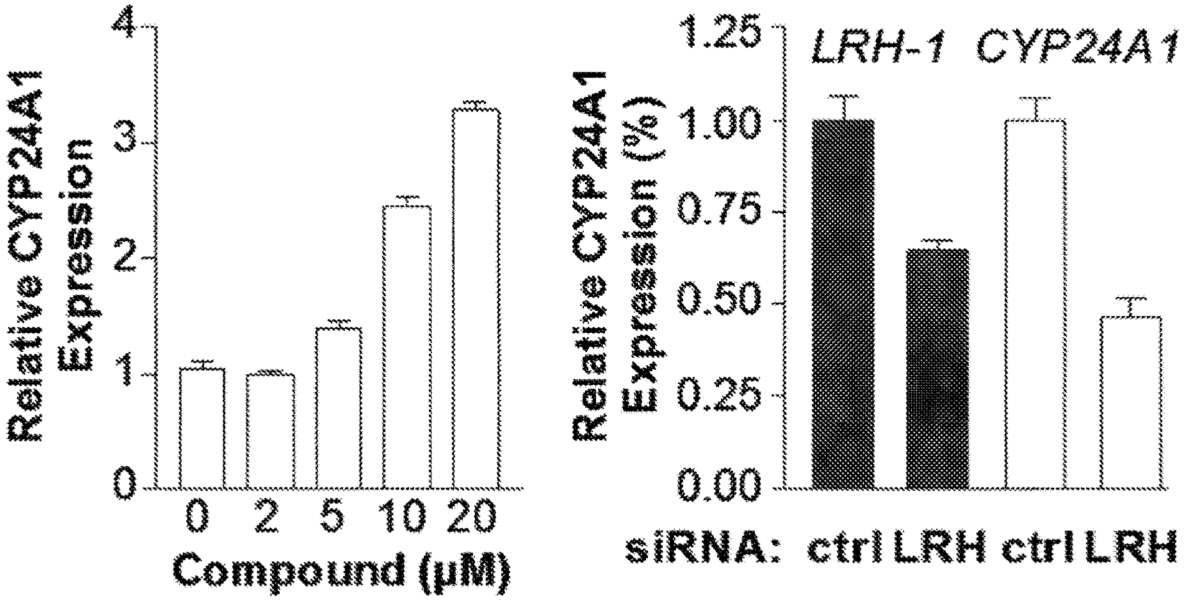
FIG. 3. Compound activity is dependent on the amount of compound and LRH-1.
Figure 4:
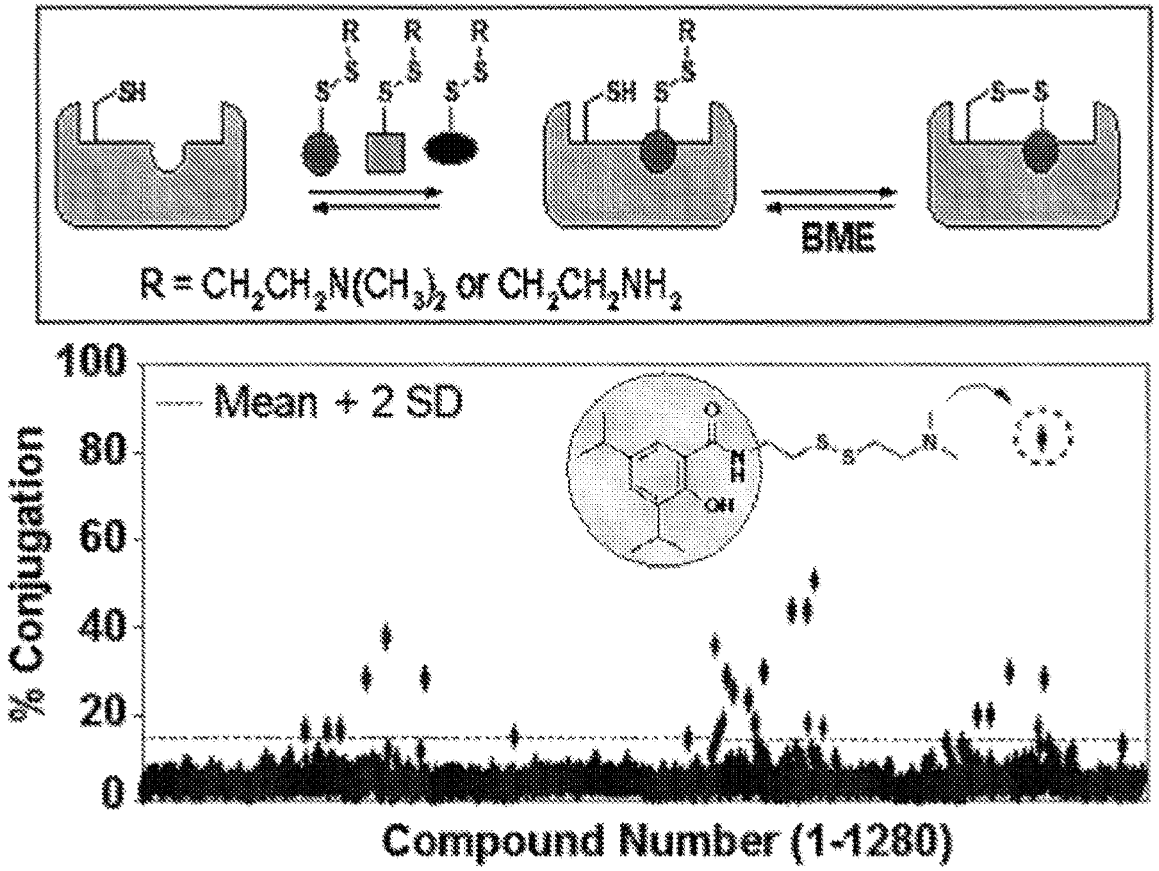
FIG. 4. Disulfide-trapping screen and structure of example compound. Cartoon depicting the screening strategy wherein each molecule in the library includes two elements: a monophore (circle, square, oval), which is the unique chemical entity, and a common linker region (—S—S—R) that can undergo disulfide exchange with thiols, including cysteine side chains; library compounds are individually incubated with the target protein (hLRH-1 LBD) under high reductant conditions (500 μM BME), such that disulfide exchange is rapid; compounds with high intrinsic affinity for a binding site near a cysteine residue (e.g., $Cys^{346}$ in hLRH-1) have superior residence time and thus encourage the lasting formation of a disulfide bond between the protein thiol and compound thiol; compounds with weak inherent affinity are readily reduced off' graph showing the conjugation efficiency for each of 1280 compounds in the library to hLRH-1; notably, the disulfide-trapping screen was carried out against hLRH-1 bound to a phospholipid (phosphatidylethanolamine) co-expressed with the receptor in bacteria; small non-polar molecules are clearly able to displace bound bacterial phospholipid ligands from the pocket.
Figure 5:
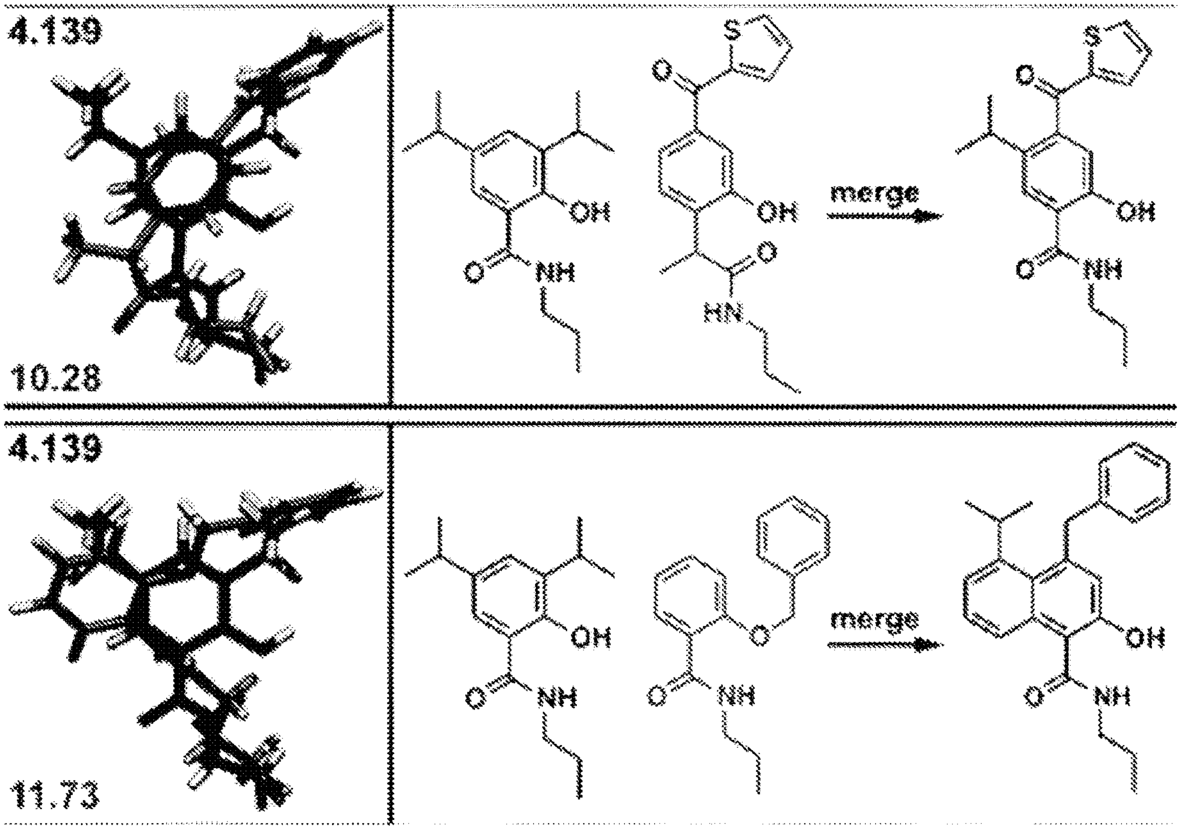
FIG. 5. LRH-1 modulators and compound modifications.

Compounds 1-10 were evaluated in HepG2 cells, a liver cancer cell line expressing endogenous human LRH-1. Specifically, compound effects were measured on the expression of the LRH-1 target gene Cyp24A1. Three compounds (8-10) proved to be surprisingly active, specifically driving Cyp24A1 expression ~3-fold over control and in one case (9), surpassing the activity of the most potent synthetic agonist described to date (RJW100) (FIG. 2). This activity was both dependent on ligand dose and LRH-1 expression (FIG. 3).

Figure 6:
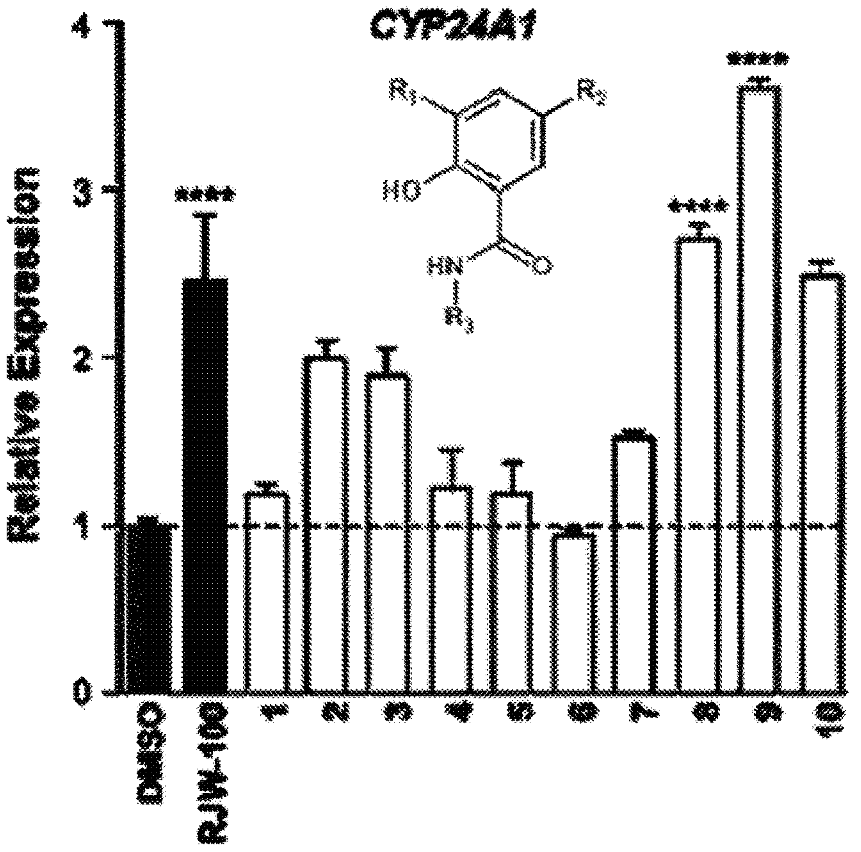
FIG. 6. Activity of PME9 Exceeds that of RJW100 in HepG2 Cells. The relative expression of CYP24A1 transcripts in HepG2 cells following 16 h treatment with either vehicle (DMSO) or compound 1 (PME1), 2 (PME2), 3 (PME3), 4 (PME4), 5 (PME5), 6 (PME6), 7 (PME7), 8 (PME8), 9 (PME9), and 10 (PME10) at 10 μM as listed on the X-axis; for reference, activity with the existing NR5A agonist RJW100 is shown (grey bar). For these experiments levels of hLRH-1 were low, as doxycycline (−Dox) was not added to HepG2-hLRH-1 cells; data are representative of at least three independent experiments with error bars representing SEM, P values=****<0.0001.
Figure 7A:
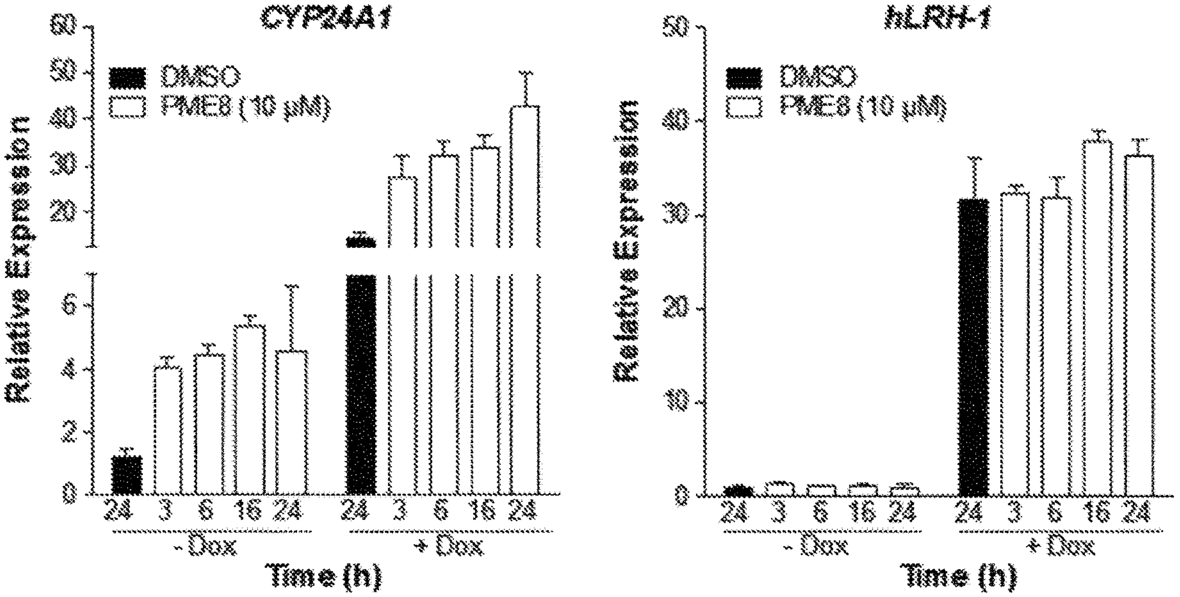
FIGS. 7A-7B. PME8 induces a hLRH-1 target gene in a both time- and dose-dependent manner with activity increasing at higher hLRH-1 levels.
Figure 7B:
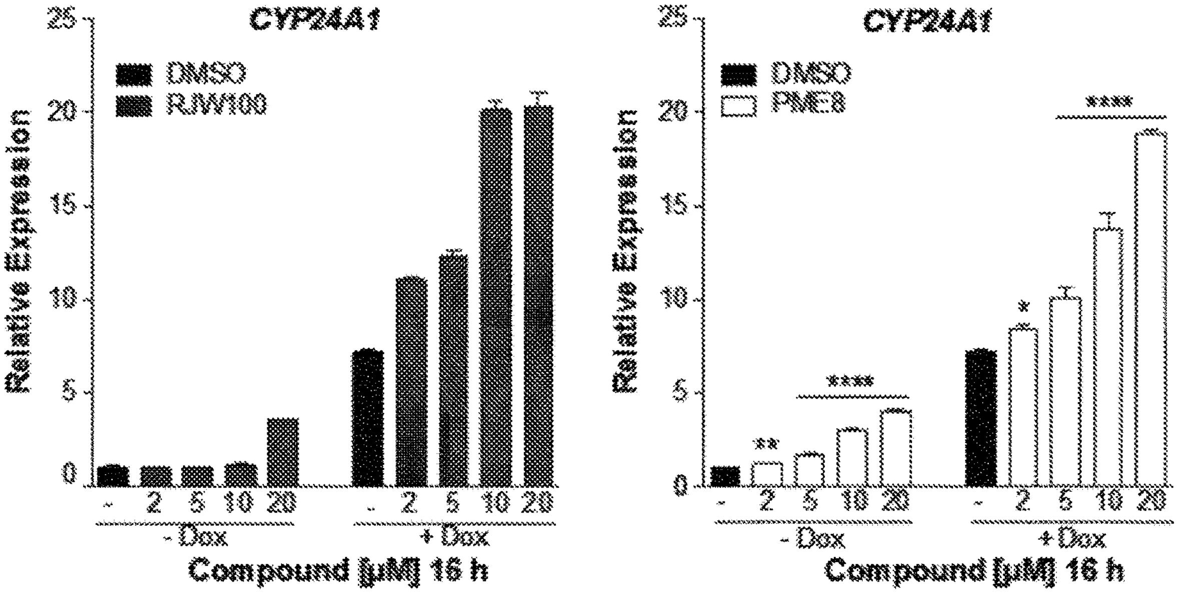

Analogs 1-10 were tested in a hepatocellular carcinoma HepG2 cell line stably expressing hLRH-1 that can be induced to express low or high levels without or with doxycycline (−Dox or +Dox), respectively. Levels of the direct hLRH-1 target gene CYP24A1 [15] were measured by RT-qPCR as described in Materials and Methods. A comparison of all analogs showed that compounds 8 (PME8) and 9 (PME9) (10 µM) consistently increased endogenous CYP24A1 transcript levels 3-4-fold following a 16 h treatment time (FIG. 6). The activity of PME9 exceeded that of RJW100. Importantly, when assayed in HepG2-hLRH-1 cells expressing low levels of hLRH-1, PME8 did not change hLRH-1 transcripts (FIG. 7A) or protein levels. Compound PME8 does increase CYP24A1 levels in a time-dependent (FIG. 7A) and dose-dependent manner with maximal activity observed at 16 h of treatment (FIG. 7B).

Figure 8:
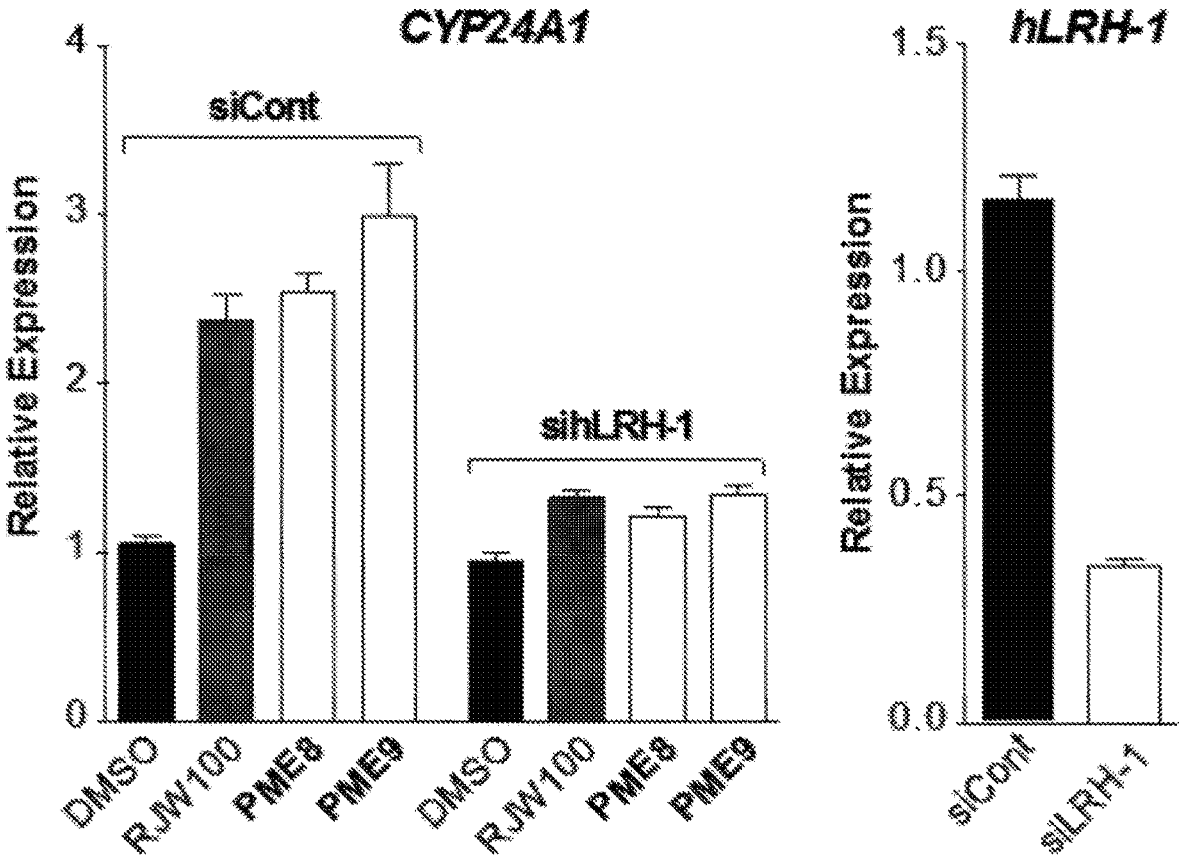
FIG. 8. Activity of PME8 and PME9 Depends on hLRH-1. The expression of CYP24A1 transcripts was determined in the presence of RJW100 (grey bar) or the two new compounds PME8 and PME9 (10 μM) without (siCont) or with knockdown (siLRH-1) of hLRH-1 (left panel). SiRNA-mediated knockdown of hLRH-1 in HepG2-hLRH-1 cells expressing low levels of hLRH-1 (−Dox) was carried out as described herein. Relative levels of hLRH-1 transcripts after siCont or siLRH-1 are shown (right panel).
Figure 9:
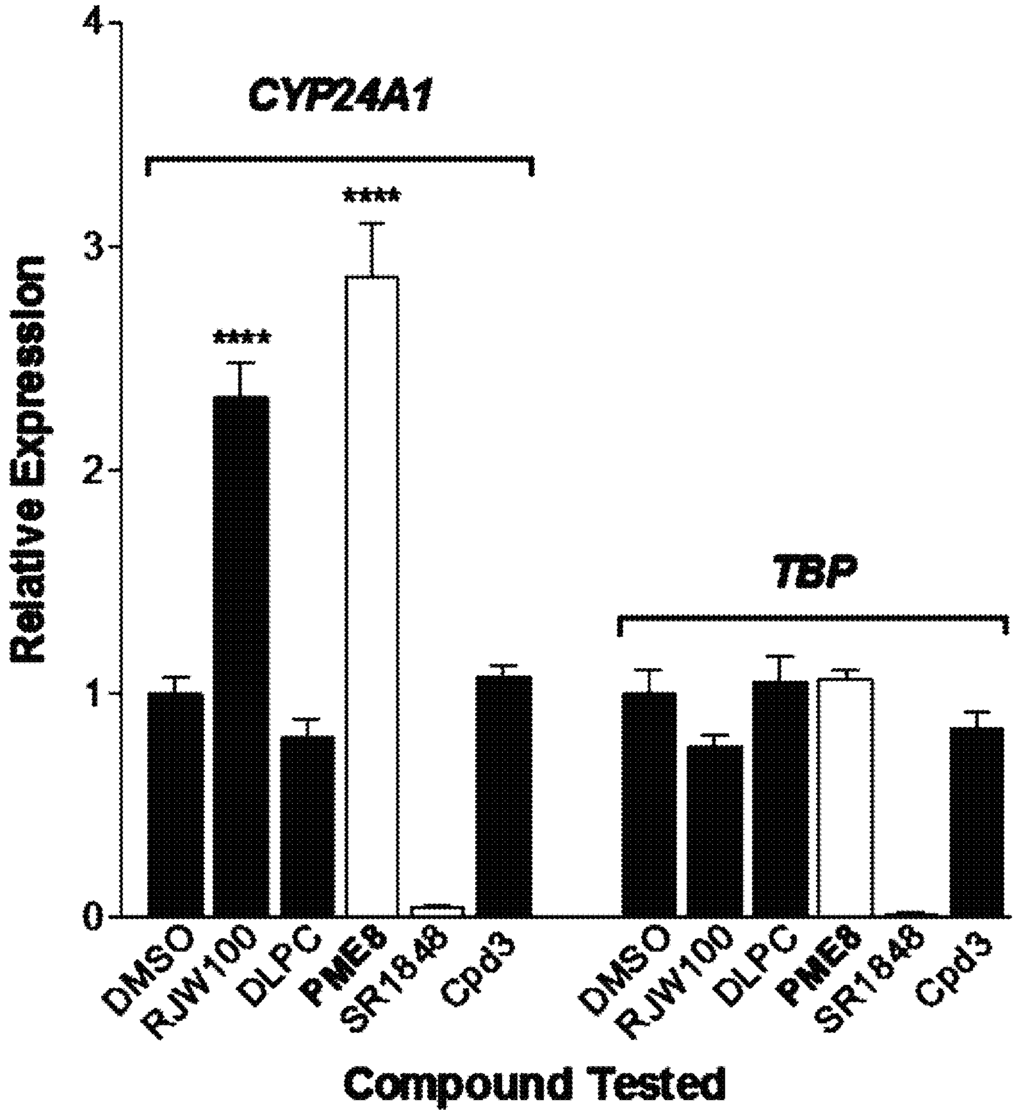
FIG. 9. Effects of select compounds targeting hLRH-1 compared to PME8. Agonists and antagonists were tested in HepG2-hLRH-1 cells expressing high levels (+Dox) of hLRH-1; activating compounds were added for 16 h relative to the DMSO control (black bars) at the following concentrations: RJW100 (10 μM) [7], DLPC (20 μM) [5], PME8 (10 μM) (bolded, this study) as well as the two putative antagonist/repressors, SR1848 (10 μM) [20] and Cpd3 (10 μM) [21]; relative levels of the hLRH-1 target, CYP24A1 (left set of bars) and the housekeeping gene, TBP (right set of bars) are shown with all values normalized to GAPDH. Error bars represents SEM and P values=****<0.0001.
Figure 10:
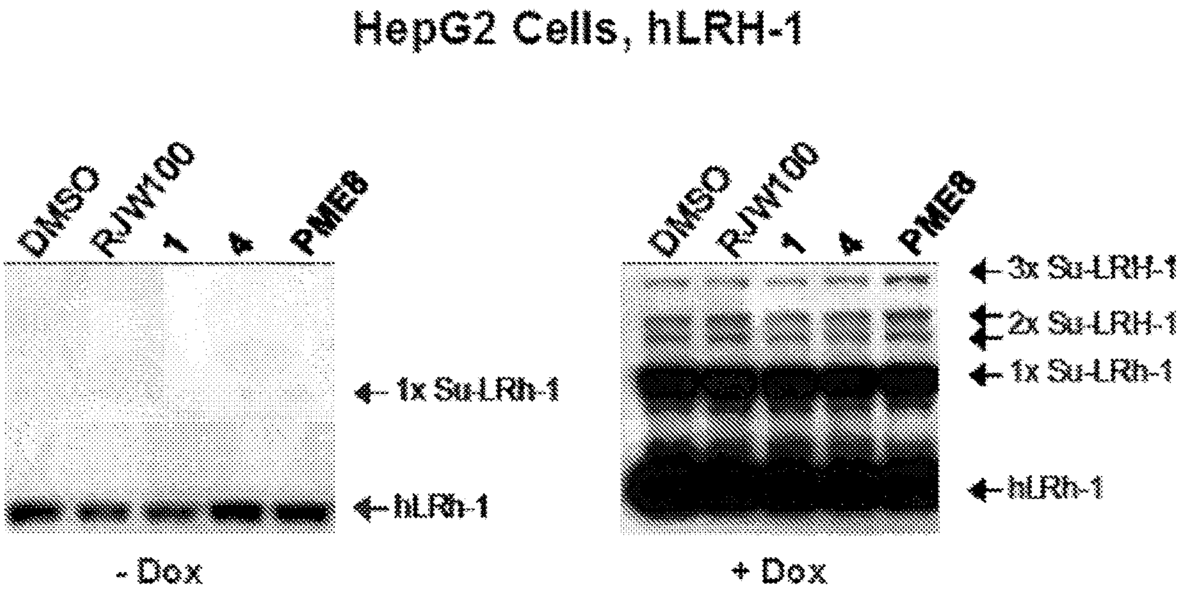
FIG. 10. Expression of hLRH-1 is unaffected by PME8. The expression of hLRH-1 detected in Western blots using anti-Flag antibody is shown in HepG2 cells expressing low (−Dox) or higher levels (+Dox) of hLRH-1. All three sumoylated species of hLRH-1 (SU-LRH-1) are observed after Induction of high levels of hLRH-1, as indicated by arrows.
Figure 11:
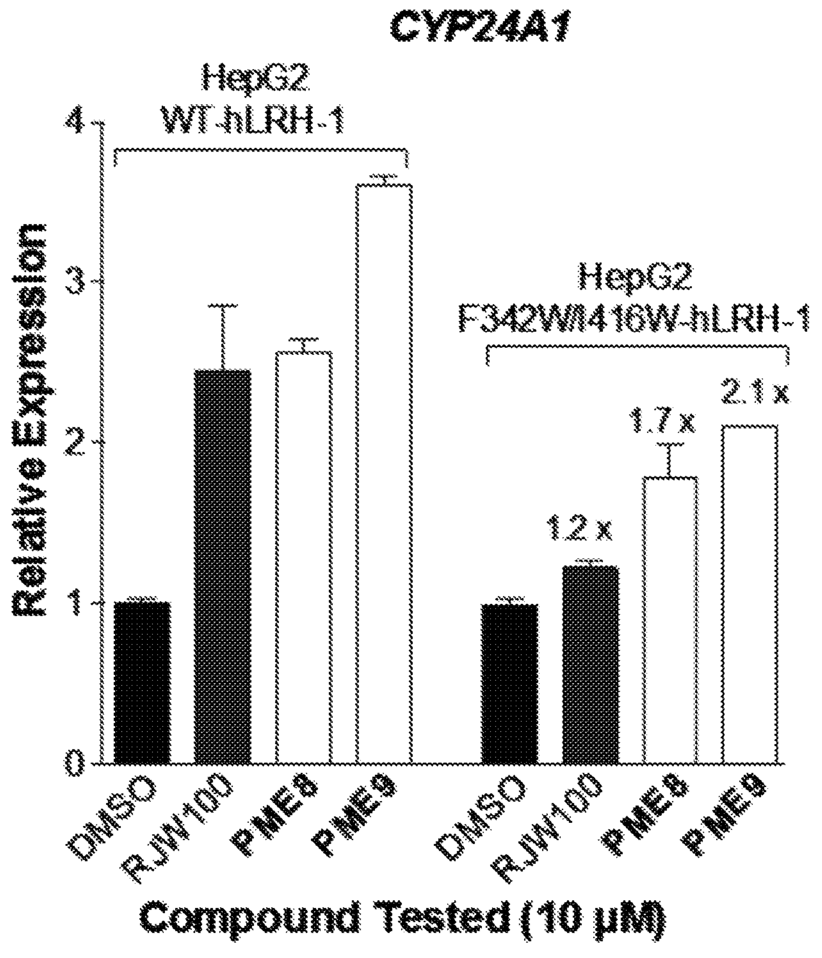
FIG. 11. Activity of RJW100, PME8 and PME9 depends on an intact hLRH-1 ligand binding pocket. Expression of CYP24A1 transcripts in the presence of DMSO (black bar), RJW100 (grey bars), PME8 and PME9 (white bars) at 10 μM for 16 h treatment in HepG2-hLRH-1 cells expressing low levels of wild type hLRH-1 or the hLRH-1 pocket mutant F342W/I416W variant as described herein.
Figure 12:
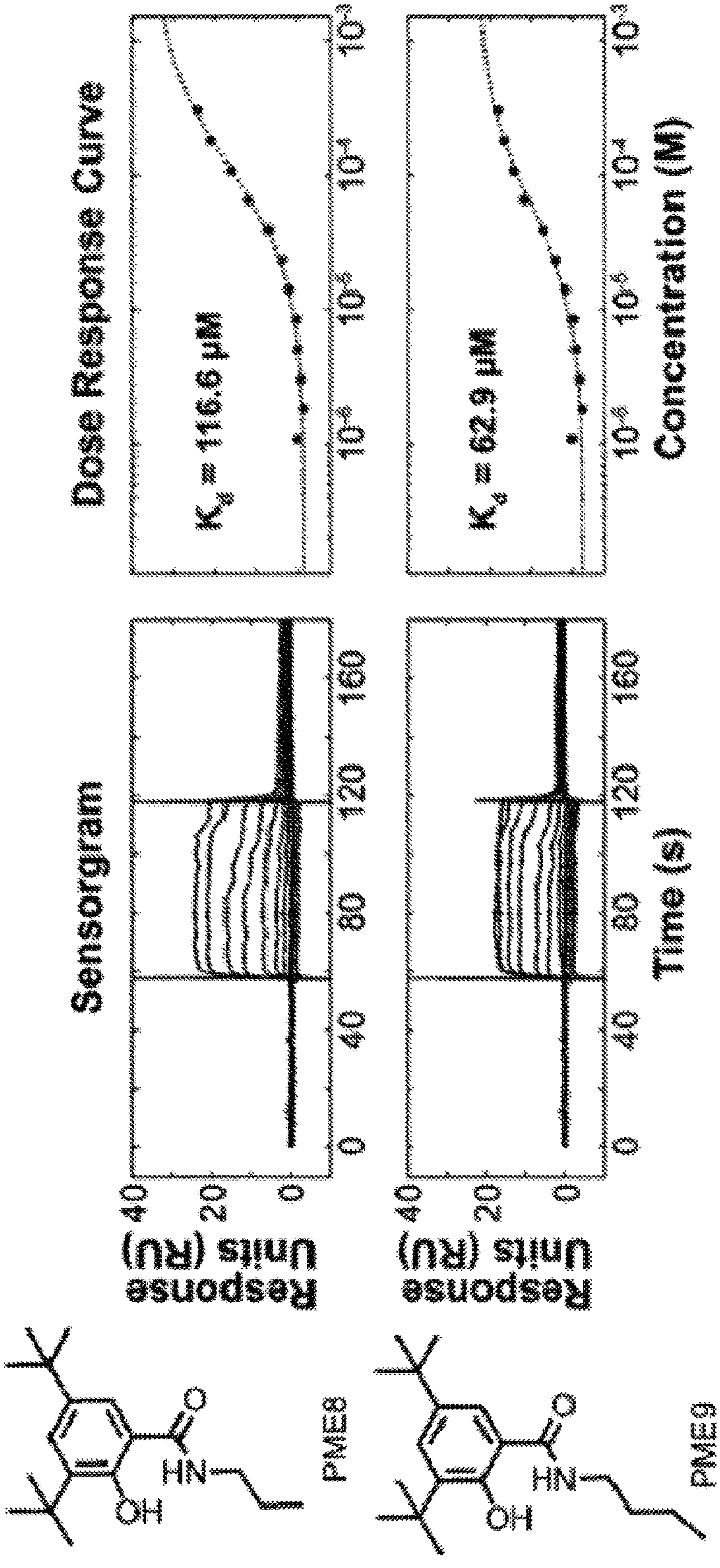
FIG. 12. PME8 and PME9 bind directly to the hLRH-1 LBD. (Left) Raw surface plasmon resonance sensorgrams (time vs response) for PME8 and PME9 show direct binding to biotinylated apo hLRH-1 LBD; (Right) Dose-response curves (log ligand concentration vs response) for PME8 and PME9 with apparent dissociation constants determined using steady state values at 20 s post injection (dots on sensorgrams) and a 1:1 binding model.
Figure 14:
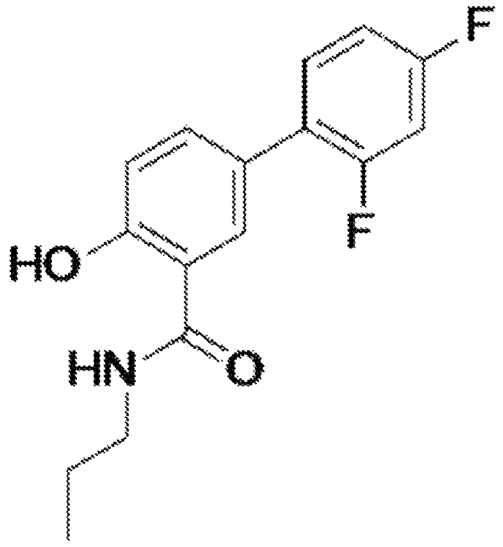
FIG. 14. Overlay of compound 10.14 on a nuclear receptor.
Figure 14:
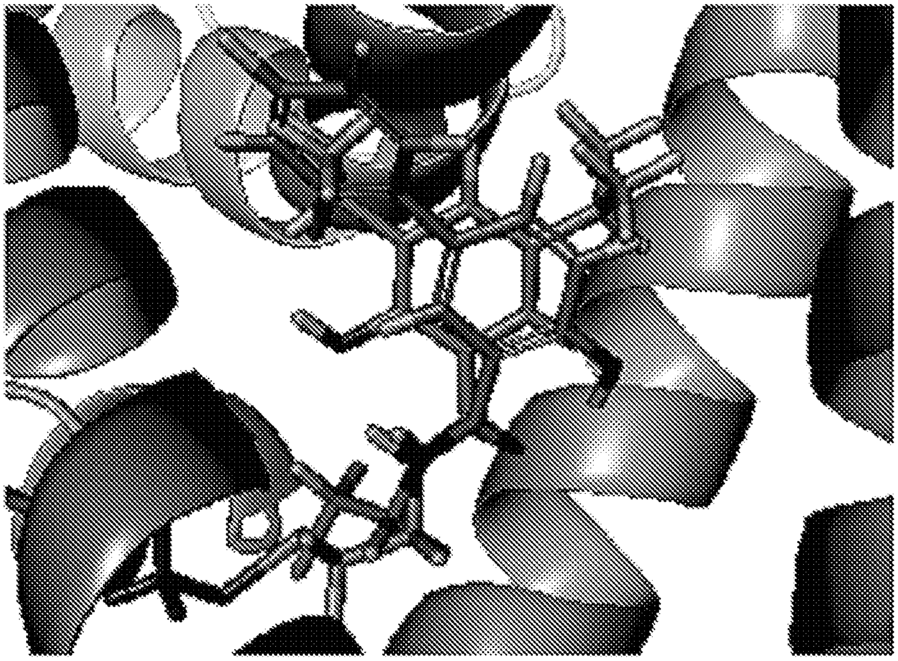
Figure 15:
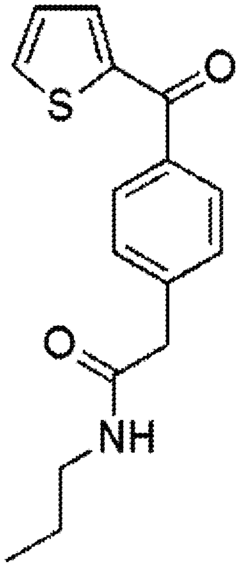
FIG. 15. Overlay of compound 10.28 on a nuclear receptor.
Figure 15:
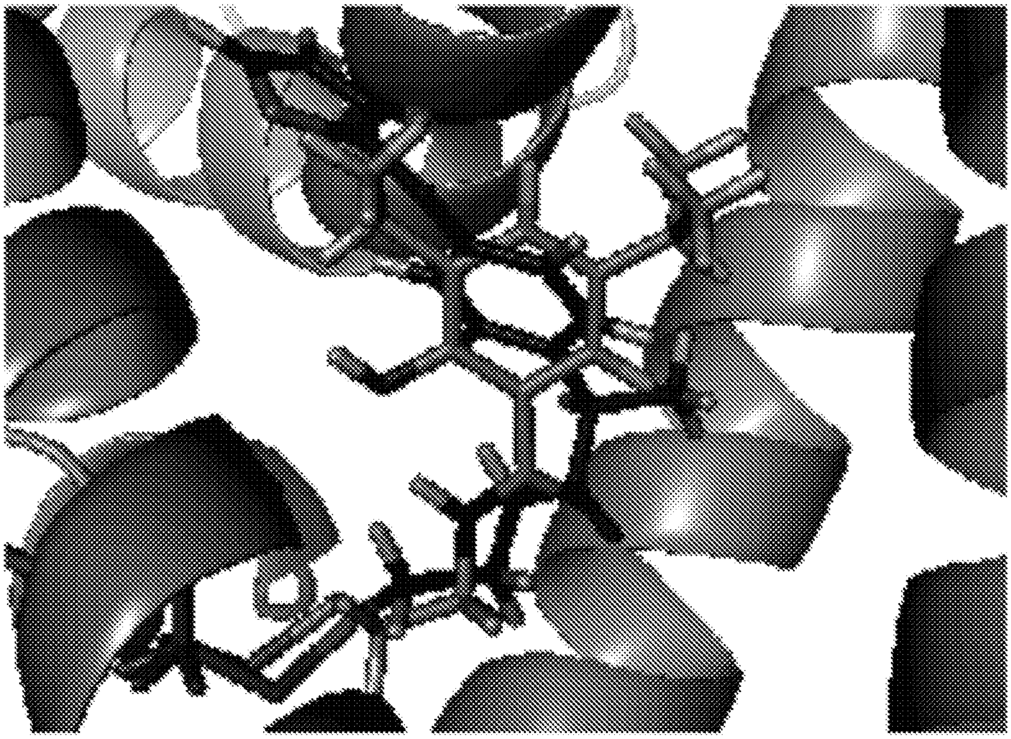

To determine whether the activity of the two most potent compounds PME8 and PME9 are specific for hLRH-1, their activities were retested after siRNA-mediated knockdown of hRH-1 in HepG2 cells. For PME8 and PME9, as well as the control RJW100 compound, a clear dependence on hLRH-1 was observed as evidenced by the precipitous drop in CYP24A1 expression following treatment with sihLRH-1, but not with siControl RNA (FIG. 8). These ligands likely bind within the ligand binding pocket as the activity of both PME8 and PME9, as well as RJW100, decreased when tested in HepG2 cells stably expressing equivalent levels of F342W/I416W hLRH-1, a "pocket" mutant harboring two large bulky tryptophan side chains designed to fill the ligand binding cavity of hLRH-1. Interestingly, although greatly reduced, there are still residual levels of CYP24A1 after treatment with PME8 and PME9 in cells expressing this variant of hLRH-1. Consistent with these data, we observed direct binding of PME8 and PME9 to the hLRH-1 LBD using surface plasmon resonance assays.

Finally, to ask how PME8 and PME9 compare to other published compounds, we directly compared the activity of all compounds with respect to the ability to activate or repress CYP24A1 expression in HepG2-hLRH-1 cells. For this experiment, assays were carried out under high levels of hLRH-1 (+Dox) to maximize our ability to see any repressive effects of compounds and the ligand concentrations used were based on published effective doses. Results from this experiment indicate that only one of the two published agonists, RJW100, showed the expected activity; DLPC failed to increase CYP24A1 expression (FIGS. 7A-7B). Of the two published antagonist/repressors, only SR1848 decreased CYP24A1 levels. However, SR1848 also exhibited substantial repression of the housekeeping gene, TBP. Similar results were also observed for another identified hLRH-1 target, SERPINE or PAII. Taken together, our findings show that PME8 and PME9 are potential new leads for creating high affinity, efficacious synthetic ligands for hLRH-1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 6. Experimental Protocol

Cell lines and Quantitative Real-time Polymerase Chain Reaction (RT-qPCR) Assay. HepG2 3G stable cells expressing 3X-Flag-tagged WT and pocket mutant (F342W/I416W) hLRH-1 were generated as described after insertion into the doxycycline (Dox)-inducible pTRE 3G vector (Clontech) to generate HepG2-hLRH-1 stable cell lines. The parental TET-On 3G HepG2 cell line was a generous gift from Dr. Stephen Hand. Induction of low or high levels of hLRH-1 was achieved by addition of DMSO or 500 ng/ml Dox, respectively.

For RT-qPCR assay, cells ($5\times10^5$) were plated on 24-well plates in 0.5 mL of media. The following day, fresh media was applied with compound or DMSO control. After an overnight treatment or indicated period of time, cells were washed with ice-cold 1×PBS and total RNA was isolated by Trizol (Life Technologies). DNase-treated total RNA was used to generate cDNA using High-Capacity cDNA Reverse Transcription kits (Life Technologies). RT-qPCR was performed with SYBR (Biotool) and data analyzed essentially as described [19]. Sequences for all primer pairs used for qPCR reactions are listed in FIG. 13. For siLRH-1 knockdowns, siLRH-1 (GS2494) and non-silencing control (SI03650318) siRNA were purchased from Qia-gen. SiRNAs were used at a final concentration of 5 nM and reverse-transfected into HepG2-hLRH-1 stable cells by RNAiMax (Life Technologies) for 72 h. Knockdown was confirmed after assaying hLRH-1 transcripts by RT-qPCR.

Surface Plasmon Resonance Assays. Data were collected on a BiaCore T100 instrument. The biotin CAPture kit (GE Healthcare Life Science) was used as directed for chip preparation and immobilization of protein. In brief, the CAP chip was first conditioned with 3×1 min injec-tions of the provided regeneration solution (6 M Guanidine HCL, 0.25 M NaOH). CAP reagent was then captured on flow cells 1 and 2 to a final density of ~2500 response units using capture buffer (25 mM HEPES, pH 7.4, 150 mM NaCl). Avi-tagged LRH-1 was then directly injected exclusively on to flow cell 2 achieving a final density of ~1000 response units (capture buffer). Flow cell 1 served as the reference flow cell and flow cell 2 served as the active flow cell. A titration series for each fragment was generated as a 0.6× dilution series starting from 300 μM. All samples were made to match the running buffer used in the experiment as closely as possible (capture buffer+3% DMSO, +0.05% Tween-20, 250 μM TCEP). Data was collected at 25° C. with a flow rate of 30 μL/min. Data processing included referencing to both the reference flow cell as well as a buffer injection. Equilibrium binding constants were determined by nonlinear regression analysis utilizing a simple 1:1 binding model. Steady state values used to generate dose-responses curve correspond to the response units achieved 20 seconds after injection.

What is claimed is:

1. A compound having the formula:

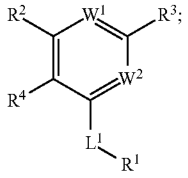

wherein $W^1$ and $W^2$ are independently CH or N;

$L^1$ is C(O)NH—, —NHC(O)—, or —NHC(NH)NH;

$R^1$ is unsubstituted alkyl;

$R^2$ is unsubstituted tert-butyl;

$R^3$ is unsubstituted tert-butyl;

$R^4$ is $—OR^{22}$;

$R^{22}$ is hydrogen, halogen, $—CX_3$, $—CHX_2$, $—CH_2X$, $—OCX_3$, $—OCH_2X$, $—OCHX_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC{=}(O)NHNH_2$, $—NHC{=}(O)\ NH_2$, $—NHSO_2H$, $—NHC{=}(O)H$, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is —Cl, —Br, —I, or —F;

wherein $R^1$ is not unsubstituted methyl or unsubstituted tert-butyl; and wherein the compound does not have the formula

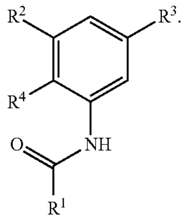

2. The compound of claim 1, wherein $R^1$ is unsubstituted $C_1$-$C_8$ alkyl.

3. The compound of claim 1, having the formula:

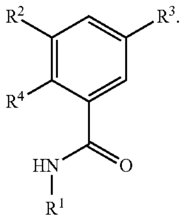

4. The compound of claim 1, wherein $R^1$ is unsubstituted $C_1$-$C_6$ alkyl.

5. The compound of claim 1, wherein $R^4$ is —OH.

6. The compound of claim 1, wherein $R^1$ is unsubstituted butyl, unsubstituted pentyl, or unsubstituted hexyl.

7. The compound of claim 1, wherein $R^1$ is unsubstituted $C_3$-$C_5$ alkyl.

8. The compound of claim 1, wherein $R^1$ is unsubstituted n-butyl.

9. A pharmaceutical composition comprising a compound of claim 1, or a pharmaceutically acceptable salt thereof, and a pharmaceutically acceptable excipient.

10. The compound of claim 1, having the formula

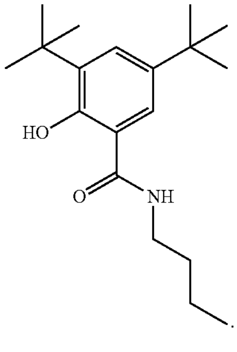 [SMILES: CCCCNC(=O)c1cc(C(C)(C)C)cc(C(C)(C)C)c1O]

* * * * *